United States Patent
Heitmeier et al.

(10) Patent No.: US 12,215,168 B2
(45) Date of Patent: *Feb. 4, 2025

(54) ANTI-A2AP ANTIBODIES AND USES THEREOF

(71) Applicant: BAYER AKTIENGESELLSCHAFT, Leverkusen (DE)

(72) Inventors: Stefan Heitmeier, Wülfrath (DE); Julia Glunz, Essen (DE); Melanie Fischer, Riedstadt (DE); Cindy Schulenburg, Zürich (CH); Hannah Jörißen, Heiligenhaus (DE); Christoph Thiel, Cologne (DE); Andreas Wilmen, Cologne (DE); Ernst Weber, Langenfeld (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/525,736

(22) Filed: Nov. 30, 2023

(65) Prior Publication Data

US 2024/0166766 A1 May 23, 2024

Related U.S. Application Data

(63) Continuation of application No. 18/329,700, filed on Jun. 6, 2023, which is a continuation of application No. 18/026,089, filed as application No. PCT/EP2021/075038 on Sep. 13, 2021.

(30) Foreign Application Priority Data

Sep. 15, 2020 (EP) .................... 20196259

(51) Int. Cl.
C07K 16/38 (2006.01)
A61K 39/395 (2006.01)
A61K 45/06 (2006.01)
A61P 9/10 (2006.01)
C12N 15/63 (2006.01)

(52) U.S. Cl.
CPC .......... *C07K 16/38* (2013.01); *A61K 39/3955* (2013.01); *A61K 45/06* (2013.01); *A61P 9/10* (2018.01); *C12N 15/63* (2013.01); *C07K 2317/21* (2013.01); *C07K 2317/24* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

2002/0086025 A1 7/2002 Reed et al.

FOREIGN PATENT DOCUMENTS

WO WO-9812329 A2 3/1998

OTHER PUBLICATIONS

"Mimuro Jun et al:""Monoclonal Antibodies to Discrete Regions in $\alpha_2$-Plasmin Inhibitor" Blood vol. 69, No. 2, 1987, 446-453.
"Sakata Yoichi et al:""Clot Lysis Induced by a Monoclonal Antibody Against $\alpha_2$-Plasmin Inhibitor" Blood, Am. Soc. Hem., vol. 74, No. 8, 1989, 2692-2697.
"Reed Guy L.:" "Functional Characterization of Monoclonal Antibody Inhibitors of $\alpha_2$-Antiplasmin that Accelerate Fibrinolysis in Different Animal Plasmas" Hybridoma vol. 16, No. 3, 1997, 281-286.
"Singh Satish El Al:" "Releasing the Brakes on the Fibrinolytic System in Pulmonary Emboli Unique Effects of Plasminogen Activation and $\alpha_2$-Antiplasmin Inactivation" Original Research Article Circulation, vol. 135, Mar. 14, 2017.
"Tone Masahide et al.;" "Structure of Human $\alpha_2$-Plasmin Inhibitor Deduced from the cDNA Sequence1" J. Biochem. 102, 1033-1041 (1987) Apr. 22, 1987.
Silverman Gary A. et al; The Serpins Are an Expanding Superfamily of Structurally Similar but Functionally Diverse Proteins The Journal of Biological Chemistry vol. 276, No. 36, Issue of Sep. 7, pp. 33293-33296, 2001.
"Collen D et al;" "Turnover of Antiplasmin, the Fast-Acting Plasmin Inhibitor of Plasma" Blood. 1979;53(2):313-324.
"Reed Guy L. et al.;""Microvascular Thrombosis, Fibrinolysis, Ischemic Injury, and Death After Cerebral Thromboembolism Are Affected by Levels of Circulating $\alpha^2$-Antiplasmin" Arterioscler Thromb Vasc Biol. Dec. 2014;34(12):2586-2593.
"Singh Satish et al: ""Alpha2-Antiplasmin: The Devil You Don't Know in Cerebrovascular and Cardiovascular Disease""", Frontiers in Cardiovascular Medicine vol. 7 Dec. 23, 2020 (Dec. 23, 2020)".

*Primary Examiner* — Kimberly Ballard
*Assistant Examiner* — Aditi Dutt
(74) *Attorney, Agent, or Firm* — Harness, Dickey & Pierce, P.L.C.

(57) ABSTRACT

The present invention relates to an isolated antibody or antigen-binding fragment thereof that binds to human A2AP. The isolated antibody or antigen-binding fragment according to the present invention i) cross-reacts with rabbit and/or cynomolgus A2AP, ii) does not inhibit human plasmin activity, and iii) increases plasmin mediated clot lysis in the presence of A2AP.

15 Claims, 36 Drawing Sheets

Figure 2:
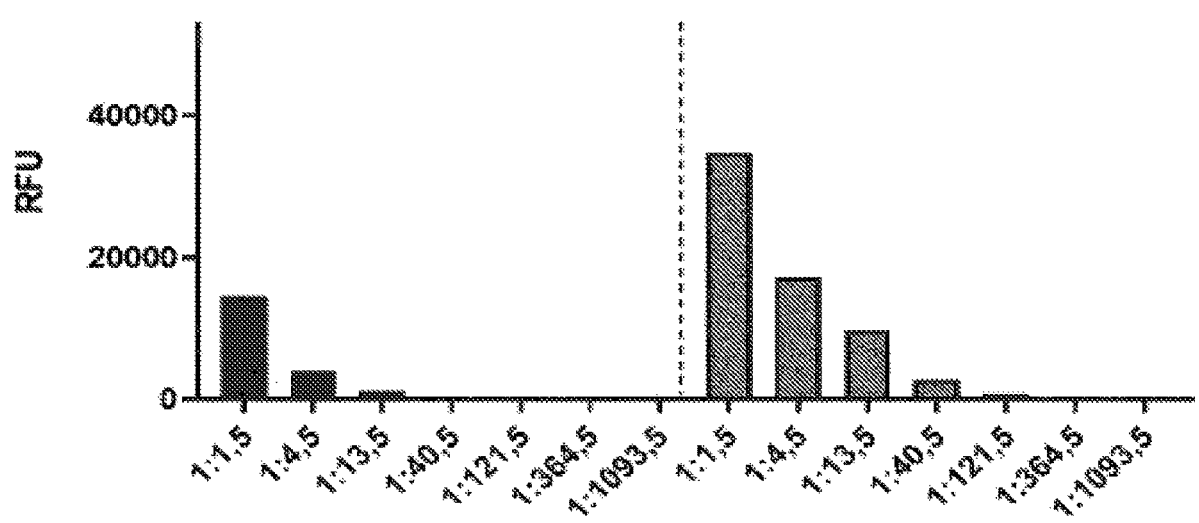

Specification includes a Sequence Listing.

| Selection Round | Strategy I:<br>btl. a2AP (NTΔ1-43) | Strategy II:<br>btl. a2AP (NTΔ1-43) | Strategy III:<br>lin. btl. peptide RCL | Strategy IV:<br>cycl. btl. peptide RCL |
|---|---|---|---|---|
| 1 | 400 nM ha2AP | 400 nM ha2AP | 400 nM ha2AP | 400 nM ha2AP |
| 2 | 200 nM ha2AP → 400 nM ra2AP | 200 nM ha2AP → 200 nM ra2AP / 400 nM ra2AP | 1.5 µM pept. lin. | 1.5 µM pept. cycl. |
| 3 | 400 nM ha2AP / 200 nM ha2AP | 400 nM ra2AP → 100 nM ha2AP | 0.8 µM pept. lin. | 0.8 µM pept. cycl. |
| Depletion | Irrelevant protein (btl.; AVI-His-tag) | btl. a2AP (NTΔ1-43; CTΔ410-464) | Irrelevant protein (btl.) | Irrelevant protein (btl.) |
| Comment | Targeting whole protein except N-terminus | Targeting Plasmin binding site (Ct-extension) | Targeting Reactive Center Loop (RCL) | Targeting Reactive Center Loop (RCL) |

Figure 1

Figure 5
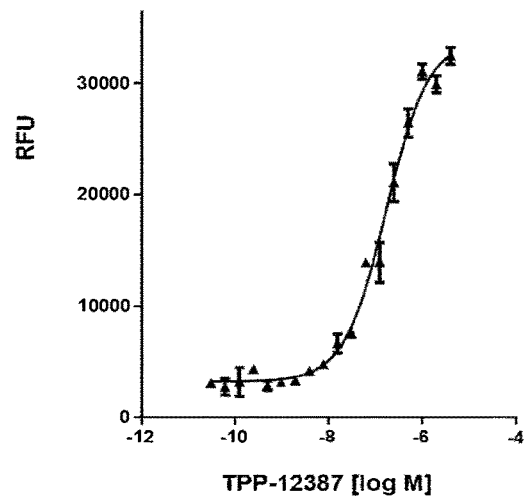
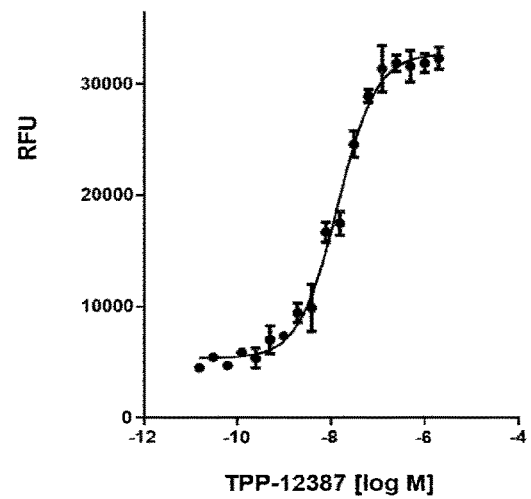
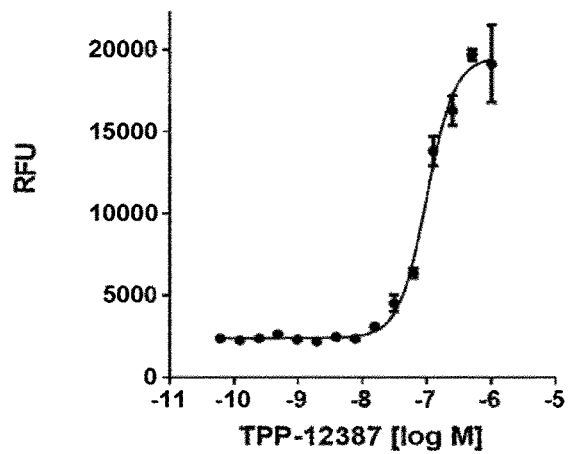
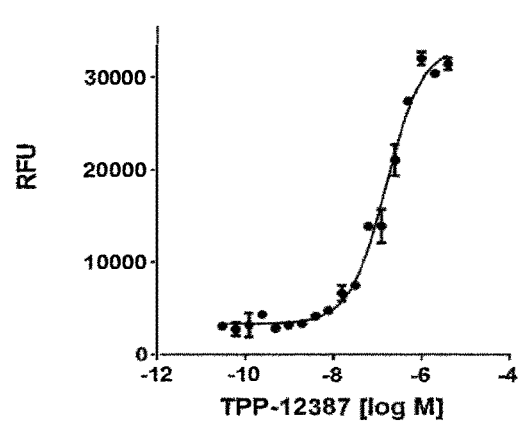
Figure 6A
Figure 6B

Figure 10A
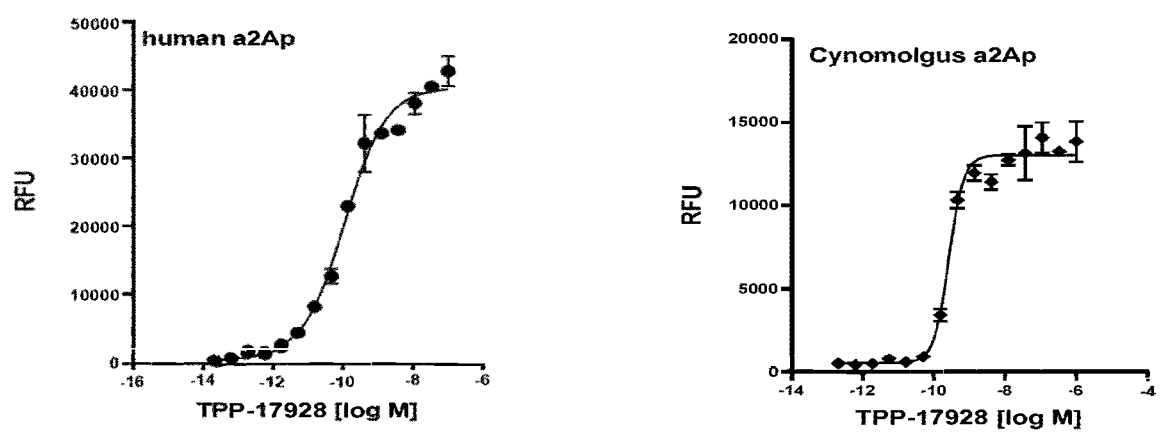
Figure 10B
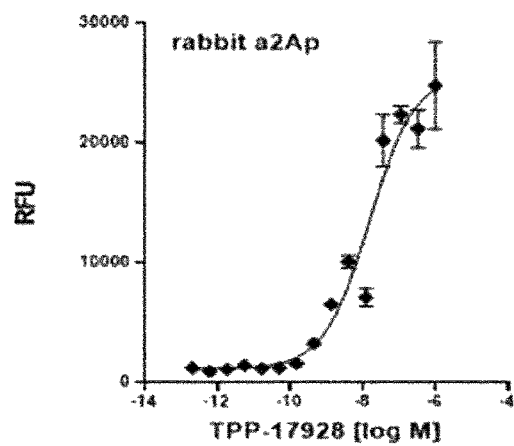
Figure 10C

Figure 12A
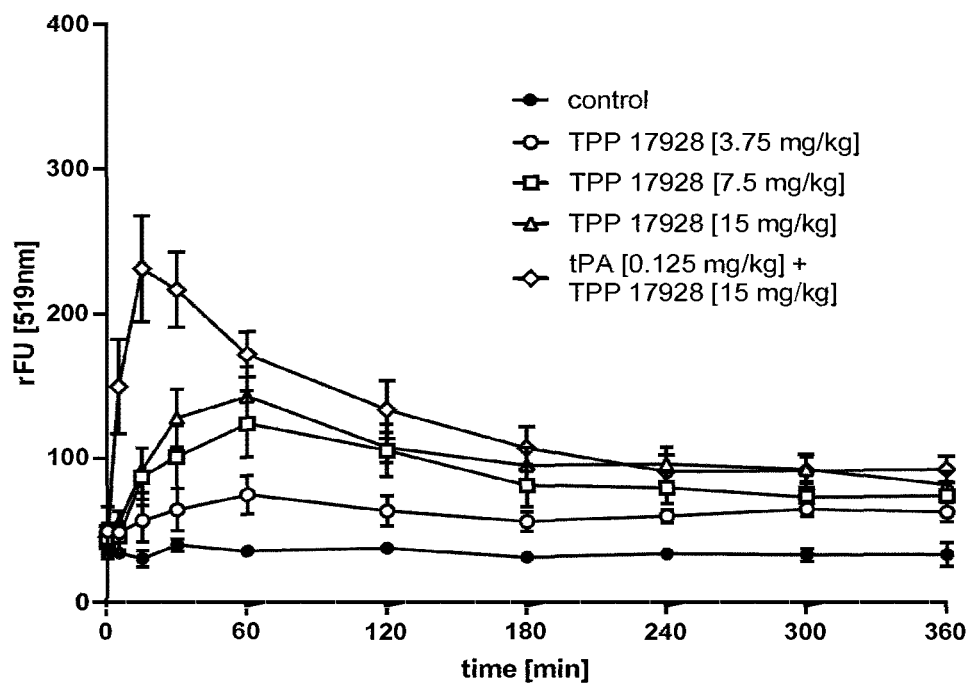
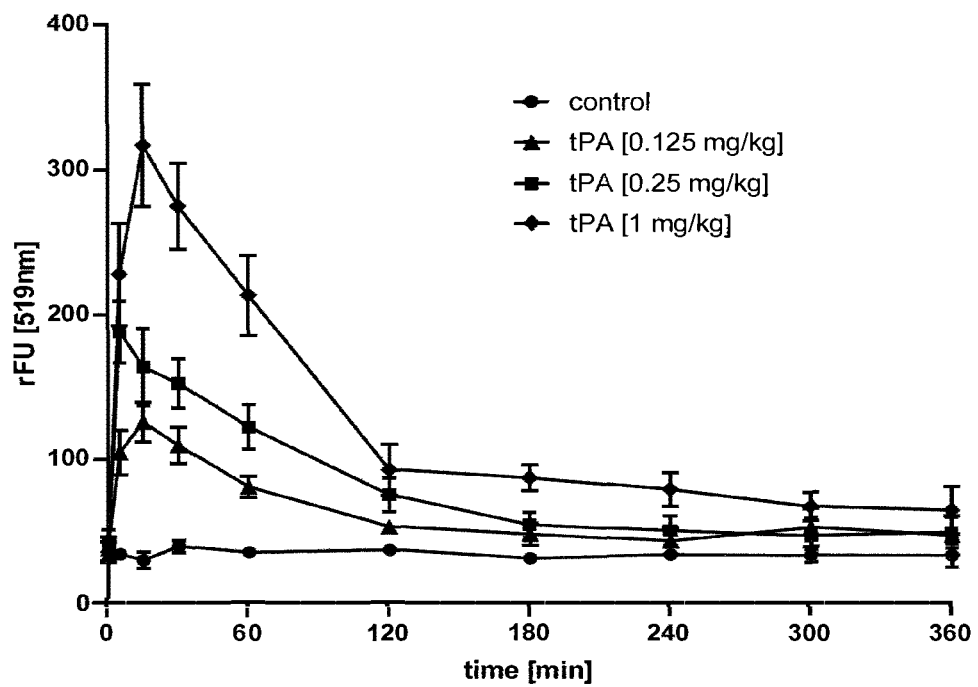
Figure 12B

15.1: TPP-12387

VH: (SEQ ID NO: 23)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLDYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 11)

EYYDSSGYYHLDY

VL: (SEQ ID NO: 37)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDDSLSGWVFGGGTKLTVL

L-CDR1 (SEQ ID NO: 9)

TGSSSNIGATYDVH

L-CDR2 (SEQ ID NO: 10)

SNNQRPS

L-CDR3 (SEQ ID NO: 17)

AAWDDSLSGWV

HC: (SEQ ID NO: 41)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPG

LC: (SEQ ID NO: 56)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDDSLSGWVFGGGTKLTVLGQPKAAPSVTLFPPS
SEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15A

15.2: TPP-14293

VH: (SEQ ID NO: 24)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCDREYYDSSGYYHLDYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 11)

EYYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1 (SEQ ID NO: 9)

TGSSSNIGATYDVH

L-CDR2 (SEQ ID NO: 10)

SNNQRPS

L-CDR3 (SEQ ID NO: 18)

AAWDWSLSGWV

HC: (SEQ ID NO: 42)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCDREYYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15B 15.3: TPP-14298

VH: (SEQ ID NO: 25)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCASEYYDSSGYYHLDYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 11)

EYYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3 (SEQ ID NO: 18)

AAWDWSLSGWV

HC: (SEQ ID NO: 43)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCASEYYDSSGYYHLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15C

15.4: TPP-14303

VH: (SEQ ID NO: 26)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREDYDSSGYYHLDYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 12)

EDYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 44)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREDYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15D

15.5: TPP-14305

VH: (SEQ ID NO: 27)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREGYDSSGYYHLDYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 13)

EGYDSSGYYHLDY

VL: (SEQ ID NO: 39)

QSVLTQPPSASGTPGQRVTISCTGSSSNIGATYDVHWYQQLPGTAPKLLIYSNNQRPSGVPDR
FSGSKSGTSASLAISGLRSEDEADYYCWAWDDSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 19)

WAWDDSLSGWV

HC: (SEQ ID NO: 45)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREGYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 58)

QSVLTQPPSASGTPGQRVTISCTGSSSNIGATYDVHWYQQLPGTAPKLLIYSNNQRPSGVPDR
FSGSKSGTSASLAISGLRSEDEADYYCWAWDDSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15E

15.6: TPP-14308

VH: (SEQ ID NO: 27)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREGYDSSGYYHLDYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 13)

EGYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 45)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREGYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15F

15.7: TPP-14313

VH: (SEQ ID NO: 28)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLVYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 14)

EYYDSSGYYHLVY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 46)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLVYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15G

15.8: TPP-14314

VH: (SEQ ID NO: 28)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLVYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 14)

EYYDSSGYYHLVY

VL: (SEQ ID NO: 40)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDVSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 20)

AAWDVSLSGWV

HC: (SEQ ID NO: 46)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLVYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPG

LC: (SEQ ID NO: 59)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDVSLSGWVFGGGTKLTVLGQPKAAPSVTLFPPS
SEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15H 15.9: TPP-14318

VH: (SEQ ID NO: 29)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLEYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 15)

EYYDSSGYYHLEY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1 (SEQ ID NO: 9)

TGSSSNIGATYDVH

L-CDR2 (SEQ ID NO: 10)

SNNQRPS

L-CDR3 (SEQ ID NO: 18)

AAWDWSLSGWV

HC: (SEQ ID NO: 47)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLEYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15I

15.10: TPP-14323

VH: (SEQ ID NO: 30)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLTYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 16)

EYYDSSGYYHLTY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 48)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAREYYDSSGYYHLTYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15J 15.11: TPP-17041

VH: (SEQ ID NO: 31)

EVQLLESGGGLVQPGGSLRLSCAASGFTFSDYAMSWVRQAPGKGLEWVSAIGTGGGTYYAD
SVKGRFTISRDNSKNTLYLQMNSLRAEDTAVYYCAREGYDSSGYYHLDYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 13)

EGYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 49)

EVQLLESGGGLVQPGGSLRLSCAASGFTFSDYAMSWVRQAPGKGLEWVSAIGTGGGTYYAD
SVKGRFTISRDNSKNTLYLQMNSLRAEDTAVYYCAREGYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15K

15.12: TPP-17044

VH: (SEQ ID NO: 32)

EVQLLESGGGLVQPGGSLRLSCAASGFTFDDYAMSWVRQAPGKGLEWVSAIGTGGSTYYAD
SVKGRFTISRDNSKNTLYLQMNSLRAEDTAVYYCAREGYDSSGYYHLDYWGQGTLVTVSS

H-CDR1: (SEQ ID NO: 6)

DYAMS

H-CDR2: (SEQ ID NO: 8)

AIGTGGSTYYADSVKG

H-CDR3: (SEQ ID NO: 13)

EGYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 50)

EVQLLESGGGLVQPGGSLRLSCAASGFTFDDYAMSWVRQAPGKGLEWVSAIGTGGSTYYAD
SVKGRFTISRDNSKNTLYLQMNSLRAEDTAVYYCAREGYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15L

15.13: TPP-17045

VH: (SEQ ID NO: 33)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAKEGYDSSGYYHLDYWGQGTLVTVSS

H-CDR1: (SEQ ID NO: 6)

DYAMS

H-CDR2: (SEQ ID NO: 7)

AIGTGGGTYYADSVKG

H-CDR3: (SEQ ID NO: 13)

EGYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 51)

EVQLLESGGGLVQPGGSLRLSCAASGFTFDDYAMSWVRQAPGKGLEWVSAIGTGGGTYYAD
SVKGRFTISRDNSKNTLYLQMNSLRAEDTAVYYCAKEGYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15M

15.14: TPP-17048

VH: (SEQ ID NO: 34)

EVQLLESGGGLVQPGGSLRLSCAASGFTFSDYAMSWVRQAPGKGLEWVSAIGTGGSTYYAD
SVKGRFTISRDNSKNTLYLQMNSLRAEDTAVYYCAREGYDSSGYYHLDYWGQGTLVTVSS

H-CDR1: (SEQ ID NO: 6)

DYAMS

H-CDR2: (SEQ ID NO: 8)

AIGTGGSTYYADSVKG

H-CDR3: (SEQ ID NO: 13)

EGYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 52)

EVQLLESGGGLVQPGGSLRLSCAASGFTFSDYAMSWVRQAPGKGLEWVSAIGTGGSTYYAD
SVKGRFTISRDNSKNTLYLQMNSLRAEDTAVYYCAREGYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15N

15.15: TPP-17051

VH: (SEQ ID NO: 35)

EVQLLESGGGLVQPGGSLRLSCAASGFTFDSYAMSWVRQAPGKGLEWVSAIGTGGSTYYAD
SVKGRFTISRDNSKNTLYLQMNSLRAEDTAVYYCAREGYDSSGYYHLDYWGQGTLVTVSS

H-CDR1: (SEQ ID NO: 21)

SYAMS

H-CDR2: (SEQ ID NO: 8)

AIGTGGSTYYADSVKG

H-CDR3: (SEQ ID NO: 13)

EGYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 53)

EVQLLESGGGLVQPGGSLRLSCAASGFTFDSYAMSWVRQAPGKGLEWVSAIGTGGSTYYAD
SVKGRFTISRDNSKNTLYLQMNSLRAEDTAVYYCAREGYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15O

15.16: TPP-17053

VH: (SEQ ID NO: 36)

EVQLLESGGGLVQPGGSLRLSCAASGFTFDDYAMSWVRQAPGKGLEWVSAIGSGGSTYYAD
SVKGRFTISRDNSKNTLYLQMNSLRAEDTAVYYCAREGYDSSGYYHLDYWGQGTLVTVSS

H-CDR1: (SEQ ID NO: 6)

DYAMS

H-CDR2: (SEQ ID NO: 22)

AIGSGGSTYYADSVKG

H-CDR3: (SEQ ID NO: 13)

EGYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 54)

EVQLLESGGGLVQPGGSLRLSCAASGFTFDDYAMSWVRQAPGKGLEWVSAIGSGGSTYYAD
SVKGRFTISRDNSKNTLYLQMNSLRAEDTAVYYCAREGYDSSGYYHLDYWGQGTLVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15P 15.17: TPP-17928

VH: (SEQ ID NO: 32)

EVQLLESGGGLVQPGGSLRLSCAASGFTFDDYAMSWVRQAPGKGLEWVSAIGTGGSTYYAD
SVKGRFTISRDNSKNTLYLQMNSLRAEDTAVYYCAREGYDSSGYYHLDYWGQGTLVTVSS

H-CDR1: (SEQ ID NO: 6)

DYAMS

H-CDR2: (SEQ ID NO: 8)

AIGTGGSTYYADSVKG

H-CDR3: (SEQ ID NO: 13)

EGYDSSGYYHLDY

VL: (SEQ ID NO: 38)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVL

L-CDR1: (SEQ ID NO: 9)

TGSSSNIGATYDVH

L-CDR2: (SEQ ID NO: 10)

SNNQRPS

L-CDR3: (SEQ ID NO: 18)

AAWDWSLSGWV

HC: (SEQ ID NO: 55)

EVQLLESGGGLVQPGGSLRLSCAASGFTFDDYAMSWVRQAPGKGLEWVSAIGTGGSTYYAD
SVKGRFTISRDNSKNTLYLQMNSLRAEDTAVYYCAREGYDSSGYYHLDYWGQGTLVTVSSAS
TKGPSVFPLAPCSRSTSESTAALGCLVKDYFPEPVTVSWNSGALTSGVHTFPAVLQSSGLYSL
SSVVTVPSSSLGTKTYTCNVDHKPSNTKVDKRVESKYGPPCPPCPAPEFLGGPSVFLFPPKPK
DTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMHEALHNH
YTQKSLSLSLG

LC: (SEQ ID NO: 57)

QSVLTQPPSASGTPGQRVTISCTGSSSNIGATYDVHWYQQLPGTAPKLLIYSNNQRPSGVPDR
FSGSKSGTSASLAISGLRSEDEADYYCAAWDWSLSGWVFGGGTKLTVLGQPKAAPSVTLFPP
SSEELQANKATLVCLISDFYPGAVTVAWKADSSPVKAGVETTTPSKQSNNKYAASSYLSLTPEQ
WKSHRSYSCQVTHEGSTVEKTVAPTECS

Figure 15Q

ANTI-A2AP ANTIBODIES AND USES THEREOF

CROSS-REFERENCE TO RELATED APPLICATIONS

This application is a continuation of U.S. patent application Ser. No. 18/329,700, filed Jun. 6, 2023, which is a continuation of U.S. patent application Ser. No. 18/026,089, filed Mar. 13, 2023, which is a U.S. national stage filing under 35 U.S.C. § 371 of International Application No. PCT/EP2021/075038, filed on Sep. 13, 2021, which claims the benefit of and priority to European Application No. 20196259.4, filed on Sep. 15, 2020. The entire disclosure of each of the above applications is incorporated herein by reference.

SEQUENCE LISTING

This application contains references to amino acid sequences and/or nucleic acid sequences which have been submitted concurrently herewith as the sequence listing .xml file entitled "000057uscob_SequenceListing.xml", file size 193,824 bytes, created on Dec. 8, 2023. The aforementioned sequence listing is hereby incorporated by reference in its entirety pursuant to 37 C.F.R. § 1.52(e)(5).

FIELD OF THE INVENTION

The present invention provides isolated antibodies or antigen-binding fragments thereof that bind to human alpha 2 antiplasmin (A2AP). The isolated antibodies or antigen-binding fragments according to the present invention i) cross-react with rabbit and/or cynomolgus A2AP, ii) do not bind to human plasmin/do not inhibit human plasmin activity, iii) do not convert A2AP from a serine protease inhibitor to a serine protease substrate, iv) bind to human A2AP of the sequence of amino acid 40-491 of SEQ ID 1 with a dissociation constant (KD) ≤100 nM, ≤50 nM, ≤25 nM, 10 nM, ≤1 nM, or ≤0.5 nM; v) bind to human A2AP of the sequence of amino acid 40-491 of SEQ ID 1 with an EC50 of ≤500 nM, ≤250 nM, ≤100 nM, ≤50 nM, ≤25 nM, ≤10 nM, ≤1 nM, or ≤0.5 nM; vi) inhibit the activity of human A2AP of amino acid 40-491 of SEQ ID 1 with an EC50 of ≤500 nM, ≤250 nM, ≤100 nM, ≤50 nM, ≤25 nM, ≤10 nM, ≤1 nM, or ≤0.5 nM; and/or and/or increase plasmin mediated clot lysis in the presence of A2AP.

The present invention further provides isolated nucleic acid sequences encoding said antibodies or antigen-binding fragments and vectors comprising same, isolated cells expressing said antibodies or antigen-binding fragments, methods of producing said antibodies or antigen-binding fragments and pharmaceutical compositions and kits comprising said antibodies or antigen-binding fragments.

Antibodies according to the present invention can be used in the treatment of diseases associated with ischemic events due to partial or complete vessel occlusion such as ischemic stroke, acute coronary syndrome, peripheral artery disease, myocardial infarction, deep vein thrombosis, pulmonary embolism, venous thrombosis, or shunt thrombosis.

BACKGROUND OF THE INVENTION

Clot formation inside blood vessels can cause multiple severe diseases like ischemic stroke, acute coronary syndrome, peripheral artery disease, myocardial infarction, deep vein thrombosis, pulmonary embolism, venous thrombosis, or shunt thrombosis. Clot generation and persistency are influenced by the rates of its formation by fibrin and platelets and its dissolution by the lytic system. The current standard of care focusses on anticoagulation for chronic prevention of thrombosis, which is despite all improvements by non-vitamin K antagonist oral anticoagulants (NOACs) still accompanied by a bleeding risk and has only an indirect effect on clot resolution.

The primary therapeutic goal for patients suffering from ischemic or embolic events is the timely restoration of blood flow. Reperfusion therapy using thrombolysis, including intravenous (IV) recombinant tissue plasminogen activator (tPA) and endovascular interventions such as mechanical thrombectomy (MT), are the only approved treatments for patients suffering e.g. from ischemic stroke. However, both treatment options have limitations. Especially for the short-acting tPA, its use is limited due to a strong increase in bleeding risk, neurotoxic effects and limited time window of efficacy.

In contrast, inhibition of the major endogenous plasmin inhibitor alpha2-Antiplasmin (a2Ap) has been reported to improve pathological parameters without accompanying hemorrhage risk. Therefore, the inhibition of alpha2-Antiplasmin might be an innovative therapeutic option for the acceleration of clot lysis and for the prevention of (secondary) thrombotic events.

Alpha2-Antiplasmin is a member of the Serpin superfamily. It is the primary physiological inhibitor of the serine protease plasmin. Plasmin in turn is an important enzyme that participates in fibrinolysis and degradation of various other proteins. (Tone M, Kikuno R, Kume-Iwaki A, Hashimoto-Gotoh T. Structure of human alpha 2-plasmin inhibitor deduced from the cDNA sequence. J Biochem. 1987; 102(5):1033-1041; Silverman G A, Bird P I, Carrell R W, et al. The serpins are an expanding superfamily of structurally similar but functionally diverse proteins. Evolution, mechanism of inhibition, novel functions, and a revised nomenclature. J Biol Chem. 2001; 276(36):33293-33296).

Alpha2-Antiplasmin is synthesized as a 491 amino acid precursor with a 27 amino acid signal peptide. The secreted form exhibits a short pro-peptide (residues 28-39) and a mature chain (residues 40-491). Liver and kidney are major sites of a2Ap production, but also other tissues such as muscle, intestine, central nervous system, and placenta also express its mRNA at a moderate level.

Plasma concentrations of alpha2-Antiplasmin are ca. 1 micromolar (~70 micrograms/ml), the half-life in plasma is determined with 2.6 days. (Collen D, Wiman B. Turnover of antiplasmin, the fast-acting plasmin inhibitor of plasma. Blood. 1979; 53(2):313-324).

Experimental therapeutic inactivation of α2-antiplasmin markedly reduces microvascular thrombosis, ischemic brain injury, brain swelling, brain hemorrhage and death after thromboembolic stroke (Reed G L, Houng A K, Wang D. Microvascular thrombosis, fibrinolysis, ischemic injury, and death after cerebral thromboembolism are affected by levels of circulating α2-antiplasmin. Arterioscler Thromb Vase Biol. 2014; 34(12):2586-2593).

Mimuro et al. describes JPTI-1, an A2AP antibody. The avidity of JPTI-1 to preformed A2AP-plasmin-complex was lower than to free A2AP. JPTI-1 inhibited A2AP activity by interfering with the formation of A2AP-plasmin-complex. However, Mimuro et al is silent about the use of JPTI-1 to enhance clot lysis (Mimuro, J. et al. Blood 1987; 69:446-453).

One of the best characterized known antibodies of the prior art is 77A3 described by Reed et al. (Reed G L. Functional characterization of monoclonal antibody inhibitors of alpha 2-antiplasmin that accelerate fibrinolysis in different animal plasmas. Hybridoma. 1997; 16(3):281-286; WO 98/12334, WO 98/12329), an antibody derived from a classical mouse immunization approach. Due to the fact that this antibody is of murine origin, at least a humanization campaign has been performed.

Other function blocking anti-alpha2-antiplasmin antibodies are not suitable as therapeutic agents, either due to their origin as non-human antibodies, e.g. the Serpin F2/alpha 2-Antiplasmin Antibody derived from goat (R&D, catalog number AF1484-SP), due to their specificity, e.g. the mouse specific antibodies clone 27C9, 4H9, and CBYY-I0956, respectively (MyBioSource, catalogue numbers MBS135095 and MBS135076, Creative Biolabs, catalogue number CBMAB-I2124-YY), or due the fact that these antibodies are polyclonal (Invitrogen, catalogue number PA5-47142).

Thus, there exists a great need for novel therapeutic A2AP antibodies useful for the treatment of diseases that are associated with ischemic events due to partial or complete vessel occlusion that has not been met so far.

OBJECTS OF THE INVENTION

In view of the prior art, it is an object of the present invention to provide novel therapeutic A2AP antibodies that overcome the shortcoming of A2AP antibodies of the prior art. In particular it is an object of the present invention to provide novel A2AP antibodies that are high affinity binders of human A2AP. Desirable A2AP antibodies are cross-reactive to rabbit and/or cynomolgus A2AP. They are non-immunogenic in human therapy, i.e. they are human or humanized antibodies. Desirable A2AP antibodies are selective to A2AP, in particular they do not bind to and inhibit human plasmin. And they are able to increase plasmin mediated clot lysis in the presence of A2AP.

Such novel A2AP antibodies would offer major advances in the treatment of diseases associated with ischemic events due to partial or complete vessel occlusion such as ischemic stroke, acute coronary syndrome, peripheral artery disease, myocardial infarction, deep vein thrombosis, pulmonary embolism, venous thrombosis or shunt thrombosis.

SUMMARY OF THE INVENTION

The above-mentioned object and other objects are achieved by the teaching of the present invention. The present invention is based on the discovery of novel antibodies that have a specific affinity for alpha2-Antiplasmin and can deliver a therapeutic benefit to a subject.

Thus, in a first aspect, the present invention relates to isolated antibodies or antigen-binding fragments thereof that bind to human A2AP, wherein said isolated antibodies or antigen-binding fragments thereof
  i) cross-react with rabbit and/or cynomolgus A2AP,
  ii) do not inhibit human plasmin activity,
  iii) do not convert A2AP from a serine protease inhibitor to a serine protease substrate,
  iv) bind to human A2AP of the sequence of amino acid 40-491 of SEQ ID 1 with a dissociation constant (KD)≤100 nM, ≤50 nM, ≤25 nM, ≤10 nM, ≤1 nM, or ≤0.5 nM;
  v) bind to human A2AP of the sequence of amino acid 40-491 of SEQ ID 1 with an EC50 of ≤500 nM, ≤250 nM, ≤100 nM, ≤50 nM, ≤25 nM, ≤10 nM, ≤1 nM, or ≤0.5 nM;
  vi) inhibit the activity of human A2AP of amino acid 40-491 of SEQ ID 1 with an EC50 of ≤500 nM, ≤250 nM, ≤100 nM, ≤50 nM, ≤25 nM, ≤10 nM, ≤1 nM, or ≤0.5 nM; and/or increase plasmin mediated clot lysis in the presence of A2AP.

The isolated antibodies or antigen-binding fragments according to the present invention are function blocking anti-alpha2-Antiplasmin antibodies or antigen-binding fragments, which induce accelerated clot lysis in vitro as well as in vivo without leading to unwanted side effects like bleeding as it is typical for other pro-thrombolytic compounds. Thus, the isolated antibodies or antigen-binding fragments according to the present invention may be used in the treatment of diseases associated with ischemic events due to vessel partial or complete occlusion such as ischemic stroke, acute coronary syndrome, peripheral artery disease, myocardial infarction, deep vein thrombosis, pulmonary embolism, venous thrombosis or shunt thrombosis. The isolated antibodies or antigen-binding fragments according to the present invention may further be used in the diagnosis of A2AP-related disorders.

In a further aspect, the present invention relates to isolated antibodies or antigen-binding fragments thereof capable of binding to A2AP and inhibiting the activity of A2AP, wherein said isolated antibodies or antigen-binding fragments thereof do not inhibit plasmin activity.

In a further aspect, the present invention relates to isolated antibodies or antigen-binding fragments thereof capable of binding to human A2AP and inhibiting activity of A2AP, wherein said isolated antibodies or antigen-binding fragments thereof bind to an epitope of A2AP comprising amino acid 402-408 (SRMSLSS) of SEQ ID NO: 1.

In a further aspect, the present invention relates to isolated antibodies or antigen-binding fragments thereof which compete with said isolated antibodies or antigen-binding fragments for binding to A2AP.

In a further aspect, the present invention relates to antibody conjugates, comprising the isolated antibodies or antigen binding fragments according to the invention.

In a further aspect, the present invention relates to isolated nucleic acid sequences that encode the antibodies or antigen-binding fragments according to the present invention.

In a further aspect, the present invention relates to vectors comprising a nucleic acid sequence according to the present invention.

In a further aspect, the present invention relates to isolated cells expressing the antibodies or antigen-binding fragments according to the present invention and/or comprising the nucleic acid according to the present invention or the vector according to the present invention.

In a further aspect, the present invention relates to methods of producing the isolated antibodies or antigen-binding fragments according to the present invention comprising culturing of the cells according to the present invention and optionally purification of the antibody or antigen-binding fragment.

In a further aspect, the present invention relates to pharmaceutical compositions comprising the isolated antibodies or antigen-binding fragments according to the present invention or the antibody conjugates according to the present invention.

In a further aspect, the present invention relates to isolated antibodies or antigen-binding fragments according to the invention or conjugates according to invention or pharmaceutical compositions according to the invention for use in the treatment or prophylaxis of a disease.

In a further aspect, the present invention relates to isolated antibodies or antigen-binding fragments according to the invention or conjugates according to invention for use as a diagnostic agent.

In a further aspect, the present invention relates to isolated antibodies or antigen-binding fragments according to the invention or conjugates according to invention or the pharmaceutical composition according to the invention for use in the treatment or prophylaxis of disorders or diseases associated with ischemic events due to partial or complete vessel occlusion, such as ischemic stroke, acute coronary syndrome, peripheral artery disease, myocardial infarction, deep vein thrombosis, pulmonary embolism, venous thrombosis, or shunt thrombosis.

In a further aspect, the present invention relates isolated antibodies or antigen-binding fragments according to the invention or conjugates according to invention or the pharmaceutical composition according to the invention for use in simultaneous, separate, or sequential combination with one or more further therapeutically active compounds, particularly selected from inhibitors of the coagulation cascade, anticoagulants and platelet aggregation inhibitors.

In a further aspect, the present invention relates to kits comprising the isolated antibodies or antigen-binding fragments according to the present invention or the conjugates according to the present invention and instructions for use.

DETAILED DESCRIPTION OF THE INVENTION

The present invention may be understood more readily by reference to the following detailed description of the invention and the examples included therein.

Definitions

Unless defined otherwise, all technical and scientific terms used herein have the meaning commonly understood by one of ordinary skill in the art to which this invention belongs. The following references, however, can provide one of skill in the art to which this invention pertains with a general definition of many of the terms used in this invention, and can be referenced and used so long as such definitions are consistent with the meaning commonly understood in the art. Such references include, but are not limited to, Singleton et al., Dictionary of Microbiology and Molecular Biology (2nd ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, 2nd Edition, W.B. Saunders Company. Any additional technical resource available to the person of ordinary skill in the art providing definitions of terms used herein having the meaning commonly understood in the art can be consulted. For the purposes of the present invention, the following terms are further defined. Additional terms are defined elsewhere in the description. As used herein and in the appended claims, the singular forms "a," and "the" include plural reference unless the context clearly dictates otherwise. Thus, for example, reference to "a gene" is a reference to one or more genes and includes equivalents thereof known to those skilled in the art, and so forth.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

In this context, the term "about" or "approximately" means within 80% to 120%, alternatively within 90% to 110%, including within 95% to 105% of a given value or range.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

As used herein "A2AP" designates "alpha2-antiplasmin", also known as "SerpinF2" (serpin family F member 2), AAP, API, PLI, or ALPHA-2-PI. A2AP is a member of the Serpin superfamily. It is the primary physiological inhibitor of the serine protease plasmin. A2AP is synthesized as a 491 amino acid precursor with a 27 amino acid signal peptide. The secreted form exhibits a short pro-peptide (residues 28-39) and a mature chain (residues 40-491). A reference sequence for human A2AP is available from UniProtKB/Swiss-Prot data base under accession number P08697-1 (SEQ-ID NO:1), including signal peptide (positions 1-27), pro-peptide (residues 28-39) and a mature chain (residues 40-491) (numbering is according to methionine in position 1).

Human A2AP (SEQ ID NO: 1):
MALLWGLLVLSWSCLQGPCSVFSPVSAMEPLGRQLTSGPNQEQVSPLTL

LKLGNQEPGGQTALKSPPGVCSRDPTPEQTHRLARAMMAFTADLFSLVA

QTSTCPNLILSPLSVALALSHLALGAQNHTLQRLQQVLHAGSGPCLPHL

LSRLCQDLGPGAFRLAARMYLQKGFPIKEDFLEQSEQLFGAKPVSLTGK

QEDDLANINQWVKEATEGKIQEFLSGLPEDTVLLLLNAIHFQGFWRNKF

DPSLTQRDSFHLDEQFTVPVEMMQARTYPLRWFLLEQPEIQVAHFPFKN

NMSFVVLVPTHFEWNVSQVLANLSWDTLHPPLVWERPTKVRLPKLYLKH

QMDLVATLSQLGLQELFQAPDLRGISEQSLVVSGVQHQSTLELSEVGVE

AAAATSIAMSRMSLSSFSVNRPFLFFIFEDTTGLPLFVGSVRNPNPSAP

RELKEQQDSPGNKDFLQSLKGFPRGDKLFGPDLKLVPPMEEDYPQFGSP

K

| Human A2AP domains | Positions on SEQ-ID NO: 1 |
|---|---|
| reactive center loop (RCL) | 400-412 |
| arginine residue forming a covalent bond with the active site serine of plasmin | R403 |

| Human A2AP domains | Positions on SEQ-ID NO: 1 |
|---|---|
| C-terminal sequence including lysines interact with the kringle domains of plasmin | 414-491 |

As used herein "plasmin" designates "plasmin". Plasmin is a that acts to dissolve fibrin e.g. in blood clots. Plasmin is released as a proenzyme called plasminogen (PLG) from the liver into the systemic circulation. Two major glycoforms of plasminogen are present in humans—type I plasminogen contains two glycosylation moieties (N-linked to N289 and O-linked to T346), whereas type II plasminogen contains only a single O-linked sugar (O-linked to T346). Type II plasminogen is preferentially recruited to the cell surface over the type I glycoform. Conversely, type I plasminogen appears more readily recruited to blood clots. In circulation, plasminogen adopts a closed, activation-resistant conformation. Upon binding to clots, or to the cell surface, plasminogen adopts an open form that can be converted into active plasmin by a variety of enzymes, including e.g. tissue plasminogen activator (tPA). Fibrin is a cofactor for plasminogen activation by tissue plasminogen activator. The conversion of plasminogen to plasmin involves the cleavage of the peptide bond between Arg-561 and Val-562 (Wikipedia).

A reference sequence for human plasmin is available from UniProtKB/Swiss-Prot data base under accession number P00747-1 (numbering is according to methionine in position 1).

| Human plasminogen domain | Positions on P00747-1 (numbering is according to methionine in position 1). |
|---|---|
| Plasmin | 98-810 |
| plasmin heavy chain A | 98-580 (SEQ ID 118) |
| plasmin light chain B | 581-810 (SEQ ID NO: 119) |
| Kringle domain 1-5 | 103-560 |
| Reactive site | S741 |

The terms "anti-A2AP antibody" or "anti-alpha2-Antiplasmin antibody" and "an antibody that binds to alpha2-Antiplasmin" or "an antibody that binds to A2AP" refer to an antibody that is capable of binding alpha2-Antiplasmin with sufficient affinity such that the antibody is useful as a diagnostic and/or therapeutic agent in targeting alpha2-Antiplasmin. In one embodiment, the extent of binding of an anti alpha2-Antiplasmin antibody to an unrelated, non-alpha2-Antiplasmin protein is less than about 10%, less than about 5%, or less than about 2% of the binding of the antibody to alpha2-Antiplasmin as measured, e.g., by standard ELISA procedure. In certain embodiments, an antibody that binds to alpha2-Antiplasmin has a binding activity (EC50) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-alpha2-Antiplasmin antibody binds to an epitope of alpha2-Antiplasmin that is conserved among alpha2-Antiplasmin from different species.

The term "antibody", as used herein, is intended to refer to immunoglobulin molecules. Antibodies may comprise four polypeptide chains, two heavy (H) chains (about 50-70 kDa) and two light (L) chains (about 25 kDa) which are typically inter-connected by disulfide bonds. In particular embodiments, the antibody is composed of two identical pairs of polypeptide chains. The amino-terminal portion of each chain includes a "variable" region of about 100 to 110 or more amino acids primarily responsible for antigen recognition. The heavy chain variable region is abbreviated herein as VH, the light chain variable region is abbreviated herein as VL. The carboxyl-terminal portion of each chain defines a constant region primarily responsible for effector function. The heavy chain constant region can comprise e.g. three domains CH1, CH2 and CH3. The light chain constant region is comprised of one domain (CL). The VH and VL regions can be further subdivided into regions of hypervariability, termed complementarity determining regions (CDR), interspersed with regions that are more conserved, termed framework regions (FR). Each VH and VL is typically composed of three CDRs and up to four FRs, arranged from amino-terminus to carboxy-terminus e.g., in the following order: FR1, CDR1, FR2, CDR2, FR3, CDR3, FR4.

As used herein, the term "Complementarity Determining Regions" (CDRs; e.g., CDR1, CDR2, and CDR3) refers to the amino acid residues of an antibody variable domain the presence of which are necessary for antigen binding. Each variable domain typically has three CDRs identified as CDR1, CDR2 and CDR3. Each complementarity determining region may comprise amino acid residues from a "complementarity determining region" as defined by Kabat (e.g. about residues 23-36 (L1), 52-58 (L2) and 91-101 (L3) in the light chain variable domain and 31-35 (H1), 50-65 (H2) and 98-110 (H3) in the heavy chain variable domain; (Kabat et al., Sequences of Proteins of Immunological Interest, 5th Ed. Public Health Service, National Institutes of Health, Bethesda, MD. (1991)) and/or those residues from a "hypervariable loop" (e.g. about residues 26-32 (L1), 50-52 (L2) and 91-96 (L3) in the light chain variable domain and 26-32 (H1), 53-55 (H2) and 96-101 (H3) in the heavy chain variable domain (Chothia and Lesk; J Mol Biol 196: 901-917 (1987)). In some instances, a complementarity determining region can include amino acids from both a CDR defined according to Kabat and a hypervariable loop.

"Framework" or FR residues are those variable domain residues other than the hypervariable region residues.

The phrase "constant region" refers to the portion of the antibody molecule that confers effector functions.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. In particular embodiments, the antibody according to the present invention is an IgG antibody. Several of these may be further divided into subclasses or isotypes, e.g. IgG1, IgG2, IgG3, IgG4, IgA1 and IgA2. In particular embodiments, the antibody according to the present invention is an IgG1, an IgG2, an IgG3 or an IgG4 antibody, more particularly an IgG1 or an IgG4 antibody. Different isotypes may have different effector functions. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hyper variable region(s) of an antibody, e.g., the CDR1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320).

Nonlimiting examples of "functional fragments" or "antigen-binding antibody fragments" include Fab, Fab', F(ab')2, Fv fragments, domain antibodies (dAb), complementarity determining region (CDR) fragments, single-chain antibodies (scFv), single chain antibody fragments, diabodies, triabodies, tetrabodies, minibodies, linear antibodies (Zapata et al., Protein Eng., 8 (10): 1057-1062 (1995)); chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity; and multispecific antibodies such as bi- and tri-specific antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "bispecific" or "bifunctional" antibody is understood to have each of its binding sites identical. The F(ab')$_2$ or Fab may be engineered to minimize or completely remove the intermolecular disulfide interactions that occur between the $C_{H1}$ and $C_L$ domains. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two "Fv" fragments. An "Fv" fragment is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen.

"Single-chain Fv" or "sFv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding. For a review of Fvs see Pluckthun in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteine residues from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteine residues between them.

The term "mutein" or "variant" can be used interchangeably and refers to an antibody or antigen-binding fragment that contains at least one amino acid substitution, deletion, or insertion in the variable region or the portion equivalent to the variable region, provided that the mutein or variant retains the desired binding affinity or biological activity. Variants of the antibodies or antigen-binding antibody fragments contemplated in the invention are molecules in which the binding activity of the antibody or antigen-binding antibody fragment is maintained.

A "chimeric antibody" or antigen-binding fragment thereof is defined herein as one, wherein the variable domains are derived from a non-human origin and some or all constant domains are derived from a human origin.

"Humanized antibodies" contain CDR regions derived from a non-human species, such as mouse, that have, for example, been engrafted, along with any necessary framework back-mutations, into human sequence-derived V regions. Thus, for the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. See, for example, U.S. Pat. Nos. 5,225,539; 5,585,089; 5,693,761; 5,693,762; 5,859,205, each herein incorporated by reference. In some instances, framework residues of the human immunoglobulin are replaced by corresponding non-human residues (see, for example, U.S. Pat. Nos. 5,585,089; 5,693,761; 5,693,762, each herein incorporated by reference). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-25 (1986); Riechmann et al., Nature 332:323-27

(1988); and Presta, Curr. Opin. Struct. Biol. 2:593-96 (1992), each herein incorporated by reference.

"Human antibodies" or "fully human antibodies" comprise human derived CDRs, i.e. CDRs of human origin. Fully human antibodies may comprise a low number of germline deviations compared with the closest human germline reference determined based on the IMGT database (http://www.imgt.org). For example, a fully human antibody according to the current invention may comprise up to 1, 2, 3, 4, 5, 6, 7, 8, 9 or 10 germline deviations in the CDRs compared with the closest human germline reference. Fully human antibodies can be developed from human derived B cells by cloning techniques in combination with a cell enrichment or immortalization step. The majority of fully human antibodies, however, are isolated either from immunized mice transgenic for the human IgG locus or from sophisticated combinatorial libraries by phage display (Bruggemann M., Osborn M. J., Ma B., Hayre J., Avis S., Lundstrom B. and Buelow R., Human Antibody Production in Transgenic Animals, Arch Immunol Ther Exp (Warsz.) 63 (2015), 101-108; Carter P. J., Potent antibody therapeutics by design, Nat Rev Immunol 6 (2006), 343-357; Frenzel A., Schirrmann T. and Hust M., Phage display-derived human antibodies in clinical development and therapy, MAbs 8 (2016), 1177-1194; Nelson A. L., Dhimolea E. and Reichert J. M., Development trends for human monoclonal antibody therapeutics, Nat Rev Drug Discov 9 (2010), 767-774.)).

Several techniques are available to generate fully human antibodies (cf. WO2008/112640 A3). Cambridge Antibody Technologies (CAT) and Dyax have obtained antibody cDNA sequences from peripheral B cells isolated from immunized humans and devised phage display libraries for the identification of human variable region sequences of a particular specificity. Briefly, the antibody variable region sequences are fused either with the Gene III or Gene VIII structure of the M13 bacteriophage. These antibody variable region sequences are expressed either as Fab or single chain Fv (scFv) structures at the tip of the phage carrying the respective sequences. Through rounds of a panning process using different levels of antigen binding conditions (stringencies), phages expressing Fab or scFv structures that are specific for the antigen of interest can be selected and isolated. The antibody variable region cDNA sequences of selected phages can then be elucidated using standard sequencing procedures. These sequences may then be used for the reconstruction of a full antibody having the desired isotype using established antibody engineering techniques. Antibodies constructed in accordance with this method are considered fully human antibodies (including the CDRs). In order to improve the immunoreactivity (antigen binding affinity and specificity) of the selected antibody, an in vitro maturation process can be introduced, including a combinatorial association of different heavy and light chains, deletion/addition/mutation at the CDR3 of the heavy and light chains (to mimic V-J, and V-D-J recombination), and random mutations (to mimic somatic hypermutation). An example of a "fully human" antibody generated by this method is the anti-tumor necrosis factor α antibody, Humira (adalimumab).

"Human Engineered™" antibodies generated by altering the parent sequence according to the methods set forth in Studnicka et al., U.S. Pat. No. 5,766,886.

An antibody of the invention may be derived from a recombinant antibody gene library. The development of technologies for making repertoires of recombinant human antibody genes, and the display of the encoded antibody fragments on the surface of filamentous bacteriophage, has provided a recombinant means for directly making and selecting human antibodies, which also can be applied to humanized, chimeric, murine or mutein antibodies. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function. Typically, the Fd fragment (VH-CH1) and light chain (VL-CL) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

A variety of procedures have been described for human antibodies deriving from phage-display libraries. Such libraries may be built on a single master framework, into which diverse in vivo-formed (i. e. human-derived) CDRs are allowed to recombine as described by Carlsson and Soderlind Exp. Rev. Mol. Diagn. 1 (1), 102-108 (2001), Soderlin et al., Nat. Biotech. 18, 852-856 (2000) and U.S. Pat. No. 6,989,250. Alternatively, such an antibody library may be based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064. For a review of phage display screening (for example see Hoet R M et al, Nat Biotechnol 2005; 23(3):344-8), the well-established hybridoma technology (for example see Köhler and Milstein Nature. 1975 Aug. 7; 256(5517):495-7), or immunization of mice inter alia immunization of hMAb mice (e.g. VelocImmune Mouse®).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the term "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The term "monoclonal" is not to be construed as to require production of the antibody by any particular method. For example, the monoclonal antibodies to be used may be made by the hybridoma method first described by Kohler et al., Nature, 256: 495 [1975, or may be made by recombinant DNA methods (see, e.g., U.S. Pat. No. 4,816,567). The "monoclonal antibodies" may also be recombinant, chimeric, humanized, human, Human Engineered™, or antibody fragments, for example.

An "isolated" antibody is one that has been identified and separated from a component of the cell that expressed it. Contaminant components of the cell are materials that would interfere with diagnostic or therapeutic uses of the antibody, and may include enzymes, hormones, and other proteinaceous or non-proteinaceous solutes.

An "isolated" nucleic acid is one that has been identified and separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

As used herein, an antibody "binds specifically to", is "specific to/for" or "specifically recognizes" an antigen of interest, e.g. A2AP, is one that binds the antigen with sufficient affinity such that the antibody is useful as a therapeutic agent in targeting a cell or tissue expressing the antigen, and does not significantly cross-react with proteins other than orthologs and variants (e.g. mutant forms, splice variants, or proteolytically truncated forms) of the aforementioned antigen target. The term "specifically recognizes" or "binds specifically to" or is "specific to/for" a particular polypeptide or an epitope on a particular polypeptide target as used herein can be exhibited, for example, by an antibody, or antigen-binding fragment thereof, having a monovalent $K_D$ for the antigen of less than about $10^{-4}$ M, alternatively less than about $10^{-5}$ M, alternatively less than about $10^{-6}$ M, alternatively less than about $10^{-7}$ M, alternatively less than about $10^{-8}$ M, alternatively less than about $10^{-9}$ M, alternatively less than about $10^{-10}$ M, alternatively less than about $10^{-11}$ M, alternatively less than about $10^{-12}$ M, or less. An antibody "binds specifically to," is "specific to/for" or "specifically recognizes" an antigen if such antibody is able to discriminate between such antigen and one or more reference antigen(s). In its most general form, "specific binding", "binds specifically to", is "specific to/for" or "specifically recognizes" is referring to the ability of the antibody to discriminate between the antigen of interest and an unrelated antigen, as determined, for example, in accordance with one of the following methods. Such methods comprise, but are not limited to surface plasmon resonance (SPR), Western blots, ELISA-, RIA-, ECL-, IRMA-tests and peptide scans. For example, a standard ELISA assay can be carried out. The scoring may be carried out by standard color development (e.g. secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative is more than 5-fold, 10-fold, 50-fold, and preferably more than 100-fold. Typically, determination of binding specificity is performed by using not a single reference antigen, but a set of about three to five unrelated antigens, such as milk powder, BSA, transferrin or the like.

"Binding affinity" or "affinity" refers to the strength of the total sum of non-covalent interactions between a single binding site of a molecule and its binding partner. Unless indicated otherwise, as used herein, "binding affinity" refers to intrinsic binding affinity which reflects a 1:1 interaction between members of a binding pair (e.g. an antibody and an antigen). The dissociation constant "$K_D$" is commonly used to describe the affinity between a molecule (such as an antibody) and its binding partner (such as an antigen) i.e. how tightly a ligand binds to a particular protein. Ligand-protein affinities are influenced by non-covalent intermolecular interactions between the two molecules. Affinity can be measured by common methods known in the art, including those described herein. In one embodiment, the "$K_D$" or "$K_D$ value" according to this invention is measured by using surface plasmon resonance assays using a Biacore T200 instrument (GE Healthcare Biacore, Inc.). Other suitable devices are BIACORE T100, BIACORE (R)-2000, BIACORe 4000, a BIACORE (R)-3000 (BIAcore, Inc., Piscataway, NJ), or ProteOn XPR36 instrument (Bio-Rad Laboratories, Inc.).

As used herein, the term "epitope" includes any protein determinant capable of specific binding to an immunoglobulin or T-cell receptor. Epitopic determinants usually consist of chemically active surface groupings of molecules such as amino acids or sugar side chains, or combinations thereof and usually have specific three-dimensional structural characteristics, as well as specific charge characteristics.

An "antibody that binds to the same epitope" as a reference antibody or "an antibody which competes for binding" to a reference antibody refers to an antibody that blocks binding of the reference antibody to its antigen in a competition assay by 10%, 20%, 30%, 40%, 50% or more, and conversely, the reference antibody blocks binding of the antibody to its antigen in a competition assay by 10%, 20%, 30%, 40%, 50% or more.

The term "maturated antibodies" or "maturated antigen-binding fragments" such as maturated Fab variants or "optimized" variants includes derivatives of an antibody or antibody fragment exhibiting stronger binding—i. e. binding with increased affinity—to a given antigen such as the extracellular domain of a target protein. Maturation is the process of identifying a small number of mutations within the six CDRs of an antibody or antibody fragment leading to this affinity increase. The maturation process is the combination of molecular biology methods for introduction of mutations into the antibody and screening for identifying the improved binders.

"Percent (%) sequence identity" with respect to a reference polynucleotide or polypeptide sequence, respectively, is defined as the percentage of nucleic acid or amino acid residues, respectively, in a candidate sequence that are identical with the nucleic acid or amino acid residues, respectively, in the reference polynucleotide or polypeptide sequence, respectively, after aligning the sequences and introducing gaps, if necessary, to achieve the maximum percent sequence identity. Conservative substitutions are not considered as part of the sequence identity. Preferred are un-gapped alignments. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

"Sequence homology" indicates the percentage of amino acids that either is identical or that represent conservative amino acid substitutions.

An "antagonistic" antibody or a "blocking" antibody is one which significantly inhibits (either partially or completely) a biological activity of the antigen it binds. In particular embodiments, antibodies or antigen-binding fragments according to the present invention are an A2AP blocking antibodies or antigen-binding fragments.

The term "antibody conjugate" refers to an antibody conjugated to one or more molecules including drugs—in which case the antibody conjugate is referred to as "antibody-drug conjugate" ("ADC")—and high molecular weight molecules such as peptides or proteins.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell", "host cell line", and "host cell culture" are used interchangeably and refer to cells into which at least one exogenous nucleic acid has been introduced, including the progeny of such cells. Host cells include "transformants" and "transformed cells", "transfectants" and "transfected cells" and "transduced cells" which include the primary transformed/transfected/transduced cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein.

As used herein, the phrase "therapeutically effective amount" is meant to refer to an amount of therapeutic or prophylactic antibody that would be appropriate to elicit the desired therapeutic or prophylactic effect or response, including alleviating some or all of such symptoms of disease or reducing the predisposition to the disease, when administered in accordance with the desired treatment regimen.

The term "pharmaceutical formulation"/"pharmaceutical composition" refers to a preparation which is in such form as to permit the biological activity of an active ingredient contained therein to be effective, and which contains no additional components which are unacceptably toxic to a subject to which the formulation would be administered.

Antibodies According to the Present Invention

In one aspect, the present invention relates to isolated antibodies or antigen-binding fragments thereof binding to human A2AP, wherein said isolated antibodies or antigen-binding fragments thereof cross-react with rabbit and/or cynomolgus A2AP. In particular embodiments, the isolated antibodies or antigen-binding fragments according to the present invention have an affinity to rabbit A2AP that is less than 100-fold, particularly less than 30-fold, even more particularly less than 15-fold and most particularly less than 5-fold different to that to human A2AP. In particular such embodiments, said affinities are to human A2AP of amino acid 40-491 of SEQ ID NO: 1 and to rabbit A2AP of amino acids 28-491 of SEQ ID NO: 2. In particular embodiments, the isolated antibodies or antigen-binding fragments according to the present invention have an affinity to cynomolgus A2AP that is less than 100-fold, particularly less than 30-fold, even more particularly less than 15-fold and most particularly less than 5-fold different to that to human A2AP. In particular such embodiments, said affinities are to human A2AP of amino acid 40-491 of SEQ ID NO: 1 and to cynomolgus A2AP of amino acid 28-491 SEQ ID NO: 3.

In another aspect, the present invention relates to isolated antibodies or antigen-binding fragments thereof capable of binding to human A2AP and inhibiting activity of A2AP, wherein said isolated antibodies or antigen-binding fragments thereof do not inhibit plasmin activity.

In particular embodiments, said isolated antibodies or antigen-binding fragments thereof according to the present invention inhibit the activity of A2AP by preventing the binding of A2AP to plasmin.

Due to the fact that the endogenous plasma concentration of A2AP is comparatively high (1 µM; and 70 µg/ml, respectively), high concentration of neutralizing antibody will be needed to block A2AP activity. Therefore, it is advantageous if an A2AP antibody does not inhibit plasmin activity up to high concentration of the antibody. Surprisingly, isolated antibodies or antigen-binding fragments thereof according to the present invention did not inhibit plasmin activity up to a concentration of 10 µM in an in vitro plasmin inhibition assay, whereas antibody 77A3 inhibited the plasmin activity with an IC50 of 1.7 µM in the same assay (see example 11, FIG. 16).

In particular embodiments, said isolated antibodies or antigen-binding fragments thereof according to the present invention do not inhibit the activity of human plasmin, particularly human plasmin comprising SEQ ID NO: 118 (plasmin heavy chain A) and SEQ ID NO: 119 (plasmin light chain B), even if present in high micromolar concentration.

In particular embodiments, said isolated antibodies or antigen-binding fragments thereof according to the present invention do not inhibit plasmin activity up to a concertation of said isolated antibodies or antigen-binding fragments thereof of 1 µM, 2 µM, 5 µM or 10 µM in an in vitro plasmin inhibition assay.

In particular embodiments, said isolated antibodies or antigen-binding fragments thereof according to the present invention do not inhibit plasmin activity up to a concertation of said isolated antibodies or antigen-binding fragments thereof of 1 µM, 2 µM, 5 µM or 10 µM in an in vitro plasmin inhibition assay, wherein the in vitro plasmin inhibition assay determines the inhibition of the proteolytic activity of plasmin.

Such an in vitro plasmin inhibition assay can be an assay, that determines the inhibition of the proteolytic activity of plasmin as described in example 11. For such assay plasmin and a labeled substrate for the plasmin proteolytic activity like fluorogenic substrate I-1275 (Bachem; MeOSuc-Ala-Phe-Lys-AMC trifluoroacetate salt; catalogue number I-1275) may be used.

In another aspect, the present invention relates to isolated antibodies or antigen-binding fragments thereof capable of binding to human A2AP and inhibiting activity of A2AP, wherein said isolated antibodies or antigen-binding fragments thereof bind to an epitope of A2AP comprising amino acid 402-408 (SRMSLSS) of SEQ ID NO: 1.

A2AP comprises the amino acid sequence SRMSLSS (amino acid 402-408 of SEQ ID NO: 1), which is located in the reactive center loop of A2AP (amino acid 400-412 of Seq ID NO: 1). In particular embodiments, said isolated antibodies or antigen-binding fragments thereof according to the present invention are capable of binding to human A2AP and inhibiting activity of A2AP, wherein said isolated antibodies or antigen-binding fragments thereof bind to an epitope of A2AP comprising amino acid 402-408 (SRMSLSS) of SEQ ID NO: 1 and wherein said isolated antibodies or antigen-binding fragments thereof do not inhibit plasmin activity.

In particular embodiments, said isolated antibodies or antigen-binding fragments thereof according to the present invention are capable of binding to human A2AP and inhibiting activity of A2AP,
wherein said isolated antibodies or antigen-binding fragments thereof bind to an epitope of A2AP comprising amino acid 402-408 (SRMSLSS) of SEQ ID NO: 1 and wherein said isolated antibodies or antigen-binding fragments thereof do not inhibit plasmin activity up to a concertation of said isolated antibodies or antigen-binding fragments thereof of 1 µM, 2 µM, 5 µM or 10 µM in an in vitro plasmin inhibition assay.

In another aspect, the present invention relates to isolated antibodies or antigen-binding fragments thereof binding to human A2AP, wherein said isolated antibodies or antigen-binding fragments thereof do not convert A2AP from a serine protease inhibitor to a serine protease substrate.

In another aspect, the present invention relates to isolated antibodies or antigen-binding fragments thereof binding to human A2AP, wherein said isolated antibodies or antigen-binding fragments thereof bind to human A2AP of the sequence of amino acid 40-491 of SEQ ID 1 with a dissociation constant (KD)≤100 nM, ≤50 nM, ≤25 nM, ≤10 nM, ≤1 nM, or ≤0.5 nM.

In another aspect, the present invention relates to isolated antibodies or antigen-binding fragments thereof binding to human A2AP, wherein said isolated antibodies or antigen-binding fragments thereof bind to human A2AP of the sequence of amino acid 40-491 of SEQ ID 1 with an EC50 of ≤500 nM, ≤250 nM, ≤100 nM, ≤50 nM, ≤25 nM, ≤10 nM, ≤1 nM, or ≤0.5 nM.

In another aspect, the present invention relates to isolated antibodies or antigen-binding fragments thereof binding to human A2AP, wherein said isolated antibodies or antigen-binding fragments thereof inhibit the activity of human A2AP of amino acid 40-491 of SEQ ID 1 with an EC50 of ≤500 nM, ≤250 nM, ≤100 nM, ≤50 nM, ≤25 nM, ≤10 nM 1 n 1 nM, or 0.5 nM in an in vitro A2AP function blocking assay.

An in vitro A2AP function blocking assay can be an assay as described in example 4. In such an assay, the test antibodies are pre-incubated with A2AP. After adding a A2AP-substrate like plasmin, trypsin or chymotrypsin to the assay, the activity of the added A2AP substrate, which is not blocked by A2AP, can be analyzed for example by the use of a labeled substrate for the A2AP-substrate. For example, for plasmin (A2AP substrate) the fluorogenic substrate I-1275 (Bachem; MeOSuc-Ala-Phe-Lys-AMC trifluoroacetate salt; catalogue number I-1275) may be used.

In particular embodiments, said isolated antibodies or antigen-binding fragments thereof according to the present invention
(i) bind to human A2AP of the sequence of amino acid 40-491 of SEQ ID NO: 1 with a dissociation constant (KD)≤100 nM, ≤50 nM, ≤25 nM, ≤10 nM, ≤1 nM, or ≤0.5 nM; and
(ii) inhibit the activity of human A2AP of amino acid 40-491 of SEQ ID NO: 1 with an EC50 of ≤500 nM, ≤250 nM, ≤100 nM, ≤50 nM, ≤25 nM, ≤10 nM, ≤1 nM, or ≤0.5 nM in an in vitro A2AP function blocking assay.

In another aspect, the present invention relates to isolated antibodies or antigen-binding fragments thereof binding to human A2AP, wherein said isolated antibodies or antigen-binding fragments thereof increase plasmin mediated clot lysis in the presence of A2AP. In particular, the isolated antibodies or antigen-binding fragments according to the present invention increase plasmin mediated clot lysis in vitro and/or in vivo. The antibody's ability to increase plasmin mediated clot lysis in vitro may be assessed as described in Example 7. The antibody's ability to increase plasmin mediated clot lysis in vivo may be assessed as described in Example 8.

The isolated antibodies or antigen-binding fragments according to the present invention may exhibit any combination of the above described characteristics.

In particular embodiments, the isolated antibodies or antigen-binding fragments according to the present invention interfere with the interaction of A2AP and plasmin, particularly with the interaction of human A2AP and human plasmin, particularly with the interaction of human A2AP of amino acid 40-491 of SEQ ID NO: 1 and human plasmin, particularly human plasmin comprising SEQ ID NO: 118 (plasmin heavy chain A) and SEQ ID NO: 119 (plasmin light chain B). Particularly, the antibodies or antigen-binding fragments according to the present invention are A2AP blocking antibodies or antigen-binding fragments.

In particular embodiments, the isolated antibodies or antigen-binding fragments according to the present invention comprise a heavy chain variable domain that is at least 90%, at least 95%, at least 98% or at least 99% identical to SEQ ID NO: 32. In particular embodiments, the isolated antibodies or antigen-binding fragments according to the present invention comprise a light chain variable domain that is at least 90% %, at least 95%, at least 98% or at least 99% identical to SEQ ID NO: 38. In particular embodiments, the isolated antibodies or antigen-binding fragments according to the present invention comprise a heavy chain variable domain that is at least 90%, at least 95%, at least 98% or at least 99% identical to SEQ ID NO: 32, and a light chain variable domain that is at least 90% %, at least 95%, at least 98% or at least 99% identical to SEQ ID NO: 38.

In particular embodiments, the isolated antibody or antigen-binding fragment according to the present invention comprises a heavy chain antigen-binding region that comprises an H-CDR3 comprising the sequence $EX_1YDSSGYYHLX_2Y$ (SEQ ID NO: 4) wherein $X_1$ is selected from the group consisting of Y, D and G and wherein $X_2$ is selected from the group consisting of D, V, E and T. In particular embodiments, $X_1$ is selected from the group consisting of D and G and $X_2$ is selected from the group consisting of V, E and T.

In particular embodiments, the isolated antibody or antigen-binding fragment according to the present invention comprises a light chain antigen-binding region that comprises an L-CDR3 comprising the sequence $X_1AWDX_2SLSGWV$ (SEQ ID NO: 5) wherein $X_1$ is selected from the group consisting of A and W and wherein $X_2$ is selected from the group consisting of D, N, L, W and V. In particular embodiments, $X_1$ is selected from the group consisting of W and $X_2$ is selected from the group consisting of N, L, W and V.

Particularly, the isolated antibody or antigen-binding fragment according to the present invention comprises i) a heavy chain antigen-binding region that comprises an H-CDR3 comprising the sequence $EX_1YDSSGYYHLX_2Y$ (SEQ ID NO: 4) wherein $X_1$ is selected from the group consisting of Y, D and G and wherein $X_2$ is selected from the group consisting of D, V, E and T and ii) a light chain antigen-binding region that comprises an L-CDR3 comprising the sequence $X_1AWDX_2SLSGWV$ (SEQ ID NO: 5), wherein $X_1$ is selected from the group consisting of A and W; and wherein $X_2$ is selected from the group consisting of D, N, L, W and V.

In particular embodiments, the two framework residues $X_1X_2$ directly adjacent to the 5' end of the H-CDR3 region (corresponding to residues 96 [$X_1$] and 97 [$X_2$] of reference VH domain of SEQ ID NO: 32) are selected as follows: $X_1$ is selected from the group consisting of A and D, in particular $X_1$ is D, and $X_2$ is selected from the group consisting of R and S, in particular $X_2$ is S.

In particular embodiments, the isolated antibody or antigen-binding fragment according to the present invention comprises a heavy chain antigen-binding region that comprises an H-CDR1 comprising SEQ ID NO: 6 or SEQ ID NO: 21 and an H-CDR2 comprising SEQ ID NO: 7, SEQ ID NO: 8 or SEQ ID NO: 22. In particular embodiments, the isolated antibody or antigen-binding fragment according to the present invention comprises a light chain antigen-binding region that comprises an L-CDR1 comprising SEQ ID NO: 9 and an L-CDR2 comprising SEQ ID NO: 10.

In particular embodiments, the isolated antibody or antigen-binding fragment according to the present invention comprises i) a heavy chain antigen-binding region that comprises an H-CDR3 comprising SEQ ID NO: 13 and a light chain antigen-binding region that comprises an L-CDR3 comprising SEQ ID NO: 18, or ii) a heavy chain antigen-binding region that comprises an H-CDR3 comprising SEQ ID NO: 11 and a light chain antigen-binding region that comprises an L-CDR3 comprising SEQ ID NO: 17, or iii) a heavy chain antigen-binding region that comprises an H-CDR3 comprising SEQ ID NO: 11 and a light chain antigen-binding region that comprises an L-CDR3 comprising SEQ ID NO: 18, or iv) a heavy chain antigen-binding region that comprises an H-CDR3 comprising SEQ ID NO: 12 and a light chain antigen-binding region that comprises an L-CDR3 comprising SEQ ID NO: 18, or v) a heavy chain antigen-binding region that comprises an H-CDR3 comprising SEQ ID NO: 13 and a light chain antigen-binding region that comprises an L-CDR3 comprising SEQ ID NO: 19, or vi) a heavy chain antigen-binding region that comprises an H-CDR3 comprising SEQ ID NO: 13 and a light chain antigen-binding region that comprises an L-CDR3 comprising SEQ ID NO: 18, or vii) a heavy chain antigen-binding region that comprises an H-CDR3 comprising SEQ ID NO: 14 and a light chain antigen-binding region that comprises an L-CDR3 comprising SEQ ID NO: 18, or viii) a heavy chain antigen-binding region that comprises an H-CDR3 comprising SEQ ID NO: 14 and a light chain antigen-binding region that comprises an L-CDR3 comprising SEQ ID NO: 20, or ix) a heavy chain antigen-binding region that comprises an H-CDR3 comprising SEQ ID NO: 15 and a light chain antigen-binding region that comprises an L-CDR3 comprising SEQ ID NO: 18, or x) a heavy chain antigen-binding region that comprises an H-CDR3 comprising SEQ ID NO: 16 and a light chain antigen-binding region that comprises an L-CDR3 comprising SEQ ID NO: 18.

In particular embodiments, the isolated antibodies or antigen-binding fragments according to the present invention comprises:

i) a heavy chain antigen-binding region that comprises an H-CDR1 comprising SEQ ID NO: 6, an H-CDR2 comprising SEQ ID NO: 8, and an H-CDR3 comprising SEQ ID NO: 13 and a light chain antigen-binding region that comprises an L-CDR1 comprising SEQ ID NO: 9, an L-CDR2 comprising SEQ ID NO: 10, and an L-CDR3 comprising SEQ ID NO:18, or ii) a heavy chain antigen-binding region that comprises an H-CDR1 comprising SEQ ID NO: 6, an H-CDR2 comprising SEQ ID NO: 7, and an H-CDR3 comprising SEQ ID NO: 13 and a light chain antigen-binding region that comprises an L-CDR1 comprising SEQ ID NO: 9, an L-CDR2 comprising SEQ ID NO: 10, and an L-CDR3 comprising SEQ ID NO:18, or iii) a heavy chain antigen-binding region that comprises an H-CDR1 comprising SEQ ID NO: 6, an H-CDR2 comprising SEQ ID NO: 7, and an H-CDR3 comprising SEQ ID NO: 11 and a light chain antigen-binding region that comprises an L-CDR1 comprising SEQ ID NO: 9, an L-CDR2 comprising SEQ ID NO: 10, and an L-CDR3 comprising SEQ ID NO:17, or iv) a heavy chain antigen-binding region that comprises an H-CDR1 comprising SEQ ID NO: 6, an H-CDR2 comprising SEQ ID NO: 7, and an H-CDR3 comprising SEQ ID NO: 11 and a light chain antigen-binding region that comprises an L-CDR1 comprising SEQ ID NO: 9, an L-CDR2 comprising SEQ ID NO: 10, and an L-CDR3 comprising SEQ ID NO:18, or v) a heavy chain antigen-binding region that comprises an H-CDR1 comprising SEQ ID NO: 6, an H-CDR2 comprising SEQ ID NO: 7, and an H-CDR3 comprising SEQ ID NO: 12 and a light chain antigen-binding region that comprises an L-CDR1 comprising SEQ ID NO: 9, an L-CDR2 comprising SEQ ID NO: 10, and an L-CDR3 comprising SEQ ID NO:18, or vi) a heavy chain antigen-binding region that comprises an H-CDR1 comprising SEQ ID NO: 6, an H-CDR2 comprising SEQ ID NO: 7, and an H-CDR3 comprising SEQ ID NO: 13 and a light chain antigen-binding region that comprises an L-CDR1 comprising SEQ ID NO: 9, an L-CDR2 comprising SEQ ID NO: 10, and an L-CDR3 comprising SEQ ID NO:19, or vii) a heavy chain antigen-binding region that comprises an H-CDR1 comprising SEQ ID NO: 6, an H-CDR2 comprising SEQ ID NO: 7, and an H-CDR3 comprising SEQ ID NO: 14 and a light chain antigen-binding region that comprises an L-CDR1 comprising SEQ ID NO: 9, an L-CDR2 comprising SEQ ID NO: 10, and an L-CDR3 comprising SEQ ID NO:18, or viii) a heavy chain antigen-binding region that comprises an H-CDR1 comprising SEQ ID NO: 6, an H-CDR2 comprising SEQ ID NO: 7, and an H-CDR3 comprising SEQ ID NO: 14 and a light chain antigen-binding region that comprises an L-CDR1 comprising SEQ ID NO: 9, an L-CDR2 comprising SEQ ID NO: 10, and an L-CDR3 comprising SEQ ID NO:20, or ix) a heavy chain antigen-binding region that comprises an H-CDR1 comprising SEQ ID NO: 6, an H-CDR2 comprising SEQ ID NO: 7, and an H-CDR3 comprising SEQ ID NO: 15 and a light chain antigen-binding region that comprises an L-CDR1 comprising SEQ ID NO: 9, an L-CDR2 comprising SEQ ID NO: 10, and an L-CDR3 comprising SEQ ID NO:18, or x) a heavy chain antigen-binding region that comprises an H-CDR1 comprising SEQ ID NO: 6, an H-CDR2 comprising SEQ ID NO: 7, and an H-CDR3 comprising SEQ ID NO: 16 and a light chain antigen-binding region that comprises an L-CDR1 comprising SEQ ID NO: 9, an L-CDR2 comprising SEQ ID NO: 10, and an L-CDR3 comprising SEQ ID NO:18, or xi) a heavy chain antigen-binding region that comprises an H-CDR1 comprising SEQ ID NO: 21, an H-CDR2 comprising SEQ ID NO: 8, and an H-CDR3 comprising SEQ ID NO: 13 and a light chain antigen-binding region that comprises an L-CDR1 comprising SEQ ID NO: 9, an L-CDR2 comprising SEQ ID NO: 10, and an L-CDR3 comprising SEQ ID NO:18, or xii) a heavy chain antigen-binding region that comprises an H-CDR1 comprising SEQ ID NO: 6, an H-CDR2 comprising SEQ ID NO: 22, and an H-CDR3 comprising SEQ ID NO: 13 and a light chain antigen-binding region that comprises an L-CDR1 comprising SEQ ID NO: 9, an L-CDR2 comprising SEQ ID NO: 10, and an L-CDR3 comprising SEQ ID NO:18.

In particular embodiments, the isolated antibodies or antigen-binding fragments according to the present invention comprise at least one, at least two, at least three or at least four or five of the heavy chain variable domain framework and CDR residues selected from the group consisting of 30S, 31S, 53S, 56S, 97K. These amino acid positions correspond to the amino acid positions of reference heavy chain variable domain of SEQ ID NO: 32 and include framework and H-CDR1 and H-CDR2 amino acid residues.

In particular embodiments, the isolated antibodies or antigen-binding fragments according to the present invention comprise:

i) a variable heavy chain domain comprising SEQ ID NO: 32 and a variable light chain domain comprising SEQ ID NO: 38; or ii) a variable heavy chain domain comprising SEQ ID NO: 23 and a variable light chain domain comprising SEQ ID NO: 37; or iii) a variable heavy chain domain comprising SEQ ID NO: 24 and a variable light chain domain comprising SEQ ID NO: 38; or iv) a variable heavy chain domain comprising SEQ ID NO: 25 and a variable light chain domain comprising SEQ ID NO: 38; or v) a variable heavy chain domain comprising SEQ ID NO: 26 and a variable light chain domain comprising SEQ ID NO: 38; or vi) a variable heavy chain domain comprising SEQ ID NO: 27 and a variable light chain domain comprising SEQ ID NO: 39; or vii) a variable heavy chain domain comprising SEQ ID NO: 27 and a variable light chain domain comprising SEQ ID NO: 38; or viii) a variable heavy chain domain comprising SEQ ID NO: 28 and a variable light chain domain comprising SEQ ID NO: 38; or ix) a variable heavy chain domain comprising SEQ ID NO: 28 and a variable light chain domain comprising SEQ ID NO: 40; or x) a variable heavy chain domain comprising SEQ ID NO: 29 and a variable light chain domain comprising SEQ ID NO: 38; or xi) a variable heavy chain domain comprising SEQ ID NO: 30 and a variable light chain domain comprising SEQ ID NO: 38; or xii) a variable heavy chain domain comprising SEQ ID NO: 31 and a variable light chain domain comprising SEQ ID NO: 38; or xiii) a variable heavy chain domain comprising SEQ ID NO: 33 and a variable light chain domain comprising SEQ ID NO: 38; or xiv) a variable heavy chain domain comprising SEQ ID NO: 34 and a variable light chain domain comprising SEQ ID NO: 38; or xv) a variable heavy chain domain comprising SEQ ID NO: 35 and a variable light chain domain comprising SEQ ID NO: 38; or xvi) a variable heavy chain domain comprising SEQ ID NO: 36 and a variable light chain domain comprising SEQ ID NO: 38.

In particular embodiments, the isolated antibodies according to the present invention are IgG antibody. In particular such embodiments, the isolated antibodies according to the present invention are an IgG1, IgG2, IgG3 or an IgG4 antibody. Most particularly, the isolated antibodies according to the present invention is an IgG1 or an IgG4 antibody.

In particular embodiments, the isolated antibodies according to the present invention comprise: i) a heavy chain comprising SEQ ID NO: 55 and a light chain comprising SEQ ID NO: 57; or ii) a heavy chain comprising SEQ ID NO: 41 and a light chain comprising SEQ ID NO: 56; or iii) a heavy chain comprising SEQ ID NO: 42 and a light chain comprising SEQ ID NO: 57; or iv) a heavy chain comprising SEQ ID NO: 43 and a light chain comprising SEQ ID NO: 57; or v) a heavy chain comprising SEQ ID NO: 44 and a light chain comprising SEQ ID NO: 57; or vi) a heavy chain comprising SEQ ID NO: 45 and a light chain comprising SEQ ID NO: 58; or vii) a heavy chain comprising SEQ ID NO: 45 and a light chain comprising SEQ ID NO: 57; or viii) a heavy chain comprising SEQ ID NO: 46 and a light chain comprising SEQ ID NO: 57; or ix) a heavy chain comprising SEQ ID NO: 46 and a light chain comprising SEQ ID NO: 59; or x) a heavy chain comprising SEQ ID NO: 47 and a light chain comprising SEQ ID NO: 57; or xi) a heavy chain comprising SEQ ID NO: 48 and a light chain comprising SEQ ID NO: 57; or xii) a heavy chain comprising SEQ ID NO: 49 and a light chain comprising SEQ ID NO: 57; or xiii) a heavy chain comprising SEQ ID NO: 50 and a light chain comprising SEQ ID NO: 57; or xiv) a heavy chain comprising SEQ ID NO: 51 and a light chain comprising SEQ ID NO: 57; or xv) a heavy chain comprising SEQ ID NO: 52 and a light chain comprising SEQ ID NO: 57; or xvi) a heavy chain comprising SEQ ID NO: 53 and a light chain comprising SEQ ID NO: 57; or xvii) a heavy chain comprising SEQ ID NO: 54 and a light chain comprising SEQ ID NO: 57.

In particular embodiments, the antigen-binding fragments according to the present invention are scFv, Fab, Fab' fragment or a F(ab')2 fragments.

In particular embodiments, the isolated antibodies or antigen-binding fragments according to the present invention are monoclonal antibodies or antigen-binding fragments.

In particular embodiments, the isolated antibodies or antigen-binding fragments according to the present invention are human, humanized or chimeric antibodies or antigen-binding fragments, more particularly fully human antibodies or antigen-binding fragments.

In particular embodiments, the isolated antibodies or antigen-binding fragments according to the present invention are monospecific antibodies. In particular other embodiments, the isolated antibodies or antigen-binding fragments according to the present invention are multispecific antibodies that bind to A2AP and at least one further antigen, such bispecific, trispecific or tetraspecific antibodies.

In a further aspect, the present invention relates to isolated antibodies or antigen-binding fragments thereof that compete with the isolated antibodies or antigen-binding fragments according to the present invention for binding to A2AP.

Amino acid sequences of preferred antibodies according to the present invention are listed in Table 1.

TABLE 1

Amino acid sequences of preferred antibodies according to the present invention

| Antibody/Isotype | SEQ ID NO: VH | SEQ ID NO: H-CDR1 | SEQ ID NO: H-CDR2 | SEQ ID NO: H-CDR3 | SEQ ID NO: VL | SEQ ID NO: L-CDR1 | SEQ ID NO: L-CDR2 | SEQ ID NO: L-CDR3 | SEQ ID NO: IgG Heavy Chain | SEQ ID NO: IgG Light Chain |
|---|---|---|---|---|---|---|---|---|---|---|
| TPP-12387 hIgG1 | 23 | 6 | 7 | 11 | 37 | 9 | 10 | 17 | 41 | 56 |
| TPP-14293 hIgG1 | 24 | 6 | 7 | 11 | 38 | 9 | 10 | 18 | 42 | 57 |
| TPP-14298 hIgG1 | 25 | 6 | 7 | 11 | 38 | 9 | 10 | 18 | 43 | 57 |
| TPP-14303 hIgG1 | 26 | 6 | 7 | 12 | 38 | 9 | 10 | 18 | 44 | 57 |
| TPP-14305 hIgG1 | 27 | 6 | 7 | 13 | 39 | 9 | 10 | 19 | 45 | 58 |
| TPP-14308 hIgG1 | 27 | 6 | 7 | 13 | 38 | 9 | 10 | 18 | 45 | 57 |
| TPP-14313 hIgG1 | 28 | 6 | 7 | 14 | 38 | 9 | 10 | 18 | 46 | 57 |
| TPP-14314 hIgG1 | 28 | 6 | 7 | 14 | 40 | 9 | 10 | 20 | 46 | 59 |
| TPP-14318 hIgG1 | 29 | 6 | 7 | 15 | 38 | 9 | 10 | 18 | 47 | 57 |
| TPP-14323 hIgG1 | 30 | 6 | 7 | 16 | 38 | 9 | 10 | 18 | 48 | 57 |
| TPP-17041 hIgG1 | 31 | 6 | 7 | 13 | 38 | 9 | 10 | 18 | 49 | 57 |
| TPP-17044 hIgG1 | 32 | 6 | 8 | 13 | 38 | 9 | 10 | 18 | 50 | 57 |
| TPP-17045 hIgG1 | 33 | 6 | 7 | 13 | 38 | 9 | 10 | 18 | 51 | 57 |
| TPP-17048 hIgG1 | 34 | 6 | 8 | 13 | 38 | 9 | 10 | 18 | 52 | 57 |
| TPP-17051 hIgG1 | 35 | 21 | 8 | 13 | 38 | 9 | 10 | 18 | 53 | 57 |
| TPP-17053 hIgG1 | 36 | 6 | 22 | 13 | 38 | 9 | 10 | 18 | 54 | 57 |
| TPP-17928 hIgG4 | 32 | 6 | 8 | 13 | 38 | 9 | 10 | 18 | 55 | 57 |

Nucleic acid sequences of preferred antibodies according to the present invention are listed in Table 2.

TABLE 2

Nucleic acid sequences of preferred antibodies according to the present invention

| Antibody/Isotype | SEQ ID NO: VH | SEQ ID NO: H-CDR1 | SEQ ID NO: H-CDR2 | SEQ ID NO: H-CDR3 | SEQ ID NO: VL | SEQ ID NO: L-CDR1 | SEQ ID NO: L-CDR2 | SEQ ID NO: L-CDR3 | SEQ ID NO: IgG Heavy Chain | SEQ ID NO: IgG Light Chain |
|---|---|---|---|---|---|---|---|---|---|---|
| TPP-12387 hIgG1 | 80 | 63 | 64 | 68 | 94 | 66 | 67 | 74 | 98 | 113 |
| TPP-14293 hIgG1 | 81 | 63 | 64 | 68 | 95 | 66 | 67 | 75 | 99 | 114 |
| TPP-14298 hIgG1 | 82 | 63 | 64 | 68 | 95 | 66 | 67 | 75 | 100 | 114 |
| TPP-14303 hIgG1 | 83 | 63 | 64 | 69 | 95 | 66 | 67 | 75 | 101 | 114 |
| TPP-14305 hIgG1 | 84 | 63 | 64 | 70 | 96 | 66 | 67 | 76 | 102 | 115 |
| TPP-14308 hIgG1 | 84 | 63 | 64 | 70 | 95 | 66 | 67 | 75 | 102 | 114 |
| TPP-14313 hIgG1 | 85 | 63 | 64 | 71 | 95 | 66 | 67 | 75 | 103 | 114 |
| TPP-14314 hIgG1 | 85 | 63 | 64 | 71 | 97 | 66 | 67 | 77 | 103 | 116 |

TABLE 2-continued

Nucleic acid sequences of preferred antibodies according to the present invention

| Antibody/Isotype | SEQ ID NO: VH | SEQ ID NO: H-CDR1 | SEQ ID NO: H-CDR2 | SEQ ID NO: H-CDR3 | SEQ ID NO: VL | SEQ ID NO: L-CDR1 | SEQ ID NO: L-CDR2 | SEQ ID NO: L-CDR3 | SEQ ID NO: IgG Heavy Chain | SEQ ID NO: IgG Light Chain |
|---|---|---|---|---|---|---|---|---|---|---|
| TPP-14318 hIgG1 | 86 | 63 | 64 | 72 | 95 | 66 | 67 | 75 | 104 | 114 |
| TPP-14323 hIgG1 | 87 | 63 | 64 | 73 | 95 | 66 | 67 | 75 | 105 | 114 |
| TPP-17041 hIgG1 | 88 | 63 | 64 | 117 | 95 | 66 | 67 | 75 | 106 | 114 |
| TPP-17044 hIgG1 | 89 | 63 | 65 | 70 | 95 | 66 | 67 | 75 | 107 | 114 |
| TPP-17045 hIgG1 | 90 | 63 | 64 | 70 | 95 | 66 | 67 | 75 | 108 | 114 |
| TPP-17048 hIgG1 | 91 | 63 | 65 | 70 | 95 | 66 | 67 | 75 | 109 | 114 |
| TPP-17051 hIgG1 | 92 | 78 | 65 | 70 | 95 | 66 | 67 | 75 | 110 | 114 |
| TPP-17053 hIgG1 | 93 | 63 | 79 | 70 | 95 | 66 | 67 | 75 | 111 | 114 |
| TPP-17928 hIgG4 | 89 | 63 | 65 | 70 | 95 | 66 | 67 | 75 | 112 | 114 |

Peptide Variants

Antibodies or antigen-binding fragments of the invention are not limited to the specific peptide sequences provided herein. Rather, the invention also embodies variants of these polypeptides. With reference to the instant disclosure and conventionally available technologies and references, the skilled worker will be able to prepare, test and utilize functional variants of the antibodies disclosed herein, while appreciating these variants having the ability to bind to A2AP fall within the scope of the present invention.

A variant can include, for example, an antibody that has at least one altered complementary determining region (CDR) (hyper-variable) and/or framework (FR) (variable) domain/position, vis-à-vis a peptide sequence disclosed herein.

By altering one or more amino acid residues in a CDR or FR region, the skilled worker routinely can generate mutated or diversified antibody sequences, which can be screened against the antigen, for new or improved properties, for example.

A further preferred embodiment of the invention is an antibody or antigen-binding fragment in which the VH and VL sequences are selected as shown in Table 1. The skilled worker can use the data in Table 1 to design peptide variants that are within the scope of the present invention. It is preferred that variants are constructed by changing amino acids within one or more CDR regions; a variant might also have one or more altered framework regions. Alterations also may be made in the framework regions. For example, a peptide FR domain might be altered where there is a deviation in a residue compared to a germline sequence.

Alternatively, the skilled worker could make the same analysis by comparing the amino acid sequences disclosed herein to known sequences of the same class of such antibodies, using, for example, the procedure described by Knappik A., et al., JMB 2000, 296:57-86.

Furthermore, variants may be obtained by using one antibody as starting point for further optimization by diversifying one or more amino acid residues in the antibody, preferably amino acid residues in one or more CDRs, and by screening the resulting collection of antibody variants for variants with improved properties. Particularly preferred is diversification of one or more amino acid residues in CDR3 of VL and/or VH. Diversification can be done e.g. by synthesizing a collection of DNA molecules using trinucleotide mutagenesis (TRIM) technology (Virnekas B. et al., Nucl. Acids Res. 1994, 22: 5600.). Antibodies or antigen-binding fragments thereof include molecules with modifications/variations including but not limited to e.g. modifications leading to altered half-life (e.g. modification of the Fc part or attachment of further molecules such as PEG), altered binding affinity or altered ADCC or CDC activity.

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophane, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Glycosylation Variants

Where the antibody comprises an Fc region, the carbohydrate attached thereto may be altered. Native antibodies produced by mammalian cells typically comprise a branched, biantennary oligosaccharide that is generally attached by an N-linkage to Asn297 using Kabat EU numbering of the CH2 domain of the Fc region; see, e.g., Wright et al. Trends Biotechnol. 15: 26-32 (1997).

In certain embodiments, an antibody provided herein is altered to increase or decrease the extent to which the antibody is glycosylated. Addition or deletion of glycosylation sites to an antibody may be conveniently accomplished by altering the expression system (e.g. host cell) and/or by altering the amino acid sequence such that one or more glycosylation sites is created or removed.

In one embodiment of this invention, aglycosyl antibodies having decreased effector function or antibody derivatives are prepared by expression in a prokaryotic host. Suitable prokaryotic hosts for include but are not limited to *E. coli, Bacillus subtilis, Salmonella typhimurium* and various species within the genera *Pseudomonas, Streptomyces*, and *Staphylococcus*.

In one embodiment, antibody variants are provided having decreased effector function, which are characterized by a modification at the conserved N-linked site in the CH2 domains of the Fc portion of said antibody. In one embodiment of present invention, the modification comprises a mutation at the heavy chain glycosylation site to prevent glycosylation at the site. Thus, in one preferred embodiment of this invention, the aglycosyl antibodies or antibody derivatives are prepared by mutation of the heavy chain glycosylation site,—i.e., mutation of N297 using Kabat EU numbering and expressed in an appropriate host cell.

In another embodiment of the present invention, aglycosyl antibodies or antibody derivatives have decreased effector function, wherein the modification at the conserved N-linked site in the CH2 domains of the Fc portion of said antibody or antibody derivative comprises the removal of the CH2 domain glycans,—i.e., deglycosylation. These aglycosyl antibodies may be generated by conventional methods and then deglycosylated enzymatically. Methods for enzymatic deglycosylation of antibodies are well known in the art (e.g. Winkelhake & Nicolson (1976), J Biol Chem. 251(4):1074-80).

In another embodiment of this invention, deglycosylation may be achieved using the glycosylation inhibitor tunicamycin (Nose & Wigzell (1983), Proc Natl Acad Sci USA, 80(21):6632-6). That is, the modification is the prevention of glycosylation at the conserved N-linked site in the CH2 domains of the Fc portion of said antibody.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function.

Examples of publications related to "defucosylated" or "fucose-deficient" antibody variants include Okazaki et al. J Mol. Biol. 336: 1239-1249 (2004); Yamane-Ohnuki et al. Biotech. Bioeng. 87: 614 (2004).

Examples of cell lines capable of producing defucosylated antibodies include Lec13 CHO cells deficient in protein fucosylation (Ripka et al. Arch. Biochem. Biophys. 249: 533-545 (1986); and WO 2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006)).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546.

Antibody variants with at least one galactose residue in the oligosaccharide attached to the Fc region are also provided. Such antibody variants may have improved CDC function. Such antibody variants are described, e.g., in WO1997/30087; WO1998/58964; and WO1999/22764.

Fc Region Variants

In certain embodiments, one or more amino acid modifications (e.g. a substitution) may be introduced into the Fc region of an antibody (e.g., a human IgG1, IgG2, IgG3 or IgG4 Fc region) provided herein, thereby generating an Fc region variant.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. In some embodiments, alterations are made in the Fc region that result in altered (i.e., either improved or diminished) C1q binding and/or Complement Dependent Cytotoxicity (CDC).

In certain embodiments, the invention contemplates an antibody variant that possesses an increased or decreased half-live. Antibodies with increased half-lives and improved binding to the neonatal Fc receptor (FcRn), which is responsible for the transfer of maternal IgGs to the fetus (Guyer et al., J Immunol. 117:587 (1976) and Kim et al., J Immunol. 24:249 (1994)), are described in US2005/0014934 (Hinton et al.). Those antibodies comprise an Fc region with one or more substitutions therein which improve binding of the Fc region to FcRn.

In a further aspect, the present invention relates to antibody conjugates, comprising the isolated antibodies or antigen binding fragments according to the present invention.

Antibody Generation

An antibody of the invention may be derived from a recombinant antibody library that is based on amino acid sequences that have been isolated from the antibodies of a large number of healthy volunteers e.g. using the n-CoDeR® technology the fully human CDRs are recombined into new antibody molecules (Carlson & Söderlind, Expert Rev Mol Diagn. 2001 May; 1(1):102-8). Or alternatively for example antibody libraries as the fully human antibody phage display library described in Hoet R M et al., Nat Biotechnol 2005; 23(3):344-8) can be used to isolate A2AP-specific antibodies. Antibodies or antibody fragments isolated from human antibody libraries are considered human antibodies or human antibody fragments herein.

Human antibodies may be further prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. For example, immunization of genetically engineered mice inter alia immunization of hMAb mice (e.g. VelocImmune Mouse® or XENOMOUSE®) may be performed.

Further antibodies may be generated using the hybridoma technology (for example see Köhler and Milstein Nature. 1975 Aug. 7; 256(5517):495-7), resulting in for example murine, rat, or rabbit antibodies which can be converted into chimeric or humanized antibodies. Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Natl Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall' Acqua et al., Methods 36:43-60 (2005) (describing "FR shuffling"); and Osboum et al., Methods 36:61-68 (2005) and Klimka et al., Br. J. Cancer, 83:252-260 (2000) (describing the "guided selection" approach to FR shuffling).

Examples are provided for the generation of antibodies using a recombinant antibody library.

DNA Molecules According to the Present Invention

The present invention also relates to an isolated nucleic acid sequence that encodes the antibody or antigen-binding fragment according to the present invention. The isolated nucleic acid sequence encoding the antibody or antigen-binding fragment according to the present invention can for instance be produced by techniques described in Sambrook et al., 1989, and Ausubel et al., 1989, or alternatively, by chemically synthesis. (e.g. techniques described in Oligonucleotide Synthesis (1984, Gait, ed., IRL Press, Oxford)). The DNA sequences used for the antibodies expressed are given in Table 2. These sequences are optimized in certain cases for mammalian expression. DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 supra and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

Functionally Equivalent DNA Variants

Yet another class of DNA variants within the scope of the invention may be described with reference to the product they encode. These functionally equivalent polynucleotides are characterized by the fact that they encode the same peptide sequences due to the degeneracy of the genetic code.

It is recognized that variants of DNA molecules provided herein can be constructed in several different ways. For example, they may be constructed as completely synthetic DNAs. Methods of efficiently synthesizing oligonucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides recombinant DNA constructs comprising one or more of the nucleotide sequences according to the present invention. The recombinant constructs of the present invention can be used in connection with a vector, such as a plasmid, phagemid, phage or viral vector, into which a DNA molecule encoding an antibody of the invention or antigen-binding fragment thereof or variant thereof is inserted.

Thus, in one aspect, the present invention relates to a vector comprising a nucleic acid sequence according to the present invention.

An antibody, antigen binding portion, or variant thereof provided herein can be prepared by recombinant expression of nucleic acid sequences encoding light and heavy chains or portions thereof in a host cell. To express an antibody, antigen binding portion, or variant thereof recombinantly a host cell can be transfected with one or more recombinant expression vectors carrying DNA fragments encoding the light and/or heavy chains or portions thereof such that the light and heavy chains are expressed in the host cell. Standard recombinant DNA methodologies are used to prepare and/or obtain nucleic acids encoding the heavy and light chains, incorporate these nucleic acids into recombinant expression vectors and introduce the vectors into host cells, such as those described in Sambrook, Fritsch and Maniatis (eds.), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al.

In addition, the nucleic acid sequences encoding variable regions of the heavy and/or light chains can be converted, for example, to nucleic acid sequences encoding full-length antibody chains, Fab fragments, or to scFv. The VL- or VH-encoding DNA fragment can be operatively linked, (such that the amino acid sequences encoded by the two DNA fragments are in-frame) to another DNA fragment encoding, for example, an antibody constant region or a flexible linker. The sequences of human heavy chain and light chain constant regions are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

To create a polynucleotide sequence that encodes a scFv, the VH- and VL-encoding nucleic acids can be operatively linked to another fragment encoding a flexible linker such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554).

To express the antibodies, antigen binding fragments thereof or variants thereof standard recombinant DNA expression methods can be used (see, for example, Goeddel; Gene Expression Technology. Methods in Enzymology 185, Academic Press, San Diego, Calif. (1990)). For example, DNA encoding the desired polypeptide can be inserted into an expression vector which is then transfected into a suitable host cell. Suitable host cells are prokaryotic and eukaryotic cells. Examples for prokaryotic host cells are e.g. bacteria, examples for eukaryotic hosts cells are yeasts, insects and insect cells, plants and plant cells, transgenic animals, or mammalian cells. Introduction of the recombinant construct into the host cell can be carried out using standard techniques such as calcium phosphate transfection, DEAE dextran mediated transfection, electroporation, transduction or phage infection.

In some embodiments, the DNAs encoding the heavy and light chains are inserted into separate vectors. In other embodiments, the DNA encoding the heavy and light chains is inserted into the same vector. It is understood that the design of the expression vector, including the selection of regulatory sequences is affected by factors such as the choice of the host cell, the level of expression of protein desired and whether expression is constitutive or inducible.

Thus, in a further aspect, the present invention relates to an isolated cell expressing the antibody or antigen-binding fragment according to the present invention and/or comprising the nucleic acid according to the present invention or the vector according to the present invention.

The isolated cell can be virtually any cell for which expression vectors are available. The isolated cell can for example a higher eukaryotic host cell, such as a mammalian cell, a lower eukaryotic host cell, such as a yeast cell, and may be a prokaryotic cell, such as a bacterial cell.

In a further aspect, the present invention relates to a method of producing the isolated antibody or antigen-binding fragment according to the present invention comprising culturing of the cell according to the present invention. In particular embodiments, the cell according to the present invention is cultivated under suitable conditions for antibody expression and the antibody or antigen-binding fragment is recovered. In particular embodiments, the antibody or antigen-binding fragment is purified, particularly to at least 95% homogeneity by weight.

Bacterial Expression

Useful expression vectors for bacterial use are constructed by inserting a DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include but are not limited to *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and a bacterial origin of replication derived from commercially available plasmids typically containing elements of the well-known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therefore, an embodiment of the present invention is an expression vector comprising a nucleic acid sequence encoding for the novel antibodies of the present invention.

Antibodies of the present invention or antigen-binding fragments thereof or variants thereof include naturally purified products, products of chemical synthetic procedures, and products produced by recombinant techniques from a prokaryotic host, including, for example, *E. coli, Bacillus subtilis, Salmonella typhimurium* and various species within the genera *Pseudomonas, Streptomyces*, and *Staphylococcus*, preferably, from *E. coli* cells.

Mammalian Expression

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Expression of the antibodies may be constitutive or regulated (e.g. inducible by addition or removal of small molecule inductors such as Tetracyclin in conjunction with Tet system). For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al. The recombinant expression vectors can also include origins of replication and selectable markers (see e.g., U.S. Pat. Nos. 4,399,216, 4,634,665 and 5,179,017). Suitable selectable markers include genes that confer resistance to drugs such as G418, puromycin, hygromycin, blasticidin, zeocin/bleomycin or methotrexate or selectable marker that exploit auxotrophies such as Glutamine Synthetase (Bebbington et al., Biotechnology (NY). 1992 February; 10(2):169-75), on a host cell into which the vector has been introduced. For example, the dihydrofolate reductase (DHFR) gene confers resistance to methotrexate, neo gene confers resistance to G418, the bsd gene from *Aspergillus terreus* confers resistance to blasticidin, puromycin N-acetyl-transferase confers resistance to puromycin, the Sh ble gene product confers resistance to zeocin, and resistance to hygromycin is conferred by the *E. coli* hygromycin resistance gene (hyg or hph). Selectable markers like DHFR or Glutamine Synthetase are also useful for amplification techniques in conjunction with MTX and MSX.

Transfection of the expression vector into a host cell can be carried out using standard techniques such as electroporation, nucleofection, calcium-phosphate precipitation, lipofection, polycation-based transfection such as polyethylenimine (PEI)-based transfection and DEAE-dextran transfection.

Suitable mammalian host cells for expressing the antibodies, antigen binding fragments thereof or variants thereof provided herein include Chinese Hamster Ovary (CHO cells) such as CHO-K1, CHO-S, CHO-KISV [including dhfr− CHO cells, described in Urlaub and Chasin, (1980) Proc. Natl. Acad. Sci. USA 77:4216-4220 and Urlaub et al., Cell. 1983 June; 33(2):405-12, used with a DHFR selectable marker, e.g., as described in R. J. Kaufman and P. A. Sharp (1982) Mol. Biol. 159:601-621; and other knockout cells exemplified in Fan et al., Biotechnol Bioeng. 2012 April; 109(4):1007-15], NS0 myeloma cells, COS cells, HEK293 cells, HKB11 cells, BHK21 cells, CAP cells, EB66 cells, and SP2 cells.

Expression might also be transient or semi-stable in expression systems such as HEK293, HEK293T, HEK293-EBNA, HEK293E, HEK293-6E, HEK293-Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for instance Durocher et al., Nucleic Acids Res. 2002 Jan. 15; 30 (2):E9).

In some embodiments, the expression vector is designed such that the expressed protein is secreted into the culture medium in which the host cells are grown. The antibodies, antigen binding fragments thereof or variants thereof can be recovered from the culture medium using standard protein purification methods.

Purification

Antibodies of the invention or antigen-binding fragments thereof or variants thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention or antigen-binding fragments thereof or variants thereof include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20.

In preferred embodiments, the antibody is purified (1) to greater than 95% by weight of antibody as determined e.g. by the Lowry method, UV-Vis spectroscopy or by by SDS-Capillary Gel electrophoresis (for example on a Caliper LabChip GXII, GX 90 or Biorad Bioanalyzer device), and in further preferred embodiments more than 99% by weight, (2) to a degree sufficient to obtain at least 15 residues of N-terminal or internal amino acid sequence, or (3) to homogeneity by SDS-PAGE under reducing or non-reducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

Therapeutic Methods

Therapeutic methods involve administering to a subject in need of treatment a therapeutically effective amount of an antibody or an antigen-binding fragment thereof or a variant thereof contemplated by the invention. A "therapeutically effective" amount hereby is defined as the amount of an antibody or antigen-binding fragment that is of sufficient quantity to increase plasmin mediated clot lysis in a subject—either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, dog, monkey or other lower-order primate).

Thus, in one aspect, the present invention relates to the isolated antibody or antigen-binding fragment according the present invention or to a conjugate comprising the isolated antibody or antigen-binding fragment according the present invention or to a pharmaceutical composition comprising the isolated antibody or antigen-binding fragment according the present invention for use in the treatment or prophylaxis of diseases.

The isolated antibodies or antigen-binding fragments according to the present invention can be used as a therapeutic or a diagnostic tool in a variety of A2AP associated disorders and/or diseases associated with ischemic events due to partial or complete vessel occlusion.

An ischemic event may be due to the partial or complete occlusion of one vessel but it may be also the result of a partial or complete occlusion of more than one vessel whereby some vessels may be partially occluded and some vessels may be complete occluded.

Thus, in a further aspect, the present invention relates to the isolated antibodies or antigen-binding fragments according the present invention or to conjugates comprising the isolated antibodies or antigen-binding fragments according the present invention or to pharmaceutical compositions comprising the isolated antibodies or antigen-binding fragments according the present invention for use in the treatment or prophylaxis of disorders or diseases associated with ischemic events due to partial or complete vessel occlusion, such as ischemic stroke, acute coronary syndrome, peripheral artery disease, myocardial infarction, deep vein thrombosis, pulmonary embolism, venous thrombosis, or shunt thrombosis.

In a further aspect, the present invention relates to the isolated antibodies or antigen-binding fragments according the present invention or to conjugates comprising the isolated antibodies or antigen-binding fragments according the present invention or to pharmaceutical compositions comprising the isolated antibodies or antigen-binding fragments according the present invention for treatment or prophylaxis of diseases, in particular of disorders or diseases associated with ischemic events due to partial or complete vessel occlusion, such as ischemic stroke, acute coronary syndrome, peripheral artery disease, myocardial infarction, deep vein thrombosis, pulmonary embolism, venous thrombosis, or shunt thrombosis.

In a further aspect, the present invention relates to the use of isolated antibodies or antigen-binding fragments according the present invention or to conjugates comprising the isolated antibodies or antigen-binding fragments according the present invention or to pharmaceutical compositions comprising the isolated antibodies or antigen-binding fragments according the present invention in a method of treatment or prophylaxis of diseases, in particular of disorders or diseases associated with ischemic events due to partial or complete vessel occlusion, such as ischemic stroke, acute coronary syndrome, peripheral artery disease, myocardial infarction, deep vein thrombosis, pulmonary embolism, venous thrombosis, or shunt thrombosis.

In a further aspect, the present invention relates to use of isolated antibodies or antigen-binding fragments according the present invention or to conjugates comprising the isolated antibodies or antigen-binding fragments according the present invention or to pharmaceutical compositions comprising the isolated antibodies or antigen-binding fragments according the present invention for the preparation of a pharmaceutical composition, preferably a medicament, for the prophylaxis or treatment of diseases, in particular of disorders or diseases associated with ischemic events due to partial or complete vessel occlusion, such as ischemic stroke, acute coronary syndrome, peripheral artery disease, myocardial infarction, deep vein thrombosis, pulmonary embolism, venous thrombosis, or shunt thrombosis.

In a further aspect, the present invention relates to methods of treatment or prophylaxis of diseases, in particular of disorders or diseases associated with ischemic events due to partial or complete vessel occlusion, such as ischemic stroke, acute coronary syndrome, peripheral artery disease, myocardial infarction, deep vein thrombosis, pulmonary embolism, venous thrombosis, or shunt thrombosis, using an effective amount of an isolated antibody or antigen-binding fragment according the present invention or to a conjugate comprising the isolated antibody or antigen-binding fragment according the present invention or to a pharmaceutical composition comprising the isolated antibody or antigen-binding fragment according the present invention. The disorders mentioned above have been well characterized in humans, but also exist with a similar etiology in other animals, including mammals, and can be treated by administering pharmaceutical compositions according to the present invention.

The antibodies or the antigen-binding fragments according to the present invention or variants thereof might be co-administered with known medications, and in some instances the antibody or antigen-binding fragment thereof might itself be modified. For example, an antibody or an antigen-binding fragment thereof or a variant thereof could be conjugated to a drug or to another peptide or protein to potentially further increase efficacy.

Antibodies of the present invention or antigen-binding fragments thereof or variants thereof may be administered as the sole pharmaceutical agent or in combination with one or more additional therapeutic agents where the combination causes no unacceptable adverse effects.

Thus, in a further aspect, the present invention relates to the isolated antibodies or antigen-binding fragments according to the present invention or the conjugates according to the present invention or the pharmaceutical compositions according to the present invention for use in simultaneous, separate, or sequential combination with one or more further therapeutically active compounds.

Non-limiting examples of therapeutically active compounds to be used in combination with the antibodies or antigen-binding fragments according to the present invention are:
  i) inhibitors of the coagulation cascade like plasminogen activators (thrombolytics/fibrinolytics) as well as compounds increasing thrombolysis and/or fibrinolysis (like tissue plasminogen activator (t-PA), streptokinase, reteplase, and urokinase) or inhibitors of the plasminogen activator inhibitor (PAI) or thrombin-activatable fibrinolysis inhibitors (TAFI);
  ii) anticoagulants like non-fractionated heparins, low molecular weight heparins, heparinoid, hirudin, bivalirudin and/or argatroban; direct oral anticoagulants/non-vitamin K anticoagulants like Factor Xa inhbitors, e.g. apixaban, edoxaban, and rivaroxaban, and Thrombin inhibitors, e.g. dabigatran.
  iii) platelet aggregation inhibitors, like aspirin, clopidogrel, cilostazol, prasugrel, ticagrelor, cangrelor, and others.

Combination therapy includes administration of a single pharmaceutical dosage formulation which comprises an antibody or antigen-binding fragment according to the present invention or a variant thereof and one or more additional therapeutic agents, as well as administration of an antibody or antigen-binding fragment according to the present invention and each additional therapeutic agent in its own separate pharmaceutical dosage formulation. For example, an antibody of the invention or an antigen-binding fragment thereof or a variant thereof and a therapeutic agent may be administered to the patient together in a single liquid composition, or each agent may be administered in separate dosage formulation.

Where separate dosage formulations are used, the antibody or antigen-binding fragment according to the present invention or the variant thereof and one or more additional therapeutic agents may be administered at essentially the same time (e.g., concurrently) or at separately staggered times (e.g., sequentially).

The antibodies or the antigen-binding fragments according to the present invention or variants thereof might be used in combination with surgical interventions, like but not limited to mechanical embolectomy, thrombectomy, clot retrieval devices, cerebral revascularization.

Diagnostic Methods

Furthermore, the antibodies or antigen-binding fragments according to the present invention may be utilized, as such or in compositions, in research and diagnostics, or as analytical reference standards, and the like.

Anti-A2AP antibodies or antigen-binding fragments thereof can be used for detecting the presence of A2AP. Thus, in a further aspect, the present invention relates to the isolated antibodies or antigen-binding fragments according to the present invention or the antibody conjugates according to the present invention for use as a diagnostic agent.

Pharmaceutical Compositions and Administration

In a further aspect, the present invention relates to pharmaceutical compositions comprising the isolated antibodies or antigen-binding fragments according to the present invention or the antibody conjugates according to the present invention. To treat any of the foregoing disorders, pharmaceutical compositions for use in accordance with the present invention may be formulated in any conventional manner using one or more physiologically acceptable carriers, excipients, or auxiliaries. Further details on techniques for formulation and administration may be found in the latest edition of Remington's Pharmaceutical Sciences (Ed. Maack Publishing Co, Easton, Pa.).

The antibody or antigen-binding fragment according to the present invention can be administered by any suitable means, which can vary, depending on the type of disorder being treated. Possible administration routes include oral, parenteral, and topical administration. Methods of parenteral delivery include intra-arterial, intramuscular, subcutaneous, intramedullary, intrathecal, intraventricular, intravenous, intraperitoneal, or intranasal administration. In addition, the antibody or antigen-binding fragment according to the present invention may be administered by pulse infusion, with, e.g., declining doses of the antibody. Preferably, administration is by injections, most preferably intravenous or subcutaneous injections, depending in part on whether the administration is brief or prolonged. The amount to be administered will depend on a variety of factors such as the clinical symptoms, weight of the individual, whether other drugs are administered, and the like. The skilled artisan will recognize that the route of administration will vary depending on the disorder or condition to be treated.

The pharmaceutical composition according to the present invention comprises the antibody or antigen-binding fragment according to the present invention alone or in combination with at least one other agent, such as a stabilizing compound. The antibody or antigen-binding fragment according to the present invention may be administered in any sterile, biocompatible pharmaceutical carrier, including, but not limited to, saline, buffered saline, dextrose, and water. In particular embodiments, the pharmaceutical composition according to the present invention may comprise one or more further pharmaceutically active compounds, in particular one or more further pharmaceutically active compounds that are suitable to treat A2AP associated disorders and/or disorders associated with ischemic events due to partial or complete vessel occlusion. Any of these agents can be administered to a patient alone, or in combination with other agents or drugs, in pharmaceutical compositions where it is mixed with excipient(s) or pharmaceutically acceptable carriers. In particular embodiments, the pharmaceutically acceptable carrier is pharmaceutically inert.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methylcellulose, hydroxypropylmethylcellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores can be provided with suitable coatings such as concentrated sugar solutions, which may also contain gum arabic, talc, polyvinyl pyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, i.e. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine or phosphate or Tris, 0.1%-2% sucrose and/or 2%-7% mannitol at a pH range of 4.5 to 7.5 optionally comprising additional substances like polysorbate that is combined with buffer prior to use.

After pharmaceutical compositions comprising a compound of the invention formulated in an acceptable carrier have been prepared, they can be placed in an appropriate container and labeled for treatment of an indicated condition. For administration of anti-A2AP antibodies or antigen-binding fragment thereof, such labeling would include amount, frequency and method of administration.

Therapeutically Effective Dose

Pharmaceutical compositions suitable for use according to the present invention include compositions wherein the active ingredients are contained in an effective amount to achieve the intended purpose, e.g., treatment of a particular disease state characterized by ischemic events due to partial or complete vessel occlusion.

The determination of an effective dose is well within the capability of those skilled in the art. Determining a therapeutically effective amount of the novel antibody of this invention or an antigen-binding fragment thereof or a variant thereof, largely will depend on particular patient characteristics, route of administration, and the nature of the disorder being treated. General guidance can be found, for example, in the publications of the International Conference on Harmonization and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

For any compound, the therapeutically effective dose can be estimated initially either in cell culture assays, or in animal models, usually mice, rabbits, dogs, pigs or monkeys. The animal model is also used to achieve a desirable concentration range and route of administration. Such information can then be used to determine useful doses and routes for administration in humans.

A therapeutically effective dose refers to that amount of antibody or antigen-binding fragment thereof, that ameliorates the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Long acting pharmaceutical compositions might be administered for example every 3 to 4 days, every week, once every two weeks, or once every three weeks, depending on half-life and clearance rate of the particular formulation.

Normal dosage amounts may vary from 0.1 to 100,000 micrograms, up to a total dose of about 10 g, depending upon the route of administration. Guidance as to particular dosages and methods of delivery is provided in the literature. See U.S. Pat. Nos. 4,657,760; 5,206,344; or 5,225,212.

Kits

In a further aspect, the present invention relates to kits comprising the isolated antibodies or antigen-binding fragments according to the present invention or the conjugates according to the present invention and instructions for use. In particular embodiments, the kits comprise one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

SHORT DESCRIPTION OF FIGURES

FIG. 1: Panning strategy for finding cross-species specific, neutralizing anti-alpha2-Antiplasmin antibodies.

Four major strategies for selections on biotinylated antigens are depicted. Where indicated, prior to each round of selection a depletion step on a relevant or a non-alpha2-Antiplasmin biotinylated protein was included.

FIG. 2: ELISA-based analysis of the binding of Fab 431A-M080-C01 to human alpha2-Antiplasmin and rabbit alpha2-Antiplasmin The specific binding of Fab 431A-M080-C01 to human (black columns) and rabbit (grey columns) alpha2-Antiplasmin as assessed in an ELISA assay is shown. Antigens were coated to microtiter plates at a final concentration of 1 µg/ml. For this, supernatants of transfected cells were diluted in Phosphate-buffered Saline (PBS) by the factor of 1:1.5, 1:4.5, 1:13.5, 1:40.5, 1:121.5, 1:364.5, 1:1093.5. Relative fluorescence units (RFU, ordinate) are plotted against the diluted Fabs (abscissa). For further details see Example 3.

Figure 3:
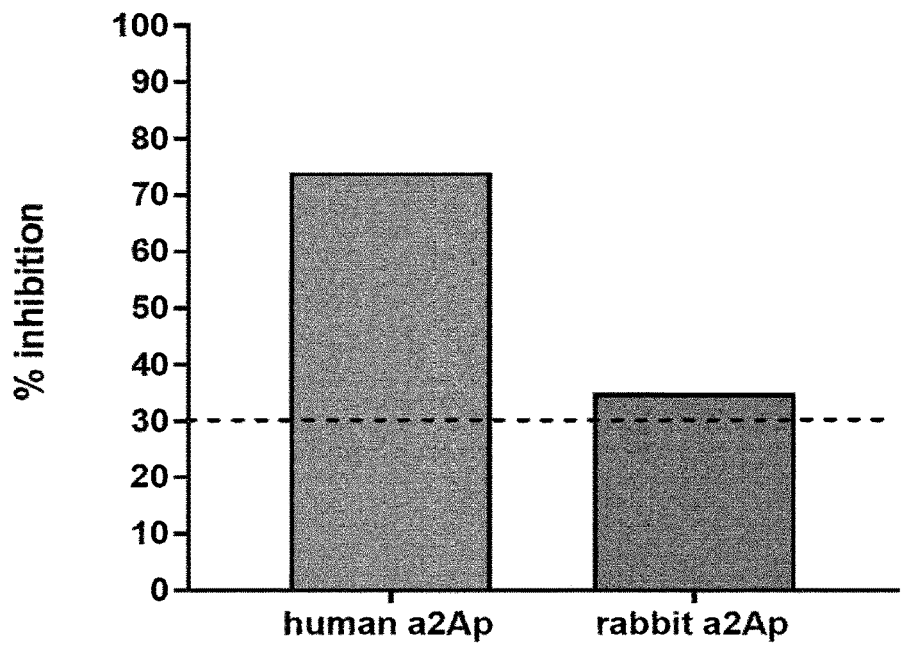

FIG. 3: Analyzing Fab 431A-M080-C01 for function blocking activity.

The function blocking activity of Fab 431A-M080-C01 as measured in the Plasmin—alpha2-Antiplasmin biochemical assay is depicted. For this, supernatants from mammalian cells containing the Fab of interest were pre-incubated with human or rabbit alpha2-Antiplasmin, followed by the addition of human Plasmin and the fluorogenic plasmin substrate. The relative fluorescence units resulting from cleavage of the substrate by Plasmin were measured. Resulting data are presented as percentage of inhibition. Left light-grey column is representing the neutralization of human alpha2-Antiplasmin, right dark-grey column is representing the neutralization of rabbit alpha2-Antiplasmin. See Example 4 for detailed description of the biochemical assay.

Figure 4:
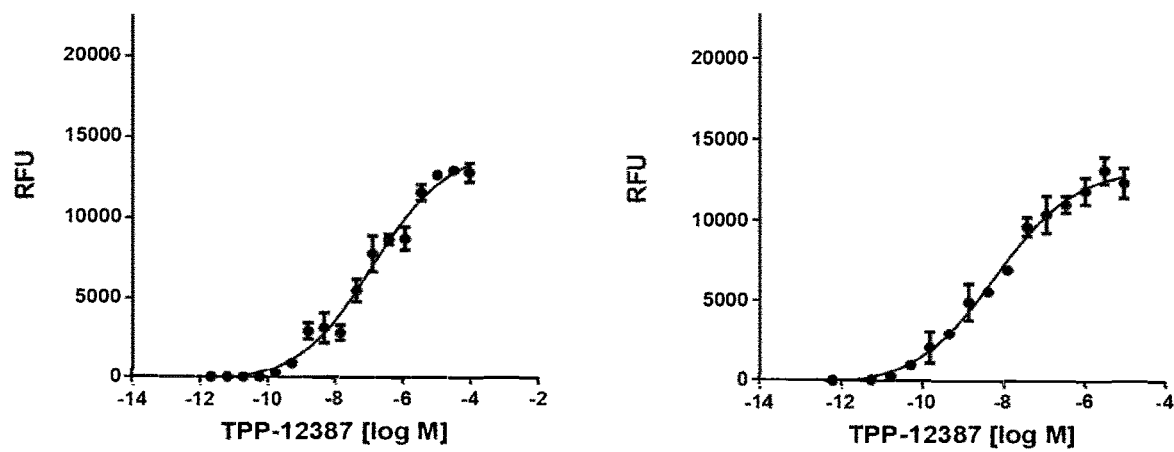

FIG. 4: Binding activity of antibody TPP-12387 on human and rabbit alpha2-Antiplasmin.

According to the method described in Example 3, antibody TPP-12387 was tested for its ability to bind human and rabbit alpha2-Antiplasmin in a dose-dependent manner. Binding activities towards human alpha2-Antiplasmin are shown in the left panel, towards rabbit alpha2-Antiplasmin are shown in the right panel of this figure. The binding activities were calculated as EC50 in M values. One dose response curve is shown as example from two to three independent experiments performed in quadruplicate: EC50 (human A2AP) was 1.2E-07 M; EC50 (rabbit A2AP) was 6.0E-09 M.

FIG. 5: Neutralizing activity of antibody TPP-12387 on human and rabbit alpha2-Antiplasmin.

According to the method described in Example 4, antibody TPP-12387 was tested for its ability to block the activity of human and rabbit alpha2-Antiplasmin in a dose-dependent manner. Neutralizing activities towards human alpha2-Antiplasmin are shown in the left panel, towards rabbit alpha2-Antiplasmin are shown in the right panel of this figure. Function blocking activities were calculated as EC50 in M values. One dose response curve is shown as example from two to three independent experiments performed in quadruplicate: EC50 (human A2AP) was 1.7E-07 M; EC50 (rabbit A2AP) was 1.4E-09 M.

FIGS. 6A-6B: Binding and function blocking activity of antibody TPP-12387 on Cynomolgus alpha2-Antiplasmin According to the methods described in Example 3 and Example 4, antibody TPP-12387 was tested for its ability to block the activity of cynomolgus alpha2-Antiplasmin in a dose-dependent manner. Binding activity of the antibody towards cynomolgus alpha-2Antiplasmin is shown in FIG. 6A, its neutralizing activity in FIG. 6B. Activities were calculated as EC50 in M values. One dose response curve is shown as example from two to three independent experiments performed in quadruplicate: EC50 (cynomolgus A2AP binding) was 9.9E-08 M; EC50 (cynomolgus A2AP activity blocking) was 1.6E-07 M.

Figure 7A:
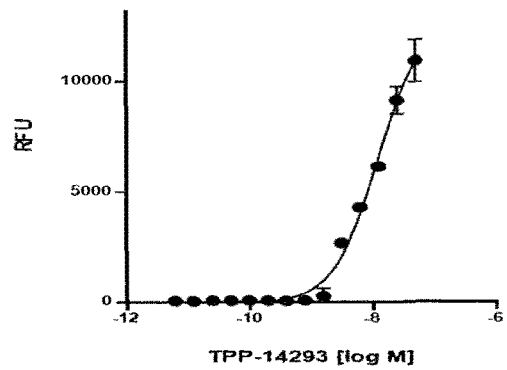
Figure 7B:
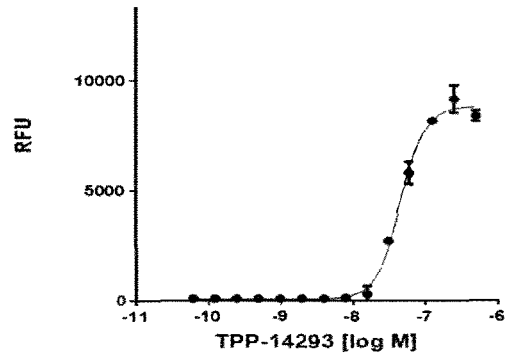
Figure 7C:
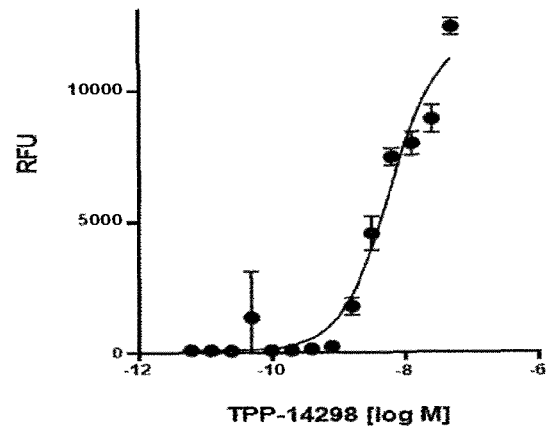
Figure 7D:
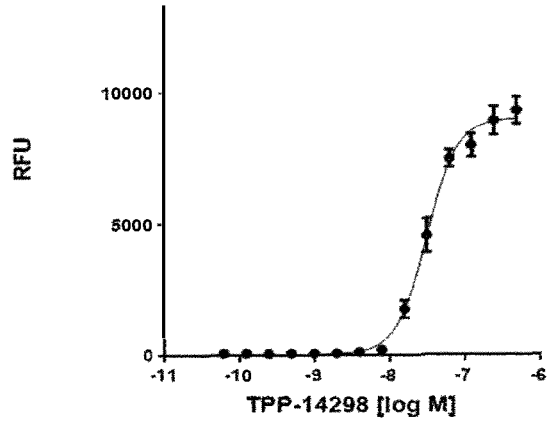
Figure 7E:
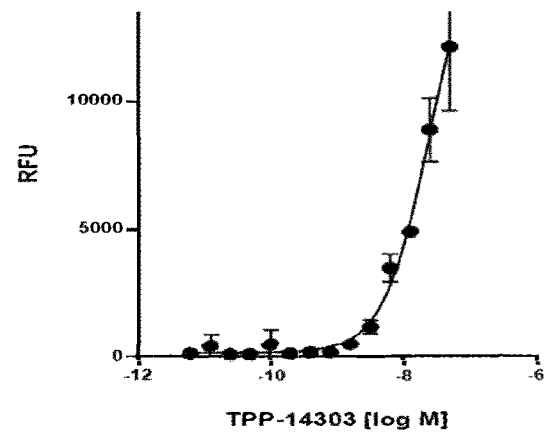
Figure 7F:
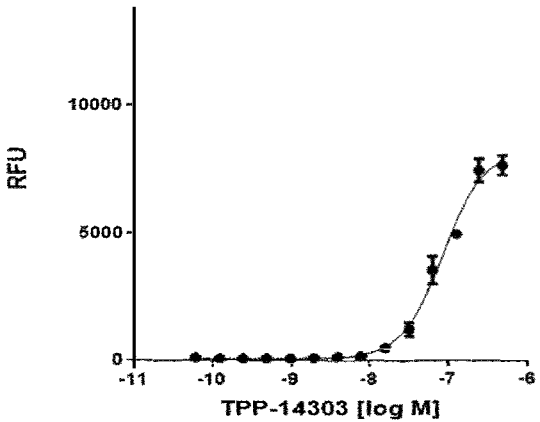
Figures 7G, 7H, 7I, 7J, 7K, 7L:
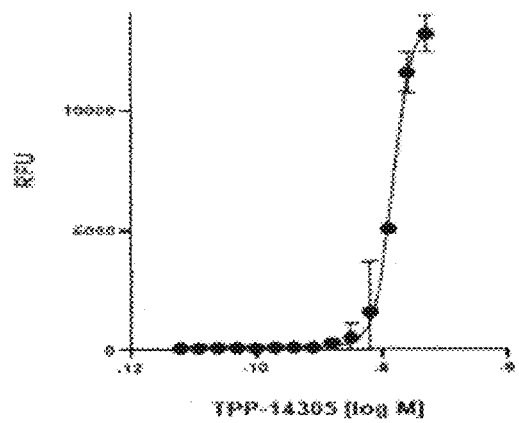
Figure 7M:
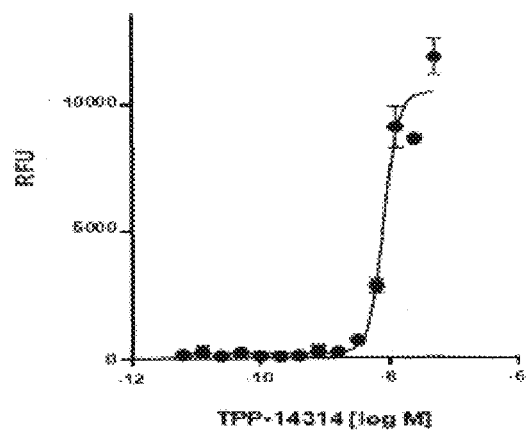
Figure 7N:
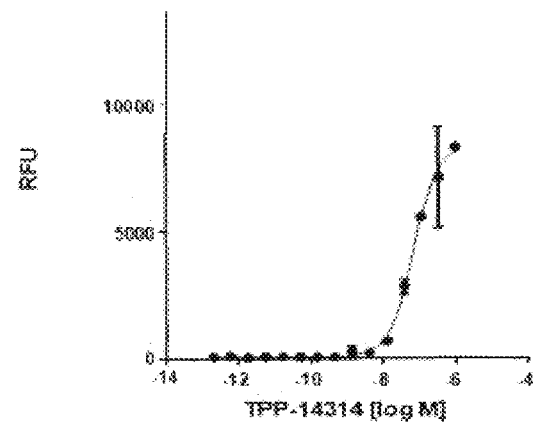
Figure 7O:
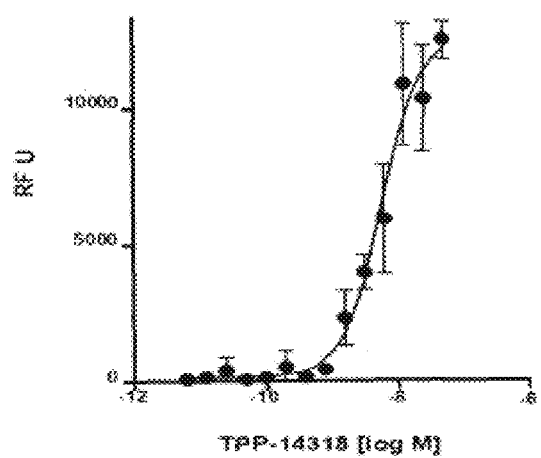
Figure 7P:
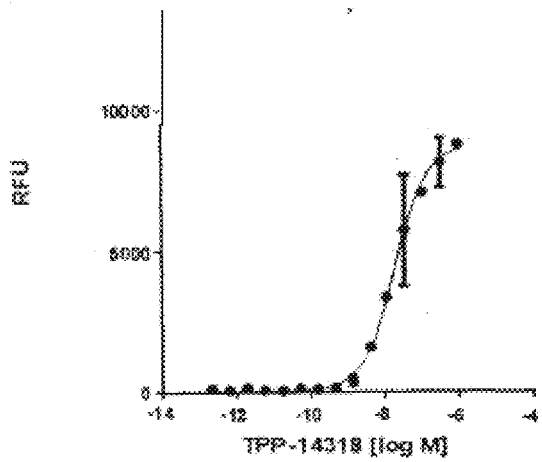
Figure 7Q:
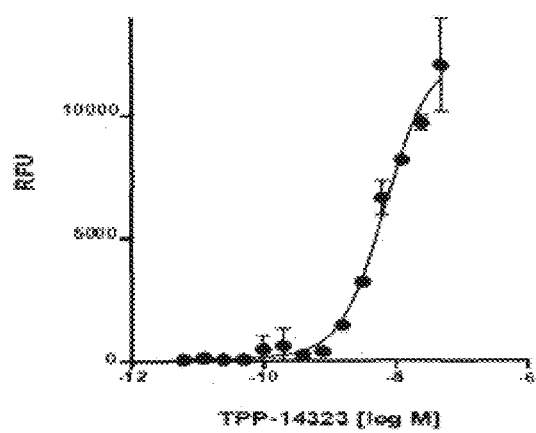
Figure 7R:
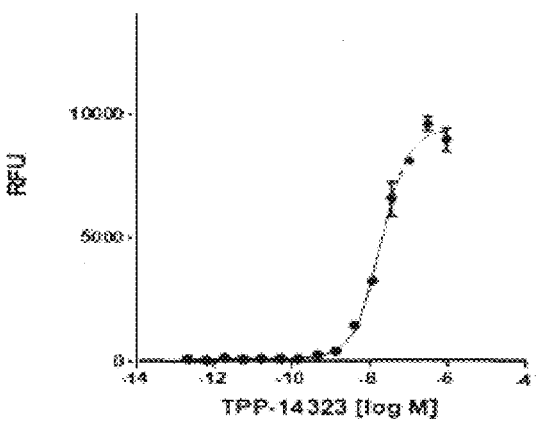
Figure 8A:
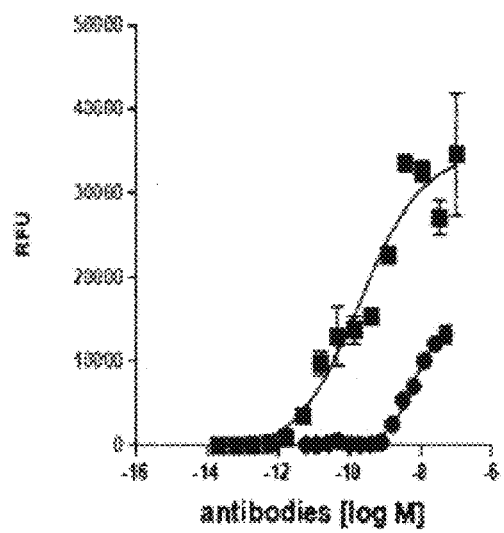
Figure 8B:
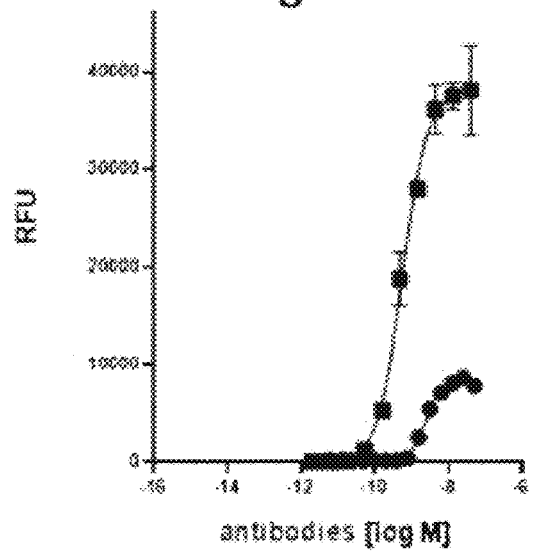
Figure 8C:
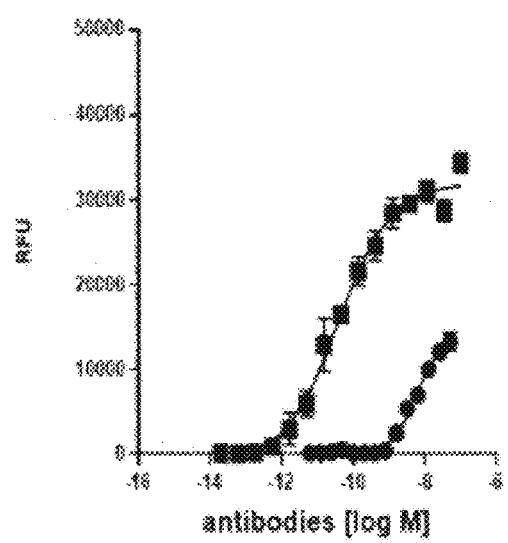
Figure 8D:
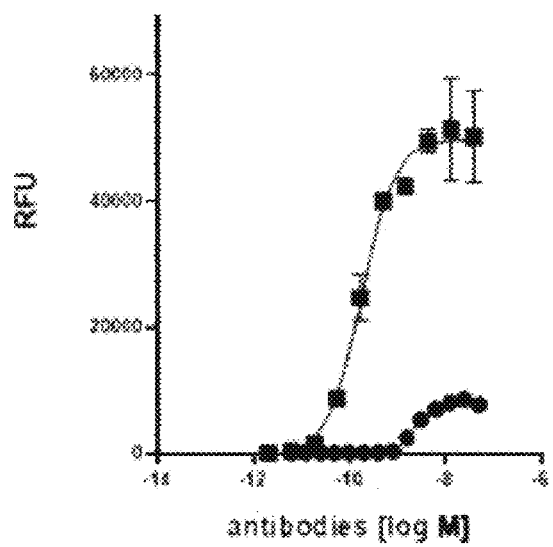
Figure 8E:
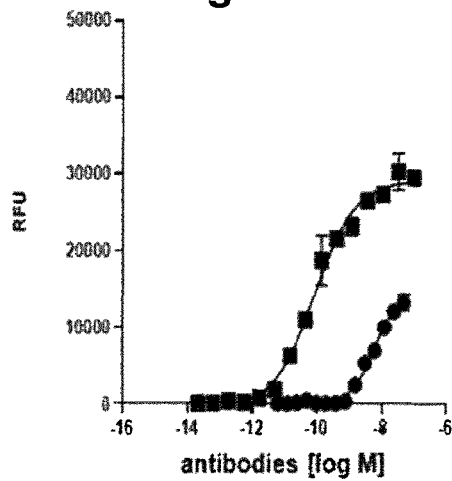
Figure 8F:
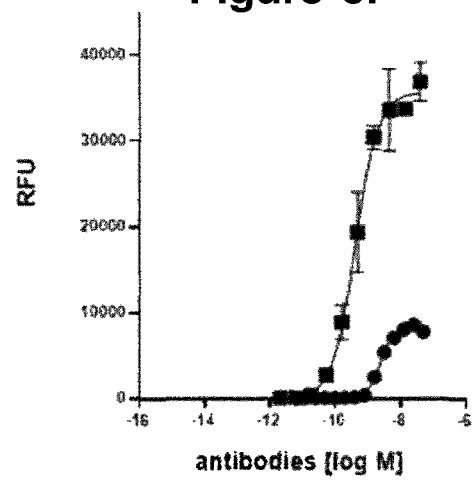
Figure 8G:
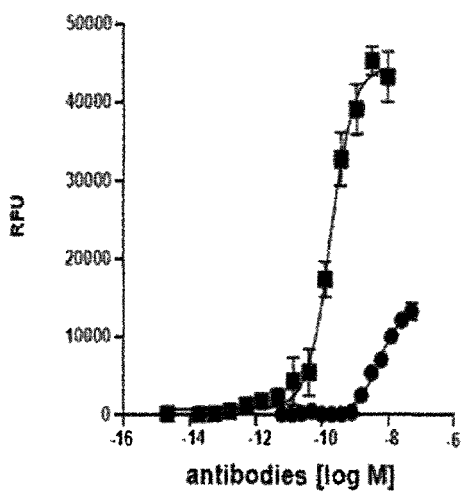
Figure 8H:
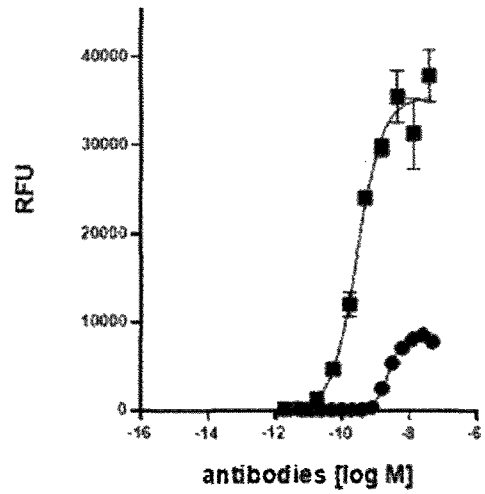
Figure 8I:
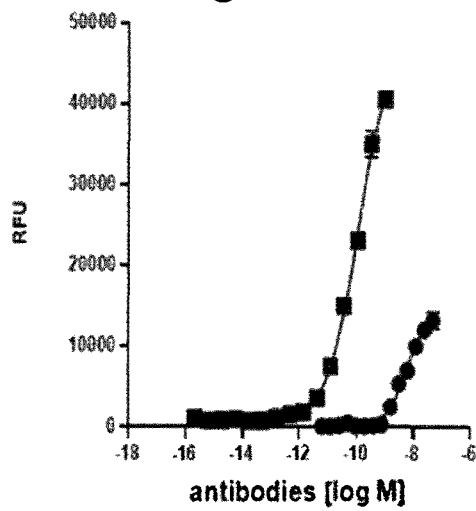
Figure 8J:
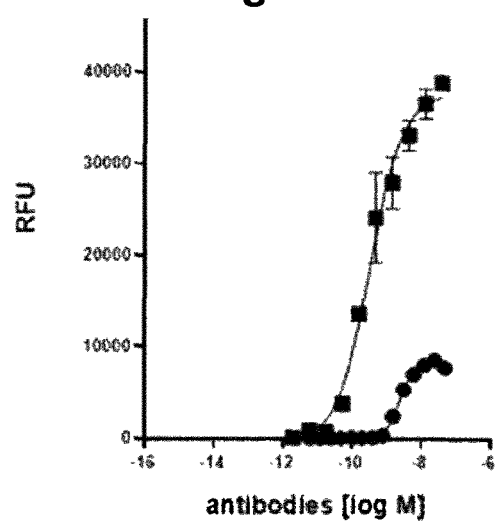
Figure 8K:
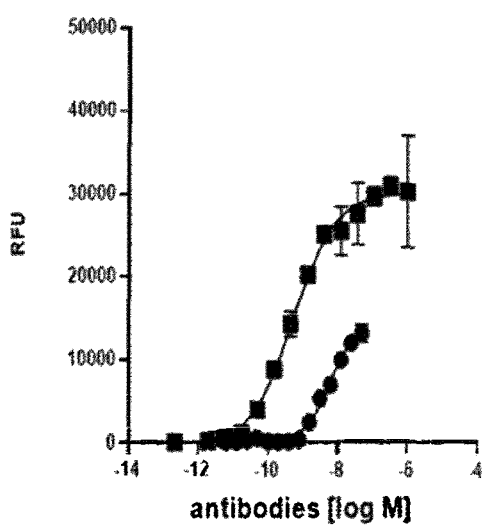
Figure 8L:
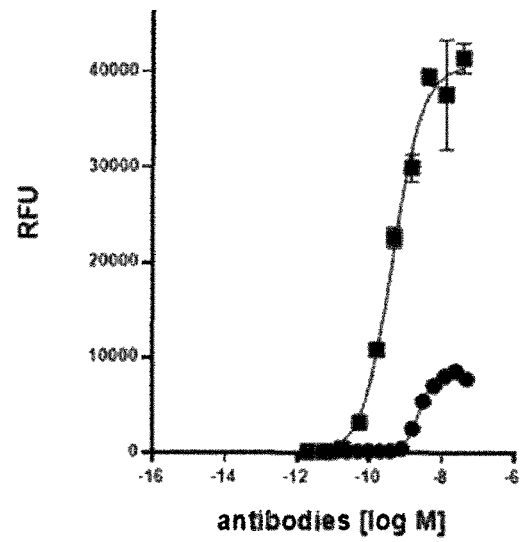

FIGS. 7A-7R: Binding and function blocking activities of TPP-12387 variants towards human alpha2-Antiplasmin.

According to the methods described in Example 3 and Example 4, antibodies TPP-14323 (FIGS. 7Q and 7R), TPP-14318 (FIGS. 7O and 7P), TPP-14314 (FIGS. 7M and 7N), TPP-14313 (FIGS. 7K and 7L), TPP-14308 (FIGS. 7I and 7J), TPP-14305 (FIGS. 7G and 7H), TPP-14303 (FIGS. 7E and 7F), TPP-14298 (FIGS. 7C and 7D), and TPP-14293 (FIGS. 7A and 7B) were tested for their ability to bind to and to block the activity of human alpha2-Antiplasmin in a dose-dependent manner. Binding activities towards human alpha2-Antiplasmin are shown in FIGS. 7A, 7C, 7E, 7G, 7I, 7K, 7M, 7O, and 7Q, neutralizing activities are shown in FIGS. 7B, 7D, 7F, 7H, 7J, 7L, 7N, 7P, and 7R. Binding and function blocking activities were calculated as EC50 in M values (table 3.3). For each antibody, one dose response curve is shown as example from two to three independent experiments performed in quadruplicate.

FIGS. 8A-8L: Testing germline variants of TPP-14308 for binding and neutralizing human alpha2-Antiplasmin.

47 antibodies resulting from the germlining approach of TPP-14308 were tested for ability to bind and to block the activity of human alpha2-Antiplasmin in a dose-dependent manner in comparison to TPP-14308. 6 antibodies resulting from the germlining approach of TPP-14308 (TPP-17041, TPP-17044, TPP-17045, TPP-17048, TPP-17051, TPP-17053), show improved binding activities and/or neutralizing activities. Binding activities towards human alpha2-Antiplasmin are shown in FIGS. 8A, 8C, 8E, 8G, 8I, and 8K, neutralizing activities are shown in FIGS. 8B, 8D, 8F, 8H, 8J, and 8L. Binding and function blocking activities were calculated as EC50 in M values (table 3.5). For each antibody, one dose response curve is shown as example from two to three independent experiments performed in quadruplicate (squares=TPP 17308, circle=TPP-17041, TPP-17044, TPP-17045, TPP-17048, TPP-17051 or TPP-17053).

Figure 9A:
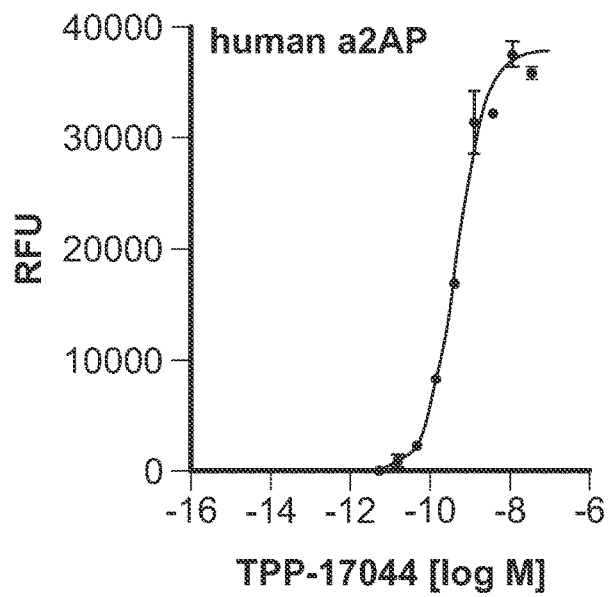
Figure 9B:
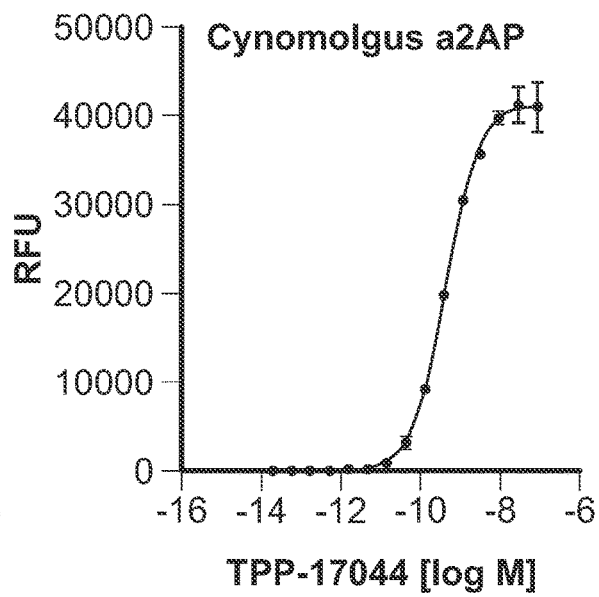
Figure 9C:
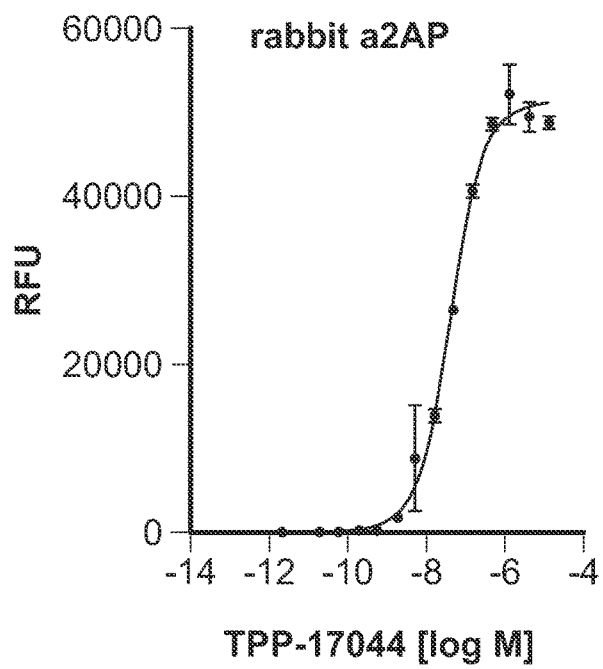

FIGS. 9A-9C: Neutralizing activity of TPP-17044 IgG1 antibody on human alpha2-Antiplasmin from different species.

Testing of TPP-17044 for function blocking activity according to the methods described in Example 4 on human (FIG. 9A), cynomolgus (FIG. 9B), and rabbit (FIG. 9C) alpha2-Antiplasmin is shown. Neutralizing activity was calculated as EC50 in M values. For this antibody, one dose response curve is shown as example from two to three independent experiments performed in quadruplicate. Function blocking activity of TPP-17044 for human alpha2-Antiplasmin was 4.4E-10 M (as shown in FIG. 9A), and 5.4E-10 M for the second and 5.0E-10 M for the third experiment. For the inhibition of Cynomolgus alpha2-Antiplasmin values were 4.6E-10 M (FIG. 9B), 4.9E-10 M for the second experiment and 5.1E-10 M for the third experiment. Rabbit alpha2-Antiplasmin was blocked in its activity by TPP-17044 with IC50 values of 2.7E-08 M (FIG. 9C), 3.6E-08 M for a second experiment and 2.9E-08 M for a third experiment.

FIGS. 10A-10C: Neutralizing activity of TPP-17928 IgG4 antibody on human alpha2-Antiplasmin from different species.

Testing of TPP-17928 for function blocking activity according to the methods described in Example 4 on human (FIG. 10A), cynomolgus (FIG. 10B), and rabbit (FIG. 10C) alpha2-Antiplasmin is shown. Neutralizing activity was calculated as EC50 in M values. For this antibody, one dose response curve is shown as example from two to three independent experiments performed in quadruplicate. Function blocking activity of TPP-17928 for human alpha2-Antiplasmin was 1.1E-10 M (as shown in FIG. 10A), and 1.6E-10 M for the second experiment. For the inhibition of Cynomolgus alpha2-Antiplasmin values were 2.6E-10 M (FIG. 10B), 3.4E-10 M for the second experiment and 2.9E-10 M for the third experiment. Rabbit alpha2-Antiplasmin was blocked in its activity by TPP-17928 with IC50 values of 1.5E-08 M (FIG. 10C), 1.9E-10 M for a second experiment and 1.6E-10 M for a third experiment.

Figure 11:
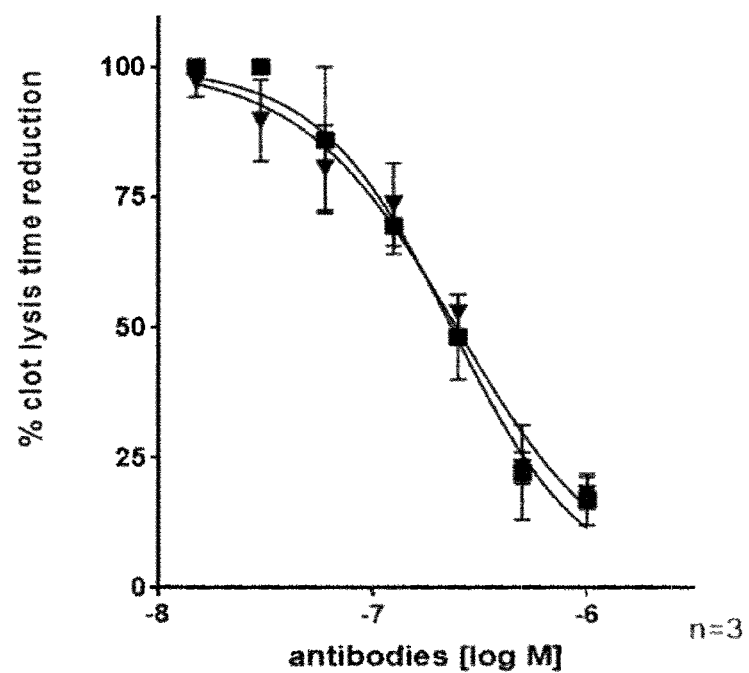

FIG. 11: Reduction of clot lysis time by TPP-17928.

Antibody TPP-17928 reduces the tPA-induced clot lysis time in human (triangles) and in rabbit (squares) plasma, respectively, in a dose-dependent manner. Activity was calculated as IC50 in M values. The curves represent the mean (+/−SD) from three independent experiments. For experimental details see Example 7. IC50 (human plasma) was 2.5E-07 M; EC50 (rabbit plasma) was 2.3E-07 M.

FIGS. 12A-12B: in vivo effects of TPP-17928 on clot lysis.

Animals received fluorescently-labeled plasma clots 30 min prior to measurement; respective treatment was administered at time point 0 min. Over 360 min plasma samples were drawn, and the amount of plasma fluorescence as indirect parameter of clot dissolution was measured. Effects of different concentrations of TPP-17928 (FIG. 12A, control circle; 3.75 mg/kg open circle; 7.5 mg/kg open square; 15 mg/kg open triangle), and effects of different concentrations of), tPA (FIG. 12B, control circle, 0.125 mg/kg triangle, 0.25 mg/kg square, 1 mg/kg diamond) or the combination of both (FIG. 12A, 15 mg/kg+0.125 mg/kg tPA (open diamond) on clot lysis were measured. Relative fluorescence units (rFU, ordinate) are plotted against the timepoints at which plasma samples have been taken (abscissa). Values are mean+/−SD. TPP-17928 alone has a dose-dependent effect on clot dissolution. After application of the antibody of the invention an activity maximum is achieved at around 60 min which then results in a lasting effect over the whole experimental time (360 min). Also, tPA-treatment shows a dose-dependent effect on clot dissolution. tPA has a fast and steep increase of clot dissolution (maximum after 15 min) but does not show a longer lasting effect as observed for TPP-17928. The co-administration of TPP-17928 to a low dose tPA leads to a faster clot dissolution than the administration of the single compounds. For details see Example 8.

Figure 13:
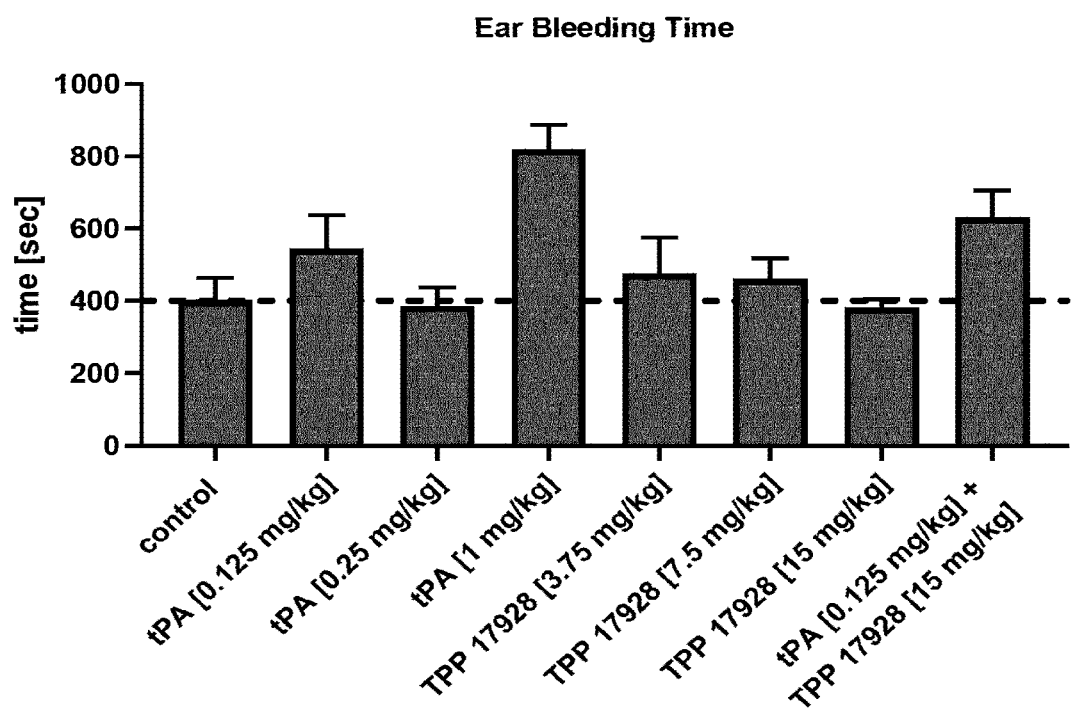

FIG. 13: Determination of tPA and TPP-17928 induced ear bleeding time.

Simultaneously to plasma fluorescence measurement (shown in FIG. 12), ear bleeding time was determined at time point 0 min following compound administration. For each treatment group, the bleeding time in seconds (sec) is shown. Values are mean+/−SEM.

Column 1: Control
Column 2: 0.125 mg/kg tPA,
Column 3: 0.25 mg/kg tPA
Column 4: 1 mg/kg tPA
Column 5: 3.75 mg/kg TPP-17928
Column 6: 7.5 mg/kg TPP-17928
Column 7: 15 mg/kg TPP-17928
Column 8: 15 mg/kg TPP-17928+0.125 mg/kg tPA FIGS. 14A-14H: Effect of 77A3 and antibodies of the invention on plasmin The results of the A2AP function blocking assay as described in example 10 are shown.

Figure 14A:
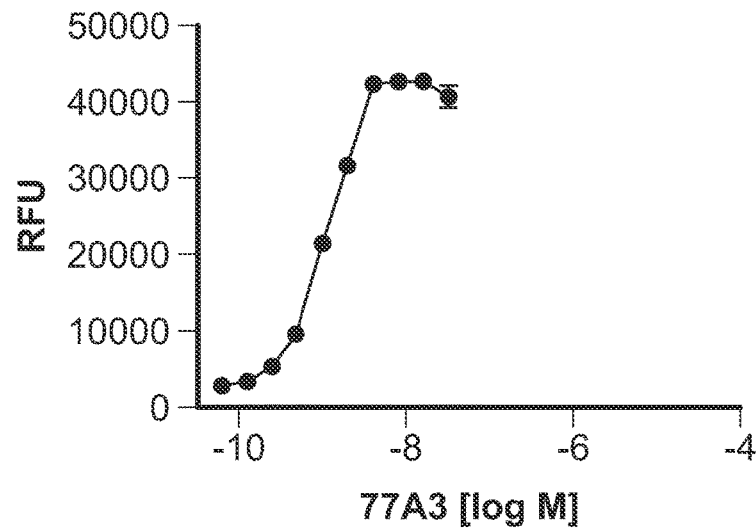
Figure 14B:
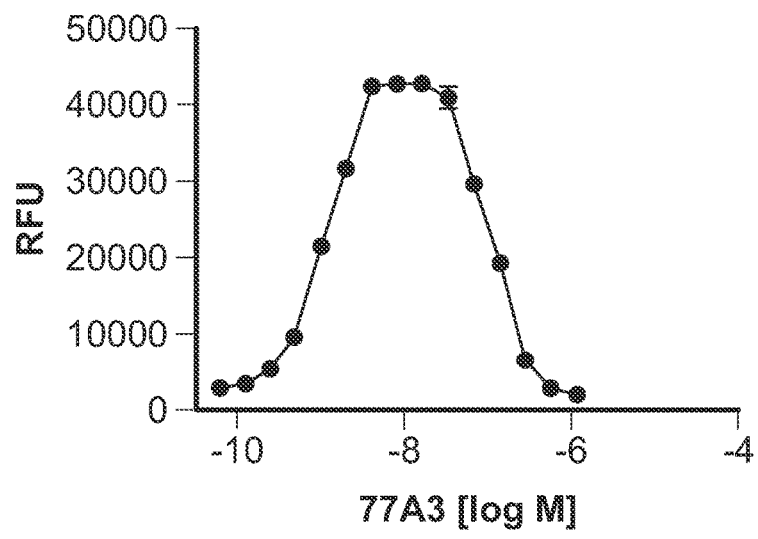
Figure 14C:
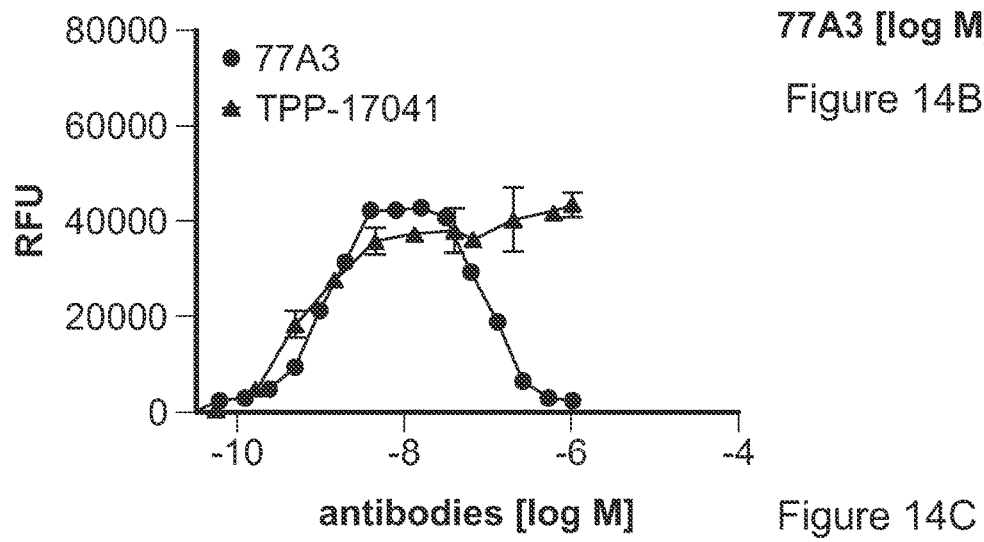
Figure 14D:
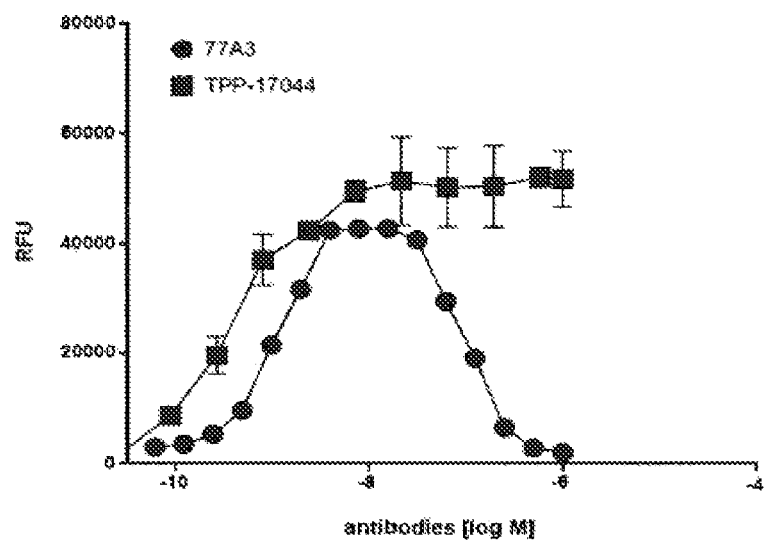
Figure 14E:
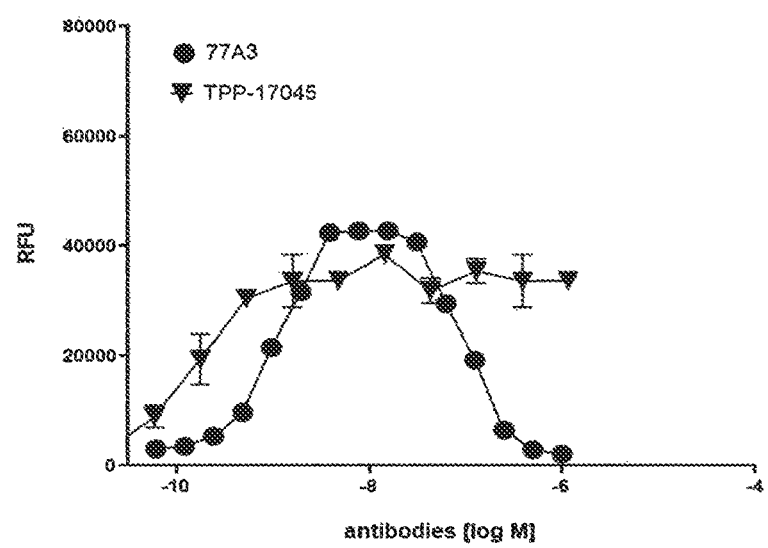
Figure 14F:
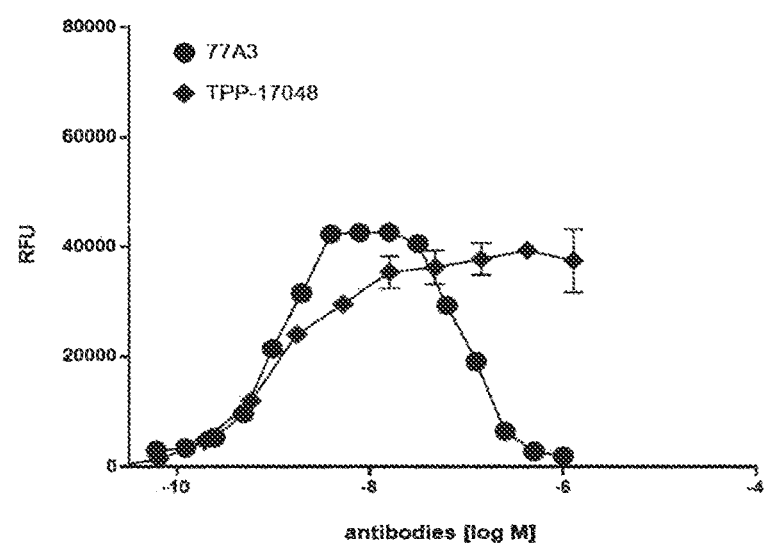
Figure 14G:
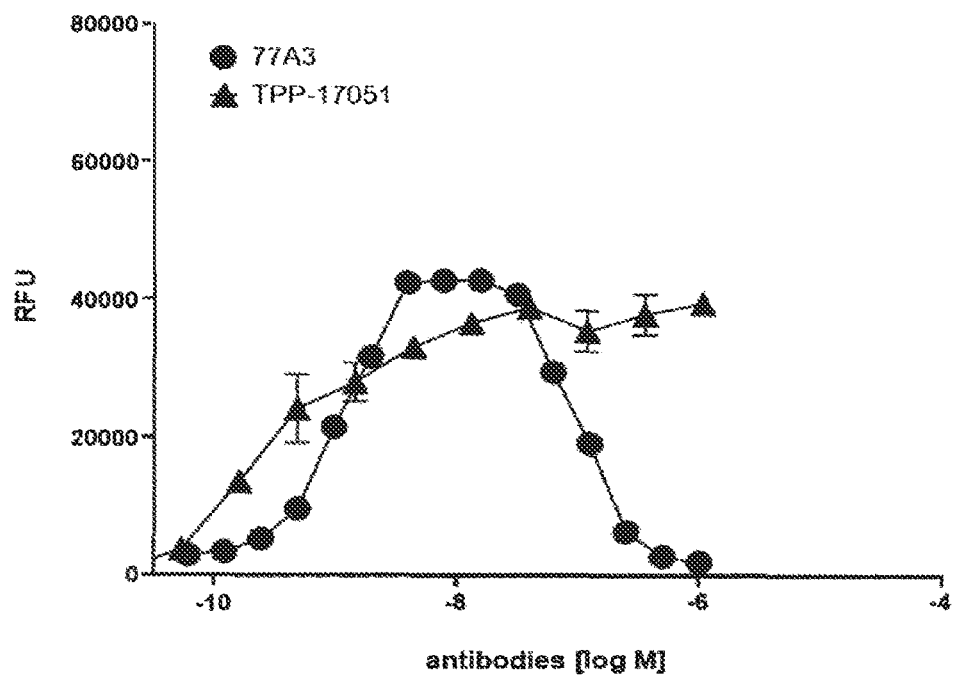
Figure 14H:
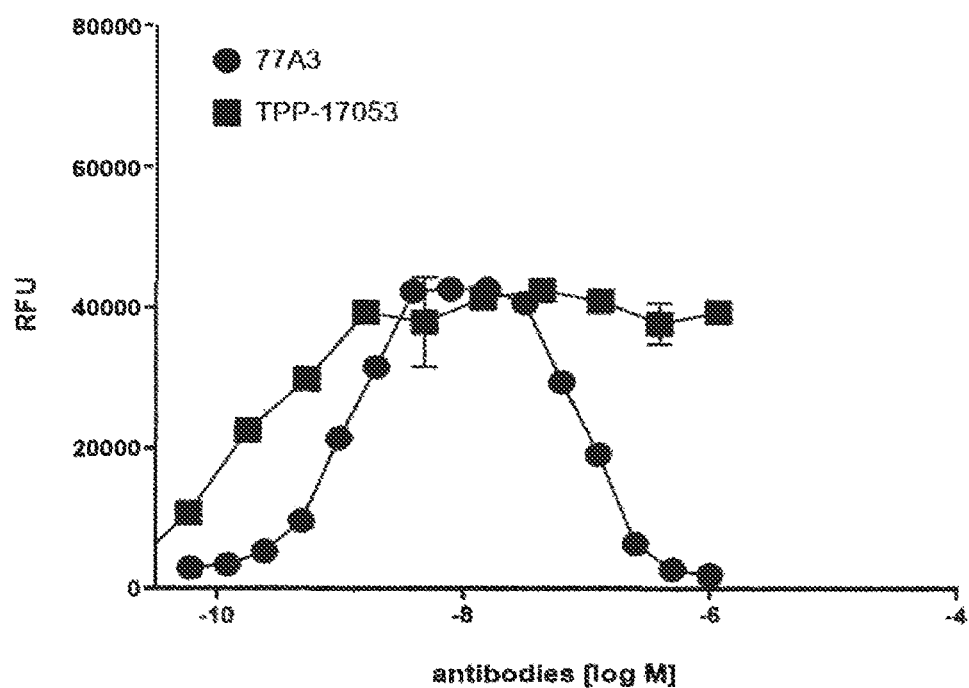

The following antibodies and antibody concentrations were used:

FIG. 14A: 6.1E-11—3.0E-08 M 77A3
FIG. 14B: 6.11E-11—1.0E-06 M 77A3
FIG. 14C: 6.11E-11-1E-06 M 77A3 (circle) and 6.1E-11—1.0E-06 M TPP-17041 (triangle)
FIG. 14D: 6.1E-11—1.0E-06 M 77A3 (circle) and 6.1E-11—1.0E-06 M TPP-17044 (square)
FIG. 14E: 6.1E-11—1Ee-06 M 77A3 (circle) and 6.1E-11—1.0E-06 M TPP-17045 (triangle)
FIG. 14F: 6.1E-11—1.0E-06 M 77A3 (circle) and 6.1E-11—1.0E-06 M TPP-17048 (diamond)
FIG. 14G: 6.1E-11—1.0E-06 M 77A3 (circle) and 6.1E-11—1.0E-06 M TPP-17051 (triangle).
FIG. 14H: 6.1E-11—1.0E-06 M 77A3 (circle) and 6.1E-11—1.0E-06 M TPP-17053 (square). An increase of 77A3 concentration up to 0.03 µM resulted into an increase of fluorescence signal due to the cleavage of the fluorogenic substrate I-1275 by plasmin. However, a further increase in 77A3 concentration resulted in a decrease of fluorescence signal. That indicates that, testing antibody 77A3 in the biochemical assay described in Example 4 up to a concentration of 0.03 µM leads to blockade of alpha2-Antiplasmin and that a further increase in 77A3 antibody concentration leads to a decline in plasmin activity, resulting in a complete inhibition of plasmin activity at a 77A3 concentration of 1 µM (FIG. 14A). Surprisingly, in comparison to this finding, testing antibodies of the invention up to 1 µM did not result into a decrease of fluorescence signal indicating that testing antibodies of the invention have no impact on plasmin activity (FIGS. 14C-14H).

FIG. 15A-15Q: Amino acid sequences of preferred antibodies according to the present invention Amino acid sequences of VH, H-CDR1, H-CDR2, H-CDR2, H-CDR3, VL, L-CDR1, L-CDR2, L-CDR3, heavy chain and light chain of preferred antibodies according to the present invention are depicted.

FIG. 15A: TPP-12387
FIG. 15B: TPP-14293
FIG. 15C: TPP-14298
FIG. 15D: TPP-14303
FIG. 15E: TPP-14305
FIG. 15F: TPP-14308
FIG. 15G: TPP-14313
FIG. 15H: TPP-14314
FIG. 15I: TPP-14318
FIG. 15J: TPP-14323
FIG. 15K: TPP-17041
FIG. 15L: TPP-17044
FIG. 15M: TPP-17045
FIG. 15N: TPP-17048
FIG. 15O: TPP-17051
FIG. 15P: TPP-17053
FIG. 15Q: TPP-17928

Figure 16:
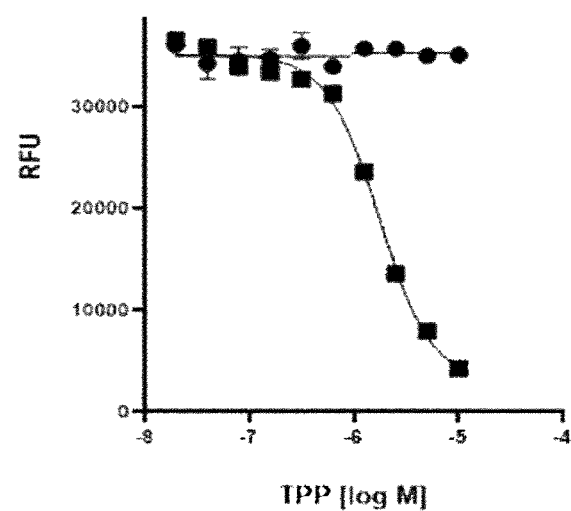

FIG. 16: Effect of 77A3 and antibodies of the invention on the proteolytic activity of plasmin The plasmin activity in dependency of the used antibody concentration as described in example 11 is shown for 77A3 (squares) and TPP-17928 (circle). One dose response curve from two to three independent experiments performed in duplicates is shown as example. 77A3 shows an inhibitory effect on plasmin activity in a concentration-dependent manner (IC50 1.7 µM) whereas TPP-17928 surprisingly does not inhibit plasmin activity up to a concentration of 10 µM (see also tabular overview of IC50 values in example 11).

SEQUENCE LISTING

A sequence listing is enclosed which discloses the following sequences:

| SEQ ID NO: | Type/sequence |
|---|---|
| SEQ ID NO: 1 | human A2AP; AA sequence<br>Met Ala Leu Leu Trp Gly Leu Leu Val Leu Ser Trp Ser Cys Leu Gln<br>Gly Pro Cys Ser Val Phe Ser Pro Val Ser Ala Met Glu Pro Leu Gly<br>Arg Gln Leu Thr Ser Gly Pro Asn Gln Glu Gln Val Ser Pro Leu Thr<br>Leu Leu Lys Leu Gly Asn Gln Glu Pro Gly Gly Gln Thr Ala Leu Lys<br>Ser Pro Pro Gly Val Cys Ser Arg Asp Pro Thr Pro Glu Gln Thr His<br>Arg Leu Ala Arg Ala Met Met Ala Phe Thr Ala Asp Leu Phe Ser Leu<br>Val Ala Gln Thr Ser Thr Cys Pro Asn Leu Ile Leu Ser Pro Leu Ser<br>Val Ala Leu Ala Leu Ser His Leu Ala Leu Gly Ala Gln Asn His Thr<br>Leu Gln Arg Leu Gln Gln Val Leu His Ala Gly Ser Gly Pro Cys Leu<br>Pro His Leu Leu Ser Arg Leu Cys Gln Asp Leu Gly Pro Gly Ala Phe |

| SEQ ID NO: | Type/sequence |
|---|---|
| | Arg Leu Ala Ala Arg Met Tyr Leu Gln Lys Gly Phe Pro Ile Lys Glu<br>Asp Phe Leu Glu Gln Ser Glu Gln Leu Phe Gly Ala Lys Pro Val Ser<br>Leu Thr Gly Lys Gln Glu Asp Asp Leu Ala Asn Ile Asn Gln Trp Val<br>Lys Glu Ala Thr Glu Gly Lys Ile Gln Glu Phe Leu Ser Gly Leu Pro<br>Glu Asp Thr Val Leu Leu Leu Leu Asn Ala Ile His Phe Gln Gly Phe<br>Trp Arg Asn Lys Phe Asp Pro Ser Leu Thr Gln Arg Asp Ser Phe His<br>Leu Asp Glu Gln Phe Thr Val Pro Val Glu Met Met Gln Ala Arg Thr<br>Tyr Pro Leu Arg Trp Phe Leu Leu Glu Gln Pro Glu Ile Gln Val Ala<br>His Phe Pro Phe Lys Asn Asn Met Ser Phe Val Val Leu Val Pro Thr<br>His Phe Glu Trp Asn Val Ser Gln Val Leu Ala Asn Leu Ser Trp Asp<br>Thr Leu His Pro Pro Leu Val Trp Glu Arg Pro Thr Lys Val Arg Leu<br>Pro Lys Leu Tyr Leu Lys His Gln Met Asp Leu Val Ala Thr Leu Ser<br>Gln Leu Gly Leu Gln Glu Leu Phe Gln Ala Pro Asp Leu Arg Gly Ile<br>Ser Glu Gln Ser Leu Val Val Ser Gly Val Gln His Gln Ser Thr Leu<br>Glu Leu Ser Glu Val Gly Val Glu Ala Ala Ala Ala Thr Ser Ile Ala<br>Met Ser Arg Met Ser Leu Ser Ser Phe Ser Val Asn Arg Pro Phe Leu<br>Phe Phe Ile Phe Glu Asp Thr Thr Gly Leu Pro Leu Phe Val Gly Ser<br>Val Arg Asn Pro Asn Pro Ser Ala Pro Arg Glu Leu Lys Glu Gln Gln<br>Asp Ser Pro Gly Asn Lys Asp Phe Leu Gln Ser Leu Lys Gly Phe Pro<br>Arg Gly Asp Lys Leu Phe Gly Pro Asp Leu Lys Leu Val Pro Pro Met<br>Glu Glu Asp Tyr Pro Gln Phe Gly Ser Pro Lys |
| SEQ ID NO: 2 | Oryctolagus cuniculus A2AP; AA sequence<br>Met Val Leu Leu Arg Gly Leu Leu Val Leu Ser Leu Ser Cys Leu Gln<br>Gly Pro Cys Ala Val Leu Pro Val Ser Ala Met Glu Pro Val Gly<br>Arg Gln Leu Thr Ser Gly Gln Ser Gln Glu Lys Leu Pro Pro Leu Ala<br>Leu Leu Lys Leu Val Asn Gln Glu Leu His Gly Gln Thr Ala Leu Lys<br>Lys Ser Pro Gly Asp Cys Arg Glu Thr Pro Thr Pro Glu Gln Thr Arg<br>Arg Leu Ala Gln Ala Met Met Ala Phe Thr Thr Asp Leu Phe Ser Leu<br>Val Val Gln Ala Ser Thr Ser Pro Asn Leu Val Leu Ser Pro Leu Ser<br>Val Ala Leu Ala Leu Ser His Leu Ala Leu Gly Ala Gln Asn His Thr<br>Leu Gln Arg Leu Gln Gln Val Leu His Ala Asp Ser Gly Pro Cys Leu<br>Pro His Leu Leu Ser His Leu Cys Arg Asn Leu Gly Pro Gly Ala Phe<br>Arg Leu Ala Ala Arg Met Tyr Leu Gln Lys Gly Phe Pro Ile Lys Glu<br>Asp Phe Leu Lys Leu Ser Glu Gln Leu Phe Gly Ala Lys Pro Val Ser<br>Leu Thr Gly Arg Gln Glu Glu Asp Leu Val Asn Ile Asn Gln Trp Val<br>Lys Glu Ala Thr Glu Gly Lys Ile Glu Asp Phe Leu Ser Glu Leu Pro<br>Asp Ser Thr Val Leu Leu Leu Asn Ala Ile His Phe Gln Gly Phe<br>Trp Arg Ser Lys Phe Asp Pro Ser Leu Thr Gln Arg Asp Ser Phe His<br>Leu Asp Glu Gln Phe Thr Val Pro Val Asp Met Met Gln Ala His Lys<br>Tyr Pro Leu Arg Trp Phe Leu Leu Glu Gln Pro Glu Ile Gln Val Ala<br>Gln Phe Pro Phe Lys Asn Asn Met Ser Phe Val Val Leu Val Pro Thr<br>Asn Phe Glu Trp Asn Val Ser Gln Val Leu Ser Asn Leu Ser Trp Asp<br>Ile Leu His Gln Pro Ser Leu Arg Glu Arg Pro Thr Lys Val Gln Leu<br>Pro Lys Leu Leu Lys His Gln Leu Asp Leu Val Thr Thr Leu Ser<br>Gln Leu Gly Leu Gln Glu Leu Phe Leu Ala Pro Asp Leu Arg Gly Ile<br>Ser Asp Glu Gly Leu Val Val Ser Ser Val Gln His Gln Ser Thr Leu<br>Glu Leu Asn Glu Ala Gly Val Glu Ala Ala Ala Thr Ser Thr Ala<br>Met Ser Arg Met Ser Leu Ser Ser Phe Ser Val Asn Arg Pro Phe Leu<br>Phe Phe Ile Leu Glu Asp Thr Ile Asp Leu Pro Ile Phe Val Gly Ile<br>Val Arg Asn Pro Asn Pro Ser Ala Gln Pro Glu Arg Lys Glu Gln Gln<br>Asp Ser Pro Asp His Arg Asp Pro Ser Gln Pro Gln Lys Ser Phe Pro<br>His Gly Asp Lys Leu Phe Ser Pro Asp Leu Lys Leu Ala Pro Pro Ser<br>Glu Glu Asp Tyr Pro Gln Leu Ser Ser Pro Lys |
| SEQ ID NO: 3 | Macaca fascicularis A2AP; AA sequence<br>Met Ala Leu Phe Trp Gly Leu Leu Val Leu Ser Trp Ser Cys Leu Gln<br>Gly Pro Leu Ser Val Phe Ser Pro Val Ser Ala Met Glu Pro Leu Gly<br>Trp Gln Leu Thr Ser Gly Pro Asn Gln Glu Lys Val Pro Pro Leu Thr<br>Leu Leu Lys Leu Gly Asn Gln Glu Pro Gly Gly Gln Thr Ala Leu Lys<br>Ser Leu Pro Gly Ile Cys Ser Arg Asp Pro Thr Pro Glu Gln Thr Arg<br>Arg Leu Ala Gln Ala Met Met Ala Phe Thr Ala Asp Leu Phe Ser Leu<br>Val Ala Gln Thr Ser Thr Cys Pro Asn Leu Ile Leu Ser Pro Leu Ser<br>Val Ala Leu Ala Leu Ser His Leu Ala Leu Gly Ala Gln Asn His Thr<br>Leu Gln Arg Leu Gln Gln Val Leu His Ala Gly Ser Gly Pro Cys Leu<br>Pro His Leu Leu Ser Arg Leu Cys Gln Asn Met Gly Pro Gly Ala Phe<br>Arg Leu Ala Ala Arg Met Tyr Leu Gln Lys Gly Phe Pro Ile Lys Glu<br>Asp Phe Leu Glu Gln Ser Glu Arg Leu Phe Gly Ala Lys Pro Val Ser<br>Leu Thr Gly Lys Gln Glu Asp Asp Leu Ala Asn Ile Asn Gln Trp Val<br>Lys Glu Ala Thr Glu Gly Lys Ile Pro Glu Phe Leu Ser Glu Leu Pro<br>Glu Asp Thr Val Leu Leu Leu Asn Ala Ile His Phe Gln Gly Phe<br>Trp Arg Ser Lys Phe Asp Pro Ser Leu Thr Gln Arg Asp Ser Phe His<br>Leu Asp Glu Gln Phe Thr Val Pro Val Glu Met Met Gln Ala Arg Thr<br>Tyr Pro Leu Arg Trp Phe Met Leu Glu Gln Pro Glu Ile Gln Val Ala<br>His Phe Pro Phe Lys Asn Asn Met Ser Phe Val Val Leu Val Pro Thr<br>His Phe Glu Trp Asn Val Ser Gln Val Leu Ala Asn Leu Ser Trp Asp<br>Thr Leu Tyr Pro Pro Ser Val Trp Glu Arg Pro Thr Lys Val Arg Leu |

| SEQ ID NO: | Type/sequence |
|---|---|
| | Pro Lys Leu Tyr Leu Lys His Gln Met Asp Leu Met Ala Thr Leu Ser<br>Arg Leu Gly Leu Gln Glu Leu Phe Gln Ala Pro Asp Leu Arg Gly Ile<br>Ser Glu Gln Ser Leu Val Val Ser Gly Val Gln His Gln Ser Thr Leu<br>Glu Leu Ser Glu Val Gly Val Glu Ala Ala Ala Thr Ser Ile Ala<br>Met Ser Arg Met Ser Leu Ser Ser Phe Ser Val Asn Arg Pro Phe Leu<br>Phe Phe Ile Phe Glu Asp Thr Thr Gly Leu Pro Leu Phe Val Gly Ser<br>Val Arg Asn Pro Asn Pro Ser Ala Pro Arg Glu Leu Lys Glu Gln Gln<br>Asp Ser Pro Gly Asp Lys Asp Phe Leu His Ser Leu Lys Ala Gly Pro<br>Arg Gly Asp Lys Leu Phe Gly Pro Asp Leu Lys Leu Ala Pro Pro Leu<br>Glu Glu Asp Tyr Pro Glu Leu Gly Ser Pro Lys |
| SEQ ID NO: 6 | antibody sequence; Artificial AA Sequence<br>Asp Tyr Ala Met Ser |
| SEQ ID NO: 7 | antibody sequence; Artificial AA Sequence<br>Ala Ile Gly Thr Gly Gly Gly Thr Tyr Tyr Ala Asp Ser Val Lys Gly |
| SEQ ID NO: 8 | antibody sequence; Artificial AA Sequence<br>Ala Ile Gly Thr Gly Gly Ser Thr Tyr Tyr Ala Asp Ser Val Lys Gly |
| SEQ ID NO: 9 | antibody sequence; Artificial AA Sequence<br>Thr Gly Ser Ser Ser Asn Ile Gly Ala Thr Tyr Asp Val His |
| SEQ ID NO: 10 | antibody sequence; Artificial AA Sequence<br>Ser Asn Asn Gln Arg Pro Ser |
| SEQ ID NO: 11 | antibody sequence; Artificial AA Sequence<br>Glu Tyr Tyr Asp Ser Ser Gly Tyr Tyr His Leu Asp Tyr |
| SEQ ID NO: 12 | antibody sequence; Artificial AA Sequence<br>Glu Asp Tyr Asp Ser Ser Gly Tyr Tyr His Leu Asp Tyr |
| SEQ ID NO: 13 | antibody sequence; Artificial AA Sequence<br>Glu Gly Tyr Asp Ser Ser Gly Tyr Tyr His Leu Asp Tyr |
| SEQ ID NO: 14 | antibody sequence; Artificial AA Sequence<br>Glu Tyr Tyr Asp Ser Ser Gly Tyr Tyr His Leu Val Tyr |
| SEQ ID NO: 15 | antibody sequence; Artificial AA Sequence<br>Glu Tyr Tyr Asp Ser Ser Gly Tyr Tyr His Leu Glu Tyr |
| SEQ ID NO: 16 | antibody sequence; Artificial AA Sequence<br>Glu Tyr Tyr Asp Ser Ser Gly Tyr Tyr His Leu Thr Tyr |
| SEQ ID NO: 17 | antibody sequence; Artificial AA Sequence<br>Ala Ala Trp Asp Asp Ser Leu Ser Gly Trp Val |
| SEQ ID NO: 18 | antibody sequence; Artificial AA Sequence<br>Ala Ala Trp Asp Trp Ser Leu Ser Gly Trp Val |
| SEQ ID NO: 19 | antibody sequence; Artificial AA Sequence<br>Trp Ala Trp Asp Asp Ser Leu Ser Gly Trp Val |
| SEQ ID NO: 20 | antibody sequence; Artificial AA Sequence<br>Ala Ala Trp Asp Val Ser Leu Ser Gly Trp Val |
| SEQ ID NO: 21 | antibody sequence; Artificial AA Sequence<br>Ser Tyr Ala Met Ser |
| SEQ ID NO: 22 | antibody sequence; Artificial AA Sequence<br>Ala Ile Gly Ser Gly Gly Ser Thr Tyr Tyr Ala Asp Ser Val Lys Gly |
| SEQ ID NO: 23 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Tyr Tyr Asp Ser Ser Gly Tyr Tyr His Leu Asp Tyr Trp Gly<br>Gln Gly Thr Leu Val Thr Val Ser Ser |
| SEQ ID NO: 24 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys |

| SEQ ID NO: | Type/sequence |
|---|---|
| | Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Asp<br>Arg Glu Tyr Tyr Asp Ser Ser Gly Tyr Tyr His Leu Asp Tyr Trp Gly<br>Gln Gly Thr Leu Val Thr Val Ser Ser |
| SEQ ID NO: 25 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Ser Glu Tyr Tyr Asp Ser Ser Gly Tyr Tyr His Leu Asp Tyr Trp Gly<br>Gln Gly Thr Leu Val Thr Val Ser Ser |
| SEQ ID NO: 26 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Asp Tyr Asp Ser Ser Gly Tyr Tyr His Leu Asp Tyr Trp Gly<br>Gln Gly Thr Leu Val Thr Val Ser Ser |
| SEQ ID NO: 27 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser |
| SEQ ID NO: 28 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Tyr Tyr Asp Ser Ser Gly Tyr Tyr His Leu Val Tyr Trp Gly<br>Gln Gly Thr Leu Val Thr Val Ser Ser |
| SEQ ID NO: 29 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Tyr Tyr Asp Ser Ser Gly Tyr Tyr His Leu Glu Tyr Trp Gly<br>Gln Gly Thr Leu Val Thr Val Ser Ser |
| SEQ ID NO: 30 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Tyr Tyr Asp Ser Ser Gly Tyr Tyr His Leu Thr Tyr Trp Gly<br>Gln Gly Thr Leu Val Thr Val Ser Ser |
| SEQ ID NO: 31 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Ser Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser |

| SEQ ID NO: | Type/sequence |
|---|---|
| SEQ ID NO: 32 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Ser Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser |
| SEQ ID NO: 33 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Lys Glu Gly Tyr Asp Ser Ser Gly Tyr Tyr His Leu Asp Tyr Trp Gly<br>Gln Gly Thr Leu Val Thr Val Ser Ser |
| SEQ ID NO: 34 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Ser Asp Tyr<br>Ala Met Ser Trp Val Arg Gln Ala Pro Gly Lys Gly Leu Glu Trp Val<br>Ser Ala Ile Gly Thr Gly Gly Ser Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser |
| SEQ ID NO: 35 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Ser Tyr<br>Ala Met Ser Trp Val Arg Gln Ala Pro Gly Lys Gly Leu Glu Trp Val<br>Ser Ala Ile Gly Thr Gly Gly Ser Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser |
| SEQ ID NO: 36 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Ser Gly Gly Ser Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser |
| SEQ ID NO: 37 | antibody sequence; Artificial AA Sequence<br>Gln Ser Val Leu Thr Gln Pro Pro Ser Ala Ser Gly Thr Pro Gly Gln<br>Arg Val Thr Ile Ser Cys Thr Gly Ser Ser Ser Asn Ile Gly Ala Thr<br>Tyr Asp Val His Trp Tyr Gln Gln Leu Pro Gly Thr Ala Pro Lys Leu<br>Leu Ile Tyr Ser Asn Asn Gln Arg Pro Ser Gly Val Pro Asp Arg Phe<br>Ser Gly Ser Lys Ser Gly Thr Ser Ala Ser Leu Ala Ile Ser Gly Leu<br>Arg Ser Glu Asp Glu Ala Asp Tyr Tyr Cys Ala Ala Trp Asp Asp Ser<br>Leu Ser Gly Trp Val Phe Gly Gly Gly Thr Lys Leu Thr Val Leu |
| SEQ ID NO: 38 | antibody sequence; Artificial AA Sequence<br>Gln Ser Val Leu Thr Gln Pro Pro Ser Ala Ser Gly Thr Pro Gly Gln<br>Arg Val Thr Ile Ser Cys Thr Gly Ser Ser Ser Asn Ile Gly Ala Thr<br>Tyr Asp Val His Trp Tyr Gln Gln Leu Pro Gly Thr Ala Pro Lys Leu<br>Leu Ile Tyr Ser Asn Asn Gln Arg Pro Ser Gly Val Pro Asp Arg Phe<br>Ser Gly Ser Lys Ser Gly Thr Ser Ala Ser Leu Ala Ile Ser Gly Leu<br>Arg Ser Glu Asp Glu Ala Asp Tyr Tyr Cys Ala Ala Trp Asp Trp Ser<br>Leu Ser Gly Trp Val Phe Gly Gly Gly Thr Lys Leu Thr Val Leu |
| SEQ ID NO: 39 | antibody sequence; Artificial AA Sequence<br>Gln Ser Val Leu Thr Gln Pro Pro Ser Ala Ser Gly Thr Pro Gly Gln<br>Arg Val Thr Ile Ser Cys Thr Gly Ser Ser Ser Asn Ile Gly Ala Thr<br>Tyr Asp Val His Trp Tyr Gln Gln Leu Pro Gly Thr Ala Pro Lys Leu<br>Leu Ile Tyr Ser Asn Asn Gln Arg Pro Ser Gly Val Pro Asp Arg Phe<br>Ser Gly Ser Lys Ser Gly Thr Ser Ala Ser Leu Ala Ile Ser Gly Leu<br>Arg Ser Glu Asp Glu Ala Asp Tyr Tyr Cys Trp Ala Trp Asp Asp Ser<br>Leu Ser Gly Trp Val Phe Gly Gly Gly Thr Lys Leu Thr Val Leu |

| SEQ ID NO: | Type/sequence |
| --- | --- |
| SEQ ID NO: 40 | antibody sequence; Artificial AA Sequence<br>Gln Ser Val Leu Thr Gln Pro Pro Ser Ala Ser Gly Thr Pro Gly Gln<br>Arg Val Thr Ile Ser Cys Thr Gly Ser Ser Ser Asn Ile Gly Ala Thr<br>Tyr Asp Val His Trp Tyr Gln Gln Leu Pro Gly Thr Ala Pro Lys Leu<br>Leu Ile Tyr Ser Asn Asn Gln Arg Pro Ser Gly Val Pro Asp Arg Phe<br>Ser Gly Ser Lys Ser Gly Thr Ser Ala Ser Leu Ala Ile Ser Gly Leu<br>Arg Ser Glu Asp Glu Ala Asp Tyr Tyr Cys Ala Ala Trp Asp Val Ser<br>Leu Ser Gly Trp Val Phe Gly Gly Gly Thr Lys Leu Thr Val Leu |
| SEQ ID NO: 41 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Tyr Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser<br>Pro Gly |
| SEQ ID NO: 42 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Asp<br>Arg Glu Tyr Tyr Asp Ser Ser Gly Tyr Tyr Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser |
| SEQ ID NO: 43 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu |

| SEQ ID NO: | Type/sequence |
|---|---|
| | Gln Met Asn Ser Leu Arg Ala Glu Asp Thr Ala Val Tyr Tyr Cys Ala<br>Ser Glu Tyr Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser |
| SEQ ID NO: 44 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Asp Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser |
| SEQ ID NO: 45 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val |

| SEQ ID NO: | Type/sequence |
|---|---|
| | Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser |
| SEQ ID NO: 46 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser |
| SEQ ID NO: 47 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Tyr Tyr Asp Ser Ser Gly Tyr Tyr His Leu Glu Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser<br>Pro Gly |
| SEQ ID NO: 48 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Tyr Tyr Asp Ser Ser Gly Tyr Tyr His Leu Thr Tyr Trp Gly<br>Gln Gly Thr Leu Val Thr Val Ser Ser Ala Ser Thr Lys Gly Pro Ser |

| SEQ ID NO: | Type/sequence |
|---|---|
| | Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser<br>Pro Gly |
| SEQ ID NO: 49 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Ser Asp Tyr<br>Ala Met Ser Trp Val Arg Gln Ala Pro Gly Lys Gly Leu Glu Trp Val<br>Ser Ala Ile Gly Thr Gly Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser<br>Pro Gly |
| SEQ ID NO: 50 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Ser Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser |

| SEQ ID NO: | Type/sequence |
|---|---|
| | Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser<br>Pro Gly |
| SEQ ID NO: 51 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Asp Tyr<br>Ala Met Ser Trp Val Arg Gln Ala Pro Gly Lys Gly Leu Glu Trp Val<br>Ser Ala Ile Gly Thr Gly Gly Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Lys Glu Gly Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser<br>Pro Gly |
| SEQ ID NO: 52 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Ser Asp Tyr<br>Ala Met Ser Trp Val Arg Gln Ala Pro Gly Lys Gly Leu Glu Trp Val<br>Ser Ala Ile Gly Thr Gly Gly Ser Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly<br>Gln Gly Thr Leu Val Thr Val Ser Ser Ala Ser Thr Lys Gly Pro Ser<br>Val Phe Pro Leu Ala Pro Ser Ser Lys Ser Thr Ser Gly Gly Thr Ala<br>Ala Leu Gly Cys Leu Val Lys Asp Tyr Phe Pro Glu Pro Val Thr Val<br>Ser Trp Asn Ser Gly Ala Leu Thr Ser Gly Val His Thr Phe Pro Ala<br>Val Leu Gln Ser Ser Gly Leu Tyr Ser Leu Ser Ser Val Val Thr Val<br>Pro Ser Ser Ser Leu Gly Thr Gln Thr Tyr Ile Cys Asn Val Asn His<br>Lys Pro Ser Asn Thr Lys Val Asp Lys Lys Val Glu Pro Lys Ser Cys<br>Asp Lys Thr His Thr Cys Pro Pro Cys Pro Ala Pro Glu Leu Leu Gly<br>Gly Pro Ser Val Phe Leu Phe Pro Pro Lys Pro Lys Asp Thr Leu Met<br>Ile Ser Arg Thr Pro Glu Val Thr Cys Val Val Val Asp Val Ser His<br>Glu Asp Pro Glu Val Lys Phe Asn Trp Tyr Val Asp Gly Val Glu Val<br>His Asn Ala Lys Thr Lys Pro Arg Glu Glu Gln Tyr Asn Ser Thr Tyr<br>Arg Val Val Ser Val Leu Thr Val Leu His Gln Asp Trp Leu Asn Gly<br>Lys Glu Tyr Lys Cys Lys Val Ser Asn Lys Ala Leu Pro Ala Pro Ile<br>Glu Lys Thr Ile Ser Lys Ala Lys Gly Gln Pro Arg Glu Pro Gln Val<br>Tyr Thr Leu Pro Pro Ser Arg Asp Glu Leu Thr Lys Asn Gln Val Ser<br>Leu Thr Cys Leu Val Lys Gly Phe Tyr Pro Ser Asp Ile Ala Val Glu<br>Trp Glu Ser Asn Gly Gln Pro Glu Asn Asn Tyr Lys Thr Thr Pro Pro<br>Val Leu Asp Ser Asp Gly Ser Phe Phe Leu Tyr Ser Lys Leu Thr Val<br>Asp Lys Ser Arg Trp Gln Gln Gly Asn Val Phe Ser Cys Ser Val Met<br>His Glu Ala Leu His Asn His Tyr Thr Gln Lys Ser Leu Ser Leu Ser<br>Pro Gly |
| SEQ ID NO: 53 | antibody sequence; Artificial AA Sequence<br>Glu Val Gln Leu Leu Glu Ser Gly Gly Gly Leu Val Gln Pro Gly Gly<br>Ser Leu Arg Leu Ser Cys Ala Ala Ser Gly Phe Thr Phe Asp Ser Tyr<br>Ala Met Ser Trp Val Arg Gln Ala Pro Gly Lys Gly Leu Glu Trp Val<br>Ser Ala Ile Gly Thr Gly Gly Ser Thr Tyr Tyr Ala Asp Ser Val Lys<br>Gly Arg Phe Thr Ile Ser Arg Asp Asn Ser Lys Asn Thr Leu Tyr Leu<br>Gln Met Asn Ser Leu Arg Ala Glu Asp Thr Ala Val Tyr Tyr Cys Ala<br>Arg Glu Gly Tyr Asp Ser Ser Gly Tyr Tyr His Leu Asp Tyr Trp Gly |

| SEQ ID NO: | Type/sequence |
|---|---|
| | Gln Gly Thr Leu Val Thr Val Ser Ser Ala Ser Thr Lys Gly Pro Ser
Val Phe Pro Leu Ala Pro Ser Ser Lys Ser Thr Ser Gly Gly Thr Ala
Ala Leu Gly Cys Leu Val Lys Asp Tyr Phe Pro Glu Pro Val Thr Val
Ser Trp Asn Ser Gly Ala Leu Thr Ser Gly Val His Thr Phe Pro Ala
Val Leu Gln Ser Ser Gly Leu Tyr Ser Leu Ser Ser Val Val Thr Val
Pro Ser Ser Ser Leu Gly Thr Gln Thr Tyr Ile Cys Asn Val Asn His
Lys Pro Ser Asn Thr Lys Val Asp Lys Lys Val Glu Pro Lys Ser Cys
Asp Lys Thr His Thr Cys Pro Pro Cys Pro Ala Pro Glu Leu Leu Gly
Gly Pro Ser Val Phe Leu Phe Pro Pro Lys Pro Lys Asp Thr Leu Met
Ile Ser Arg Thr Pro Glu Val Thr Cys Val Val Val Asp Val Ser His
Glu Asp Pro Glu Val Lys Phe Asn Trp Tyr Val Asp Gly Val Glu Val
His Asn Ala Lys Thr Lys Pro Arg Glu Glu Gln Tyr Asn Ser Thr Tyr
Arg Val Val Ser Val Leu Thr Val Leu His Gln Asp Trp Leu Asn Gly
Lys Glu Tyr Lys Cys Lys Val Ser Asn Lys Ala Leu Pro Ala Pro Ile
Glu Lys Thr Ile Ser Lys Ala Lys Gly Gln Pro Arg Glu Pro Gln Val
Tyr Thr Leu Pro Pro Ser Arg Asp Glu Leu Thr Lys Asn Gln Val Ser
Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro
Val Leu Asp Ser Asp Gly Ser Phe Phe Leu Tyr Ser Lys Leu Thr Val
Asp Lys Ser Arg Trp Gln Gln Gly Asn Val Phe Ser Cys Ser Val Met
His Glu Ala Leu His Asn His Tyr Thr Gln Lys Ser Leu Ser Leu Ser
Pro Gly |
| SEQ ID NO: 54 | antibody sequence; Artificial AA Sequence
Glu Val Gln Leu Leu Glu Ser Gly Gly Gly Leu Val Gln Pro Gly Gly
Ser Leu Arg Leu Ser Cys Ala Ala Ser Gly Phe Thr Phe Asp Asp Tyr
Ala Met Ser Trp Val Arg Gln Ala Pro Gly Lys Gly Leu Glu Trp Val
Ser Ala Ile Gly Ser Gly Gly Ser Thr Tyr Tyr Ala Asp Ser Val Lys
Gly Arg Phe Thr Ile Ser Arg Asp Asn Ser Lys Asn Thr Leu Tyr Leu
Gln Met Asn Ser Leu Arg Ala Glu Asp Thr Ala Val Tyr Tyr Cys Ala
Arg Glu Gly Tyr Asp Ser Ser Gly Tyr Tyr His Leu Asp Tyr Trp Gly
Gln Gly Thr Leu Val Thr Val Ser Ser Ala Ser Thr Lys Gly Pro Ser
Val Phe Pro Leu Ala Pro Ser Ser Lys Ser Thr Ser Gly Gly Thr Ala
Ala Leu Gly Cys Leu Val Lys Asp Tyr Phe Pro Glu Pro Val Thr Val
Ser Trp Asn Ser Gly Ala Leu Thr Ser Gly Val His Thr Phe Pro Ala
Val Leu Gln Ser Ser Gly Leu Tyr Ser Leu Ser Ser Val Val Thr Val
Pro Ser Ser Ser Leu Gly Thr Gln Thr Tyr Ile Cys Asn Val Asn His
Lys Pro Ser Asn Thr Lys Val Asp Lys Lys Val Glu Pro Lys Ser Cys
Asp Lys Thr His Thr Cys Pro Pro Cys Pro Ala Pro Glu Leu Leu Gly
Gly Pro Ser Val Phe Leu Phe Pro Pro Lys Pro Lys Asp Thr Leu Met
Ile Ser Arg Thr Pro Glu Val Thr Cys Val Val Val Asp Val Ser His
Glu Asp Pro Glu Val Lys Phe Asn Trp Tyr Val Asp Gly Val Glu Val
His Asn Ala Lys Thr Lys Pro Arg Glu Glu Gln Tyr Asn Ser Thr Tyr
Arg Val Val Ser Val Leu Thr Val Leu His Gln Asp Trp Leu Asn Gly
Lys Glu Tyr Lys Cys Lys Val Ser Asn Lys Ala Leu Pro Ala Pro Ile
Glu Lys Thr Ile Ser Lys Ala Lys Gly Gln Pro Arg Glu Pro Gln Val
Tyr Thr Leu Pro Pro Ser Arg Asp Glu Leu Thr Lys Asn Gln Val Ser
Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro
Val Leu Asp Ser Asp Gly Ser Phe Phe Leu Tyr Ser Lys Leu Thr Val
Asp Lys Ser Arg Trp Gln Gln Gly Asn Val Phe Ser Cys Ser Val Met
His Glu Ala Leu His Asn His Tyr Thr Gln Lys Ser Leu Ser Leu Ser
Pro Gly |
| SEQ ID NO: 55 | antibody sequence; Artificial AA Sequence
Glu Val Gln Leu Leu Glu Ser Gly Gly Gly Leu Val Gln Pro Gly Gly
Ser Leu Arg Leu Ser Cys Ala Ala Ser Gly Phe Thr Phe Asp Asp Tyr
Ala Met Ser Trp Val Arg Gln Ala Pro Gly Lys Gly Leu Glu Trp Val
Ser Ala Ile Gly Thr Gly Gly Ser Thr Tyr Tyr Ala Asp Ser Val Lys
Gly Arg Phe Thr Ile Ser Arg Asp Asn Ser Lys Asn Thr Leu Tyr Leu
Gln Met Asn Ser Leu Arg Ala Glu Asp Thr Ala Val Tyr Tyr Cys Ala
Arg Glu Gly Tyr Asp Ser Ser Gly Tyr Tyr His Leu Asp Tyr Trp Gly
Gln Gly Thr Leu Val Thr Val Ser Ser Ala Ser Thr Lys Gly Pro Ser
Val Phe Pro Leu Ala Pro Cys Ser Arg Ser Thr Ser Glu Ser Thr Ala
Ala Leu Gly Cys Leu Val Lys Asp Tyr Phe Pro Glu Pro Val Thr Val
Ser Trp Asn Ser Gly Ala Leu Thr Ser Gly Val His Thr Phe Pro Ala
Val Leu Gln Ser Ser Gly Leu Tyr Ser Leu Ser Ser Val Val Thr Val
Pro Ser Ser Ser Leu Gly Thr Lys Thr Tyr Thr Cys Asn Val Asp His
Lys Pro Ser Asn Thr Lys Val Asp Lys Arg Val Glu Ser Lys Tyr Gly
Pro Pro Cys Pro Pro Cys Pro Ala Pro Glu Phe Leu Gly Gly Pro Ser
Val Phe Leu Phe Pro Pro Lys Pro Lys Asp Thr Leu Met Ile Ser Arg
Thr Pro Glu Val Thr Cys Val Val Val Asp Val Ser Gln Glu Asp Pro
Glu Val Gln Phe Asn Trp Tyr Val Asp Gly Val Glu Val His Asn Ala
Lys Thr Lys Pro Arg Glu Glu Gln Phe Asn Ser Thr Tyr Arg Val Val
Ser Val Leu Thr Val Leu His Gln Asp Trp Leu Asn Gly Lys Glu Tyr
Lys Cys Lys Val Ser Asn Lys Gly Leu Pro Ser Ser Ile Glu Lys Thr
Ile Ser Lys Ala Lys Gly Gln Pro Arg Glu Pro Gln Val Tyr Thr Leu |

| SEQ ID NO: | Type/sequence |
|---|---|
| | Pro Pro Ser Gln Glu Glu Met Thr Lys Asn Gln Val Ser Leu Thr Cys<br>Leu Val Lys Gly Phe Tyr Pro Ser Asp Ile Ala Val Glu Trp Glu Ser<br>Asn Gly Gln Pro Glu Asn Asn Tyr Lys Thr Thr Pro Pro Val Leu Asp<br>Ser Asp Gly Ser Phe Phe Leu Tyr Ser Arg Leu Thr Val Asp Lys Ser<br>Arg Trp Gln Glu Gly Asn Val Phe Ser Cys Ser Val Met His Glu Ala<br>Leu His Asn His Tyr Thr Gln Lys Ser Leu Ser Leu Ser Leu Gly |
| SEQ ID NO: 56 | antibody sequence; Artificial AA Sequence<br>Gln Ser Val Leu Thr Gln Pro Pro Ser Ala Ser Gly Thr Pro Gly Gln<br>Arg Val Thr Ile Ser Cys Thr Gly Ser Ser Ser Asn Ile Gly Ala Thr<br>Tyr Asp Val His Trp Tyr Gln Gln Leu Pro Gly Thr Ala Pro Lys Leu<br>Leu Ile Tyr Ser Asn Asn Gln Arg Pro Ser Gly Val Pro Asp Arg Phe<br>Ser Gly Ser Lys Ser Gly Thr Ser Ala Ser Leu Ala Ile Ser Gly Leu<br>Arg Ser Glu Asp Glu Ala Asp Tyr Tyr Cys Ala Ala Trp Asp Asp Ser<br>Leu Ser Gly Trp Val Phe Gly Gly Gly Thr Lys Leu Thr Val Leu Gly<br>Gln Pro Lys Ala Ala Pro Ser Val Thr Leu Phe Pro Pro Ser Ser Glu<br>Glu Leu Gln Ala Asn Lys Ala Thr Leu Val Cys Leu Ile Ser Asp Phe<br>Tyr Pro Gly Ala Val Thr Val Ala Trp Lys Ala Asp Ser Ser Pro Val<br>Lys Ala Gly Val Glu Thr Thr Thr Pro Ser Lys Gln Ser Asn Asn Lys<br>Tyr Ala Ala Ser Ser Tyr Leu Ser Leu Thr Pro Glu Gln Trp Lys Ser<br>His Arg Ser Tyr Ser Cys Gln Val Thr His Glu Gly Ser Thr Val Glu<br>Lys Thr Val Ala Pro Thr Glu Cys Ser |
| SEQ ID NO: 57 | antibody sequence; Artificial AA Sequence<br>Gln Ser Val Leu Thr Gln Pro Pro Ser Ala Ser Gly Thr Pro Gly Gln<br>Arg Val Thr Ile Ser Cys Thr Gly Ser Ser Ser Asn Ile Gly Ala Thr<br>Tyr Asp Val His Trp Tyr Gln Gln Leu Pro Gly Thr Ala Pro Lys Leu<br>Leu Ile Tyr Ser Asn Asn Gln Arg Pro Ser Gly Val Pro Asp Arg Phe<br>Ser Gly Ser Lys Ser Gly Thr Ser Ala Ser Leu Ala Ile Ser Gly Leu<br>Arg Ser Glu Asp Glu Ala Asp Tyr Tyr Cys Ala Ala Trp Asp Trp Ser<br>Leu Ser Gly Trp Val Phe Gly Gly Gly Thr Lys Leu Thr Val Leu Gly<br>Gln Pro Lys Ala Ala Pro Ser Val Thr Leu Phe Pro Pro Ser Ser Glu<br>Glu Leu Gln Ala Asn Lys Ala Thr Leu Val Cys Leu Ile Ser Asp Phe<br>Tyr Pro Gly Ala Val Thr Val Ala Trp Lys Ala Asp Ser Ser Pro Val<br>Lys Ala Gly Val Glu Thr Thr Thr Pro Ser Lys Gln Ser Asn Asn Lys<br>Tyr Ala Ala Ser Ser Tyr Leu Ser Leu Thr Pro Glu Gln Trp Lys Ser<br>His Arg Ser Tyr Ser Cys Gln Val Thr His Glu Gly Ser Thr Val Glu<br>Lys Thr Val Ala Pro Thr Glu Cys Ser |
| SEQ ID NO: 58 | antibody sequence; Artificial AA Sequence<br>Gln Ser Val Leu Thr Gln Pro Pro Ser Ala Ser Gly Thr Pro Gly Gln<br>Arg Val Thr Ile Ser Cys Thr Gly Ser Ser Ser Asn Ile Gly Ala Thr<br>Tyr Asp Val His Trp Tyr Gln Gln Leu Pro Gly Thr Ala Pro Lys Leu<br>Leu Ile Tyr Ser Asn Asn Gln Arg Pro Ser Gly Val Pro Asp Arg Phe<br>Ser Gly Ser Lys Ser Gly Thr Ser Ala Ser Leu Ala Ile Ser Gly Leu<br>Arg Ser Glu Asp Glu Ala Asp Tyr Tyr Cys Trp Ala Trp Asp Asp Ser<br>Leu Ser Gly Trp Val Phe Gly Gly Gly Thr Lys Leu Thr Val Leu Gly<br>Gln Pro Lys Ala Ala Pro Ser Val Thr Leu Phe Pro Pro Ser Ser Glu<br>Glu Leu Gln Ala Asn Lys Ala Thr Leu Val Cys Leu Ile Ser Asp Phe<br>Tyr Pro Gly Ala Val Thr Val Ala Trp Lys Ala Asp Ser Ser Pro Val<br>Lys Ala Gly Val Glu Thr Thr Thr Pro Ser Lys Gln Ser Asn Asn Lys<br>Tyr Ala Ala Ser Ser Tyr Leu Ser Leu Thr Pro Glu Gln Trp Lys Ser<br>His Arg Ser Tyr Ser Cys Gln Val Thr His Glu Gly Ser Thr Val Glu<br>Lys Thr Val Ala Pro Thr Glu Cys Ser |
| SEQ ID NO: 59 | antibody sequence; Artificial AA Sequence<br>Gln Ser Val Leu Thr Gln Pro Pro Ser Ala Ser Gly Thr Pro Gly Gln<br>Arg Val Thr Ile Ser Cys Thr Gly Ser Ser Ser Asn Ile Gly Ala Thr<br>Tyr Asp Val His Trp Tyr Gln Gln Leu Pro Gly Thr Ala Pro Lys Leu<br>Leu Ile Tyr Ser Asn Asn Gln Arg Pro Ser Gly Val Pro Asp Arg Phe<br>Ser Gly Ser Lys Ser Gly Thr Ser Ala Ser Leu Ala Ile Ser Gly Leu<br>Arg Ser Glu Asp Glu Ala Asp Tyr Tyr Cys Ala Ala Trp Asp Val Ser<br>Leu Ser Gly Trp Val Phe Gly Gly Gly Thr Lys Leu Thr Val Leu Gly<br>Gln Pro Lys Ala Ala Pro Ser Val Thr Leu Phe Pro Pro Ser Ser Glu<br>Glu Leu Gln Ala Asn Lys Ala Thr Leu Val Cys Leu Ile Ser Asp Phe<br>Tyr Pro Gly Ala Val Thr Val Ala Trp Lys Ala Asp Ser Ser Pro Val<br>Lys Ala Gly Val Glu Thr Thr Thr Pro Ser Lys Gln Ser Asn Asn Lys<br>Tyr Ala Ala Ser Ser Tyr Leu Ser Leu Thr Pro Glu Gln Trp Lys Ser<br>His Arg Ser Tyr Ser Cys Gln Val Thr His Glu Gly Ser Thr Val Glu<br>Lys Thr Val Ala Pro Thr Glu Cys Ser |
| SEQ ID NO: 60 | DNA; Homo sapiens<br>atggcgctgc tctgggggct cctggtgctc agctggtcct gcctgcaagg cccctgctcc    60<br>gtgttctccc ctgtgagcgc catggagccc ttgggccggc agctaactag cgggccgaac   120<br>caggagcagg tgtcccact taccctcctc aagttgggca accaggagcc tggtggccag   180<br>actgccctga agagtccccc aggagtctgc agcagagacc ccacccagaa gcagacccac   240<br>aggctggccc gggccatgat ggccttcact gccgacctgt tctccctggt ggctcaaacg   300 |

| SEQ ID NO: | Type/sequence | |
|---|---|---|
| | tccacctgcc ccaacctcat cctgtcaccc ctgagtgtgg ccctggcgct gtctcacctg | 360 |
| | gcactaggtg ctcagaacca cacgttgcag aggctgcaac aggtgctgca cgcaggctca | 420 |
| | gggccctgcc tcccccatct gctgagccgc ctctgccaga acctgggccc cggcgcgttc | 480 |
| | cgactggctg ccaggatgta cctgcagaaa ggatttccca tcaaagaaga tttcctggaa | 540 |
| | caatccgaac agctatttgg ggcaaagccc gtgagcctga cgggaaagca ggaagatgac | 600 |
| | ctggcaaaca tcaaccaatg ggtgaaggag ccacggagg gaagattca ggaattcctc | 660 |
| | tctgggctgc cggaagacac cgtgttgctt ctcctcaacg ccatccactt ccagggtttc | 720 |
| | tggaggaaca gtttgaccc gagcctacc cagagagact ccttccacct ggacgagcag | 780 |
| | ttcacggtgc ccgtggaaat gatgcaggcc cgcacgtacc cgctgcgctg gttcttgctg | 840 |
| | gagcagcctg agatccaggt ggctcatttc ccctttaaga caaacatgag ctttgtggtc | 900 |
| | cttgtaccca cccactttga atggaacgtg tccaggtac tggccaacct gagttgggac | 960 |
| | accctgcacc cacctctggt gtgggagagg cccaccaagg tccggctgcc taagctgtat | 1020 |
| | ctgaaacacc aaatggacct ggtggccacc ctcagccagc tgggcctgca ggagttgttc | 1080 |
| | caggcccag acctgcgtgg gatctccgag cagagcctgg tggtgtccgg cgtgcagcat | 1140 |
| | cagtccaccc tggagctcag cgaggtcggc gtggaggcgg cggcggccac cagcattgcc | 1200 |
| | atgtcccgca tgtccctgtc ctccttcagc gtgaaccgcc ccttcctctt cttcatcttc | 1260 |
| | gaggacacca caggccttcc cctcttcgtg ggcagtgg gaacccaa ccccagtgca | 1320 |
| | ccgcgggagc tcaaggaaca gcaggattcc ccgggcaaca aggactccct ccagagcctg | 1380 |
| | aaaggcttcc ccgcggaga caagctttc ggccctgact aaaacttgt gccccccatg | 1440 |
| | gaggaggatt accccagtt tggcagcccc aagtga | 1476 |
| SEQ ID NO: 61 | DNA; Oryctolagus cuniculus | |
| | atggtgctgc tccgggggct cctggtgctc agcttgtcct gcctgcaagg ccctgcgcg | 60 |
| | gtgctccctc ccgtgagcgc catggagccc gtgggccggc agctaactag tggtcagagc | 120 |
| | caagaaaagc tgcctccgct cgcccctcc aagttggtca ccaggagct gcacggtcag | 180 |
| | actgccctga gaagtcccc aggagactgc agggaaaccc gacccccgga gcagacgcgc | 240 |
| | aggctggcgc aggccatgat ggccttcacc actgacctgt tttccctggt ggtgcaagca | 300 |
| | tccaccagcc ccaacctggt cttgtcgccc ctgagtgtgg ccctggctct gtctcacctg | 360 |
| | gcattaggtg ctcagaacca cacgctacag aggttgcagc aggtgctgca tgcggactca | 420 |
| | gggccctgcc tcccccacct gctgagccac ctctgccgga acctgggccc aggggcgttc | 480 |
| | cgattggctg ccagaatgta cctgcagaaa ggctttccca tcaaagagga cttcctgaag | 540 |
| | ctgtcagagc agctgtttgg tgcaaagcct gtgagcctga caggaaggca agaggaggac | 600 |
| | ctggtgaaca tcaatcaatg ggtgaaggag gccacagagg gaagattga ggatttcctc | 660 |
| | tcggaattgc cagacagcac cgtgctgctc ctcctcaatg ccatccactt ccagggtttc | 720 |
| | tggaggagca aatttgaccc gagcctcacc cagagagact cttccacct ggacgagcag | 780 |
| | ttcacggtgc cagtggacat gatgcaagcc cacaagtacc ctctgcgctg gttcttgctg | 840 |
| | gagcagcctg agatccaggt ggcccaattc ccctttaaga caaacatgag ctttgtggtc | 900 |
| | ctcgtgccca cgaactttga gtggaacgtg tccaggtgc tgagcaacct gagctgggac | 960 |
| | atcctgcacc agccctcact gcgggagagg cccaccaaag tccagctgcc caagctgctc | 1020 |
| | ctgaaacacc agctggacct ggtgaccacc ctcagccagc tgggcctgca ggagctgttc | 1080 |
| | ctggcccag acctgcgtgg gatctccgac gagggcctgg tggtgtccag tgtacaacat | 1140 |
| | cagtccaccc tggagctcaa cgaggctggt gtggaggcgg ccgcggccac cagcacggcc | 1200 |
| | atgtcgcgca tgtcccttc ctccttcagc gtgaaccgcc ccttcctctt cttcatcttc | 1260 |
| | gaggacacca tagacctgcc catcttgtg ggcatagtgc ggaacccaa tcctagcgcg | 1320 |
| | cagccagagc gcaaggagca gcaggattcc cctgaccaca gggacccctc gcagcccag | 1380 |
| | aaatccttcc cccacgggga caagctcttc agccccgact gaaactggc gccccgtcg | 1440 |
| | gaagaggatt accccagct cagcagcccc aagtga | 1476 |
| SEQ ID NO: 62 | DNA; Macaca fascicularis | |
| | atggcgctgt tctgggggct cctggtgctc agctggtcct gcctgcaagg tccctctcc | 60 |
| | gtgttctccc ctgtgagcgc catggagccc ttgggctggc agctaactag tgggccaaac | 120 |
| | caagagaagg tgccccact tactctcctc aagttgggca accaggagcc tggcggcag | 180 |
| | actgccctga agagtctccc aggaatctgc acagagacc caccccga gcagacccgc | 240 |
| | aggctggccc aggccatgat ggccttcact gccgaccgtg tctccctggt ggctcaaacg | 300 |
| | tccacctgcc ccaacctcat cctgtcacct ctgagtgtgg ccctggcgct gtctcacctg | 300 |
| | gcactaggtg ctcagaacca cacgctgcag aggctgcaac aggtgctgca cgcaggctca | 420 |
| | gggccctgcc taccccatct gctgagccgc ctctgccaga catgggcccc ggggccttc | 480 |
| | cgactggctg ccaggatgta cctgcagaaa ggatttccca tcaaagaaga tttcctggaa | 540 |
| | cagtctgaac ggctatttgg ggcaaagccc gtgagcctga cgggaaagca ggaagatgac | 600 |
| | ctggcaaaca tcaaccaatg ggtgaaggag ccacggagg gaagattcc ggagttcctc | 720 |
| | tctgagctac cggaagacac cgtgttgctt ctcctcaacg ccatccactt ccagggtttc | 900 |
| | tggaggagca gtttgaccc gagcctcacc cagagagact ccttccacct ggacgagcag | 660 |
| | ttcacggtgc ccgtggaaat gatgcaagcc cgcacgtatc ctctgcgctg gttcatgctg | 780 |
| | gagcagcccg agatccaggt ggctcatttt ccctttaaga caaacatgag ctttgtggtc | 840 |
| | cttgtaccca cccactttga atggaacgtg tccaggtac tggccaacct gagttgggac | 960 |
| | accctgtacc caccttccgt gtgggagagg cccaccaagg tccggctgcc taagctgtat | 1020 |
| | ctgaaacacc aaatggacct gatggccacc ctcagccggc tgggcctgca ggagctgttc | 1080 |
| | caggcccag acctgcgcgg gatctctgag cagagcctgg tggtgtccgg cgtgcagcat | 1140 |
| | cagtccaccc tggagctcag cgaggtggc gtgggccac cagcatcgcc | 1200 |
| | atgtcccgca tgtccctgtc ctccttcagc gtgaaccgcc ccttcctctt cttcatcttt | 1260 |
| | gaggacacca caggccttcc cctcttgtg ggcagcgtga gaacccaa cccagcgcg | 1320 |
| | ccacgggagc tcaaggagca gcaggattcc ccgggagaca aggactccct ccacagcctg | 1380 |
| | aaagccggcc ccgcggaga caagctcttc ggccctgact gaaactggc gccccgttg | 1440 |
| | gaggaggatt accctgagct tggcagccct aagtga | 1476 |

| SEQ ID NO: | Type/sequence | |
|---|---|---|
| SEQ ID NO: 63 | DNA; Artificial Sequence, antibody sequence<br>gattacgcca tgagc | 15 |
| SEQ ID NO: 64 | DNA; Artificial Sequence, antibody sequence<br>gccatcggaa caggcggcgg aacatattac gccgacagcg tgaagggc | 48 |
| SEQ ID NO: 65 | DNA; Artificial Sequence, antibody sequence<br>gccatcggca caggcggcag cacatattac gccgactctg tgaagggc | 48 |
| SEQ ID NO: 66 | DNA; Artificial Sequence, antibody sequence<br>accggcagca gctccaatat cggcgccacc tatgacgtgc ac | 42 |
| SEQ ID NO: 67 | DNA; Artificial Sequence, antibody sequence<br>agcaacaacc agcggcctag c | 21 |
| SEQ ID NO: 68 | DNA; Artificial Sequence, antibody sequence<br>gagtactacg acagcagcgg ctactaccac ctggactat | 39 |
| SEQ ID NO: 69 | DNA; Artificial Sequence, antibody sequence<br>gaggattacg acagcagcgg ctactaccac ctggactat | 39 |
| SEQ ID NO: 70 | DNA; Artificial Sequence, antibody sequence<br>gaggggtacg acagcagcgg ctactaccac ctggactat | 39 |
| SEQ ID NO: 71 | DNA; Artificial Sequence, antibody sequence<br>gagtactacg acagcagcgg ctactaccac ctggtttat | 39 |
| SEQ ID NO: 72 | DNA; Artificial Sequence, antibody sequence<br>gagtactacg acagcagcgg ctactaccac ctggagtat | 39 |
| SEQ ID NO: 73 | DNA; Artificial Sequence, antibody sequence<br>gagtactacg acagcagcgg ctactaccac ctgacgtat | 39 |
| SEQ ID NO: 74 | DNA; Artificial Sequence, antibody sequence<br>gccgcctggg atgattctct gagcggctgg gtt | 33 |
| SEQ ID NO: 75 | DNA; Artificial Sequence, antibody sequence<br>gccgcctggg attggtctct gagcggctgg gtt | 33 |
| SEQ ID NO: 76 | DNA; Artificial Sequence, antibody sequence<br>tgggcctggg atgattctct gagcggctgg gtt | 33 |
| SEQ ID NO: 77 | DNA; Artificial Sequence, antibody sequence<br>gccgcctggg atgtttctct gagcggctgg gt | 33 |
| SEQ ID NO: 78 | DNA; Artificial Sequence, antibody sequence<br>agctacgcca tgagc | 15 |
| SEQ ID NO: 79 | DNA; Artificial Sequence, antibody sequence<br>gccatcggca gcggaggcag cacatattac gccgactctg tgaagggc | 48 |
| SEQ ID NO: 80 | DNA; Artificial Sequence, antibody sequence<br>gaagttcagc tgctggaatc tggcggcgga ctggttcaac tggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgccag agagtactac | 300 |
| | gacagcagcg gctactacca cctggactat tggggccagg caccctggt cacagttct | 360 |
| | tca | 363 |
| SEQ ID NO: 81 | DNA; Artificial Sequence, antibody sequence<br>gaagttcagc tgctggaatc tggcggcgga ctggttcaac tggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgcgat agagtactac | 300 |
| | gacagcagcg gctactacca cctggactat tggggccagg caccctggt cacagttct | 360 |
| | tca | 363 |

| SEQ ID NO: | Type/sequence | |
|---|---|---|
| SEQ ID NO: 82 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgccag tgagtactac | 300 |
| | gacagcagcg gctactacca cctggactat tggggccagg gcaccctggt cacagtttct | 360 |
| | tca | 363 |
| SEQ ID NO: 83 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgccag agaggattac | 300 |
| | gacagcagcg gctactacca cctggactat tggggccagg gcaccctggt cacagtttct | 360 |
| | tca | 363 |
| SEQ ID NO: 84 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgccag agaggggtac | 300 |
| | gacagcagcg gctactacca cctggactat tggggccagg gcaccctggt cacagtttct | 360 |
| | tca | 363 |
| SEQ ID NO: 85 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgccag agtactac | 300 |
| | gacagcagcg gctactacca cctggtttat tggggccagg gcaccctggt cacagtttct | 360 |
| | tca | 363 |
| SEQ ID NO: 86 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgccag agtactac | 300 |
| | gacagcagcg gctactacca cctggagtat tggggccagg gcaccctggt cacagtttct | 360 |
| | tca | 363 |
| SEQ ID NO: 87 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgccag agtactac | 300 |
| | gacagcagcg gctactacca cctgacgtat tggggccagg gcaccctggt cacagtttct | 360 |
| | tca | 363 |
| SEQ ID NO: 88 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttagc gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgtgccag agagggctac | 300 |
| | gacagcagcg gctactacca cctggattat tggggccagg gcaccctggt tacagtgtca | 360 |
| | tca | 363 |
| SEQ ID NO: 89 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggacag gcggcagcac atattacgcc | 180 |
| | gactctgtga agggcagatt caccatcagc cggacaacaa gcaagaacac cctgtacctg | 240 |
| | cagatgaaca gcctgagagc cgaggacacc gccgtgtact attgtgccag agagggctac | 300 |
| | gacagcagcg gctactacca cctggattat tggggccagg gcaccctggt tacagtgtca | 360 |
| | tca | 363 |

| SEQ ID NO: | Type/sequence |
|---|---|
| SEQ ID NO: 90 | DNA; Artificial Sequence, antibody sequence |

```
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cggacaacaa gcaagaacac cctgtacctg   240
cagatgaaca gcctgagagc cgaggacacc gccgtgtact actgtgccaa agagggctac   300
gacagcagcg gctactacca cctggattat tggggccagg gcaccctggt tacagtgtca   360
tca                                                                 363
```

| SEQ ID NO: 91 | DNA; Artificial Sequence, antibody sequence |
|---|---|

```
gaagttcagc tgctggaatc tggcggcgga ctggttcaac ctggcggatc tctgagactg    60
agctgtgccg ccagcggctt cacctttagc gattacgcca tgagctgggt ccgacaggcc   120
cctggaaaag gccttgaatg ggtgtccgcc atcggcacag gcggcagcac atattacgcc   180
gactctgtga agggcagatt caccatcagc cggacaacaa gcaagaacac cctgtacctg   240
cagatgaaca gcctgagagc cgaggacacc gccgtgtact attgtgccag agagggctac   300
gacagcagcg gctactacca cctggattat tggggccagg gcaccctggt tacagtgtca   360
tca                                                                 363
```

| SEQ ID NO: 92 | DNA; Artificial Sequence, antibody sequence |
|---|---|

```
gaagttcagc tgctggaatc tggcggcgga ctggttcaac ctggcggatc tctgagactg    60
agctgtgccg ccagcggctt cacctttgat agctacgcca tgagctgggt ccgacaggcc   120
cctggaaaag gccttgaatg ggtgtccgcc atcggcacag gcggcagcac atattacgcc   180
gactctgtga agggcagatt caccatcagc cggacaacaa gcaagaacac cctgtacctg   240
cagatgaaca gcctgagagc cgaggacacc gccgtgtact attgtgccag agagggctac   300
gacagcagcg gctactacca cctggattat tggggccagg gcaccctggt tacagtgtca   360
tca                                                                 363
```

| SEQ ID NO: 93 | DNA; Artificial Sequence, antibody sequence |
|---|---|

```
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggcagcg gaggcagcac atattacgcc   180
gactctgtga agggcagatt caccatcagc cggacaacaa gcaagaacac cctgtacctg   240
cagatgaaca gcctgagagc cgaggacacc gccgtgtact attgtgccag agagggctac   300
gacagcagcg gctactacca cctggattat tggggccagg gcaccctggt tacagtgtca   360
tca                                                                 363
```

| SEQ ID NO: 94 | DNA; Artificial Sequence, antibody sequence |
|---|---|

```
cagtctgttc tgacacagcc tcctagcgcc tctggcacac tggacagag agtgaccatc     60
agctgtaccg gcagcagctc aatatcggc gccacctatg acgtgcactg gtatcagcag    120
ctgcctggca cagcccctaa actgctgatc tacagcaaca accagcggcc tagcggcgtg   180
cccgatagat tttctggcag caagagcggc acaagcgcca gcctggctat ctctggactg   240
agatctgagg acgaggccga ctactattgc gccgcctggg atgattctct gagcggctgg   300
gttttcggcg gaggcacaaa actgacagtg cta                                333
```

| SEQ ID NO: 95 | DNA; Artificial Sequence, antibody sequence |
|---|---|

```
cagtctgttc tgacacagcc tcctagcgcc tctggcacac tggacagag agtgaccatc     60
agctgtaccg gcagcagctc aatatcggc gccacctatg acgtgcactg gtatcagcag    120
ctgcctggca cagcccctaa actgctgatc tacagcaaca accagcggcc tagcggcgtg   180
cccgatagat tttctggcag caagagcggc acaagcgcca gcctggctat ctctggactg   240
agatctgagg acgaggccga ctactattgc gccgcctggg attggtctct gagcggctgg   300
gttttcggcg gaggcacaaa actgacagtg cta                                333
```

| SEQ ID NO: 96 | DNA; Artificial Sequence, antibody sequence |
|---|---|

```
cagtctgttc tgacacagcc tcctagcgcc tctggcacac tggacagag agtgaccatc     60
agctgtaccg gcagcagctc aatatcggc gccacctatg acgtgcactg gtatcagcag    120
ctgcctggca cagcccctaa actgctgatc tacagcaaca accagcggcc tagcggcgtg   180
cccgatagat tttctggcag caagagcggc acaagcgcca gcctggctat ctctggactg   240
agatctgagg acgaggccga ctactattgc tgggcctggg atgattctct gagcggctgg   300
gttttcggcg gaggcacaaa actgacagtg cta                                333
```

| SEQ ID NO: 97 | DNA; Artificial Sequence, antibody sequence |
|---|---|

```
cagtctgttc tgacacagcc tcctagcgcc tctggcacac tggacagag agtgaccatc     60
agctgtaccg gcagcagctc aatatcggc gccacctatg acgtgcactg gtatcagcag    120
ctgcctggca cagcccctaa actgctgatc tacagcaaca accagcggcc tagcggcgtg   180
cccgatagat tttctggcag caagagcggc acaagcgcca gcctggctat ctctggactg   240
agatctgagg acgaggccga ctactattgc gccgcctggg atgtttctct gagcggctgg   300
gttttcggcg gaggcacaaa actgacagtg cta                                333
```

| SEQ ID NO: 98 | DNA; Artificial Sequence, antibody sequence |
|---|---|

```
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cggacaacaa gcaagaacac cctgtacctg   240
cagatgaaca gcctgagagc cgaggacacc gccgtgtact attgcgccag agagtactac   300
gacagcagcg gctactacca cctggactat tggggccagg gcaccctggt cacagtttct   360
tcagccagca ccaagggccc cagcgtgttc cctctggccc ctagcagcaa gagcacatct   420
```

| SEQ ID NO: | Type/sequence | |
|---|---|---|
| | ggcggaacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccttgtc ctgcccccga actgctggga | 720 |
| | ggcccttccg tgttcctgtt ccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacggc | 960 |
| | aaagagtaca agtgcaaggt gtccaacaag gccctgcctg ccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aggcttcta cccctccgat | 1140 |
| | atcgccgtgg aatgggagag caacgccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 99 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cgggacaaca gcaagaacac cctgtacctg | 240 |
| | cagatgaaca gcctgagagc cgaggacacc gccgtgtact attgcgatag agagtactac | 300 |
| | gacagcagcg gctactacca cctggactat tggggccagg gcaccctggt cacagtttct | 360 |
| | tcagccagca ccaagggccc cagcgtgttc cctctggccc ctagcagcaa gagcacatct | 420 |
| | ggcggaacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccttgtc ctgcccccga actgctggga | 720 |
| | ggcccttccg tgttcctgtt ccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacggc | 960 |
| | aaagagtaca agtgcaaggt gtccaacaag gccctgcctg ccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aggcttcta cccctccgat | 1140 |
| | atcgccgtgg aatgggagag caacgccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 100 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cgggacaaca gcaagaacac cctgtacctg | 240 |
| | cagatgaaca gcctgagagc cgaggacacc gccgtgtact attgcgccag tgagtactac | 300 |
| | gacagcagcg gctactacca cctggactat tggggccagg gcaccctggt cacagtttct | 360 |
| | tcagccagca ccaagggccc cagcgtgttc cctctggccc ctagcagcaa gagcacatct | 420 |
| | ggcggaacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccttgtc ctgcccccga actgctggga | 720 |
| | ggcccttccg tgttcctgtt ccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacggc | 960 |
| | aaagagtaca agtgcaaggt gtccaacaag gccctgcctg ccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aggcttcta cccctccgat | 1140 |
| | atcgccgtgg aatgggagag caacgccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 101 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cgggacaaca gcaagaacac cctgtacctg | 240 |
| | cagatgaaca gcctgagagc cgaggacacc gccgtgtact attgcgccag agaggattac | 300 |
| | gacagcagcg gctactacca cctggactat tggggccagg gcaccctggt cacagtttct | 360 |
| | tcagccagca ccaagggccc cagcgtgttc cctctggccc ctagcagcaa gagcacatct | 420 |
| | ggcggaacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |

| SEQ ID NO: | Type/sequence | |
|---|---|---|
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccccttgtc ctgcccccga actgctggga | 720 |
| | ggcccttccg tgttcctgtt cccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacgcc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aggcttcta cccctccgat | 1140 |
| | atcgccgtgg aatgggagag caacggccag cccgagaaca actacaagac caccccccct | 1200 |
| | gtgctgaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 102 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cgggacaaca gcaagaacac cctgtacctg | 240 |
| | cagatgaaca gcctgagagc cgaggacacc gccgtgtact attgcgccag agaggggtac | 300 |
| | gacagcagcg gctactacca cctggactat tggggccagg gcaccctggt cacagtttct | 360 |
| | tcagccgca ccaagggccc cagcgtgttc cctctggccc ctagcagcaa gagcacatct | 420 |
| | ggcggaacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccccttgtc ctgcccccga actgctggga | 720 |
| | ggcccttccg tgttcctgtt cccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacgcc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aggcttcta cccctccgat | 1140 |
| | atcgccgtgg aatgggagag caacggccag cccgagaaca actacaagac caccccccct | 1200 |
| | gtgctgaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 103 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cgggacaaca gcaagaacac cctgtacctg | 240 |
| | cagatgaaca gcctgagagc cgaggacacc gccgtgtact attgcgccag agagtactac | 300 |
| | gacagcagcg gctactacca cctggtttat tggggccagg gcaccctggt cacagtttct | 360 |
| | tcagccgca ccaagggccc cagcgtgttc cctctggccc ctagcagcaa gagcacatct | 420 |
| | ggcggaacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccccttgtc ctgcccccga actgctggga | 720 |
| | ggcccttccg tgttcctgtt cccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacgcc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aggcttcta cccctccgat | 1140 |
| | atcgccgtgg aatgggagag caacggccag cccgagaaca actacaagac caccccccct | 1200 |
| | gtgctgaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 104 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cgggacaaca gcaagaacac cctgtacctg | 240 |
| | cagatgaaca gcctgagagc cgaggacacc gccgtgtact attgcgccag agagtactac | 300 |
| | gacagcagcg gctactacca cctggagtat tggggccagg gcaccctggt cacagtttct | 360 |
| | tcagccgca ccaagggccc cagcgtgttc cctctggccc ctagcagcaa gagcacatct | 420 |
| | ggcggaacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |

| SEQ ID NO: | Type/sequence | |
|---|---|---|
| | cccaagagct gcgacaagac ccacacctgt cccccttgtc ctgcccccga actgctggga | 720 |
| | ggcccttccg tgttcctgtt ccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacggc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca gaaccaggt gtccctgacc tgtctcgtga aaggcttcta ccctccgat | 1140 |
| | atcgccgtgg aatgggagag caacggccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 105 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgcgccag agagtactac | 300 |
| | gacagcagcg gctactacca cctggagtat tggggccagg gcaccctggt cacagtttct | 360 |
| | tcagccagca ccaagggccc cagcgtgttc cctctggccc ctagcagcaa gagcacatct | 420 |
| | ggcggaacag ccgccctggg ctgcctcgtg aaggactact tccccgagcc cgtgaccgtg | 480 |
| | tcctggaact ctggcgctct gacaagcggc gtgcacacct tccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt cccccttgtc ctgcccccga actgctggga | 720 |
| | ggcccttccg tgttcctgtt ccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacggc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca gaaccaggt gtccctgacc tgtctcgtga aaggcttcta ccctccgat | 1140 |
| | atcgccgtgg aatgggagag caacggccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 106 | DNA; Artificial Sequence, antibody sequence | |
| | gaagttcagc tgctggaatc tggcggcgga ctggttcaac ctggcggatc tctgagactg | 60 |
| | agctgtgccg ccagcggctt cacctttagc gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cggacaacaa gcaagaacac cctgtacctg | 240 |
| | cagatgaaca gcctgagagc cgaggacacc gccgtgtact attgtgccag agagggctac | 300 |
| | gacagcagcg gctactacca cctggattat tggggccagg gcaccctggt tacagtgtca | 360 |
| | tcagccagca ccaagggccc cagcgtgttc cctctggccc ctagcagcaa gagcacatct | 420 |
| | ggcggaacag ccgccctggg ctgcctcgtg aaggactact tccccgagcc cgtgaccgtg | 480 |
| | tcctggaact ctggcgctct gacaagcggc gtgcacacct tccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt cccccttgtc ctgcccccga actgctggga | 720 |
| | ggcccttccg tgttcctgtt ccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtggt gtccgtgctg acagtgctgc accaggactg gctgaacggc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca gaaccaggt gtccctgacc tgtctcgtga aaggcttcta ccctccgat | 1140 |
| | atcgccgtgg aatgggagag caacggccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 107 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggacacag gcggcagcac atattacgcc | 180 |
| | gactctgtga agggcagatt caccatcagc cggacaacaa gcaagaacac cctgtacctg | 240 |
| | cagatgaaca gcctgagagc cgaggacacc gccgtgtact attgtgccag agagggctac | 300 |
| | gacagcagcg gctactacca cctggattat tggggccagg gcaccctggt tacagtgtca | 360 |
| | tcagccagca ccaagggccc cagcgtgttc cctctggccc ctagcagcaa gagcacatct | 420 |
| | ggcggaacag ccgccctggg ctgcctcgtg aaggactact tccccgagcc cgtgaccgtg | 480 |
| | tcctggaact ctggcgctct gacaagcggc gtgcacacct tccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt cccccttgtc ctgcccccga actgctggga | 720 |
| | ggcccttccg tgttcctgtt ccccccaaag cccaaggaca ccctgatgat cagccggacc | 780 |

| SEQ ID NO: | Type/sequence | |
|---|---|---|
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtgct gtccgtgctg acagtgctgc accaggactg gctgaacggc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aaggcttcta cccctccgat | 1140 |
| | atcgccgtgg aatgggagag caacggccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 108 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggaacag gcggcggaac atattacgcc | 180 |
| | gacagcgtga agggcagatt caccatcagc cgggacaaca gcaagaacac cctgtacctg | 240 |
| | cagatgaaca gcctgagagc cgaggacacc gccgtgtact actgtgccaa agagggctac | 300 |
| | gacagcagcg gctactacca cctggattat tggggccagg cacccctggt tacagtgtca | 360 |
| | tcagccagca ccaagggccc cagcgtgttc cctctggccc ctagcagcaa gagcacatct | 420 |
| | ggcggaacag ccgccctggg ctgcctcgtg aaggactact tccccgagcc cgtgaccgtg | 480 |
| | tcctggaact ctggcgctct gacaagcggc gtgcacacct tccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccttgtc ctgccccga actgctggga | 720 |
| | ggcccttccg tgttcctgtt cccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtgct gtccgtgctg acagtgctgc accaggactg gctgaacggc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aaggcttcta cccctccgat | 1140 |
| | atcgccgtgg aatgggagag caacggccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 109 | DNA; Artificial Sequence, antibody sequence | |
| | gaagttcagc tgctggaatc tggcggcgga ctggttcaac ctggcggatc tctgagactg | 60 |
| | agctgtgccg ccagcggctt cacctttagc gattacgcca tgagctgggt ccgacaggcc | 120 |
| | cctggaaaag gccttgaatg ggtgtccgcc atcggcacag gcggcagcac atattacgcc | 180 |
| | gactctgtga agggcagatt caccatcagc cgggacaaca gcaagaacac cctgtacctg | 240 |
| | cagatgaaca gcctgagagc cgaggacacc gccgtgtact attgtgccag agagggctac | 300 |
| | gacagcagcg gctactacca cctggattat tggggccagg cacccctggt tacagtgtca | 360 |
| | tcagccagca ccaagggccc cagcgtgttc cctctggccc ctagcagcaa gagcacatct | 420 |
| | ggcggaacag ccgccctggg ctgcctcgtg aaggactact tccccgagcc cgtgaccgtg | 480 |
| | tcctggaact ctggcgctct gacaagcggc gtgcacacct tccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccttgtc ctgccccga actgctggga | 720 |
| | ggcccttccg tgttcctgtt cccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |
| | aacagcacct accgggtgct gtccgtgctg acagtgctgc accaggactg gctgaacggc | 960 |
| | aaagagtaca agtgcaaggt gtccaacaag gccctgcctg cccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aaggcttcta cccctccgat | 1140 |
| | atcgccgtgg aatgggagag caacggccag cccgagaaca actacaagac cacccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 110 | DNA; Artificial Sequence, antibody sequence | |
| | gaagttcagc tgctggaatc tggcggcgga ctggttcaac ctggcggatc tctgagactg | 60 |
| | agctgtgccg ccagcggctt cacctttgat agctacgcca tgagctgggt ccgacaggcc | 120 |
| | cctggaaaag gccttgaatg ggtgtccgcc atcggcacag gcggcagcac atattacgcc | 180 |
| | gactctgtga agggcagatt caccatcagc cgggacaaca gcaagaacac cctgtacctg | 240 |
| | cagatgaaca gcctgagagc cgaggacacc gccgtgtact attgtgccag agagggctac | 300 |
| | gacagcagcg gctactacca cctggattat tggggccagg cacccctggt tacagtgtca | 360 |
| | tcagccagca ccaagggccc cagcgtgttc cctctggccc ctagcagcaa gagcacatct | 420 |
| | ggcggaacag ccgccctggg ctgcctcgtg aaggactact tccccgagcc cgtgaccgtg | 480 |
| | tcctggaact ctggcgctct gacaagcggc gtgcacacct tccagccgt gctgcagagc | 540 |
| | agcggcctgt actctctgag cagcgtcgtg acagtgccca gcagctctct gggcacccag | 600 |
| | acctacatct gcaacgtgaa ccacaagccc agcaacacca aggtggacaa gaaggtggaa | 660 |
| | cccaagagct gcgacaagac ccacacctgt ccccttgtc ctgccccga actgctggga | 720 |
| | ggcccttccg tgttcctgtt cccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca agcctagaga ggaacagtac | 900 |

| SEQ ID NO: | Type/sequence | |
|---|---|---|
| | aacagcacct accgggtggt gtccgtgctg acagtgctgc accaggactg gctgaacggc | 960 |
| | aaagagtaca agtgcaaggt gtccaacaag gccctgcctg ccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aaggcttcta cccctccgat | 1140 |
| | atcgccgtgg aatgggagag caacgccag cccgagaaca actacaagac caccccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 111 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggcagcg gaggcagcac atattacgcc | 180 |
| | gactctgtga agggcagatt caccatcagc cggacaacaa gcaagaacac cctgtacctg | 240 |
| | cagatgaaca gcctgagagc cgaggacacc gccgtgtact attgtgccag agagggctac | 300 |
| | gacagcagcg gctactacca cctggattat tgggggcagg gcaccctggt tacagtgtca | 360 |
| | tcagccagca ccaaggcccc cagcgtgttc cctctggccc ctagcagcaa gagcacatct | 420 |
| | ggcggaacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |
| | agcggcctgt actctctgag cagcgtggtg acagtgccca gcagctctct gggcacccag | 600 |
| | acctacatct gcaacgtgaa ccacaagccc agcaacacca aggtggacaa gaaggttgaa | 660 |
| | cccaagagct gcgacaagac ccacacctgt cccccttgtc ctgcccccga actgctggga | 720 |
| | ggcccttccg tgttcctgtt ccccccaaag cccaaggaca ccctgatgat cagccggacc | 780 |
| | cccgaagtga cctgcgtggt ggtggatgtg tcccacgagg accctgaagt gaagttcaat | 840 |
| | tggtacgtgg acggcgtgga agtgcacaac gccaagacca gcctagaga ggaacagtac | 900 |
| | aacagcacct accgggtggt gtccgtgctg acagtgctgc accaggactg gctgaacggc | 960 |
| | aaagagtaca agtgcaaggt gtccaacaag gccctgcctg ccccatcga gaaaaccatc | 1020 |
| | agcaaggcca agggccagcc ccgcgaaccc caggtgtaca cactgccccc aagcagggac | 1080 |
| | gagctgacca agaaccaggt gtccctgacc tgtctcgtga aaggcttcta cccctccgat | 1140 |
| | atcgccgtgg aatgggagag caacgccag cccgagaaca actacaagac caccccccct | 1200 |
| | gtgctggaca gcgacggctc attcttcctg tacagcaagc tgaccgtgga caagtcccgg | 1260 |
| | tggcagcagg gcaacgtgtt cagctgcagc gtgatgcacg aggccctgca caaccactac | 1320 |
| | acccagaagt ccctgagcct gagccctggc | 1350 |
| SEQ ID NO: 112 | DNA; Artificial Sequence, antibody sequence | |
| | gaagttcagc tgctggaatc tggcggcgga ctggttcaac ctggcggatc tctgagactg | 60 |
| | agctgtgccg ccagcggctt caccttcgat gattacgcca tgagctgggt ccgacaggcc | 120 |
| | cctggaaaag gccttgaatg ggtgtccgcc atcggcagcg ggcgcagcac atattacgcc | 180 |
| | gactctgtga agggcagatt caccatcagc cggacaacaa gcaagaacac cctgtacctg | 240 |
| | cagatgaaca gcctgagagc cgaggacacc gccgtgtact attgtgccag agagggctac | 300 |
| | gacagcagcg gctactacca cctggattat tgggggcagg gcaccctggt tacagtgtca | 360 |
| | tcagccagca ccaaggcccc cagcgtgttc cctctggccc cttgtagcag aagcaccagc | 420 |
| | gagtctacag ccgccctggg ctgcctcgtg aaggactact ttcccgagcc cgtgaccgtg | 480 |
| | tcctggaact ctggcgctct gacaagcggc gtgcacacct ttccagccgt gctgcagagc | 540 |
| | agcggcctgt actctctgag cagcgtggtg acagtgccca gcagcagctct gggcacccag | 600 |
| | acctacacct gtaacgtgga ccacaagccc agcaacacca aggtggacaa gcgggtggaa | 660 |
| | tctaagtacg gccctccctg ccctccttgc ccagcccctg aatttctggg cggaccctcc | 720 |
| | gtgttcctgt tccccccaaa gcccaaggac accctgatga tcagccggac ccccgaagtg | 780 |
| | acctgcgtgg tggtggatgt gtcccaggaa gatcccgagg tgcagttcaa ttggtacgtg | 840 |
| | gacggcgtgg aagtgcacaa cgccaagacc aagcccagag gaacagtt caacagcacc | 900 |
| | taccgggtgg tgtccgtgct gacagtgctg caccaggact ggctgaacgg caaagagtac | 960 |
| | aagtgcaagg tgtccaacaa gggcctgccc agctccatcg agaaaaccat cagcaaggcc | 1020 |
| | aaggggccagc cccgcgaacc ccaggtgtac aactactgcc caagcagga agatgaccc | 1080 |
| | aagaaccagg tgtccctgac ctgtctcgtg aaaggcttct acccctccga tatcgccgtg | 1140 |
| | gaatgggaga gcaacgcca gcccgagaac aactacaaga ccaccccccc tgtgctggac | 1200 |
| | agcgacggct cattcttcct gtacagcaga ctgaccgtgg acaagagccg gtggcaggaa | 1260 |
| | ggcaacgtgt tcagctgcag cgtgatgcac gaggccctgc acaaccacta cacccagaag | 1320 |
| | tccctgtctc tgagcctggg c | 1341 |
| SEQ ID NO: 113 | DNA; Artificial Sequence, antibody sequence | |
| | agtctgttc tgacacagcc tcctagcgcc tctggcacac ctggacagag agtgaccatc | 60 |
| | agctgtaccg gcagcagctc caatatcggc gccacctatg acgtgcactg gtatcagcag | 120 |
| | ctgcctggca cagcccctaa actgctgatc tacagcaaca accagcggcc tagcggcgtg | 180 |
| | cccgatagat tttctggcag caagagcggc acaagcgcca gcctggctat ctctggactg | 240 |
| | agatctgagg acgaggccga ctactattgc gccgcctggg atgattctct gagcggctgg | 300 |
| | gttttcggcg gaggcacaaa actgacagtg ctaggccagc ctaaagccgc ccctagcgtg | 360 |
| | accctgttcc ctccaagcca cgaggaactg caggccacaa aggccaccct cgtgtgcctg | 420 |
| | atcagcgact tctatcctgg cgccgtgacc gtggcctgga aggccgatag ctctcctgtg | 480 |
| | aaggccggcg tggaaaccac caccccctagc aagcagagca acaacaaata cgccgccagc | 540 |
| | agctacctga gcctgacccc cgagcagtgg aagtcccaca tctccttacg ctgccaagtg | 600 |
| | acccacgagg gcagcaccgt ggaaaagaca gtggccccta ccgagtgcag c | 651 |
| SEQ ID NO: 114 | DNA; Artificial Sequence, antibody sequence | |
| | cagtctgttc tgacacagcc tcctagcgcc tctggcacac ctggacagag agtgaccatc | 60 |
| | agctgtaccg gcagcagctc caatatcggc gccacctatg acgtgcactg gtatcagcag | 120 |
| | ctgcctggca cagcccctaa actgctgatc tacagcaaca accagcggcc tagcggcgtg | 180 |
| | cccgatagat tttctggcag caagagcggc acaagcgcca gcctggctat ctctggactg | 240 |

| SEQ ID NO: | Type/sequence | |
|---|---|---|
| | agatctgagg acgaggccga ctactattgc gccgcctggg attggtctct gagcggctgg | 300 |
| | gttttcggcg gaggcacaaa actgacagtg ctaggccagc taaagccgc ccctagcgtg | 360 |
| | accctgttcc ctccaagcag cgaggaactg caggccaaca aggccaccct cgtgtgcctg | 420 |
| | atcagcgact tctatcctgg cgccgtgacc gtggcctgga aggccgatag ctctcctgtg | 480 |
| | aaggccggcg tggaaaccac caccccctagc aagcagagca acaacaaata cgccgccagc | 540 |
| | agctacctga gcctgacccc cgagcagtgg aagtcccaca gatcctacag ctgccaagtg | 600 |
| | acccacgagg gcagcaccgt ggaaaagaca gtggccccta ccgagtgcag c | 651 |
| SEQ ID NO: 115 | DNA; Artificial Sequence, antibody sequence | |
| | cagtctgttc tgacacagcc tcctagcgcc tctggcacac tggacagag agtgaccatc | 60 |
| | agctgtaccg gcagcagctc aatatcggc gccacctatg acgtgcactg gtatcagcag | 120 |
| | ctgcctggca cagcccctaa actgctgatc tacagcaaca ccagcggcc tagcggcctg | 180 |
| | cccgatagat ttctggcag caagagcggc acaagcgcca gcctggctat ctctggactg | 240 |
| | agatctgagg acgaggccga ctactattgc tgggcctggg atgattctct gagcggctgg | 300 |
| | gttttcggcg gaggcacaaa actgacagtg ctaggccagc taaagccgc ccctagcgtg | 360 |
| | accctgttcc ctccaagcag cgaggaactg caggccaaca aggccaccct cgtgtgcctg | 420 |
| | atcagcgact tctatcctgg cgccgtgacc gtggcctgga aggccgatag ctctcctgtg | 480 |
| | aaggccggcg tggaaaccac caccccctagc aagcagagca acaacaaata cgccgccagc | 540 |
| | agctacctga gcctgacccc cgagcagtgg aagtcccaca gatcctacag ctgccaagtg | 600 |
| | acccacgagg gcagcaccgt ggaaaagaca gtggccccta ccgagtgcag c | 651 |
| SEQ ID NO: 116 | DNA; Artificial Sequence, antibody sequence | |
| | cagtctgttc tgacacagcc tcctagcgcc tctggcacac tggacagag agtgaccatc | 60 |
| | agctgtaccg gcagcagctc aatatcggc gccacctatg acgtgcactg gtatcagcag | 120 |
| | ctgcctggca cagcccctaa actgctgatc tacagcaaca ccagcggcc tagcggcgtg | 180 |
| | cccgatagat ttctggcag caagagcggc acaagcgcca gcctggctat ctctggactg | 240 |
| | agatctgagg acgaggccga ctactattgc gccgcctggg atgtttctct gagcggctgg | 300 |
| | gttttcggcg gaggcacaaa actgacagtg ctaggccagc taaagccgc ccctagcgtg | 360 |
| | accctgttcc ctccaagcag cgaggaactg caggccaaca aggccaccct cgtgtgcctg | 420 |
| | atcagcgact tctatcctgg cgccgtgacc gtggcctgga aggccgatag ctctcctgtg | 480 |
| | aaggccggcg tggaaaccac caccccctagc aagcagagca acaacaaata cgccgccagc | 540 |
| | agctacctga gcctgacccc cgagcagtgg aagtcccaca gatcctacag ctgccaagtg | 600 |
| | acccacgagg gcagcaccgt ggaaaagaca gtggccccta ccgagtgcag c | 651 |
| SEQ ID NO: 117 | DNA; Artificial Sequence, antibody sequence | |
| | gagggctacg acagcagcgg ctactaccac ctggattat | 39 |
| SEQ ID NO: 118 | human plasmin; AA sequence | |
| | Glu Pro Leu Asp Asp Tyr Val Asn Thr Gln Gly Ala Ser Leu Phe Ser | |
| | Val Thr Lys Lys Gln Leu Gly Ala Gly Ser Ile Glu Glu Cys Ala Ala | |
| | Lys Cys Glu Glu Asp Glu Glu Phe Thr Cys Arg Ala Phe Gln Tyr His | |
| | Ser Lys Glu Gln Gln Cys Val Ile Met Ala Glu Asn Arg Lys Ser Ser | |
| | Ile Ile Ile Arg Met Arg Asp Val Val Leu Phe Glu Lys Lys Val Tyr | |
| | Leu Ser Glu Cys Lys Thr Gly Asn Gly Lys Asn Tyr Arg Gly Thr Met | |
| | Ser Lys Thr Lys Asn Gly Ile Thr Cys Gln Lys Trp Ser Ser Thr Ser | |
| | Pro His Arg Pro Arg Phe Ser Pro Ala Thr His Pro Ser Glu Gly Leu | |
| | Glu Glu Asn Tyr Cys Arg Asn Pro Asp Asn Asp Pro Gln Gly Pro Trp | |
| | Cys Tyr Thr Thr Asp Pro Glu Lys Arg Tyr Asp Tyr Cys Asp Ile Leu | |
| | Glu Cys Glu Glu Glu Cys Met His Cys Ser Gly Glu Asn Tyr Asp Gly | |
| | Lys Ile Ser Lys Thr Met Ser Gly Leu Glu Cys Gln Ala Trp Asp Ser | |
| | Gln Ser Pro His Ala His Gly Tyr Ile Pro Ser Lys Phe Pro Asn Lys | |
| | Asn Leu Lys Lys Asn Tyr Cys Arg Asn Pro Asp Arg Glu Leu Arg Pro | |
| | Trp Cys Phe Thr Thr Asp Pro Asn Lys Arg Trp Glu Leu Cys Asp Ile | |
| | Pro Arg Cys Thr Thr Pro Pro Pro Ser Ser Gly Pro Thr Tyr Gln Cys | |
| | Leu Lys Gly Thr Gly Glu Asn Tyr Arg Gly Asn Val Ala Val Thr Val | |
| | Ser Gly His Thr Cys Gln His Trp Ser Ala Gln Thr Pro His Thr His | |
| | Asn Arg Thr Pro Glu Asn Phe Pro Cys Lys Asn Leu Asp Glu Asn Tyr | |
| | Cys Arg Asn Pro Asp Gly Lys Arg Ala Pro Trp Cys His Thr Thr Asn | |
| | Ser Gln Val Arg Trp Glu Tyr Cys Lys Ile Pro Ser Cys Asp Ser Ser | |
| | Pro Val Ser Thr Glu Gln Leu Ala Pro Thr Ala Pro Pro Glu Leu Thr | |
| | Pro Val Val Gln Asp Cys Tyr His Gly Asp Gly Gln Ser Tyr Arg Gly | |
| | Thr Ser Ser Thr Thr Thr Thr Gly Lys Lys Cys Gln Ser Trp Ser Ser | |
| | Met Thr Pro His Arg His Gln Lys Thr Pro Glu Asn Tyr Pro Asn Ala | |
| | Gly Leu Thr Met Asn Tyr Cys Arg Asn Pro Asp Ala Asp Lys Gly Pro | |
| | Trp Cys Phe Thr Thr Asp Pro Ser Val Arg Trp Glu Tyr Cys Asn Leu | |
| | Lys Lys Cys Ser Gly Thr Glu Ala Ser Val Val Ala Pro Pro Pro Val | |
| | Val Leu Leu Pro Asp Val Glu Thr Pro Ser Glu Glu Asp Cys Met Phe | |
| | Gly Asn Gly Lys Gly Tyr Arg Gly Lys Arg Ala Thr Thr Val Thr Gly | |
| | Thr Pro Cys Gln Asp Trp Ala Ala Gln Glu Pro His Arg His Ser Ile | |
| | Phe Thr Pro Glu Thr Asn Pro Arg Ala Gly Leu Glu Lys Asn Tyr Cys | |
| | Arg Asn Pro Asp Gly Asp Val Gly Gly Pro Trp Cys Tyr Thr Thr Asn | |
| | Pro Arg Lys Leu Tyr Asp Tyr Cys Asp Val Pro Gln Cys Ala Ala Pro | |
| | Ser Phe Asp Cys Gly Lys Pro Gln Val Glu Pro Lys Lys Cys Pro Gly | |
| | Arg | |

-continued

| SEQ ID NO: | Type/sequence |
|---|---|
| SEQ ID NO: 115 | human plasmin; AA sequence<br>Val Val Gly Gly Cys Val Ala His Pro His Ser Trp Pro Trp Gln Val<br>Ser Leu Arg Thr Arg Phe Gly Met His Phe Cys Gly Gly Thr Leu Ile<br>Ser Pro Glu Trp Val Leu Thr Ala Ala His Cys Leu Glu Lys Ser Pro<br>Arg Pro Ser Ser Tyr Lys Val Ile Leu Gly Ala His Gln Glu Val Asn<br>Leu Glu Pro His Val Gln Glu Ile Glu Val Ser Arg Leu Phe Leu Glu<br>Pro Thr Arg Lys Asp Ile Ala Leu Leu Lys Leu Ser Ser Pro Ala Val<br>Ile Thr Asp Lys Val Ile Pro Ala Cys Leu Pro Ser Pro Asn Tyr Val<br>Val Ala Asp Arg Thr Glu Cys Phe Ile Thr Gly Trp Gly Glu Thr Gln<br>Gly Thr Phe Gly Ala Gly Leu Leu Lys Glu Ala Gln Leu Pro Val Ile<br>Glu Asn Lys Val Cys Asn Arg Tyr Glu Phe Leu Asn Gly Arg Val Gln<br>Ser Thr Glu Leu Cys Ala Gly His Leu Ala Gly Gly Thr Asp Ser Cys<br>Gln Gly Asp Ser Gly Gly Pro Leu Val Cys Phe Glu Lys Asp Lys Tyr<br>Ile Leu Gln Gly Val Thr Ser Trp Gly Leu Gly Cys Ala Arg Pro Asn<br>Lys Pro Gly Val Tyr Val Arg Val Ser Arg Phe Val Thr Trp Ile Glu<br>Gly Val Met Arg Asn Asn |

EXAMPLES

Example 1: Generation of Antibody TPP-12387 from BioInvent Antibody Library

A fully human antibody phage display library (BioInvent n-CoDeR Fab lambda library) was used to isolate human monoclonal antibodies by selection against soluble biotinylated antigens, which are human alpha2-Antiplasmin from human and from rabbit origin.

The human alpha2-Antiplasmin was used from a commercial source (antibodies online; catalogue number ABIN2544306) whereas the rabbit antigen was produced in house by recombinant expression and purification. For this, the cDNA from rabbit alpha2-Antiplasmin was cloned into standard expression vector and HEK293 cells were transiently transfected with this construct using 293fectin transfection reagent (Invitrogen, catalogue number 12347-019) following manufactures instructions. Expressed rabbit alpha2-Antiplasmin were purified from the cell culture supernatant via Ni-IMAC and size exclusion chromatography.

Antigens were biotinylated using a Sulfo-NHS-LC-Biotin kit (Thermo Scientific, catalogue number A39257). Free biotin was removed from the reactions by dialysis against the appropriate buffer.

For the panning procedure the following protocol was applied: Streptavidin-coupled Dynabeads M-280 (Invitrogen, catalogue number 11205D) were coated for one hour at room temperature (RT) with the biotinylated antigen (1 tube) and the biotinylated off-target (3 tubes), respectively. Dynabeads were washed and subsequently blocked for 1 h at RT with end-over-end rotation. For depletion of off-target binders the blocked phage library was added to the blocked off-target loaded Dynabeads and incubated for 10 min at room temperature with end-over-end rotation. This depletion step was repeated 2 times. The depleted phage library was added to the blocked target loaded Dynabeads and incubated for 60 min at RT with end-over-end rotation. After stringent washing (3× in blocking buffer and 9× in PBS (150 mM NaCl; 8 mM Na2HPO4; 1.5 mM KH2PO4; adjusted to pH=7.4-7.6) with 0.05% Tween-20) Dynabeads with Fab-phages binding specifically to the coated target were directly used to infect *Escherichia coli* strain HB101. Subsequently the phages are amplified in *Escherichia coli* strain HB101 using M13KO7 Helper Phage (Invitrogen, catalogue number 18311019). In the following selection rounds the target concentration was decreased to augment the selection pressure for high affinity binders.

During panning of this library, four different selection strategies were carried out:

Strategy I was designed in such a way to identify antibodies exhibiting binding activity towards the full length human alpha2-Antiplasmin and rabbit alpha2-Antiplasmin, respectively, both lacking the N-terminus. A depletion step was included using a biotinylated irrelevant protein.

Strategy II aimed for antibodies recognizing Plasmin binding site of alpha2-Antiplasmin. Like in Strategy I and in order to increase the probability of success, a depletion step was included using an alpha2-Antiplasmin variant missing the Plasmin-binding site as antigen.

In two further strategies (strategy III and IV) a biotinylated linear and a biotinylated cyclic peptide, respectively, representing the so-called Reactive Center Loop (RCL) of alpha2-Antiplasmin, were used. In both cases, an irrelevant biotinylated protein was used for the depletion step.

A detailed overview of the panning strategies is given in FIG. 1.

Example 2: Recombinant DNA Constructs and Expression, Purification and Quantification of Fabs and Full-Length Antibodies Production in HEK293-6E Cells Fabs as well as full length antibodies were produced by mammalian cell culture using transiently transfected HEK293-6E cells. Heavy and light chains were cloned into a suitable expression vector system. Cells were incubated for 3-4 days. Supernatants were collected and Fabs and antibodies were purified as described.

Purification and Quantification of Fabs and Antibodies

Antibodies were purified by Protein A chromatography (ThermoFischer, catalogue number A26455) according to manufacturer's instructions.

The antibodies, antigen binding portions, or derivatives thereof were recovered from the culture medium by using standard protein purification methods.

Fabs were purified from sterile filtered mammalian cell supernatants using a 3-step research downstream process. As capture step a "Capture Select IgG-CH1" affinity column (ThermoFisher, catalogue number 494320005) equilibrated in PBS pH 7.4 was used. After washing in wash buffer (PBS pH 7.4) for 10 column volumes, elution of the Fab was achieved using glycine 0.1 M pH 3.0 (6 CV). Upon neutralization with Tris Base a size exclusion chromatography (GE Healthcare, Superdex 200, catalogue number GE29321905) was used for buffer exchange into DPBS pH 7.4 and aggregate removal. Analytical size exclusion chromatography demonstrated that no dimer was present in the resulting batch.

For quantification of full-length antibodies, the anti-human IgG Fc specific antibody (Sigma, catalogue number 12136) was coated at a concentration of 5 µg/ml over night at 4° C. to 384-well microtiter plates (Nunc). Solutions containing the IgGs of interest were added at different concentrations an incubated for 1 hour at room temperature. For detection, the detection antibody A0170 (Sigma) and as substrate Amplex Red were added. Fluorescence was monitored at 535/590 nm using a SpectraFluorplus Reader (Tecan).

For quantification of antibody variants like Fabs, the Human Kappa ELISA Kit (Abcam, catalogue number ab157709) was used according to the manufacturer's instructions.

Example 3: Enzyme-Linked Immunosorbent Assay (ELISA) for Testing Anti-Alpha2-Antiplasmin Binding Activity A standard ELISA format was used for analyzing the binding affinity of Fabs of this invention to human and rabbit alpha-2-Antiplasmin, respectively. Antigens were coated to black 384 well Maxisorp microtiter plates (Nunc; catalogue number 460518), diluted to a concentration of 1 µg/ml in 1× Coating Buffer (Candor Bioscience; catalogue number 121125). Plates were incubated overnight at 4° C. After overnight incubation, plates were washed 2× with 50 µl/well using PBS+0.05% Tween 20. Following this, 50 µl/well of blocking buffer (Smart Block; Candor Bioscience; catalogue number 113500) was added and the plates were incubated for 1 hour at room temperature. Afterwards, plates were washed for 3× using 50 µl/well of a PBS+0.05% Tween 20 buffer. Fabs of this invention were added at different concentrations in a final volume of 30 µl/well. Plates were incubated for 1 hour at room temperature. Following this incubation step, plates were washed for 3× using 50 µl/well of a PBS+0.05% Tween 20 buffer. For the detection of bound Fabs and full-length antibodies, the anti-Human Lambda Light Chains (Bound and Free)-Peroxidase antibody (Sigma; catalogue number A5175) was diluted by the factor of 1:10.000 in 10% Blocking Buffer. 30 µl/well of this diluted detection antibody was added and plates are incubated for 1 hour at room temperature. Following this incubation step, plates were washed for 3× using 50 µl/well of a PBS+0.05% Tween 20 buffer. As substrate, a mixture of 30 µl/well of 1:1000 diluted Amplex red (Invitrogen; catalogue number 12222; stock solution 10 mM in DMSO) and 1:10.000 of Hydrogen peroxide (Merck; catalogue number 107209; 30% stock solution) was added and the plates incubated for 20 minutes in the dark.

For measurement, the Infinite f500 reader (Tecan) was used. Measurement mode: Fluorescence; Top reading; Ex 535 nm; Em 590 nm.

From an overall number of $2 \times 10^{10}$ Fab variants screened, 2944 variants were selected as potential candidates to be tested for binding human and rabbit alpha2-Antiplasmin, respectively.

As described in Example 2, HEK293 cells were transiently transfected. Resulting supernatants were used directly without further purification or dilution for testing their ability to bind the human and rabbit antigen. From these 2944 Fabs, 88 candidates exhibiting distinct sequences showed the requested cross-species binding activity towards the two antigens.

For conformation, 88 variants of this invention were re-tested for their binding capacity. For this, supernatants of transfected cells were diluted in Phosphate-buffered Saline (PBS) by the factor of 1:1.5, 1:4.5, 1:13.5, 1:40.5, 1:121.5, 1:364.5, 1:1093.5. These diluted samples were tested for binding human and rabbit alpha-2-Antiplasmin.

One dose response curve is shown in FIG. 4 as an example from two to three independent experiments performed in quadruplicate. For the three independent experiments, the EC50 value for the binding activity of TPP-12387 towards human alpha2-Antiplasmin were as follows: 1.2E-07 M (as shown in FIG. 4), 1.0E-07 M, and 1.3E-07 M, respectively. The binding activity towards rabbit alpha2-Antiplasmin were 6.0E-09 M (as shown in FIG. 4), 6.07E-09 M and 6.2E-09 M, respectively.

Example 4: Biochemical Assay for Testing Selected Candidates for Alpha2-Antiplasmin Function Blocking Activity For testing the anti-alpha2-Antiplasmin molecules for functional blocking activity, Fabs or full-length antibodies were pre-incubated with 1 nM of human alpha2-Antiplasmin (antibodies online; catalogue number ABIN2544306) or in house produced rabbit alpha2-Antiplasmin or in house produced cynomolgus alpha2-Antiplasmin in a buffer consisting of 50 mM TRIS-HCl (GIBCO; catalogue number 15567-027 (50 mM)), 100 mM NaCl (Sigma; catalogue number S7653), 5 mM CaCl2) (Sigma; catalogue number 21115-100ML), 0.1% Albumin 0.1% (Sigma; BSA, catalogue number A4503-100g), pH 7,4 for 20 minutes at 37° C.

Afterwards, human Plasmin (Haematologic Technologies INC.; catalogue number HCPM0140) at a final concentration of 400 µM and the fluorogenic substrate I-1275 (Bachem; MeOSuc-Ala-Phe-Lys-AMC trifluoroacetate salt; catalogue number I-1275 (stock: 10 mM in DMSO)) at a final concentration of 50 µm were added and the reaction was incubated for 1 hour at 37° C. This reaction was carried out in 384 well microtiter plates (Nunc; catalogue number 262260). The fluorogenic signals were measured at the following conditions: modus fluorescence top reading, Ex 360 nM, Em 465 nm, Ex bandwidth 5 nm, Em bandwidth 5 nm.

For determination of dose dependencies of Fabs and/or full-length antibodies function blocking activity, the concentrations of these molecules were measured as described above. Different concentrations of Fabs and/or full-length antibodies starting at a defined concentration, followed by 1:3 or 1:4 dilution steps, were pre-incubated with 1 nM of human, cynomolgus, or rabbit alpha2-Antiplasmin, respectively.

The 88 Fab candidates were tested for function blocking activity in single-point measurement on human and rabbit alpha2-Antiplasmin, meaning that from the supernatants resulting from transiently transfected HEK293 cells the maximal possible volume was added to the activity assay. Hereby, 17 Fabs were identified showing at least a reduction of alpha2-Antiplasmin activity of ca. 30%.

In a next step, these 17 Fabs were reformatted into the full length IgG1 antibody format. 12 of these showed reasonable expression rates.

According to the method described in Example 3, these 12 antibodies were tested for ability to bind human and rabbit alpha2-Antiplasmin in a dose-dependent manner. Data generated were analyzed using the GraphPadPrism software. The binding activities of the antibodies were calculated as EC50 values. Two to three independent experiments were performed in quadruplicate.

In a next step, these 12 full length antibodies were re-tested dose-dependently for blocking the activity towards human and rabbit alpha2-Antiplasmin.

Based on its binding activity and function blocking activity towards human and rabbit alpha2-Antiplasmin antibody TPP-12387 was chosen for further testing and optimization. FIG. 2 shows the binding activity of the Fab fragment corresponding to TPP-12387 for human and rabbit alpha2-Antiplasmin as determined in Example 3. FIG. 3 shows the function blocking activity of the Fab fragment corresponding to TPP-12387 towards human and rabbit alpha2-Antiplasmin as determined in Example 4. FIG. 4 shows the binding activity of the IgG1 antibody TPP-12387 for human and rabbit alpha2-Antiplasmin as determined in a binding assay described in Example 3. FIG. 5 shows the function blocking activity of the IgG1 antibody TPP-12387 towards human and rabbit alpha2-Antiplasmin as determined in a function blocking assay described in Example 4. One dose response curve for the neutralizing activity of TPP-12387 on human and rabbit alpha2-Antiplasmin is shown in FIG. 5 as an example of two to three independent experiments performed in quadruplicate. For the three independent experiments, the IC50 value for the function blocking activity of TPP-12387 towards human alpha2-Antiplasmin were as follows: 1.7E-07 M (as shown in FIG. 5), 1.8E-07 M, and 1.8E-07 M, respectively. The binding activity towards rabbit alpha2-Antiplasmin were 1.4E-08 M (as shown in FIG. 4), 1.3E-08 M and 1.5E-08 M.

In a next step, TPP-12387 was tested for its binding activity as well as for its function blocking activity towards cynomolgus alpha2-Antiplasmin. Cynomolgus alpha2-Antiplasmin was made in the same way as the rabbit alpha2-Antiplasmin. Values of the binding activity as well as its function blocking activity of TPP-12387 towards cynomolgus alpha2-Antiplasmin are shown in FIG. 6. One dose response curve for the binding and function blocking activity of antibody TPP-12387 on Cynomolgus alpha2-Antiplasmin is shown in FIG. 6 as example of two to three independent experiments performed in quadruplicate. Hereby, the EC50 values for the binding activity of TPP-12387 towards Cynomolgus alpha2-Antiplasmin was 9.0E-08 M (as shown in FIG. 6A) and 9.0E-08 M in a second, independent experiment, and the IC50 for the function blocking activity of Cynomolgus alpha2-Antiplasmin was 1.6E-07 M (as shown in FIG. 6B) and 1.6E-07 M in a second experiment.

Example 5: Affinity Optimization of Lead Antibody TPP-12387

Antibody TPP-12387 was subjected to lead optimization procedures aiming to optimize its affinity and to increase its functional efficiency.

Affinity maturation was done by a first single mutation gathering round followed by recombination of the most affinity- and potency-increasing amino acid exchanges followed by germlining and sequence optimization campaign. For mutation gathering NNK (N=A or G or C or T, K=G or T) randomizations at the following individual amino acid positions were generated by site directed mutagenesis using synthetic oligonucleotides including NNK codon-diversification of residues AAWDDSLSGWV (residues 91 to 101, comprising CDR-L3), and AREYYDSSGYYHLDY (residues 96 to 110, comprising CDR-H3 residues 98-110 plus two additional amino acids flanking the CDR at its N-terminal site).

The resulting single NNK libraries were sequenced and 139 amino acid exchange variants of TPP-12387 for CDR-L3 and 156 CDR-H3 were identified (see Table 3.1 and 3.2).

TABLE 3.1

List of exchanges in the CDRL3 of TPP-12387

| A91 | A92 | W93 | D94 | D95 | S96 | L97 | S98 | G99 | W100 | V101 |
|-----|-----|-----|-----|-----|-----|-----|-----|-----|------|------|
| R | R | A | A | A | A | R | A | R | R | A |
| D | N | R | N | R | R | D | R | N | N | |
| Q | D | C | C | N | D | C | N | D | C | |
| E | C | E | Q | C | C | G | D | C | E | |
| G | G | G | E | E | E | H | C | E | G | |
| H | H | L | G | G | I | K | E | I | I | |
| I | I | K | L | I | M | M | G | L | L | |
| L | L | M | K | L | T | F | I | K | F | |
| M | K | S | S | M | W | P | L | F | S | |
| F | M | T | T | P | Y | S | M | P | Y | |
| S | S | Y | W | S | V | T | W | S | V | |
| W | T | V | V | T | | W | Y | W | D | |
| Y | Y | | | W | | V | V | Y | C | |
| V | V | | | V | | | | V | E | |
| | | | | | | | | | G | |
| | | | | | | | | | I | |
| | | | | | | | | | L | |
| | | | | | | | | | K | |
| | | | | | | | | | F | |

TABLE 3.2

List of exchanges in the CDRH3 plus two N-terminally adjacent amino acids of TPP-12387

| A96 | R97 | E98 | Y99 | Y100 | D101 | S102 | S103 | G104 | Y105 | Y106 | H107 | L108 | D109 | Y110 |
|---|---|---|---|---|---|---|---|---|---|---|---|---|---|---|
| R | N | R | A | R | A | R | A | A | A | A | C | C | E | C |
| N | Q | N | R | D | R | N | R | N | D | R | D | D | F | E |
| D | G | C | D | G | H | C | N | C | G | N | E | E | G | F |
| H | I | L | E | L | I | E | E | E | I | D | K | F | K | G |
| L | L | K | G | K | L | G | G | H | L | Q | L | G | L | I |
| K | S | F | H | W | F | L | L | L | I | I | M | I | M | L |
| M | Y | P | L | V | S | K | K | K | S | L | N | M | S | Q |
| S | V | T | K | | | F | M | M | T | M | Q | P | T | R |
| T | | V | M | | | T | P | P | W | S | R | S | V | S |
| V | | | P | | | W | T | S | V | T | S | T | W | V |
| | | | S | | | Y | W | W | | | T | W | Y | X |
| | | | T | | | V | | V | | | V | | | |
| | | | W | | | | | | | | W | | | |

All variants were expressed by transient transfection of the mammalian cell line HEK293 and resulting expression supernatants were directly tested for their binding ability as well as their function blocking activity towards human alpha2-Antiplasmin.

Those variants showing higher binding and function blocking activity than the antibody TPP-12387 were expressed one more time in HEK293 cells, the antibodies were purified and quantified as described in Example 2 and re-tested in direct comparison with the parental variant TPP-12387 for their binding ability and their function blocking ability towards human alpha2-Antiplasmin.

By this, 5 exchanges within the CDR-L3 and 7 exchanges within CDR-H3 were identified with improved activity compared to the parental antibody TPP-12387. These 11 single substitution variants with improved affinity and functional efficiency were recombined in one recombination library based on TPP-12387. Here oligonucleotides were generated to introduce selected mutations or the corresponding wild type amino acid at each selected position. Library construction was performed using sequential rounds of overlap extension PCR. The final PCR product was ligated into a mammalian IgG1 expression vector and variants were sequenced.

Antibodies generated in this recombination library were TPP-14290, TPP-14291, TPP-14292, TPP-14293, TPP-14294, TPP-14295, TPP-14296, TPP-14297, TPP-14298, TPP-14299, TPP-14300, TPP-14301, TPP-14302, TPP-14303, TPP-14304, TPP-14305, TPP-14306, TPP-14307, TPP-14308, TPP-14309, TPP-14310, TPP-14311, TPP-14312, TPP-14313, TPP-14314, TPP-14315, TPP-14316, TPP-14317, TPP-14318, TPP-14319, TPP-14320, TPP-14322, TPP-14323, TPP-14324.

As described in Example 2 antibodies were purified from supernatants and their concentration determined. Next, antibodies were tested for their ability of binding human alpha2-Antiplasmin and their ability of blocking human alpha2-Antiplasmin (as described in Example 3 and 4).

Antibodies TPP-14293, TPP-14298, TPP-14303, TPP-14305, TPP-14308, TPP-14313, TPP-14314, TPP-14318, TPP-14323 represent the most improved recombined mutants of TPP-12387 as identified as being most potent in terms of binding human alpha2-Antiplasmin and blocking the activity of human alpha2-Antiplasmin. Binding as well as activity data for these antibodies are given in FIG. 7.

According to the methods described in Example 3 and Example 4, antibodies TPP-14323, TPP-14318, TPP-14314, TPP-14313, TPP-14308, TPP-14305, TPP-14303, TPP-14298, and TPP-14293 were tested for their ability to bind to and to block the activity of human alpha2-Antiplasmin in a dose-dependent manner. For each antibody, one dose response curve from two to three independent experiments performed in quadruplicate is shown as example in FIG. 7A to FIG. 7R. (see Table 3.3)

TABLE 3.3

Binding activity EC [M] and function blocking activity IC50 [M] of the three independent experiments

| antibody | binding activity [EC50 M] | | | function blocking activity [IC50 M] | | |
|---|---|---|---|---|---|---|
| | 1st exp*. | 2nd exp. | 3rd exp. | 1st exp*. | 2nd exp. | 3rd exp. |
| TPP-14293 | 1.2E−08 | 1.2E−08 | 1.2E−08 | 4.6E−08 | 4.8E−08 | 5.0E−08 |
| TPP-14298 | 5.7E−09 | 6.2E−08 | 5.8E−08 | 3.1E−08 | 3.7E−08 | 4.0E−08 |
| TPP-14303 | 2.4E−08 | 2.9E−08 | 2.7E−05 | 8.5E−08 | 8.9E−08 | 9.4E−08 |
| TPP-14305 | 1.5E−08 | 1.6E−08 | 1.6E−08 | 6.4E−08 | 6.9E−08 | 6.6E−08 |
| TPP-14308 | 5.7E−09 | 6.1E−08 | 6.0E−08 | 2.4E−09 | 3.0E−08 | 2.4E−08 |
| TPP-14313 | 3.3E−09 | 3.5E−08 | 3.4E−08 | 1.2E−08 | 2.0E−08 | 1.3E−08 |
| TPP-14314 | 8.1E−09 | 8.2E−08 | 8.4E−08 | 6.8E−08 | 7.3E−08 | 6.9E−08 |
| TPP-14318 | 5.7E−09 | 5.9E−08 | 6.1E−08 | 2.0E−08 | 2.5E−08 | 2.2E−08 |
| TPP-14323 | 7.0E−09 | 7.3E−08 | 7.1E−08 | 2.0E−08 | 2.0E−08 | 2.9E−08 |

*Shown in FIG. 7

Example 6: Risk Reduction for Sequence-Based Immunogenicity

In order to reduce the risk for sequence-based immunogenicity antibody TPP-14308 was chosen for further optimization. For this, amino acids which differ from the nearest germline sequence were exchanged, the corresponding cDNAs were synthesized, HEK293 cells were transiently transfected, the expressed antibodies of this invention were quantified but not purified and tested for their ability to bind human alpha2-Antiplasmin and to block the function of human alpha2-Antiplasmin.

Outcome of this approach were 47 antibodies.

Most germline exchanges show only minor improvement in both functionalities.

Although only amino acids within the framework sequences and CDRH1 and CDRH2 have been exchanged, surprisingly, compared to antibody TPP-14308, 6 variants were identified exhibiting even higher binding activity and/or improved function blocking activity.

Dose response curves of binding and function blocking activities of these variants are given in FIG. 8.

TABLE 3.5

Binding activity EC [M] and function blocking activity IC50 [M] of two to three independent experiments

| | binding activity [EC50 M] | | | function blocking activity [IC50 M] | | |
|---|---|---|---|---|---|---|
| | 1st exp.* | 2nd exp. | 3rd exp. | 1st exp*. | 2nd exp. | 3rd exp. |
| TPP-17041 | 1.9E−10 | 2.3E−10 | | 5.6E−10 | 6.9E−10 | |
| TPP-17044 | 3.7E−11 | 4.9E−11 | 1.0E−10 | 1.7E−10 | 2.3E−10 | 2.0E−10 |
| TPP-17045 | 8.5E−11 | 1.2E−10 | 1.1E−10 | 4.0E−10 | 5.0E−10 | |
| TPP-17048 | 1.8E−10 | 3.6E−10 | | 2.8E−10 | 3.9E−10 | 3.0E−10 |
| TPP-17051 | 1.1E−10 | 1.6E−10 | 2.2E−10 | 3.3E−10 | 4.4E−10 | |
| TPP-17053 | 5.2E−10 | 5.8E−10 | 6.3E−10 | 4.3E−10 | 6.5E−10 | 5.0E−10 |

*Shown in FIG. 8

In a next step, the most active antibody TPP-17044 was expressed in larger amounts and was purified and quantified. The purified and quantified antibody was retested for its function blocking activity of human, cynomolgus, and rabbit alpha2-Antiplasmin. Results are shown in FIG. 9. One dose response curve from two to three independent experiments performed in quadruplicate is shown as an example. Function blocking activity of TPP-17044 for human alpha2-Antiplasmin was 4.4E-10 M (as shown in FIG. 9A), and 5.4E-10 M for the second and 5E-10 M for the third experiment. For the inhibition of Cynomolgus alpha2-Antiplasmin values were 4.6E-10 M (FIG. 9B), 4.9E-10 M for the second experiment and 5.1E-10 M for the third experiment. Rabbit alpha2-Antiplasmin was blocked in its activity by TPP-17044 with IC50 values of 2.7E-08 M (FIG. 9C), 3.6E-08 M for a second experiment and 2.9E-08 M for a third experiment.

Finally, in order to further minimize the theoretic risk of an immunogenic reaction TPP-17044 was re-cloned into the human IgG4 Fc version of human antibodies. The resulting antibody TPP-17928 was again tested for its function blocking activity on human, cynomolgus, and rabbit alpha2-Antiplasmin. Results are shown in FIG. 10. One dose response curve from two to three independent experiments performed in quadruplicate is shown as an example. Function blocking activity of TPP-17928 for human alpha2-Antiplasmin was 1.1E-10 M (as shown in FIG. 10A), and 1.6E-10 M for the second experiment. For the inhibition of Cynomolgus alpha2-Antiplasmin values were 2.6E-10 M (FIG. 10B), 3.4E-10 M for the second experiment and 2.9E-10 M for the third experiment. Rabbit alpha2-Antiplasmin was blocked in its activity by TPP-17928 with IC50 values of 1.5E-08 M (FIG. 10C), 1.9E-10 M for a second experiment and 1.6E-10 M for a third experiment.

Example 7: In Vitro Clot Lysis

Human blood was collected by venipuncture from healthy subjects who had not been medicated during the last 10 days (procedure approved by Ethics Committee "Ärztekammer Nordrhein", #2017029). Blood was collected into plastic tubes containing ⅟10 volume of 3.8% trisodium citrate. Platelet-Poor Plasma (PPP) was obtained by immediate centrifugation at 2500 g for 10 min at 4° C., and stored at −20° C.

For all experiments plasma from at least n=3 independent donors was used. Clot lysis assay was performed as followed. Frozen plasma was thawed (at 37° C. for 30 min) and mixed with defined concentrations of the test compounds [varying between 0.015 μM-1 μM] or solvent only as control in a 96-well plate. On a second 96-well plate CaCl$_2$) (Sigma; catalogue number 21115-100ML) [final concentration: 12.5 mM] as clot inducer and low dose tPA (Actilyse®, Boehringer Ingelheim) [final concentration 0.3 μg/ml] as lysis initiator were prepared. After short incubation of test compound in plasma (5 min at 37° C.) the mixture was added to the second plate and directly transferred to a microplate reader (Tecan infinite 200 Pro) to measure absorption (at 405 nm, 37° C., 1/min) over time for 3 h. For final determination of lysis time reduction tPA-induced lysis time was set as 100% (individually for every donor plasma) and lysis time reduction was calculated for each test compound in a dose-response curve.

For analysis of rabbit plasma, whole blood from male New Zealand White rabbits was obtained via venipuncture and prepared and used as described above for human plasma.

As shown in FIG. 11, antibody TPP-17928 reduces the tPA-induced clot lysis time in a dose-dependent manner in human and in rabbit plasma, respectively. For human plasma, value for the function blocking activity of TPP-17928 was 2.5E-07 M and for rabbit plasma 2.3E-07 M.

Example 8: In Vivo Testing of TPP-17928 in an Acute Pulmonary Embolism in Rabbits To study the effects of the anti-anti-alpha2-Antiplasmin antibody of this invention on clot dissolution in pulmonary embolism a rabbit in vivo model was used.

Male New Zealand White Rabbits were anesthetized by an intramuscular injection of Xylazine/Ketamine (5 mg/kg+ 40 mg/kg, Sigma, catalogue numbers X1126 and K2753). Ears, neck and the left hind limb (in the area of the femoral triangle) were shaved. To keep the rabbit anesthetized an infusion of Xylazine/Ketamine (80 ml+800 ml ad 60 ml NaCl 0.9%) with 5 ml/h was given via the ear vein. The rabbits were placed on a heating plate and kept at 37° C. for the whole experimental time. The left vena femoralis was cannulated for compound application and blood sampling, the right vena jugularis for clot injection.

For preparation of fluorescently labeled clots, rabbit platelet poor plasma was mixed with ALEXA 488 fluorescently-labeled human Fibrinogen (Thermo Fisher Scientific, catalogue number F13191). Clotting was initiated by adding 2.5 µl Batroxobin [20 U/ml] (LOXO, catalogue number 101-04) and 2.5 µl $CaCl_2$) [0.1 mM] to 45 µl of plasma mixture; final clot volume 50 µl containing 75 µg of fluorescently-labeled Fibrinogen.

After clot maturation (30 min at 37° C.) 2 clots/kg bodyweight were injected into the jugular vein of the anesthetized rabbit which led to embolization of clots in the lung. 30 min after embolization treatment was started by bolus i.v. injection of either saline, antibody TPP-17928, tPA or a combination of antibody TPP-17928 and tPA. Over a time period of 360 min blood samples were taken from the rabbits' vein and plasma fluorescence was analyzed as indirect parameter of clot dissolution. Simultaneously, directly after treatment onset and 300 min post treatment the ear bleeding time was determined. To access the ear bleeding time an incision of app. 3-5 mm was made with a scalpel blade in parallel to the outer edge of the ear (close to the outer ear vein). Every 30 sec it was proven whether the incision was still bleeding by gently dabbing with a small filter tip directly besides the incision.

As shown in FIG. 12A, treatment of pulmonary embolism in rabbits with antibody TPP-17928 led to an increased clot dissolution which is considered over time comparable to tPA treatment. TPP-17928 dose-dependently increases the plasma fluorescence (2.1-fold increase of AUC in comparison to control) as indirect measurement parameter for clot dissolution. Combination of the 15 mg/kg of TPP-17928 with a low concentration of tPA (0,125 mg/kg) accelerates clot dissolution even faster. tPA-treatment also shows a dose-dependent effect on clot dissolution (FIG. 12B).

Similar results with an increase of plasma fluorescence as parameter for clot dissolution were observed for 30 mg/kg TPP-12387 (2.6-fold increase of AUC in comparison to control) and 15 mg/kg TPP-17044 (2.1-fold increase of AUC in comparison to control) in further rabbit pulmonary embolism experiments.

Determination of Ear Bleeding Time

In the above described experiment, simultaneously, the ear bleeding time was determined. Directly after treatment application (at 0 min) the ear bleeding time was measured as follows. To access the ear bleeding time an incision of app. 3-5 mm was made with a scalpel blade in parallel to the outer edge of the ear (close to the outer ear vein). Every 30 sec it was proven whether the incision was still bleeding by gently dabbing with a small filter tip directly besides the incision. Ear bleeding time unravels a superior safety profile for anti-α2AP-antibody treatment in comparison to tPA treatment. Directly after compound administration there is no increase in bleeding time detectable for none of the used antibody concentrations whereas tPA treatment especially at the highest concentration of 1 mg/kg shows an immediate effect on ear bleeding time prolongation. Surprisingly, also the combination of the 15 mg/kg of TPP-17928 in combination with the low dose of tPA (0.125 mg/kg) does not lead to a significant increase in bleeding time. This clearly proofs for superiority of the anti-α2AP-antibody treatment over tPA treatment in respect of adverse events, in this case bleeding. Results are shown in FIG. 13. Bleeding time prolongation for tPA [1 mg/kg] 2.03-fold, for TPP-17928 [15 mg/kg] 0.95-fold and for the combination of tPA [0.125 mg/kg]+TPP-17928 [15 mg/kg] 1.56-fold. Similar results with no effect on ear bleeding time prolongation were observed for 30 mg/kg TPP-12387 (0.91-fold) and 15 mg/kg TPP-17044 (1.05-fold) in further rabbit ear bleeding experiments.

Example 9: Determination of the Binding Affinity of Antibodies of the Invention

Binding assays were performed on a Biacore T200 instrument at 25° C. with a protein G sensor chip and assay buffer HBS-EP+. Antibodies were captured to ~150 RU and analytes were used at concentrations between 1.56 and 200 nM for full kinetics. As interaction partner, alpha2-Antiplasmin from human, cynomolgus and rabbit was used. Regeneration was performed with glycine-HCl pH 1.5. Kinetic parameters were derived by fitting experimental sensorgrams to a 1:1 Langmuir binding model. Results are given in Table 4.

TABLE 4

Affinity values of antibodies of the invention.

| Ligand | Analyte | $K_D$ [M] |
| --- | --- | --- |
| TPP-12387 | Human | 1.8 E−07 |
|  | Rabbit | 4.3 E−08 |
|  | Cyno | 1.0 E−07 |
| TPP-14308 | Human | 3.9 E−09 |
|  | Rabbit | 7.8 E−09 |
|  | Cyno | 3.1 E−09 |
| TPP-17041 | Human | 1.1 E−08 |
|  | Rabbit | 1.8 E−08 |
|  | Cyno | 7.6 E−09 |
| TPP-17044 | Human | 5.1 E−09 |
|  | Rabbit | 5.4 E−09 |
|  | Cyno | 3.8 E−09 |
| TPP-17045 | Human | 1.4 E−08 |
|  | Rabbit | 4.9 E−08 |
|  | Cyno | 1.1 E−08 |
| TPP-17048 | Human | 7.9 E−09 |
|  | Rabbit | 9.7 E−09 |
|  | Cyno | 5.8 E−09 |
| TPP-17051 | Human | 1.8 E−08 |
|  | Rabbit | 1.7 E−08 |
|  | Cyno | 1.3 E−08 |
| TPP-17053 | Human | 1.1 E−08 |
|  | Rabbit | 2.8 E−08 |
|  | Cyno | 8.7 E−09 |
| TPP-17928 | Human | 1 E−09 |
|  | Rabbit | 5 E−09 |
|  | Cyno | 2 E−09 |

Example 10: Direct Comparison of the Function Blocking Activity of 77A3 and of Antibodies of the Invention In order to compare the blocking activity of the test antibody 77A3 with the test antibodies of the invention against the A2AP activity the function blocking assay as described in detail in example 4 was used. In brief, the test antibodies were pre-incubated at a concentration of 6.1E-11—3.0E-08 M and .0E-06 M, respectively with A2AP. After adding plasmin and I-1275 (a fluorogenic substrate for plasmin serine protease activity) to the assay the fluorescence signal as a measure for the serine protease activity of plasmin was determined.

An increase of 77A3 concentration up to 0.03 µM resulted into an increase of fluorescence signal due to the cleavage of the fluorogenic substrate I-1275 by plasmin. However, a further increase in 77A3 concentration resulted in a decrease of fluorescence signal. That indicates that, testing the antibody 77A3 in the biochemical assay described in Example 4 up to a concentration of 0.03 µM leads to blockade of alpha2-Antiplasmin and that a further increase in 77A3 antibody concentration leads to a decline in plasmin activity, resulting in a complete inhibition of plasmin activity at a 77A3 concentration of 1 µM (FIG. 14A). For the antibodies of the invention, the following IC50 values for the function blocking activity of A2AP were generated: TPP-17041-6.4 E-10 M, TPP-17044-3.9 E-10 M, TPP-17045-1.4 E-10 M, TPP-17048-1.2 E-09 M, TPP-17051-3.3 E-10 M, TPP-17053-1.5 E-10 M. None of the antibodies of the invention tested up to a concentration of 1 µM results in a decrease of fluorescence signal indicating that testing antibodies of the invention have no impact on plasmin activity (FIGS. 14B-14G).

Example 11: Biochemical Assay for Testing Antibodies of the Invention for Inhibiting the Proteolytic Activity of Plasmin To further investigate the surprising results obtained for the antibody 77A3 in Example 10 anti-alpha2-Antiplasmin antibodies of the invention as well as the antibody 77A3 were tested for inhibiting activity in a biochemical Plasmin assay. For this, different concentrations of antibodies starting at a defined concentration, followed by 1:2 or 1:3 dilution steps, were incubated for 1 hour at 37° C. with 400 µM of human Plasmin obtained from Haematologic Technologies INC.; catalogue number HCPM0140) and the fluorogenic substrate I-1275 (Bachem; MeOSuc-Ala-Phe-Lys-AMC trifluoroacetate salt; catalogue number I-1275 (stock: 10 mM in DMSO)) at a final concentration of 1 µM. This reaction was carried out in 384 well microtiter plates (Nunc; catalogue number 262260). The fluorogenic signals were measured at the following conditions: modus fluorescence top reading, Ex 360 nM, Em 465 nm, Ex bandwidth 5 nm, Em bandwidth 5 nm.

As shown in FIG. 16, TPP-17928 (exemplarily shown for all antibodies of the invention) has no impact on the biochemical activity whereas 77A3 blocks the proteolytic activity of Plasmin with an IC50 value of 1.7 µM.

TABLE 5

Inhibition of plasmin proteolytic activity by 77A3 and test antibodies of the invention.

| antibody | IC$_{50}$ [M] |
|---|---|
| 77A3* | 1.7 E-06 |
| TPP-12387 | >1.0 E-05 |
| TPP-14293 | >5.0 E-06 |
| TPP-14298 | >5.0 E-06 |
| TPP-14303 | >1.0 E-05 |
| TPP-14305 | >2.0 E-06 |
| TPP-14308 | >5.0 E-06 |
| TPP-14313 | >5.0 E-06 |
| TPP-14314 | >2.0 E-06 |
| TPP-14318 | >1.0 E-05 |
| TPP-14323 | >1.0 E-5 |
| TPP-17041 | >1 E-05 |
| TPP-17044 | >1.0 E-05 |
| TPP-17045 | >1.0 E-05 |
| TPP-17048 | >1.0 E-05 |
| TPP-17051 | >1.0 E-05 |
| TPP-17053 | >1.0 E-05 |
| TPP-17928* | >1.0 E-05 |

*dose response curve from two to three independent experiments performed in duplicates are shown as example in Figure 16 for 77A3 and TPP-17928.

Example 12: Epitope Mapping of TPP-12387 and 77A3

Epitope mapping was performed by the company PEPperPRINT (Heidelberg, Germany) by using the PEPperCHIP® Peptide Microarray platform.

For linear epitope mappings, the antigen sequence was translated into overlapping linear 15 amino acid peptides with a peptide-peptide overlap of 14 amino acids. The resulting peptide microarrays contained 491 different peptides printed in duplicate.

For the conformational epitope mappings, the antigen sequence was translated into overlapping 7, 10 and 13 amino acid peptides with peptide-peptide overlaps of 6, 9 and 12 amino acids. After peptide synthesis, all peptides were cyclized via a thioether linkage between a C-terminal cysteine side chain and an appropriately modified N-terminus. The resulting conformational peptide microarrays contained 1,488 different cyclic constrained peptides printed in duplicate.

Microarray were blocked by using Rockland blocking buffer MB-070 (30 min before the first assay), antibody incubation was performed in Incubation buffer consisting of PBS, pH 7.4 with 0.05% (linear epitope mappings) or 0.005% (conformational epitope mappings) Tween 20 with 10% blocking buffer.

Following incubation, arrays were washed using PBS, pH 7.4 with 0.05% (linear epitope mappings) or 0.005% (conformational epitope mappings) Tween 20. Arrays were washed 3×1 min (linear epitope mappings) or 2×10 sec (conformational epitope mappings).

Antibodies were incubated on the Microarray in concentrations of 1 µg/ml, 10 µg/ml and 100 µg/ml in incubation buffer. Incubation time was 16 h at 4° C. and shaking at 140 rpm.

As control, the mouse monoclonal anti-HA (12CA5) DyLight800 was used at a dilution of 1:2000; this detection antibody was incubated on the Microarray at 45 min staining in incubation buffer at room temperature.

As secondary antibody the goat anti-human IgG (Fc) DyLight680 was used at a dilution of 1:5000. This detection antibody was incubated on the Microarray at 45 min staining in incubation buffer at room temperature.

Signals were detected by using the LI-COR Odyssey Imaging System with a scanning offset 0.65 mm, a resolution 21 µm, and scanning intensities of 7/7 (red=700 nm/green=800 nm).

Quantification of spot intensities and peptide annotation were based on the 16-bit gray scale tiff files at scanning intensities of 7/7 that exhibit a higher dynamic range than the 24-bit colorized tiff files. Microarray image analysis was done with PepSlide® Analyzer. A software algorithm was used to break down fluorescence intensities of each spot into raw, foreground and background signal, and calculated averaged median foreground intensities and spot-to-spot deviations of spot duplicates. Based on averaged median foreground intensities, an intensity map was generated and interactions in the peptide map highlighted by an intensity color code with red for high and white for low spot intensities. Averaged spot intensities of the assays were plotted with the antibody samples against the antigen sequence from the N- to the C-terminus to visualize overall spot intensities and signal-to-noise ratios. The intensity plots were correlated with peptide and intensity maps as well as with visual inspection of the microarray scans to identify the epitopes of the tested antibodies.

Pre-staining of a linear and a conformational peptide microarray with secondary goat anti-human IgG (Fc) DyLight680 antibody (1:5000) and control mouse monoclonal anti-HA (12CA5) DyLight800 antibody (1:2000) did not show any background interaction with the linear or cyclic constrained peptides of the antigen. In contrast incubation with the antibodies of interest resulted in the following observations:

As shown in table 6, TPP-12387 showed a high signal-to-noise ratio against peptides with the consensus motif SRMSLSS, which corresponds to amino acid 402-408 of SEQ ID NO: 1 which is located in the reactive center loop of A2AP (amino acid 400-412 of Seq ID NO: 1).

In contrast, for the antibody 77A3, a very weak signal-to-noise ratio against peptides with the basic consensus motif RPTKVRLPK was identified, that corresponds to amino acid 330-338 of SEQ ID NO: 1. For this part of A2AP no distinct have been described.

TABLE 6

A2AP binding sites for TPP-12387 and 77A3

| peptide | sequence | signal-to-noise-ratio at 1 µg/ml | signal-to-noise-ratio at 10 µg/ml | signal-to-noise-ratio at 100 µg/ml |
|---|---|---|---|---|
| TPP-12387 | SRMSLSS | 659.0 | 2,255.0 | |
| 77A3 | RPTKVRLPK | 11.5 | 40.0 | 134.0 |

---

What is claimed is:

1. An isolated antibody or antigen-binding fragment thereof capable of binding to alpha 2 antiplasmin (A2AP) and inhibiting the activity of A2AP, comprising:
a heavy chain antigen-binding region that comprises an H-CDR1 comprising SEQ ID NO: 6, an H-CDR2 comprising SEQ ID NO: 8, and an H-CDR3 comprising SEQ ID NO: 13 and a light chain antigen-binding region that comprises an L-CDR1 comprising SEQ ID NO: 9, an L-CDR2 comprising SEQ ID NO: 10, and an L-CDR3 comprising SEQ ID NO:18.

2. The isolated antibody or antigen-binding fragment according to claim 1, comprising a variable heavy chain domain comprising SEQ ID NO: 32 and a variable light chain domain comprising SEQ ID NO: 38.

3. The isolated antibody or antigen-binding fragment according to claim 2, which is a human, humanized or chimeric antibody or antigen-binding fragment.

4. The isolated antibody or antigen-binding fragment according to claim 1, wherein the isolated antibody is an IgG antibody.

5. The isolated antibody or antigen-binding fragment according to claim 4, comprising a heavy chain comprising SEQ ID NO: 55 and a light chain comprising SEQ ID NO: 57.

6. The isolated antibody or antigen-binding fragment according to claim 5, wherein the IgG antibody is an IgG1 or an IgG4 antibody.

7. The isolated antibody or antigen-binding fragment according to claim 5, which is a human, humanized or chimeric antibody or antigen-binding fragment.

8. The isolated antibody or antigen-binding fragment according to claim 4, wherein the IgG antibody is an IgG1 or an IgG4 antibody.

9. The isolated antibody or antigen-binding fragment according to claim 4, wherein the antigen-binding fragment is selected from the group consisting of an scFv, Fab, Fab' fragment, and a F(ab')2 fragment.

10. The isolated antibody or antigen-binding fragment according to claim 1, which is an scFv, Fab, Fab' fragment or a F(ab')2 fragment.

11. The isolated antibody or antigen-binding fragment according to claim 1, which is a monoclonal antibody or antigen-binding fragment.

12. The isolated antibody or antigen-binding fragment according to claim 1, which is a human, humanized or chimeric antibody or antigen-binding fragment.

13. An antibody conjugate, comprising the isolated antibody or antigen binding fragment according to claim 1.

14. A pharmaceutical composition comprising the isolated antibody or antigen-binding fragment according to claim 1, or an antibody conjugate comprising the isolated antibody or antigen binding fragment according to claim 1.

15. A kit comprising the isolated antibody or antigen-binding fragment according to claim 1, a conjugate thereof, or a pharmaceutical composition comprising the isolated antibody or antigen-binding fragment, the conjugate, or the pharmaceutical composition, and instructions for use.

* * * * *

SEQUENCE LISTING

```
Sequence total quantity: 119
SEQ ID NO: 1              moltype = AA  length = 491
FEATURE                   Location/Qualifiers
source                    1..491
                          mol_type = protein
                          organism = Homo sapiens
SEQUENCE: 1
MALLWGLLVL SWSCLQGPCS VFSPVSAMEP LGRQLTSGPN QEQVSPLTLL KLGNQEPGGQ   60
TALKSPPGVC SRDPTPEQTH RLARAMMAFT ADLFSLVAQT STCPNLILSP LSVALALSHL  120
ALGAQNHTLQ RLQQVLHAGS GPCLPHLLSR LCQDLGPGAF RLAARMYLQK GFPIKEDFLE  180
QSEQLFGAKP VSLTGKQEDD LANINQWVKE ATEGKIQEFL SGLPEDTVLL LLNAIHFQGF  240
WRNKFDPSLT QRDSFHLDEQ FTVPVEMMQA RTYPLRWFLL EQPEIQVAHF PFKNNMSFVV  300
LVPTHFEWNV SQVLANLSWD TLHPPLVWER PTKVRLPKLY LKHQMDLVAT LSQLGLQELF  360
QAPDLRGISE QSLVVSGVQH QSTLELSEVG VEAAAATSIA MSRMSLSSFS VNRPFLFFIF  420
EDTTGLPLFV GSVRNPNPSA PRELKEQQDS PGNKDFLQSL KGFPRGDKLF GPDLKLVPPM  480
EEDYPQFGSP K                                                     491

SEQ ID NO: 2              moltype = AA  length = 491
FEATURE                   Location/Qualifiers
source                    1..491
                          mol_type = protein
                          organism = Oryctolagus cuniculus
SEQUENCE: 2
MVLLRGLLVL SLSCLQGPCA VLPPVSAMEP VGRQLTSGQS QEKLPPLALL KLVNQELHGQ   60
TALKKSPGDC RETPTPEQTR RLAQAMMAFT TDLFSLVVQA STSPNLVLSP LSVALALSHL  120
ALGAQNHTLQ RLQQVLHADS GPCLPHLLSH LCRNLGPGAF RLAARMYLQK GFPIKEDFLK  180
LSEQLFGAKP VSLTGRQEED LVNINQWVKE ATEGKIEDFL SELPDSTVLL LLNAIHFQGF  240
WRSKFDPSLT QRDSFHLDEQ FTVPVDMMQA HKYPLRWFLL EQPEIQVAQF PFKNNMSFVV  300
LVPTNFEWNV SQVLSNLSWD ILHQPSLRER PTKVQLPKLL LKHQLDLVTT LSQLGLQELF  360
LAPDLRGISD EGLVVSSVQH QSTLELNEAG VEAAAATSTA MSRMSLSSFS VNRPFLFFIL  420
EDTIDLPIFV GIVRNPNPSA QPERKEQQDS PDHRDPSQPQ KSFPHGDKLF SPDLKLAPPS  480
EEDYPQLSSP K                                                     491

SEQ ID NO: 3              moltype = AA  length = 491
FEATURE                   Location/Qualifiers
source                    1..491
                          mol_type = protein
                          organism = Macaca fascicularis
SEQUENCE: 3
MALFWGLLVL SWSCLQGPLS VFSPVSAMEP LGWQLTSGPN QEKVPPLTLL KLGNQEPGGQ   60
TALKSLPGIC SRDPTPEQTR RLAQAMMAFT ADLFSLVAQT STCPNLILSP LSVALALSHL  120
ALGAQNHTLQ RLQQVLHAGS GPCLPHLLSR LCQNMGPGAF RLAARMYLQK GFPIKEDFLE  180
QSERLFGAKP VSLTGKQEDD LANINQWVKE ATEGKIPEFL SELPEDTVLL LLNAIHFQGF  240
WRSKFDPSLT QRDSFHLDEQ FTVPVEMMQA RTYPLRWFML EQPEIQVAHF PFKNNMSFVV  300
LVPTHFEWNV SQVLANLSWD TLYPPSVWER PTKVRLPKLY LKHQMDLMAT LSRLGLQELF  360
QAPDLRGISE QSLVVSGVQH QSTLELSEVG VEAAAATSIA MSRMSLSSFS VNRPFLFFIF  420
EDTTGLPLFV GSVRNPNPSA PRELKEQQDS PGDKDFLHSL KAGPRGDKLF GPDLKLAPPL  480
EEDYPELGSP K                                                     491

SEQ ID NO: 4              moltype = AA  length = 13
FEATURE                   Location/Qualifiers
REGION                    1..13
                          note = antibody sequence
VAR_SEQ                   2
                          note = Xaa can be any naturally occuring amino acid
VAR_SEQ                   12
                          note = Xaa can be any naturally occuring amino acid
source                    1..13
```

```
                              mol_type = protein
                              organism = synthetic construct
SEQUENCE: 4
EXYDSSGYYH LXY                                                                  13

SEQ ID NO: 5                  moltype = AA  length = 11
FEATURE                       Location/Qualifiers
REGION                        1..11
                              note = antibody sequence
VAR_SEQ                       1
                              note = Xaa can be any naturally occurring amino acid
VAR_SEQ                       5
                              note = Xaa can be any naturally occurring amino acid
source                        1..11
                              mol_type = protein
                              organism = synthetic construct
SEQUENCE: 5
XAWDXSLSGW V                                                                    11

SEQ ID NO: 6                  moltype = AA  length = 5
FEATURE                       Location/Qualifiers
REGION                        1..5
                              note = antibody sequence
source                        1..5
                              mol_type = protein
                              organism = synthetic construct
SEQUENCE: 6
DYAMS                                                                            5

SEQ ID NO: 7                  moltype = AA  length = 16
FEATURE                       Location/Qualifiers
REGION                        1..16
                              note = antibody sequence
source                        1..16
                              mol_type = protein
                              organism = synthetic construct
SEQUENCE: 7
AIGTGGGTYY ADSVKG                                                               16

SEQ ID NO: 8                  moltype = AA  length = 16
FEATURE                       Location/Qualifiers
REGION                        1..16
                              note = antibody sequence
source                        1..16
                              mol_type = protein
                              organism = synthetic construct
SEQUENCE: 8
AIGTGGSTYY ADSVKG                                                               16

SEQ ID NO: 9                  moltype = AA  length = 14
FEATURE                       Location/Qualifiers
REGION                        1..14
                              note = antibody sequence
source                        1..14
                              mol_type = protein
                              organism = synthetic construct
SEQUENCE: 9
TGSSSNIGAT YDVH                                                                 14

SEQ ID NO: 10                 moltype = AA  length = 7
FEATURE                       Location/Qualifiers
REGION                        1..7
                              note = antibody sequence
source                        1..7
                              mol_type = protein
                              organism = synthetic construct
SEQUENCE: 10
SNNQRPS                                                                          7

SEQ ID NO: 11                 moltype = AA  length = 13
FEATURE                       Location/Qualifiers
REGION                        1..13
                              note = antibody sequence
source                        1..13
                              mol_type = protein
                              organism = synthetic construct
SEQUENCE: 11
EYYDSSGYYH LDY                                                                  13
```

```
SEQ ID NO: 12           moltype = AA  length = 13
FEATURE                 Location/Qualifiers
REGION                  1..13
                        note = antibody sequence
source                  1..13
                        mol_type = protein
                        organism = synthetic construct
SEQUENCE: 12
EDYDSSGYYH LDY                                                          13

SEQ ID NO: 13           moltype = AA  length = 13
FEATURE                 Location/Qualifiers
REGION                  1..13
                        note = antibody sequence
source                  1..13
                        mol_type = protein
                        organism = synthetic construct
SEQUENCE: 13
EGYDSSGYYH LDY                                                          13

SEQ ID NO: 14           moltype = AA  length = 13
FEATURE                 Location/Qualifiers
REGION                  1..13
                        note = antibody sequence
source                  1..13
                        mol_type = protein
                        organism = synthetic construct
SEQUENCE: 14
EYYDSSGYYH LVY                                                          13

SEQ ID NO: 15           moltype = AA  length = 13
FEATURE                 Location/Qualifiers
REGION                  1..13
                        note = antibody sequence
source                  1..13
                        mol_type = protein
                        organism = synthetic construct
SEQUENCE: 15
EYYDSSGYYH LEY                                                          13

SEQ ID NO: 16           moltype = AA  length = 13
FEATURE                 Location/Qualifiers
REGION                  1..13
                        note = antibody sequence
source                  1..13
                        mol_type = protein
                        organism = synthetic construct
SEQUENCE: 16
EYYDSSGYYH LTY                                                          13

SEQ ID NO: 17           moltype = AA  length = 11
FEATURE                 Location/Qualifiers
REGION                  1..11
                        note = antibody sequence
source                  1..11
                        mol_type = protein
                        organism = synthetic construct
SEQUENCE: 17
AAWDDSLSGW V                                                            11

SEQ ID NO: 18           moltype = AA  length = 11
FEATURE                 Location/Qualifiers
REGION                  1..11
                        note = antibody sequence
source                  1..11
                        mol_type = protein
                        organism = synthetic construct
SEQUENCE: 18
AAWDWSLSGW V                                                            11

SEQ ID NO: 19           moltype = AA  length = 11
FEATURE                 Location/Qualifiers
REGION                  1..11
                        note = antibody sequence
source                  1..11
                        mol_type = protein
                        organism = synthetic construct
SEQUENCE: 19
WAWDDSLSGW V                                                            11
```

```
SEQ ID NO: 20            moltype = AA   length = 11
FEATURE                  Location/Qualifiers
REGION                   1..11
                         note = antibody sequence
source                   1..11
                         mol_type = protein
                         organism = synthetic construct
SEQUENCE: 20
AAWDVSLSGW V                                                                  11

SEQ ID NO: 21            moltype = AA   length = 5
FEATURE                  Location/Qualifiers
REGION                   1..5
                         note = antibody sequence
source                   1..5
                         mol_type = protein
                         organism = synthetic construct
SEQUENCE: 21
SYAMS                                                                          5

SEQ ID NO: 22            moltype = AA   length = 16
FEATURE                  Location/Qualifiers
REGION                   1..16
                         note = antibody sequence
source                   1..16
                         mol_type = protein
                         organism = synthetic construct
SEQUENCE: 22
AIGSGGSTYY ADSVKG                                                             16

SEQ ID NO: 23            moltype = AA   length = 121
FEATURE                  Location/Qualifiers
REGION                   1..121
                         note = antibody sequence
source                   1..121
                         mol_type = protein
                         organism = synthetic construct
SEQUENCE: 23
EVQLLESGGG LVQPGGSLRL SCAASGFTFD DYAMSWVRQA PGKGLEWVSA IGTGGGTYYA             60
DSVKGRFTIS RDNSKNTLYL QMNSLRAEDT AVYYCAREYY DSSGYYHLDY WGQGTLVTVS            120
S                                                                           121

SEQ ID NO: 24            moltype = AA   length = 121
FEATURE                  Location/Qualifiers
REGION                   1..121
                         note = antibody sequence
source                   1..121
                         mol_type = protein
                         organism = synthetic construct
SEQUENCE: 24
EVQLLESGGG LVQPGGSLRL SCAASGFTFD DYAMSWVRQA PGKGLEWVSA IGTGGGTYYA             60
DSVKGRFTIS RDNSKNTLYL QMNSLRAEDT AVYYCDREYY DSSGYYHLDY WGQGTLVTVS            120
S                                                                           121

SEQ ID NO: 25            moltype = AA   length = 121
FEATURE                  Location/Qualifiers
REGION                   1..121
                         note = antibody sequence
source                   1..121
                         mol_type = protein
                         organism = synthetic construct
SEQUENCE: 25
EVQLLESGGG LVQPGGSLRL SCAASGFTFD DYAMSWVRQA PGKGLEWVSA IGTGGGTYYA             60
DSVKGRFTIS RDNSKNTLYL QMNSLRAEDT AVYYCASEYY DSSGYYHLDY WGQGTLVTVS            120
S                                                                           121

SEQ ID NO: 26            moltype = AA   length = 121
FEATURE                  Location/Qualifiers
REGION                   1..121
                         note = antibody sequence
source                   1..121
                         mol_type = protein
                         organism = synthetic construct
SEQUENCE: 26
EVQLLESGGG LVQPGGSLRL SCAASGFTFD DYAMSWVRQA PGKGLEWVSA IGTGGGTYYA             60
DSVKGRFTIS RDNSKNTLYL QMNSLRAEDT AVYYCAREDY DSSGYYHLDY WGQGTLVTVS            120
S                                                                           121
```

```
SEQ ID NO: 27            moltype = AA  length = 121
FEATURE                  Location/Qualifiers
REGION                   1..121
                         note = antibody sequence
source                   1..121
                         mol_type = protein
                         organism = synthetic construct
SEQUENCE: 27
EVQLLESGGG LVQPGGSLRL SCAASGFTFD DYAMSWVRQA PGKGLEWVSA IGTGGGTYYA  60
DSVKGRFTIS RDNSKNTLYL QMNSLRAEDT AVYYCAREGY DSSGYYHLDY WGQGTLVTVS 120
S                                                                121

SEQ ID NO: 28            moltype = AA  length = 121
FEATURE                  Location/Qualifiers
REGION                   1..121
                         note = antibody sequence
source                   1..121
                         mol_type = protein
                         organism = synthetic construct
SEQUENCE: 28
EVQLLESGGG LVQPGGSLRL SCAASGFTFD DYAMSWVRQA PGKGLEWVSA IGTGGGTYYA  60
DSVKGRFTIS RDNSKNTLYL QMNSLRAEDT AVYYCAREYY DSSGYYHLVY WGQGTLVTVS 120
S                                                                121

SEQ ID NO: 29            moltype = AA  length = 121
FEATURE                  Location/Qualifiers
REGION                   1..121
                         note = antibody sequence
source                   1..121
                         mol_type = protein
                         organism = synthetic construct
SEQUENCE: 29
EVQLLESGGG LVQPGGSLRL SCAASGFTFD DYAMSWVRQA PGKGLEWVSA IGTGGGTYYA  60
DSVKGRFTIS RDNSKNTLYL QMNSLRAEDT AVYYCAREYY DSSGYYHLEY WGQGTLVTVS 120
S                                                                121

SEQ ID NO: 30            moltype = AA  length = 121
FEATURE                  Location/Qualifiers
REGION                   1..121
                         note = antibody sequence
source                   1..121
                         mol_type = protein
                         organism = synthetic construct
SEQUENCE: 30
EVQLLESGGG LVQPGGSLRL SCAASGFTFD DYAMSWVRQA PGKGLEWVSA IGTGGGTYYA  60
DSVKGRFTIS RDNSKNTLYL QMNSLRAEDT AVYYCAREYY DSSGYYHLTY WGQGTLVTVS 120
S                                                                121

SEQ ID NO: 31            moltype = AA  length = 121
FEATURE                  Location/Qualifiers
REGION                   1..121
                         note = antibody sequence
source                   1..121
                         mol_type = protein
                         organism = synthetic construct
SEQUENCE: 31
EVQLLESGGG LVQPGGSLRL SCAASGFTFS DYAMSWVRQA PGKGLEWVSA IGTGGGTYYA  60
DSVKGRFTIS RDNSKNTLYL QMNSLRAEDT AVYYCAREGY DSSGYYHLDY WGQGTLVTVS 120
S                                                                121

SEQ ID NO: 32            moltype = AA  length = 121
FEATURE                  Location/Qualifiers
REGION                   1..121
                         note = antibody sequence
source                   1..121
                         mol_type = protein
                         organism = synthetic construct
SEQUENCE: 32
EVQLLESGGG LVQPGGSLRL SCAASGFTFD DYAMSWVRQA PGKGLEWVSA IGTGGSTYYA  60
DSVKGRFTIS RDNSKNTLYL QMNSLRAEDT AVYYCAREGY DSSGYYHLDY WGQGTLVTVS 120
S                                                                121

SEQ ID NO: 33            moltype = AA  length = 121
FEATURE                  Location/Qualifiers
REGION                   1..121
                         note = antibody sequence
source                   1..121
                         mol_type = protein
                         organism = synthetic construct
```

```
SEQUENCE: 33
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCAKEGY DSSGYYHLDY WGQGTLVTVS   120
S                                                                  121

SEQ ID NO: 34           moltype = AA  length = 121
FEATURE                 Location/Qualifiers
REGION                  1..121
                        note = antibody sequence
source                  1..121
                        mol_type = protein
                        organism = synthetic construct
SEQUENCE: 34
EVQLLESGGG LVQPGGSLRL SCAASGFTFS DYAMSWVRQA PGKGLEWVSA IGTGGGTYYA    60
DSVKGRFTIS RDNSKNTLYL QMNSLRAEDT AVYYCAREGY DSSGYYHLDY WGQGTLVTVS   120
S                                                                  121

SEQ ID NO: 35           moltype = AA  length = 121
FEATURE                 Location/Qualifiers
REGION                  1..121
                        note = antibody sequence
source                  1..121
                        mol_type = protein
                        organism = synthetic construct
SEQUENCE: 35
EVQLLESGGG LVQPGGSLRL SCAASGFTFD SYAMSWVRQA PGKGLEWVSA IGTGGGTYYA    60
DSVKGRFTIS RDNSKNTLYL QMNSLRAEDT AVYYCAREGY DSSGYYHLDY WGQGTLVTVS   120
S                                                                  121

SEQ ID NO: 36           moltype = AA  length = 121
FEATURE                 Location/Qualifiers
REGION                  1..121
                        note = antibody sequence
source                  1..121
                        mol_type = protein
                        organism = synthetic construct
SEQUENCE: 36
EVQLLESGGG LVQPGGSLRL SCAASGFTFD DYAMSWVRQA PGKGLEWVSA IGSGGSTYYA    60
DSVKGRFTIS RDNSKNTLYL QMNSLRAEDT AVYYCAREGY DSSGYYHLDY WGQGTLVTVS   120
S                                                                  121

SEQ ID NO: 37           moltype = AA  length = 111
FEATURE                 Location/Qualifiers
REGION                  1..111
                        note = antibody sequence
source                  1..111
                        mol_type = protein
                        organism = synthetic construct
SEQUENCE: 37
QSVLTQPPSA SGTPGQRVTI SCTGSSSNIG ATYDVHWYQQ LPGTAPKLLI YSNNQRPSGV    60
PDRFSGSKSG TSASLAISGL RSEDEADYYC AAWDDSLSGW VFGGGTKLTV L           111

SEQ ID NO: 38           moltype = AA  length = 111
FEATURE                 Location/Qualifiers
REGION                  1..111
                        note = antibody sequence
source                  1..111
                        mol_type = protein
                        organism = synthetic construct
SEQUENCE: 38
QSVLTQPPSA SGTPGQRVTI SCTGSSSNIG ATYDVHWYQQ LPGTAPKLLI YSNNQRPSGV    60
PDRFSGSKSG TSASLAISGL RSEDEADYYC AAWDWSLSGW VFGGGTKLTV L           111

SEQ ID NO: 39           moltype = AA  length = 111
FEATURE                 Location/Qualifiers
REGION                  1..111
                        note = antibody sequence
source                  1..111
                        mol_type = protein
                        organism = synthetic construct
SEQUENCE: 39
QSVLTQPPSA SGTPGQRVTI SCTGSSSNIG ATYDVHWYQQ LPGTAPKLLI YSNNQRPSGV    60
PDRFSGSKSG TSASLAISGL RSEDEADYYC WAWDDSLSGW VFGGGTKLTV L           111

SEQ ID NO: 40           moltype = AA  length = 111
FEATURE                 Location/Qualifiers
REGION                  1..111
                        note = antibody sequence
source                  1..111
```

```
                        mol_type = protein
                        organism = synthetic construct
SEQUENCE: 40
QSVLTQPPSA SGTPGQRVTI SCTGSSSNIG ATYDVHWYQQ LPGTAPKLLI YSNNQRPSGV    60
PDRFSGSKSG TSASLAISGL RSEDEADYYC AAWDVSLSGW VFGGGTKLTV L            111

SEQ ID NO: 41           moltype = AA  length = 450
FEATURE                 Location/Qualifiers
REGION                  1..450
                        note = antibody sequence
source                  1..450
                        mol_type = protein
                        organism = synthetic construct
SEQUENCE: 41
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCAREYY DSSGYYHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 42           moltype = AA  length = 450
FEATURE                 Location/Qualifiers
REGION                  1..450
                        note = antibody sequence
source                  1..450
                        mol_type = protein
                        organism = synthetic construct
SEQUENCE: 42
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCDREYY DSSGYYHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 43           moltype = AA  length = 450
FEATURE                 Location/Qualifiers
REGION                  1..450
                        note = antibody sequence
source                  1..450
                        mol_type = protein
                        organism = synthetic construct
SEQUENCE: 43
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCASEYY DSSGYYHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 44           moltype = AA  length = 450
FEATURE                 Location/Qualifiers
REGION                  1..450
                        note = antibody sequence
source                  1..450
                        mol_type = protein
                        organism = synthetic construct
SEQUENCE: 44
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCAREDY DSSGYYHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 45           moltype = AA  length = 450
FEATURE                 Location/Qualifiers
REGION                  1..450
                        note = antibody sequence
source                  1..450
```

```
                        mol_type = protein
                        organism = synthetic construct
SEQUENCE: 45
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCAREGY DSSGYYHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 46           moltype = AA   length = 450
FEATURE                 Location/Qualifiers
REGION                  1..450
                        note = antibody sequence
source                  1..450
                        mol_type = protein
                        organism = synthetic construct
SEQUENCE: 46
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCAREYY DSSGYYHLVY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 47           moltype = AA   length = 450
FEATURE                 Location/Qualifiers
REGION                  1..450
                        note = antibody sequence
source                  1..450
                        mol_type = protein
                        organism = synthetic construct
SEQUENCE: 47
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCAREYY DSSGYYHLEY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 48           moltype = AA   length = 450
FEATURE                 Location/Qualifiers
REGION                  1..450
                        note = antibody sequence
source                  1..450
                        mol_type = protein
                        organism = synthetic construct
SEQUENCE: 48
EVQLLESGGG LVQPGGSLRL SCAASGFTFD DYAMSWVRQA PGKGLEWVSA IGTGGGTYYA    60
DSVKGRFTIS RDNSKNTLYL QMNSLRAEDT AVYYCAREYY DSSGYYHLTY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 49           moltype = AA   length = 450
FEATURE                 Location/Qualifiers
REGION                  1..450
                        note = antibody sequence
source                  1..450
                        mol_type = protein
                        organism = synthetic construct
SEQUENCE: 49
EVQLLESGGG LVQPGGSLRL SCAASGFTFS DYAMSWVRQA PGKGLEWVSA IGTGGGTYYA    60
DSVKGRFTIS RDNSKNTLYL QMNSLRAEDT AVYYCAREGY DSSGYYHLDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450
```

```
SEQ ID NO: 50             moltype = AA  length = 450
FEATURE                   Location/Qualifiers
REGION                    1..450
                          note = antibody sequence
source                    1..450
                          mol_type = protein
                          organism = synthetic construct
SEQUENCE: 50
EVQLLESGGG LVQPGGSLRL SCAASGFTFD DYAMSWVRQA PGKGLEWVSA IGTGGSTYYA   60
DSVKGRFTIS RDNSKNTLYL QMNSLRAEDT AVYYCAREGY DSSGYYHLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 51             moltype = AA  length = 450
FEATURE                   Location/Qualifiers
REGION                    1..450
                          note = antibody sequence
source                    1..450
                          mol_type = protein
                          organism = synthetic construct
SEQUENCE: 51
EVQLLESGGG LVQPGGSLRL SCAASGFTFD DYAMSWVRQA PGKGLEWVSA IGTGGSTYYA   60
DSVKGRFTIS RDNSKNTLYL QMNSLRAEDT AVYYCAKEGY DSSGYYHLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 52             moltype = AA  length = 450
FEATURE                   Location/Qualifiers
REGION                    1..450
                          note = antibody sequence
source                    1..450
                          mol_type = protein
                          organism = synthetic construct
SEQUENCE: 52
EVQLLESGGG LVQPGGSLRL SCAASGFTFS DYAMSWVRQA PGKGLEWVSA IGTGGSTYYA   60
DSVKGRFTIS RDNSKNTLYL QMNSLRAEDT AVYYCAREGY DSSGYYHLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 53             moltype = AA  length = 450
FEATURE                   Location/Qualifiers
REGION                    1..450
                          note = antibody sequence
source                    1..450
                          mol_type = protein
                          organism = synthetic construct
SEQUENCE: 53
EVQLLESGGG LVQPGGSLRL SCAASGFTFD SYAMSWVRQA PGKGLEWVSA IGTGGSTYYA   60
DSVKGRFTIS RDNSKNTLYL QMNSLRAEDT AVYYCAREGY DSSGYYHLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 54             moltype = AA  length = 450
FEATURE                   Location/Qualifiers
REGION                    1..450
                          note = antibody sequence
source                    1..450
                          mol_type = protein
                          organism = synthetic construct
SEQUENCE: 54
EVQLLESGGG LVQPGGSLRL SCAASGFTFD DYAMSWVRQA PGKGLEWVSA IGSGGSTYYA   60
DSVKGRFTIS RDNSKNTLYL QMNSLRAEDT AVYYCAREGY DSSGYYHLDY WGQGTLVTVS  120
```

```
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG                                    450

SEQ ID NO: 55           moltype = AA  length = 447
FEATURE                 Location/Qualifiers
REGION                  1..447
                        note = antibody sequence
source                  1..447
                        mol_type = protein
                        organism = synthetic construct
SEQUENCE: 55
EVQLLESGGG LVQPGGSLRL SCAASGFTFD DYAMSWVRQA PGKGLEWVSA IGTGGSTYYA    60
DSVKGRFTIS RDNSKNTLYL QMNSLRAEDT AVYYCAREGY DSSGYYHLDY WGQGTLVTVS    120
SASTKGPSVF PLAPCSRSTS ESTAALGCLV KDYFPEPVTV SWNSGALTSG VHTFPAVLQS    180
SGLYSLSSVV TVPSSSLGTK TYTCNVDHKP SNTKVDKRVE SKYGPPCPPC PAPEFLGGPS    240
VFLFPPKPKD TLMISRTPEV TCVVVDVSQE DPEVQFNWYV DGVEVHNAKT KPREEQFNST    300
YRVVSVLTVL HQDWLNGKEY KCKVSNKGLP SSIEKTISKA KGQPREPQVY TLPPSQEEMT    360
KNQVSLTCLV KGFYPSDIAV EWESNGQPEN NYKTTPPVLD SDGSFFLYSR LTVDKSRWQE    420
GNVFSCSVMH EALHNHYTQK SLSLSLG                                       447

SEQ ID NO: 56           moltype = AA  length = 217
FEATURE                 Location/Qualifiers
REGION                  1..217
                        note = antibody sequence
source                  1..217
                        mol_type = protein
                        organism = synthetic construct
SEQUENCE: 56
QSVLTQPPSA SGTPGQRVTI SCTGSSSNIG ATYDVHWYQQ LPGTAPKLLI YSNNQRPSGV    60
PDRFSGSKSG TSASLAISGL RSEDEADYYC AAWDDSLSGL VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                            217

SEQ ID NO: 57           moltype = AA  length = 217
FEATURE                 Location/Qualifiers
REGION                  1..217
                        note = antibody sequence
source                  1..217
                        mol_type = protein
                        organism = synthetic construct
SEQUENCE: 57
QSVLTQPPSA SGTPGQRVTI SCTGSSSNIG ATYDVHWYQQ LPGTAPKLLI YSNNQRPSGV    60
PDRFSGSKSG TSASLAISGL RSEDEADYYC AAWDWSLSGW VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                            217

SEQ ID NO: 58           moltype = AA  length = 217
FEATURE                 Location/Qualifiers
REGION                  1..217
                        note = antibody sequence
source                  1..217
                        mol_type = protein
                        organism = synthetic construct
SEQUENCE: 58
QSVLTQPPSA SGTPGQRVTI SCTGSSSNIG ATYDVHWYQQ LPGTAPKLLI YSNNQRPSGV    60
PDRFSGSKSG TSASLAISGL RSEDEADYYC WAWDDSLSGW VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                            217

SEQ ID NO: 59           moltype = AA  length = 217
FEATURE                 Location/Qualifiers
REGION                  1..217
                        note = antibody sequence
source                  1..217
                        mol_type = protein
                        organism = synthetic construct
SEQUENCE: 59
QSVLTQPPSA SGTPGQRVTI SCTGSSSNIG ATYDVHWYQQ LPGTAPKLLI YSNNQRPSGV    60
PDRFSGSKSG TSASLAISGL RSEDEADYYC AAWDVSLSGW VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                            217

SEQ ID NO: 60           moltype = DNA  length = 1476
FEATURE                 Location/Qualifiers
source                  1..1476
```

```
                        mol_type = other DNA
                        organism = Homo sapiens
SEQUENCE: 60
atggcgctgc tctgggggct cctggtgctc agctggtcct gcctgcaagg cccctgctcc    60
gtgttctccc ctgtgagcgc catggagccc ttgggccggc agctaactag cgggccgaac   120
caggagcagg tgtccccact tacccctcct caagttgggca accaggagcc tggtggccag   180
actgccctga agagtccccc aggagtctgc agcagagacc ccaccccaga gcagaccac    240
aggctggccc gggccatgat ggccttcact gccgacctgt tctccctggt ggctcaaacg   300
tccacctgcc ccaacctcat cctgtcaccc ctgagtgtgg ccctggcgct gtctcacctg   360
gcactaggtg ctcagaacca cacgttgcag aggctgcaac aggtgctgca cgcaggctca   420
gggccctgcc tccccatct gctgagccgc ctctgccagg acctgggccc cggcgcgttc   480
cgactggctg ccaggatgta cctgcagaaa ggatttccca tcaaagaaga tttcctggaa   540
caatccgaac agctatttgg ggcaaagccc gtgagcctga cgggaaagca ggaagatgac   600
ctggcaaaca tcaaccaatg ggtgaaggag gccacgaggg ggaagattca ggaattcctc   660
tctgggctgc cggaagacac cgtgttgctt ctcctcaacg ccatccactt ccagggtttc   720
tggaggaaca agtttgaccc gagccttacc cagagagact ccttccacct ggacgagcag   780
ttcacggtgc ccgtggaaat gatgcaggcc cgcacgtacc cgctgcgctg gttcttgctg   840
gagcagcctg agatccaggt ggctcatttc ccctttaaga acaacatgag ctttgtggtc   900
cttgtaccca cccactttga atggaacgtg tcccaggtac tggccaacct gagttgggac   960
accctgcacc cacctctggt gtgggagagg cccaccaagg tccggctgcc taagctgtat  1020
ctgaaacacc aaatggacct ggtggccacc ctcagccagc tgggcctgca ggagttgttc  1080
caggcccccag acctgcgtgg gatctccgag cagagcctgg tggtgtccgg ctgcagcat  1140
cagtccaccc tggagctcag cgaggtcggc gtggaggcgg ccggcggccac cagcattgcc  1200
atgtccgca tgtccctgtc ctccttcagc gtgaaccgcc cctcctctt cttcatcttc   1260
gaggacacca caggccttcc cctcttcgtg ggcagcgtga ggaaccccaa ccccagtgca  1320
ccgcgggagc tcaaggaaca gcaggattcc ccgggcaaca aggacttcct ccagagcctg  1380
aaaggcttcc cccgcggaga caagcttttc ggccctgact taaaacttgt gccccccatg  1440
gaggaggatt accccagtt tggcagcccc aagtga                             1476

SEQ ID NO: 61           moltype = DNA  length = 1476
FEATURE                 Location/Qualifiers
source                  1..1476
                        mol_type = other DNA
                        organism = Oryctolagus cuniculus
SEQUENCE: 61
atggtgctgc tccgggggct cctggtgctc agcttgtcct gcctgcaagg cccctgcgcg    60
gtgctccctc ccgtgagcgc catggagccc gtgggccggc agctaactag tggtcagagc   120
caagaaaagc tgcctccgct cgcccctcctc aagttggtca accaggagct gcacggtcag   180
actgccctga agaagtcccc aggagactgc agggaaaacc cgacccccgga gcagacgcgc  240
aggctggcgc aggccatgat ggccttcacc actgacctgt tttccctggt ggtgcaagca   300
tccaccagcc caacctggt cttgtcgccc ctgagtgtgg ccctggctct gtctcacctg   360
gcattaggtg ctcagaacca cacgctacag aggttgcagc aggtgctgca tgcggactca   420
gggccctgcc tccccacct gctgagccac ctctgccagg acctgggcc aggggcgttc   480
cgattggctg ccagaatgta cctgcagaaa ggctttccca tcaaagagga cttcctgaag   540
ctgtcagagc agctgtttgg tgcaaagcct gtgagcctga caggaagca agaggaggac   600
ctggtgaaca tcaatcaatg ggtgaaggag gccacagagg ggaagattga ggatttcctc   660
tcggaattgc cagacagcac cgtgctgctc ctcctcaacg ccatccactt ccagggtttc   720
tggaggagca aatttgaccc gagcctcacc cagagagact ccttccacct ggacgagcag   780
ttcacggtgc cagtggacat gatgcaagcc cacaagtacc ctctgcgctg gttcttgctg   840
gagcagcctg agatccaggt ggcccaattc ccctttaaga caacatgag ctttgtggtc   900
ctcgtgccca cgaactttga gtggaacgtg tcccaggtgc tgagcaacct gagctgggac   960
atcctgcacc agccctcact gcgggagagg cccaccaaag tccagctgcc caagctgctc  1020
ctgaaacacc agctggacct ggtgaccacc ctcagccagc tgggcctgca ggagctgttc  1080
ctggccccag acctgcgtgg gatctccgac gagggcctgg tggtgtccag tgtacaacat  1140
cagtccaccc tggagctcaa cgaggctggt gtggaggcgg ccgcggccac cagcacggcc  1200
atgtcgcgca tgtcccttc ctccttcagc gtgaaccgcc cctcctctt cttcatcctg   1260
gaggacacca tagacctgcc catctttgtg ggcatagtgc ggaaccccaa tcctagcgcg  1320
cagccagagc gcaaggagca gcaggattcc cctgaccaca gggacccctc gcagcccag  1380
aaaatccttc cccacgggga caagcttctc agccccgact tgaaactggc gccccgtcg  1440
gaagaggatt accccagct cagcagcccc aagtga                              1476

SEQ ID NO: 62           moltype = DNA  length = 1476
FEATURE                 Location/Qualifiers
source                  1..1476
                        mol_type = other DNA
                        organism = Macaca fascicularis
SEQUENCE: 62
atggcgctgt tctgggggct cctggtgctc agctggtcct gcctgcaagg tccctctcc    60
gtgttctccc ctgtgagcgc catggagccc ttgggctggc agctaactag tgggccaaac   120
caagagaagg tgccccact tactctcctc aagttgggca accaggagcc tggcggccag   180
actgccctga agagtctccc aggaatctgc agcagagacc ccaccccga gcagaccgc    240
aggctggccc aggccatgat ggccttcact gccgacctgt tctccctggt ggctcaaacg   300
tccacctgcc caacctcat cctgtcacct ctgagtgtgg ccctggcgct gtctcacctg   360
gcactaggtg ctcagaacca cacgctgcag aggctgctgca aggtgctgca cgcaggctca   420
gggccctgcc tacccatct gctgagccgc ctctgccaga acatgggccc cggggccttc   480
cgactggctg ccaggatgta cctgcagaaa ggatttccca tcaaagaaga tttcctggaa   540
cagtctgaac ggctatttgg ggcaaagccc gtgagcctga cgggaaagca ggaagatgac   600
ctggcaaaca tcaaccaatg ggtgaaggag gccacgaggg ggaagattcc ggagttcctc   660
tctgagctac cggaagacac cgtgttgctt ctcctcaacg ccatccactt ccagggtttc   720
```

```
tggaggagca agtttgaccc gagcctcacc cagagagact ccttccacct ggacgagcag    780
ttcacggtgc ccgtggaaat gatgcaagcc cgcacgtatc ctctgcgctg gttcatgctg    840
gagcagcccg agatccaggt ggctcatttt ccctttaaga acaacatgag ctttgtggtc    900
cttgtaccca cccactttga atggaacgtg tcccaggtac tggccaacct gagttgggac    960
accctgtacc caccttccgt gtgggagagg cccaccaagg tccggctgcc taagctgtat   1020
ctgaaacacc aaatggacct gatgccacc ctcagccggc tgggcctgca ggagctgttc    1080
caggccccag acctgcgcgg gatctctgag cagagcctgg tggtgtccgg cgtgcagcat   1140
cagtccaccc tggagctcag cgaggtcggc gtggaggcgg cggcggccac cagcatcgcc   1200
atgtcccgca tgtccctgtc ctccttcagc gtgaaccgcc ccttcctctt cttcatcttt   1260
gaggacacca caggccttcc cctctttgtg ggcagcgtga ggaacccca ccccagcgcg    1320
ccacgggagc tcaaggagca gcaggattcc ccgggagaca aggacttcct ccacagcctg   1380
aaagccggcc ccgcggaga caagctcttc ggccctgact tgaaacttgc gccccccttg   1440
gaggaggatt accctgagct tggcagccct aagtga                              1476

SEQ ID NO: 63            moltype = DNA   length = 15
FEATURE                  Location/Qualifiers
misc_feature             1..15
                         note = antibody sequence
source                   1..15
                         mol_type = other DNA
                         organism = synthetic construct
SEQUENCE: 63
gattacgcca tgagc                                                      15

SEQ ID NO: 64            moltype = DNA   length = 48
FEATURE                  Location/Qualifiers
misc_feature             1..48
                         note = antibody sequence
source                   1..48
                         mol_type = other DNA
                         organism = synthetic construct
SEQUENCE: 64
gccatcggaa caggcggcgg aacatattac gccgacagcg tgaagggc                  48

SEQ ID NO: 65            moltype = DNA   length = 48
FEATURE                  Location/Qualifiers
misc_feature             1..48
                         note = antibody sequence
source                   1..48
                         mol_type = other DNA
                         organism = synthetic construct
SEQUENCE: 65
gccatcggca caggcggcag cacatattac gccgactctg tgaagggc                  48

SEQ ID NO: 66            moltype = DNA   length = 42
FEATURE                  Location/Qualifiers
misc_feature             1..42
                         note = antibody sequence
source                   1..42
                         mol_type = other DNA
                         organism = synthetic construct
SEQUENCE: 66
accggcagca gctccaatat cggcgccacc tatgacgtgc ac                        42

SEQ ID NO: 67            moltype = DNA   length = 21
FEATURE                  Location/Qualifiers
misc_feature             1..21
                         note = antibody sequence
source                   1..21
                         mol_type = other DNA
                         organism = synthetic construct
SEQUENCE: 67
agcaacaacc agcggcctag c                                               21

SEQ ID NO: 68            moltype = DNA   length = 39
FEATURE                  Location/Qualifiers
misc_feature             1..39
                         note = antibody sequence
source                   1..39
                         mol_type = other DNA
                         organism = synthetic construct
SEQUENCE: 68
gagtactacg acacagcgg ctactaccac ctggactat                             39

SEQ ID NO: 69            moltype = DNA   length = 39
FEATURE                  Location/Qualifiers
misc_feature             1..39
                         note = antibody sequence
source                   1..39
```

```
                        mol_type = other DNA
                        organism = synthetic construct
SEQUENCE: 69
gaggattacg acagcagcgg ctactaccac ctggactat                                39

SEQ ID NO: 70           moltype = DNA   length = 39
FEATURE                 Location/Qualifiers
misc_feature            1..39
                        note = antibody sequence
source                  1..39
                        mol_type = other DNA
                        organism = synthetic construct
SEQUENCE: 70
gaggggtacg acagcagcgg ctactaccac ctggactat                                39

SEQ ID NO: 71           moltype = DNA   length = 39
FEATURE                 Location/Qualifiers
misc_feature            1..39
                        note = antibody sequence
source                  1..39
                        mol_type = other DNA
                        organism = synthetic construct
SEQUENCE: 71
gagtactacg acagcagcgg ctactaccac ctggtttat                                39

SEQ ID NO: 72           moltype = DNA   length = 39
FEATURE                 Location/Qualifiers
misc_feature            1..39
                        note = antibody sequence
source                  1..39
                        mol_type = other DNA
                        organism = synthetic construct
SEQUENCE: 72
gagtactacg acagcagcgg ctactaccac ctggagtat                                39

SEQ ID NO: 73           moltype = DNA   length = 39
FEATURE                 Location/Qualifiers
misc_feature            1..39
                        note = antibody sequence
source                  1..39
                        mol_type = other DNA
                        organism = synthetic construct
SEQUENCE: 73
gagtactacg acagcagcgg ctactaccac ctgacgtat                                39

SEQ ID NO: 74           moltype = DNA   length = 33
FEATURE                 Location/Qualifiers
misc_feature            1..33
                        note = antibody sequence
source                  1..33
                        mol_type = other DNA
                        organism = synthetic construct
SEQUENCE: 74
gccgcctggg atgattctct gagcggctgg gtt                                      33

SEQ ID NO: 75           moltype = DNA   length = 33
FEATURE                 Location/Qualifiers
misc_feature            1..33
                        note = antibody sequence
source                  1..33
                        mol_type = other DNA
                        organism = synthetic construct
SEQUENCE: 75
gccgcctggg attggtctct gagcggctgg gtt                                      33

SEQ ID NO: 76           moltype = DNA   length = 33
FEATURE                 Location/Qualifiers
misc_feature            1..33
                        note = antibody sequence
source                  1..33
                        mol_type = other DNA
                        organism = synthetic construct
SEQUENCE: 76
tgggcctggg atgattctct gagcggctgg gtt                                      33

SEQ ID NO: 77           moltype = DNA   length = 33
FEATURE                 Location/Qualifiers
misc_feature            1..33
                        note = antibody sequence
```

```
source                       1..33
                             mol_type = other DNA
                             organism = synthetic construct
SEQUENCE: 77
gccgcctggg atgtttctct gagcggctgg gtt                            33

SEQ ID NO: 78                moltype = DNA  length = 15
FEATURE                      Location/Qualifiers
misc_feature                 1..15
                             note = antibody sequence
source                       1..15
                             mol_type = other DNA
                             organism = synthetic construct
SEQUENCE: 78
agctacgcca tgagc                                                15

SEQ ID NO: 79                moltype = DNA  length = 48
FEATURE                      Location/Qualifiers
misc_feature                 1..48
                             note = antibody sequence
source                       1..48
                             mol_type = other DNA
                             organism = synthetic construct
SEQUENCE: 79
gccatcggca gcggaggcag cacatattac gccgactctg tgaagggc            48

SEQ ID NO: 80                moltype = DNA  length = 363
FEATURE                      Location/Qualifiers
misc_feature                 1..363
                             note = antibody sequence
source                       1..363
                             mol_type = other DNA
                             organism = synthetic construct
SEQUENCE: 80
gaagttcagc tgctggaatc tggcggcgga ctggttcaac ctggcggatc tctgagactg   60
agctgtgccg ccagcggctt caccttcgat gattacgcca tgagctgggt ccgacaggcc  120
cctggaaaag gccttgaatg ggtgtccgcc atcggaacag gcggcggaac atattacgcc  180
gacagcgtga agggcagatt caccatcagc cgggacaaca gcaagaacac cctgtacctg  240
cagatgaaca gcctgagagc cgaggacacc gccgtgtact attgcgccag agagtactac  300
gacagcagcg gctactacca cctggactat tggggccagg gcaccctggt cacagtttct  360
tca                                                               363

SEQ ID NO: 81                moltype = DNA  length = 363
FEATURE                      Location/Qualifiers
misc_feature                 1..363
                             note = antibody sequence
source                       1..363
                             mol_type = other DNA
                             organism = synthetic construct
SEQUENCE: 81
gaagttcagc tgctggaatc tggcggcgga ctggttcaac ctggcggatc tctgagactg   60
agctgtgccg ccagcggctt caccttcgat gattacgcca tgagctgggt ccgacaggcc  120
cctggaaaag gccttgaatg ggtgtccgcc atcggaacag gcggcggaac atattacgcc  180
gacagcgtga agggcagatt caccatcagc cgggacaaca gcaagaacac cctgtacctg  240
cagatgaaca gcctgagagc cgaggacacc gccgtgtact attgcgatag agagtactac  300
gacagcagcg gctactacca cctggactat tggggccagg gcaccctggt cacagtttct  360
tca                                                               363

SEQ ID NO: 82                moltype = DNA  length = 363
FEATURE                      Location/Qualifiers
misc_feature                 1..363
                             note = antibody sequence
source                       1..363
                             mol_type = other DNA
                             organism = synthetic construct
SEQUENCE: 82
gaagttcagc tgctggaatc tggcggcgga ctggttcaac ctggcggatc tctgagactg   60
agctgtgccg ccagcggctt caccttcgat gattacgcca tgagctgggt ccgacaggcc  120
cctggaaaag gccttgaatg ggtgtccgcc atcggaacag gcggcggaac atattacgcc  180
gacagcgtga agggcagatt caccatcagc cgggacaaca gcaagaacac cctgtacctg  240
cagatgaaca gcctgagagc cgaggacacc gccgtgtact attgcgccag tgagtactac  300
gacagcagcg gctactacca cctggactat tggggccagg gcaccctggt cacagtttct  360
tca                                                               363

SEQ ID NO: 83                moltype = DNA  length = 363
FEATURE                      Location/Qualifiers
misc_feature                 1..363
                             note = antibody sequence
source                       1..363
```

```
                        mol_type = other DNA
                        organism = synthetic construct
SEQUENCE: 83
gaagttcagc tgctggaatc tggcggcgga ctggttcaac ctggcggatc tctgagactg      60
agctgtgccg ccagcggctt caccttcgat gattacgcca tgagctgggt ccgacaggcc     120
cctggaaaag gccttgaatg ggtgtccgcc atcggaacag gcggcggaac atattacgcg     180
gacagcgtga agggcagatt caccatcagc cgggacaaca gcaagaacac cctgtacctg     240
cagatgaaca gcctgagagc cgaggacacc gccgtgtact attgcgccag agaggattac     300
gacagcagcg gctactacca cctggactat tggggccagg gcaccctggt cacagtttct     360
tca                                                                   363

SEQ ID NO: 84           moltype = DNA   length = 363
FEATURE                 Location/Qualifiers
misc_feature            1..363
                        note = antibody sequence
source                  1..363
                        mol_type = other DNA
                        organism = synthetic construct
SEQUENCE: 84
gaagttcagc tgctggaatc tggcggcgga ctggttcaac ctggcggatc tctgagactg      60
agctgtgccg ccagcggctt caccttcgat gattacgcca tgagctgggt ccgacaggcc     120
cctggaaaag gccttgaatg ggtgtccgcc atcggaacag gcggcggaac atattacgcc     180
gacagcgtga agggcagatt caccatcagc cgggacaaca gcaagaacac cctgtacctg     240
cagatgaaca gcctgagagc cgaggacacc gccgtgtact attgcgccag agaggggtac     300
gacagcagcg gctactacca cctggactat tggggccagg gcaccctggt cacagtttct     360
tca                                                                   363

SEQ ID NO: 85           moltype = DNA   length = 363
FEATURE                 Location/Qualifiers
misc_feature            1..363
                        note = antibody sequence
source                  1..363
                        mol_type = other DNA
                        organism = synthetic construct
SEQUENCE: 85
gaagttcagc tgctggaatc tggcggcgga ctggttcaac ctggcggatc tctgagactg      60
agctgtgccg ccagcggctt caccttcgat gattacgcca tgagctgggt ccgacaggcc     120
cctggaaaag gccttgaatg ggtgtccgcc atcggaacag gcggcggaac atattacgcc     180
gacagcgtga agggcagatt caccatcagc cgggacaaca gcaagaacac cctgtacctg     240
cagatgaaca gcctgagagc cgaggacacc gccgtgtact attgcgccag agagtactac     300
gacagcagcg gctactacca cctggtttat tggggccagg gcaccctggt cacagtttct     360
tca                                                                   363

SEQ ID NO: 86           moltype = DNA   length = 363
FEATURE                 Location/Qualifiers
misc_feature            1..363
                        note = antibody sequence
source                  1..363
                        mol_type = other DNA
                        organism = synthetic construct
SEQUENCE: 86
gaagttcagc tgctggaatc tggcggcgga ctggttcaac ctggcggatc tctgagactg      60
agctgtgccg ccagcggctt caccttcgat gattacgcca tgagctgggt ccgacaggcc     120
cctggaaaag gccttgaatg ggtgtccgcc atcggaacag gcggcggaac atattacgcc     180
gacagcgtga agggcagatt caccatcagc cgggacaaca gcaagaacac cctgtacctg     240
cagatgaaca gcctgagagc cgaggacacc gccgtgtact attgcgccag agagtactac     300
gacagcagcg gctactacca cctggagtat tggggccagg gcaccctggt cacagtttct     360
tca                                                                   363

SEQ ID NO: 87           moltype = DNA   length = 363
FEATURE                 Location/Qualifiers
misc_feature            1..363
                        note = antibody sequence
source                  1..363
                        mol_type = other DNA
                        organism = synthetic construct
SEQUENCE: 87
gaagttcagc tgctggaatc tggcggcgga ctggttcaac ctggcggatc tctgagactg      60
agctgtgccg ccagcggctt caccttcgat gattacgcca tgagctgggt ccgacaggcc     120
cctggaaaag gccttgaatg ggtgtccgcc atcggaacag gcggcggaac atattacgcc     180
gacagcgtga agggcagatt caccatcagc cgggacaaca gcaagaacac cctgtacctg     240
cagatgaaca gcctgagagc cgaggacacc gccgtgtact attgcgccag agagtactac     300
gacagcagcg gctactacca cctgacgtat tggggccagg gcaccctggt cacagtttct     360
tca                                                                   363

SEQ ID NO: 88           moltype = DNA   length = 363
FEATURE                 Location/Qualifiers
misc_feature            1..363
                        note = antibody sequence
```

| source | 1..363 |
| --- | --- |
| | mol_type = other DNA |
| | organism = synthetic construct |

SEQUENCE: 88

```
gaagttcagc tgctggaatc tggcggcgga ctggttcaac ctggcggatc tctgagactg   60
agctgtgccg ccagcggctt cacctttagc gattacgcca tgagctgggt ccgacaggcc  120
cctggaaaag gccttgaatg ggtgtccgcc atcggaacag gcggcggaac atattacgcc  180
gacagcgtga agggcagatt caccatcagc cgggacaaca gcaagaacac cctgtacctg  240
cagatgaaca gcctgagagc cgaggacacc gccgtgtact attgtgccag agagggctac  300
gacagcagcg gctactacca cctggattat tggggccagg gcaccctggt tacagtgtca  360
tca                                                                 363
```

| SEQ ID NO: 89 | moltype = DNA   length = 363 |
| --- | --- |
| FEATURE | Location/Qualifiers |
| misc_feature | 1..363 |
| | note = antibody sequence |
| source | 1..363 |
| | mol_type = other DNA |
| | organism = synthetic construct |

SEQUENCE: 89

```
gaagttcagc tgctggaatc tggcggcgga ctggttcaac ctggcggatc tctgagactg   60
agctgtgccg ccagcggctt cacctttcgat gattacgcca tgagctgggt ccgacaggcc  120
cctggaaaag gccttgaatg ggtgtccgcc atcggcacag gcggcagcac atattacgcc  180
gactctgtga agggcagatt caccatcagc cgggacaaca gcaagaacac cctgtacctg  240
cagatgaaca gcctgagagc cgaggacacc gccgtgtact attgtgccag agagggctac  300
gacagcagcg gctactacca cctggattat tggggccagg gcaccctggt tacagtgtca  360
tca                                                                 363
```

| SEQ ID NO: 90 | moltype = DNA   length = 363 |
| --- | --- |
| FEATURE | Location/Qualifiers |
| misc_feature | 1..363 |
| | note = antibody sequence |
| source | 1..363 |
| | mol_type = other DNA |
| | organism = synthetic construct |

SEQUENCE: 90

```
gaagttcagc tgctggaatc tggcggcgga ctggttcaac ctggcggatc tctgagactg   60
agctgtgccg ccagcggctt cacctttcgat gattacgcca tgagctgggt ccgacaggcc  120
cctggaaaag gccttgaatg ggtgtccgcc atcggaacag gcggcggaac atattacgcc  180
gacagcgtga agggcagatt caccatcagc cgggacaaca gcaagaacac cctgtacctg  240
cagatgaaca gcctgagagc cgaggacacc gccgtgtact actgtgccaa agagggctac  300
gacagcagcg gctactacca cctggattat tggggccagg gcaccctggt tacagtgtca  360
tca                                                                 363
```

| SEQ ID NO: 91 | moltype = DNA   length = 363 |
| --- | --- |
| FEATURE | Location/Qualifiers |
| misc_feature | 1..363 |
| | note = antibody sequence |
| source | 1..363 |
| | mol_type = other DNA |
| | organism = synthetic construct |

SEQUENCE: 91

```
gaagttcagc tgctggaatc tggcggcgga ctggttcaac ctggcggatc tctgagactg   60
agctgtgccg ccagcggctt cacctttagc gattacgcca tgagctgggt ccgacaggcc  120
cctggaaaag gccttgaatg ggtgtccgcc atcggaacag gcggcagcac atattacgcc  180
gactctgtga agggcagatt caccatcagc cgggacaaca gcaagaacac cctgtacctg  240
cagatgaaca gcctgagagc cgaggacacc gccgtgtact attgtgccag agagggctac  300
gacagcagcg gctactacca cctggattat tggggccagg gcaccctggt tacagtgtca  360
tca                                                                 363
```

| SEQ ID NO: 92 | moltype = DNA   length = 363 |
| --- | --- |
| FEATURE | Location/Qualifiers |
| misc_feature | 1..363 |
| | note = antibody sequence |
| source | 1..363 |
| | mol_type = other DNA |
| | organism = synthetic construct |

SEQUENCE: 92

```
gaagttcagc tgctggaatc tggcggcgga ctggttcaac ctggcggatc tctgagactg   60
agctgtgccg ccagcggctt cacctttgat agctacgcca tgagctgggt ccgacaggcc  120
cctggaaaag gccttgaatg ggtgtccgcc atcggcacag gcggcagcac atattacgcc  180
gactctgtga agggcagatt caccatcagc cgggacaaca gcaagaacac cctgtacctg  240
cagatgaaca gcctgagagc cgaggacacc gccgtgtact attgtgccag agagggctac  300
gacagcagcg gctactacca cctggattat tggggccagg gcaccctggt tacagtgtca  360
tca                                                                 363
```

| SEQ ID NO: 93 | moltype = DNA   length = 363 |
| --- | --- |
| FEATURE | Location/Qualifiers |
| misc_feature | 1..363 |

```
                        note = antibody sequence
source                  1..363
                        mol_type = other DNA
                        organism = synthetic construct
SEQUENCE: 93
gaagttcagc tgctggaatc tggcggcgga ctggttcaac ctgcggatc tctgagactg    60
agctgtgccg ccagcggctt caccttcgat gattacgcca tgagctgggt ccgacaggcc   120
cctggaaaag gccttgaatg ggtgtccgcc atcggcagcg gaggcagcac atattacgcc   180
gactctgtga agggcagatt caccatcagc cgggacaaca gcaagaacac cctgtacctg   240
cagatgaaca gcctgagagc cgaggacacc gccgtgtact attgtgccag agagggctac   300
gacagcagcg gctactacca cctggattat tggggccagg gcacccttggt tacagtgtca   360
tca                                                                 363

SEQ ID NO: 94           moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 94
cagtctgttc tgacacagcc tcctagcgcc tctggcacac ctggacagag agtgaccatc    60
agctgtaccg gcagcagctc caatatcggc gccacctatg acgtgcactg gtatcagcag   120
ctgcctggca cagcccctaa actgctgatc tacagcaaca accagcggcc tagcggcgtg   180
cccgatagat tttctggcag caagagcggc acaagcgcca gcctggctat ctctggactg   240
agatctgagg acgaggccga ctactattgc gccgcctggg atgattctct gagcggctgg   300
gttttcggcg gaggcacaaa actgacagtg cta                                333

SEQ ID NO: 95           moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 95
cagtctgttc tgacacagcc tcctagcgcc tctggcacac ctggacagag agtgaccatc    60
agctgtaccg gcagcagctc caatatcggc gccacctatg acgtgcactg gtatcagcag   120
ctgcctggca cagcccctaa actgctgatc tacagcaaca accagcggcc tagcggcgtg   180
cccgatagat tttctggcag caagagcggc acaagcgcca gcctggctat ctctggactg   240
agatctgagg acgaggccga ctactattgc gccgcctggg attggtctct gagcggctgg   300
gttttcggcg gaggcacaaa actgacagtg cta                                333

SEQ ID NO: 96           moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 96
cagtctgttc tgacacagcc tcctagcgcc tctggcacac ctggacagag agtgaccatc    60
agctgtaccg gcagcagctc caatatcggc gccacctatg acgtgcactg gtatcagcag   120
ctgcctggca cagcccctaa actgctgatc tacagcaaca accagcggcc tagcggcgtg   180
cccgatagat tttctggcag caagagcggc acaagcgcca gcctggctat ctctggactg   240
agatctgagg acgaggccga ctactattgc tgggcctggg atgattctct gagcggctgg   300
gttttcggcg gaggcacaaa actgacagtg cta                                333

SEQ ID NO: 97           moltype = DNA   length = 333
FEATURE                 Location/Qualifiers
misc_feature            1..333
                        note = antibody sequence
source                  1..333
                        mol_type = other DNA
                        organism = synthetic construct
SEQUENCE: 97
cagtctgttc tgacacagcc tcctagcgcc tctggcacac ctggacagag agtgaccatc    60
agctgtaccg gcagcagctc caatatcggc gccacctatg acgtgcactg gtatcagcag   120
ctgcctggca cagcccctaa actgctgatc tacagcaaca accagcggcc tagcggcgtg   180
cccgatagat tttctggcag caagagcggc acaagcgcca gcctggctat ctctggactg   240
agatctgagg acgaggccga ctactattgc gccgcctggg atgtttctct gagcggctgg   300
gttttcggcg gaggcacaaa actgacagtg cta                                333

SEQ ID NO: 98           moltype = DNA   length = 1350
FEATURE                 Location/Qualifiers
misc_feature            1..1350
                        note = antibody sequence
source                  1..1350
                        mol_type = other DNA
```

-continued

```
                        organism = synthetic construct
SEQUENCE: 98
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cgggacaaca gcaagaacac cctgtacctg   240
cagatgaaca gcctgagagc cgaggacacc gccgtgtact attgcgccag agagtactac   300
gacagcagcg gctactacca cctggactat tggggccagg gcaccctggt cacagtttct   360
tcagccagca ccaagggccc cagcgtgttc cctctggccc ctagcagcaa gagcacatct   420
ggcggaacag ccgccctggg ctgcctcgtg aaggactact ttcccgagcc cgtgaccgtg   480
tcctggaact ctggcgctct gacaagcggc gtgcacacct ttccagccgt gctgcagagc   540
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt cccccttgtc ctgccccgga actgctggga   720
ggcccttccg tgttcctgtt cccccccaaag cccaaggaca ccctgatgat cagccggacc   780
cccgaagtga cctgcgtggt ggtggatgtg tcccacgagg accctgaagt gaagttcaat   840
tggtacgtgg acggcgtgga agtgcacaac gccaagacca gcctagaga ggaacagtac   900
aacagcacct accgggtggt gtccgtgctg acagtgccca accaggactg gctgaacggc   960
aaagagtaca agtgcaaggt gtccaacaag gccctgcctg cccccatcga gaaaaccatc  1020
agcaaggcca agggccagcc ccgcgaaccc caggtgtaca cactgccccc aagcagggac  1080
gagctgacca gaaccaggt gtccctgacc tgtctcgtga aaggcttcta ccctccgat   1140
atcgccgtgg aatgggagag caacggccag cccgagaaca actacaagac cacccccct   1200
gtgctggaca gcgacggctc attcttcctg tacagcaagc tgaccgtgga caagtcccgg  1260
tggcagcagg gcaacgtgtt cagctgcagc gtgatgcacg aggccctgca caaccactac  1320
acccagaagt ccctgagcct gagccctggc                                    1350

SEQ ID NO: 99           moltype = DNA  length = 1350
FEATURE                 Location/Qualifiers
misc_feature            1..1350
                        note = antibody sequence
source                  1..1350
                        mol_type = other DNA
                        organism = synthetic construct
SEQUENCE: 99
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cgggacaaca gcaagaacac cctgtacctg   240
cagatgaaca gcctgagagc cgaggacacc gccgtgtact attgcgatag agagtactac   300
gacagcagcg gctactacca cctggactat tggggccagg gcaccctggt cacagtttct   360
tcagccagca ccaagggccc cagcgtgttc cctctggccc ctagcagcaa gagcacatct   420
ggcggaacag ccgccctggg ctgcctcgtg aaggactact ttcccgagcc cgtgaccgtg   480
tcctggaact ctggcgctct gacaagcggc gtgcacacct ttccagccgt gctgcagagc   540
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt cccccttgtc ctgccccgga actgctggga   720
ggcccttccg tgttcctgtt cccccccaaag cccaaggaca ccctgatgat cagccggacc   780
cccgaagtga cctgcgtggt ggtggatgtg tcccacgagg accctgaagt gaagttcaat   840
tggtacgtgg acggcgtgga agtgcacaac gccaagacca gcctagaga ggaacagtac   900
aacagcacct accgggtggt gtccgtgctg acagtgctgc accaggactg gctgaacggc   960
aaagagtaca agtgcaaggt gtccaacaag gccctgcctg cccccatcga gaaaaccatc  1020
agcaaggcca agggccagcc ccgcgaaccc caggtgtaca cactgccccc aagcagggac  1080
gagctgacca gaaccaggt gtccctgacc tgtctcgtga aaggcttcta ccctccgat   1140
atcgccgtgg aatgggagag caacggccag cccgagaaca actacaagac cacccccct   1200
gtgctggaca gcgacggctc attcttcctg tacagcaagc tgaccgtgga caagtcccgg  1260
tggcagcagg gcaacgtgtt cagctgcagc gtgatgcacg aggccctgca caaccactac  1320
acccagaagt ccctgagcct gagccctggc                                    1350

SEQ ID NO: 100          moltype = DNA  length = 1350
FEATURE                 Location/Qualifiers
misc_feature            1..1350
                        note = antibody sequence
source                  1..1350
                        mol_type = other DNA
                        organism = synthetic construct
SEQUENCE: 100
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cgggacaaca gcaagaacac cctgtacctg   240
cagatgaaca gcctgagagc cgaggacacc gccgtgtact attgcgccag tgagtactac   300
gacagcagcg gctactacca cctggactat tggggccagg gcaccctggt cacagtttct   360
tcagccagca ccaagggccc cagcgtgttc cctctggccc ctagcagcaa gagcacatct   420
ggcggaacag ccgccctggg ctgcctcgtg aaggactact ttcccgagcc cgtgaccgtg   480
tcctggaact ctggcgctct gacaagcggc gtgcacacct ttccagccgt gctgcagagc   540
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt cccccttgtc ctgccccgga actgctggga   720
ggcccttccg tgttcctgtt cccccccaaag cccaaggaca ccctgatgat cagccggacc   780
```

```
cccgaagtga cctgcgtggt ggtggatgtg tcccacgagg accctgaagt gaagttcaat    840
tggtacgtgg acggcgtgga agtgcacaac gccaagacca agcctagaga ggaacagtac    900
aacagcacct accgggtggt gtccgtgctg acagtgctgc accaggactg gctgaacggc    960
aaagagtaca agtgcaaggt gtccaacaag gccctgcctg cccccatcga gaaaaccatc    1020
agcaaggcca agggccagcc ccgcgaaccc caggtgtaca cactgccccc aagcagggac    1080
gagctgacca agaaccaggt gtccctgacc tgtctcgtga aaggcttcta ccctccgat    1140
atcgccgtgg aatgggagag caacggccag cccgagaaca actacaagac cccccccct    1200
gtgctggaca gcgacggctc attcttcctg tacagcaagc tgaccgtgga caagtcccgg    1260
tggcagcagg gcaacgtgtt cagctgcagc gtgatgcacg aggccctgca caaccactac    1320
acccagaagt ccctgagcct gagccctggc                                     1350

SEQ ID NO: 101          moltype = DNA   length = 1350
FEATURE                 Location/Qualifiers
misc_feature            1..1350
                        note = antibody sequence
source                  1..1350
                        mol_type = other DNA
                        organism = synthetic construct
SEQUENCE: 101
gaagttcagc tgctggaatc tggcggcgga ctggttcaac ctggcggatc tctgagactg     60
agctgtgccg ccagcggctt caccttcgat gattacgcca tgagctgggt ccgacaggcc    120
cctggaaaag gccttgaatg ggtgtccgcc atcggaacag gcggcggaac atattacgcc    180
gacagcgtga agggcagatt caccatcagc cgggacaaca gcaagaacac cctgtacctg    240
cagatgaaca gcctgagagc cgaggacacc gccgtgtact attgcgccag agaggattac    300
gacagcagcg gctactacca cctggactat tggggccagg gcaccctggt cacagtttct    360
tcagccgcca ccaagggccc cagcgtgttc cctctggccc ctagcagcaa gagcacatct    420
ggcggaacag ccgccctggg ctgcctcgtg aaggactact tccccgagcc cgtgaccgtg    480
tcctggaact ctggcgctct gacaagcggg gtgcacacct ttccagccgt gctgcagagc    540
agcggcctgt actctctgag cagcgtcgtg acagtgccca gcagctctct gggcacccag    600
acctacatct gcaacgtgaa ccacaagccc agcaacacca aggtggacaa gaaggtggaa    660
cccaagagct gcgacaagac ccacacctgt ccccttgtc ctgccccga actgctggga     720
ggccct tccg tgttcctgtt ccccccaaag cccaaggaca ccctgatgat cagccggacc    780
cccgaagtga cctgcgtggt ggtggatgtg tcccacgagg accctgaagt gaagttcaat    840
tggtacgtgg acggcgtgga agtgcacaac gccaagacca agcctagaga ggaacagtac    900
aacagcacct accgggtggt gtccgtgctg acagtgctgc accaggactg gctgaacggc    960
aaagagtaca agtgcaaggt gtccaacaag gccctgcctg cccccatcga gaaaaccatc    1020
agcaaggcca agggccagcc ccgcgaaccc caggtgtaca cactgccccc aagcagggac    1080
gagctgacca agaaccaggt gtccctgacc tgtctcgtga aaggcttcta ccctccgat    1140
atcgccgtgg aatgggagag caacggccag cccgagaaca actacaagac cccccccct    1200
gtgctggaca gcgacggctc attcttcctg tacagcaagc tgaccgtgga caagtcccgg    1260
tggcagcagg gcaacgtgtt cagctgcagc gtgatgcacg aggccctgca caaccactac    1320
acccagaagt ccctgagcct gagccctggc                                     1350

SEQ ID NO: 102          moltype = DNA   length = 1350
FEATURE                 Location/Qualifiers
misc_feature            1..1350
                        note = antibody sequence
source                  1..1350
                        mol_type = other DNA
                        organism = synthetic construct
SEQUENCE: 102
gaagttcagc tgctggaatc tggcggcgga ctggttcaac ctggcggatc tctgagactg     60
agctgtgccg ccagcggctt caccttcgat gattacgcca tgagctgggt ccgacaggcc    120
cctggaaaag gccttgaatg ggtgtccgcc atcggaacag cggcggaac atattacgcc    180
gacagcgtga agggcagatt caccatcagc cgggacaaca gcaagaacac cctgtacctg    240
cagatgaaca gcctgagagc cgaggacacc gccgtgtact attgcgccag agaggggtac    300
gacagcagcg gctactacca cctggactat tggggccagg gcaccctggt cacagtttct    360
tcagccgcca ccaagggccc cagcgtgttc cctctggccc ctagcagcaa gagcacatct    420
ggcggaacag ccgccctggg ctgcctcgtg aaggactact tccccgagcc cgtgaccgtg    480
tcctggaact ctggcgctct gacaagcggg gtgcacacct ttccagccgt gctgcagagc    540
agcggcctgt actctctgag cagcgtcgtg acagtgccca gcagctctct gggcacccag    600
acctacatct gcaacgtgaa ccacaagccc agcaacacca aggtggacaa gaaggtggaa    660
cccaagagct gcgacaagac ccacacctgt ccccttgtc ctgccccga actgctggga     720
ggcccttccg tgttcctgtt ccccccaaag cccaaggaca ccctgatgat cagccggacc    780
cccgaagtga cctgcgtggt ggtggatgtg tcccacgagg accctgaagt gaagttcaat    840
tggtacgtgg acggcgtgga agtgcacaac gccaagacca agcctagaga ggaacagtac    900
aacagcacct accgggtggt gtccgtgctg acagtgctgc accaggactg gctgaacggc    960
aaagagtaca agtgcaaggt gtccaacaag gccctgcctg cccccatcga gaaaaccatc    1020
agcaaggcca agggccagcc ccgcgaaccc caggtgtaca cactgccccc aagcagggac    1080
gagctgacca agaaccaggt gtccctgacc tgtctcgtga aaggcttcta ccctccgat    1140
atcgccgtgg aatgggagag caacggccag cccgagaaca actacaagac cccccccct    1200
gtgctggaca gcgacggctc attcttcctg tacagcaagc tgaccgtgga caagtcccgg    1260
tggcagcagg gcaacgtgtt cagctgcagc gtgatgcacg aggccctgca caaccactac    1320
acccagaagt ccctgagcct gagccctggc                                     1350

SEQ ID NO: 103          moltype = DNA   length = 1350
FEATURE                 Location/Qualifiers
misc_feature            1..1350
                        note = antibody sequence
```

```
source                  1..1350
                        mol_type = other DNA
                        organism = synthetic construct
SEQUENCE: 103
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cgggacaaca gcaagaacac cctgtacctg   240
cagatgaaca gcctgagagc cgaggacacc gccgtgtact attgcgccag agagtactac   300
gacagcagcg gctactacca cctggtttat tggggccagg gcaccctggt cacagttttct   360
tcagccagca ccaagggccc cagcgtgttc cctctggccc ctagcagcaa gagcacatct   420
ggcggaacag ccgccctggg ctgcctcgtg aaggactact tccccgagcc cgtgaccgtg   480
tcctggaact ctggcgctct gacaagcggc gtgcacacct tccagcgt gctgcagagc    540
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt cccccttgtc ctgccccga actgctggga   720
ggcccttccg tgttcctgtt ccccccaaag cccaaggaca cctgatgat cagccggacc    780
cccgaagtga cctgcgtggt ggtggatgtg tcccacgagg accctgaagt gaagttcaat   840
tggtacgtgg acggcgtgga agtgcacaac gccaagacca gcctagaga ggaacagtac    900
aacagcacct accgggtggt gtccgtgctg acagtgctgc accaggactg gctgaacggc   960
aaagagtaca agtgcaaggt gtccaacaag gccctgcctg cccccatcga gaaaaccatc   1020
agcaaggcca agggccagcc ccgcgaaccc caggtgtaca cactgccccc aagcagggac   1080
gagctgacca gaaccaggt gtccctgacc tgtctcgtga aaggcttcta cccctccgat    1140
atcgccgtgg aatgggagag caacggccag cccgagaaca actacaagac caccccccct   1200
gtgctggaca gcgacggctc attcttcctg tacagcaagc tgaccgtgga caagtcccgg   1260
tggcagcagg gcaacgtgtt cagctgcagc gtgatgcacg aggccctgca caaccactac   1320
acccagaagt ccctgagcct gagccctggc                                   1350

SEQ ID NO: 104         moltype = DNA    length = 1350
FEATURE                Location/Qualifiers
misc_feature           1..1350
                       note = antibody sequence
source                 1..1350
                       mol_type = other DNA
                       organism = synthetic construct
SEQUENCE: 104
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cgggacaaca gcaagaacac cctgtacctg   240
cagatgaaca gcctgagagc cgaggacacc gccgtgtact attgcgccag agagtactac   300
gacagcagcg gctactacca cctggagtat tggggccagg gcaccctggt cacagttttct   360
tcagccagca ccaagggccc cagcgtgttc cctctggccc ctagcagcaa gagcacatct   420
ggcggaacag ccgccctggg ctgcctcgtg aaggactact tccccgagcc cgtgaccgtg   480
tcctggaact ctggcgctct gacaagcggc gtgcacacct tccagcgt gctgcagagc    540
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt cccccttgtc ctgccccga actgctggga   720
ggcccttccg tgttcctgtt ccccccaaag cccaaggaca cctgatgat cagccggacc    780
cccgaagtga cctgcgtggt ggtggatgtg tcccacgagg accctgaagt gaagttcaat   840
tggtacgtgg acggcgtgga agtgcacaac gccaagacca gcctagaga ggaacagtac    900
aacagcacct accgggtggt gtccgtgctg acagtgctgc accaggactg gctgaacggc   960
aaagagtaca agtgcaaggt gtccaacaag gccctgcctg cccccatcga gaaaaccatc   1020
agcaaggcca agggccagcc ccgcgaaccc caggtgtaca cactgccccc aagcagggac   1080
gagctgacca gaaccaggt gtccctgacc tgtctcgtga aaggcttcta cccctccgat    1140
atcgccgtgg aatgggagag caacggccag cccgagaaca actacaagac caccccccct   1200
gtgctggaca gcgacggctc attcttcctg tacagcaagc tgaccgtgga caagtcccgg   1260
tggcagcagg gcaacgtgtt cagctgcagc gtgatgcacg aggccctgca caaccactac   1320
acccagaagt ccctgagcct gagccctggc                                   1350

SEQ ID NO: 105         moltype = DNA    length = 1350
FEATURE                Location/Qualifiers
misc_feature           1..1350
                       note = antibody sequence
source                 1..1350
                       mol_type = other DNA
                       organism = synthetic construct
SEQUENCE: 105
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cgggacaaca gcaagaacac cctgtacctg   240
cagatgaaca gcctgagagc cgaggacacc gccgtgtact attgcgccag agagtactac   300
gacagcagcg gctactacca cctgacgtat tggggccagg gcaccctggt cacagttttct   360
tcagccagca ccaagggccc cagcgtgttc cctctggccc ctagcagcaa gagcacatct   420
ggcggaacag ccgccctggg ctgcctcgtg aaggactact tccccgagcc cgtgaccgtg   480
tcctggaact ctggcgctct gacaagcggc gtgcacacct tccagcgt gctgcagagc    540
agcggcctgt actctctgag cagcgtcgtg acagtgccca gcagctctct gggcacccag   600
acctacatct gcaacgtgaa ccacaagccc agcaacacca aggtggacaa gaaggtggaa   660
```

```
cccaagagct gcgacaagac ccacacctgt cccccttgtc ctgccccga actgctggga    720
ggcccttccg tgttcctgtt ccccccaaag cccaaggaca ccctgatgat cagccggacc    780
cccgaagtga cctgcgtggt ggtggatgtg tcccacgagg accctgaagt gaagttcaat    840
tggtacgtgg acggcgtgga agtgcacaac gccaagacca gcctagaga ggaacagtac    900
aacagcacct accgggtggt gtccgtgctg acagtgctgc accaggactg gctgaacggc    960
aaagagtaca agtgcaaggt gtccaacaag gccctgcctg ccccatcga gaaaaccatc   1020
agcaaggcca agggccagcc ccgcgaaccc caggtgtaca cactgccccc aagcagggac   1080
gagctgacca gaaccaggt gtccctgacc tgtctcgtga aaggcttcta cccctccgat   1140
atcgccgtgg aatgggagag caacggccag cccgagaaca actacaagac cacccccct   1200
gtgctggaca gcgacggctc attcttcctg tacagcaagc tgaccgtgga caagtcccgg   1260
tggcagcagg gcaacgtgtt cagctgcagc gtgatgcacg aggccctgca caaccactac   1320
acccagaagt ccctgagcct gagccctggc                                    1350

SEQ ID NO: 106        moltype = DNA  length = 1350
FEATURE               Location/Qualifiers
misc_feature          1..1350
                      note = antibody sequence
source                1..1350
                      mol_type = other DNA
                      organism = synthetic construct
SEQUENCE: 106
gaagttcagc tgctggaatc tggcggcgga ctggttcaac ctggcggatc tctgagactg     60
agctgtgccg ccagcggctt cacctttagc gattacgcca tgagctgggt ccgacaggcc    120
cctggaaaag gccttgaatg ggtgtccgcc atcggaacag gcggcggaac atattacgcc    180
gacagcgtga agggcagatt caccatcagc cgggacaaca gcaagaacac cctgtacctg    240
cagatgaaca gcctgagagc cgaggacacc gccgtgtact attgtgccag agagggctac    300
gacagcagcg gctactacca cctggattat tggggccagg gcaccctggt tacagtgtca    360
tcagccagca ccaagggccc cagcgtgttc cctctggccc ctagcagcaa gagcacatct    420
ggcggaacag ccgccctggg ctgcctcgtg aaggactact ttcccgagcc cgtgaccgtg    480
tcctggaact ctggcgctct gacaagcggc gtgcacacct tccagccgt gctgcagagc    540
agcggcctgt actctctgag cagcgtcgtg acagtgccca gcagctctct gggcacccag    600
acctacatct gcaacgtgaa ccacaagccc agcaacacca aggtggacaa gaaggtggaa    660
cccaagagct gcgacaagac ccacacctgt cccccttgtc ctgccccga actgctggga    720
ggcccttccg tgttcctgtt ccccccaaag cccaaggaca ccctgatgat cagccggacc    780
cccgaagtga cctgcgtggt ggtggatgtg tcccacgagg accctgaagt gaagttcaat    840
tggtacgtgg acggcgtgga agtgcacaac gccaagacca gcctagaga ggaacagtac    900
aacagcacct accgggtggt gtccgtgctg acagtgctgc accaggactg gctgaacggc    960
aaagagtaca agtgcaaggt gtccaacaag gccctgcctg ccccatcga gaaaaccatc   1020
agcaaggcca agggccagcc ccgcgaaccc caggtgtaca cactgccccc aagcagggac   1080
gagctgacca gaaccaggt gtccctgacc tgtctcgtga aaggcttcta cccctccgat   1140
atcgccgtgg aatgggagag caacggccag cccgagaaca actacaagac cacccccct   1200
gtgctggaca gcgacggctc attcttcctg tacagcaagc tgaccgtgga caagtcccgg   1260
tggcagcagg gcaacgtgtt cagctgcagc gtgatgcacg aggccctgca caaccactac   1320
acccagaagt ccctgagcct gagccctggc                                    1350

SEQ ID NO: 107        moltype = DNA  length = 1350
FEATURE               Location/Qualifiers
misc_feature          1..1350
                      note = antibody sequence
source                1..1350
                      mol_type = other DNA
                      organism = synthetic construct
SEQUENCE: 107
gaagttcagc tgctggaatc tggcggcgga ctggttcaac ctggcggatc tctgagactg     60
agctgtgccg ccagcggctt cacctttgat gattacgcca tgagctgggt ccgacaggcc    120
cctggaaaag gccttgaatg ggtgtccgcc atcggcacag gcggcagcac atattacgcc    180
gactctgtga agggcagatt caccatcagc cgggacaaca gcaagaacac cctgtacctg    240
cagatgaaca gcctgagagc cgaggacacc gccgtgtact attgtgccag agagggctac    300
gacagcagcg gctactacca cctggattat tggggccagg gcaccctggt tacagtgtca    360
tcagccagca ccaagggccc cagcgtgttc cctctggccc ctagcagcaa gagcacatct    420
ggcggaacag ccgccctggg ctgcctcgtg aaggactact ttcccgagcc cgtgaccgtg    480
tcctggaact ctggcgctct gacaagcggc gtgcacacct tccagccgt gctgcagagc    540
agcggcctgt actctctgag cagcgtcgtg acagtgccca gcagctctct gggcacccag    600
acctacatct gcaacgtgaa ccacaagccc agcaacacca aggtggacaa gaaggtggaa    660
cccaagagct gcgacaagac ccacacctgt cccccttgtc ctgccccga actgctggga    720
ggcccttccg tgttcctgtt ccccccaaag cccaaggaca ccctgatgat cagccggacc    780
cccgaagtga cctgcgtggt ggtggatgtg tcccacgagg accctgaagt gaagttcaat    840
tggtacgtgg acggcgtgga agtgcacaac gccaagacca gcctagaga ggaacagtac    900
aacagcacct accgggtggt gtccgtgctg acagtgctgc accaggactg gctgaacggc    960
aaagagtaca agtgcaaggt gtccaacaag gccctgcctg ccccatcga gaaaaccatc   1020
agcaaggcca agggccagcc ccgcgaaccc caggtgtaca cactgccccc aagcagggac   1080
gagctgacca gaaccaggt gtccctgacc tgtctcgtga aaggcttcta cccctccgat   1140
atcgccgtgg aatgggagag caacggccag cccgagaaca actacaagac cacccccct   1200
gtgctggaca gcgacggctc attcttcctg tacagcaagc tgaccgtgga caagtcccgg   1260
tggcagcagg gcaacgtgtt cagctgcagc gtgatgcacg aggccctgca caaccactac   1320
acccagaagt ccctgagcct gagccctggc                                    1350

SEQ ID NO: 108        moltype = DNA  length = 1350
FEATURE               Location/Qualifiers
```

```
misc_feature            1..1350
                        note = antibody sequence
source                  1..1350
                        mol_type = other DNA
                        organism = synthetic construct
SEQUENCE: 108
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggaacag gcggcggaac atattacgcc   180
gacagcgtga agggcagatt caccatcagc cgggacaaca gcaagaacac cctgtacctg   240
cagatgaaca gcctgagagc cgaggacacc gccgtgtact actgtgccaa agagggctac   300
gacagcagcg gctactacca cctggattat tggggccagg gcaccctggt tacagtgtca   360
tcagccagca ccaagggccc cagcgtgttc cctctggccc ctagcagcaa gagcacatct   420
ggcggaacag ccgccctggg ctgcctcgtg aaggactact ttcccgagcc cgtgaccgtg   480
tcctggaact ctggcgctct gacaagcggc gtgcacacct ttccagccgt gctgcagagc   540
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt ccccccttgtc ctgcccccga actgctggga   720
ggcccttccg tgttcctgtt cccccccaaag cccaaggaca ccctgatgat cagccggacc   780
cccgaagtga cctgcgtggt ggtggatgtg tcccacgagg accctgaagt gaagttcaat   840
tggtacgtgg acggcgtgga agtgcacaac gccaagacca gcctagaga ggaacagtac   900
aacagcacct accgggtggt gtccgtgctg acagtgctgc accaggactg gctgaacggc   960
aaagagtaca agtgcaaggt gtccaacaag gccctgcctg cccccatcga gaaaaccatc  1020
agcaaggcca agggccagcc ccgcgaaccc caggtgtaca cactgccccc aagcagggac  1080
gagctgacca gaaccaggt gtccctgacc tgtctcgtga aaggcttcta ccctccgat  1140
atcgccgtgg aatgggagag caacggccag cccgagaaca actacaagac cacccccct  1200
gtgctggaca gcgacggctc attcttcctg tacagcaagc tgaccgtgga caagtccgg  1260
tggcagcagg gcaacgtgtt cagctgcagc gtgatgcacg aggccctgca caaccactac  1320
acccagaagt ccctgagcct gagccctggc                                   1350

SEQ ID NO: 109           moltype = DNA  length = 1350
FEATURE                  Location/Qualifiers
misc_feature             1..1350
                         note = antibody sequence
source                   1..1350
                         mol_type = other DNA
                         organism = synthetic construct
SEQUENCE: 109
gaagttcagc tgctggaatc tggcggcgga ctggttcaac ctggcggatc tctgagactg    60
agctgtgccg ccagcggctt cacctttagc gattacgcca tgagctgggt ccgacaggcc   120
cctggaaaag gccttgaatg ggtgtccgcc atcggcacag cggcagcac atattacgcc   180
gactctgtga agggcagatt caccatcagc cgggacaaca gcaagaacac cctgtacctg   240
cagatgaaca gcctgagagc cgaggacacc gccgtgtact attgtgccag agagggctac   300
gacagcagcg gctactacca cctggattat tggggccagg gcaccctggt tacagtgtca   360
tcagccagca ccaagggccc cagcgtgttc cctctggccc ctagcagcaa gagcacatct   420
ggcggaacag ccgccctggg ctgcctcgtg aaggactact ttcccgagcc cgtgaccgtg   480
tcctggaact ctggcgctct gacaagcggc gtgcacacct ttccagccgt gctgcagagc   540
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt cccccttgtc ctgcccccga actgctggga   720
ggcccttccg tgttcctgtt cccccccaaag cccaaggaca ccctgatgat cagccggacc   780
cccgaagtga cctgcgtggt ggtggatgtg tcccacgagg accctgaagt gaagttcaat   840
tggtacgtgg acggcgtgga agtgcacaac gccaagacca gcctagaga ggaacagtac   900
aacagcacct accgggtggt gtccgtgctg acagtgctgc accaggactg gctgaacggc   960
aaagagtaca agtgcaaggt gtccaacaag gccctgcctg cccccatcga gaaaaccatc  1020
agcaaggcca agggccagcc ccgcgaaccc caggtgtaca cactgccccc aagcagggac  1080
gagctgacca gaaccaggt gtccctgacc tgtctcgtga aaggcttcta ccctccgat  1140
atcgccgtgg aatgggagag caacggccag cccgagaaca actacaagac cacccccct  1200
gtgctggaca gcgacggctc attcttcctg tacagcaagc tgaccgtgga caagtccgg  1260
tggcagcagg gcaacgtgtt cagctgcagc gtgatgcacg aggccctgca caaccactac  1320
acccagaagt ccctgagcct gagccctggc                                   1350

SEQ ID NO: 110           moltype = DNA  length = 1350
FEATURE                  Location/Qualifiers
misc_feature             1..1350
                         note = antibody sequence
source                   1..1350
                         mol_type = other DNA
                         organism = synthetic construct
SEQUENCE: 110
gaagttcagc tgctggaatc tggcggcgga ctggttcaac ctggcggatc tctgagactg    60
agctgtgccg ccagcggctt cacctttgat agctacgcca tgagctgggt ccgacaggcc   120
cctggaaaag gccttgaatg ggtgtccgcc atcggcacag cggcagcac atattacgcc   180
gactctgtga agggcagatt caccatcagc cgggacaaca gcaagaacac cctgtacctg   240
cagatgaaca gcctgagagc cgaggacacc gccgtgtact attgtgccag agagggctac   300
gacagcagcg gctactacca cctggattat tggggccagg gcaccctggt tacagtgtca   360
tcagccagca ccaagggccc cagcgtgttc cctctggccc ctagcagcaa gagcacatct   420
ggcggaacag ccgccctggg ctgcctcgtg aaggactact ttcccgagcc cgtgaccgtg   480
tcctggaact ctggcgctct gacaagcggc gtgcacacct ttccagccgt gctgcagagc   540
```

```
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt cccccttgtc ctgccccga actgctggga    720
ggcccttccg tgttcctgtt cccccaaag cccaaggaca ccctgatgat cagccggacc    780
cccgaagtga cctgcgtggt ggtggatgtg tcccacgagg accctgaagt gaagttcaat   840
tggtacgtgg acggcgtgga agtgcacaac gccaagacca gcctagaga ggaacagtac    900
aacagcacct accgggtggt gtccgtgcta caagtgctgc accaggactg gctgaacggc   960
aaagagtaca agtgcaaggt gtccaacaag gccctgcctg cccccatcga gaaaaccatc  1020
agcaaggcca agggccagcc ccgcgaaccc caggtgtaca cactgccccc aagcagggac  1080
gagctgacca agaaccaggt gtccctgacc tgtctcgtga aaggcttcta cccctccgat  1140
atcgccgtgg aatgggagag caacggccag cccgagaaca actacaagac cacccccct   1200
gtgctggaca gcgacggctc attcttcctg tacagcaagc tgaccgtgga caagtcccgg  1260
tggcagcagg gcaacgtgtt cagctgcagc gtgatgcacg aggccctgca caaccactac  1320
acccagaagt ccctgagcct gagccctggc                                   1350

SEQ ID NO: 111          moltype = DNA  length = 1350
FEATURE                 Location/Qualifiers
misc_feature            1..1350
                        note = antibody sequence
source                  1..1350
                        mol_type = other DNA
                        organism = synthetic construct
SEQUENCE: 111
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggcacgg cggcagcac atattacgcc    180
gactctgtga agggcagatt caccatcagc cgggacaaca gcaagaacac cctgtacctg   240
cagatgaaca gcctgagagc cgaggacacc gccgtgtact attgtgccag agagggctac   300
gacagcagcg gctactacca cctggattat tgggccagg gcaccctggt tacagtgtca    360
tcagccagca ccaagggccc cagcgtgttc cctctggccc ctagcagcaa gagcacatct   420
ggcgaacag ccgccctggg ctgcctcgtg aaggactact ttcccgagcc cgtgaccgtg    480
tcctggaact ctggcgctct gacaagcggc gtgcacacct ttccagcgt gctgcagagc    540
agcggcctgt actctctgag cagcgtcgtg acagtgccca gcagctctct gggcacccag   600
acctacatct gcaacgtgaa ccacaagccc agcaacacca aggtggacaa gaaggtggaa   660
cccaagagct gcgacaagac ccacacctgt cccccttgtc ctgccccga actgctggga    720
ggcccttccg tgttcctgtt cccccaaag cccaaggaca ccctgatgat cagccggacc    780
cccgaagtga cctgcgtggt ggtggatgtg tcccacgagg accctgaagt gaagttcaat   840
tggtacgtgg acggcgtgga agtgcacaac gccaagacca gcctagaga ggaacagtac    900
aacagcacct accgggtggt gtccgtgcta caagtgctgc accaggactg gctgaacggc   960
aaagagtaca agtgcaaggt gtccaacaag gccctgcctg cccccatcga gaaaaccatc  1020
agcaaggcca agggccagcc ccgcgaaccc caggtgtaca cactgccccc aagcagggac  1080
gagctgacca agaaccaggt gtccctgacc tgtctcgtga aaggcttcta cccctccgat  1140
atcgccgtgg aatgggagag caacggccag cccgagaaca actacaagac cacccccct   1200
gtgctggaca gcgacggctc attcttcctg tacagcaagc tgaccgtgga caagtcccgg  1260
tggcagcagg gcaacgtgtt cagctgcagc gtgatgcacg aggccctgca caaccactac  1320
acccagaagt ccctgagcct gagccctggc                                   1350

SEQ ID NO: 112          moltype = DNA  length = 1341
FEATURE                 Location/Qualifiers
misc_feature            1..1341
                        note = antibody sequence
source                  1..1341
                        mol_type = other DNA
                        organism = synthetic construct
SEQUENCE: 112
gaagttcagc tgctggaatc tggcggcgga ctggttcaac ctggcggatc tctgagactg    60
agctgtgccg ccagcggctt caccttcgat gattacgcca tgagctgggt ccgacaggcc   120
cctggaaaag gccttgaatg ggtgtccgcc atcggcacag cggcagcac atattacgcc    180
gactctgtga agggcagatt caccatcagc cgggacaaca gcaagaacac cctgtacctg   240
cagatgaaca gcctgagagc cgaggacacc gccgtgtact attgtgccag agagggctac   300
gacagcagcg gctactacca cctggattat tgggccagg gcaccctggt tacagtgtca    360
tcagccagca ccaagggccc cagcgtgttc cctctggccc cttgtagcag aagcaccagc   420
gagtctacag ccgccctggg ctgcctcgtg aaggactact ttcccgagcc cgtgaccgtg    480
tcctggaact ctggcgctct gacaagcggc gtgcacacct ttccagcgt gctgcagagc    540
agcggcctgt actctctgag cagcgtcgtg acagtgccca gcagcagcct gggcaccaag   600
acctacacct gtaacgtgga ccacaagccc agcaacacca aggtgacaa gcgggtggaa    660
tctaagtacg gccctcctg ccctccttgc ccagcccctg aatttctggg cggacctctc    720
gtgttcctgt tcccccaaa gcccaaggac accctgatga tcagccggac cccgaagtg    780
acctgcgtgg tggtggatgt gtcccaggaa gatcccgag ttggtacgtg                840
gacgcgtgg aagtgcacaa cgccaagacc aagcccagag gaacagtt caacagcacc      900
taccgggtgg tgtccgtgct gacagtgctg caccaggact ggctgaacgg caaagagtac   960
aagtgcaagg tgtccaacaa gggcctgcct agctccatcg agaaaaccat cagcaaggcc  1020
aagggccagc ccgcgaacc ccaggtgtac acactgcctc aagcagga agagatgacc     1080
aagaaccagg tgtccctgac ctgtctcgtg aaaggcttct accctccga tatcgccgtg   1140
gaatgggaga gcaacggcca gcccgagaac aactacaaga ccaccccccc tgtgctggac  1200
agcgacggct cattcttcct gtacagcaga ctgaccgtgg acaagagccg gtggcaggaa  1260
ggcaacgtgt tcagctgcag cgtgatgcac gaggccctgc acaaccacta cacccagaag  1320
tccctgtctc tgagcctggg c                                            1341
```

```
SEQ ID NO: 113            moltype = DNA   length = 651
FEATURE                   Location/Qualifiers
misc_feature              1..651
                          note = antibody sequence
source                    1..651
                          mol_type = other DNA
                          organism = synthetic construct
SEQUENCE: 113
cagtctgttc tgacacagcc tcctagcgcc tctggcacac ctggacagag agtgaccatc     60
agctgtaccg gcagcagctc caatatcggc gccacctatg acgtgcactg gtatcagcag    120
ctgcctggca cagcccctaa actgctgatc tacagcaaca accagcggcc tagcggcgtg    180
cccgatagat tttctggcag caagagcggc acaagcgcca gcctggctat ctctggactg    240
agatctgagg acgaggccga ctactattgc gccgcctggg atgattctct gagcggctgg    300
gttttcggcg gaggcacaaa actgacagtg ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac cacccctagc aagcagagca acaacaaata cgccgccagc    540
agctacctga gcctgacccc cgagcagtgg aagtcccaca tgatcctacag ctgccaagtg   600
acccacgagg gcagcaccgt ggaaaagaca gtggccccta ccgagtgcag c              651

SEQ ID NO: 114            moltype = DNA   length = 651
FEATURE                   Location/Qualifiers
misc_feature              1..651
                          note = antibody sequence
source                    1..651
                          mol_type = other DNA
                          organism = synthetic construct
SEQUENCE: 114
cagtctgttc tgacacagcc tcctagcgcc tctggcacac ctggacagag agtgaccatc     60
agctgtaccg gcagcagctc caatatcggc gccacctatg acgtgcactg gtatcagcag    120
ctgcctggca cagcccctaa actgctgatc tacagcaaca accagcggcc tagcggcgtg    180
cccgatagat tttctggcag caagagcggc acaagcgcca gcctggctat ctctggactg    240
agatctgagg acgaggccga ctactattgc gccgcctggg attggtctct gagcggctgg    300
gttttcggcg gaggcacaaa actgacagtg ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac cacccctagc aagcagagca acaacaaata cgccgccagc    540
agctacctga gcctgacccc cgagcagtgg aagtcccaca tgatcctacag ctgccaagtg   600
acccacgagg gcagcaccgt ggaaaagaca gtggccccta ccgagtgcag c              651

SEQ ID NO: 115            moltype = DNA   length = 651
FEATURE                   Location/Qualifiers
misc_feature              1..651
                          note = antibody sequence
source                    1..651
                          mol_type = other DNA
                          organism = synthetic construct
SEQUENCE: 115
cagtctgttc tgacacagcc tcctagcgcc tctggcacac ctggacagag agtgaccatc     60
agctgtaccg gcagcagctc caatatcggc gccacctatg acgtgcactg gtatcagcag    120
ctgcctggca cagcccctaa actgctgatc tacagcaaca accagcggcc tagcggcgtg    180
cccgatagat tttctggcag caagagcggc acaagcgcca gcctggctat ctctggactg    240
agatctgagg acgaggccga ctactattgc tgggcctggg atgattctct gagcggctgg    300
gttttcggcg gaggcacaaa actgacagtg ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac cacccctagc aagcagagca acaacaaata cgccgccagc    540
agctacctga gcctgacccc cgagcagtgg aagtcccaca tgatcctacag ctgccaagtg   600
acccacgagg gcagcaccgt ggaaaagaca gtggccccta ccgagtgcag c              651

SEQ ID NO: 116            moltype = DNA   length = 651
FEATURE                   Location/Qualifiers
misc_feature              1..651
                          note = antibody sequence
source                    1..651
                          mol_type = other DNA
                          organism = synthetic construct
SEQUENCE: 116
cagtctgttc tgacacagcc tcctagcgcc tctggcacac ctggacagag agtgaccatc     60
agctgtaccg gcagcagctc caatatcggc gccacctatg acgtgcactg gtatcagcag    120
ctgcctggca cagcccctaa actgctgatc tacagcaaca accagcggcc tagcggcgtg    180
cccgatagat tttctggcag caagagcggc acaagcgcca gcctggctat ctctggactg    240
agatctgagg acgaggccga ctactattgc gccgcctggg atgtttctct gagcggctgg    300
gttttcggcg gaggcacaaa actgacagtg ctaggccagc ctaaagccgc ccctagcgtg    360
accctgttcc ctccaagcag cgaggaactg caggccaaca aggccaccct cgtgtgcctg    420
atcagcgact tctatcctgg cgccgtgacc gtggcctgga aggccgatag ctctcctgtg    480
aaggccggcg tggaaaccac cacccctagc aagcagagca acaacaaata cgccgccagc    540
agctacctga gcctgacccc cgagcagtgg aagtcccaca tgatcctacag ctgccaagtg   600
acccacgagg gcagcaccgt ggaaaagaca gtggccccta ccgagtgcag c              651
```

```
SEQ ID NO: 117         moltype = DNA  length = 39
FEATURE                Location/Qualifiers
misc_feature           1..39
                       note = antibody sequence
source                 1..39
                       mol_type = other DNA
                       organism = synthetic construct
SEQUENCE: 117
gagggctacg acagcagcgg ctactaccac ctggattat                                  39

SEQ ID NO: 118         moltype = AA  length = 561
FEATURE                Location/Qualifiers
source                 1..561
                       mol_type = protein
                       organism = Homo sapiens
SEQUENCE: 118
EPLDDYVNTQ GASLFSVTKK QLGAGSIEEC AAKCEEDEEF TCRAFQYHSK EQQCVIMAEN    60
RKSSIIIRMR DVVLFEKKVY LSECKTGNGK NYRGTMSKTK NGITCQKWSS TSPHRPRFSP   120
ATHPSEGLEE NYCRNPDNDP QGPWCYTTDP EKRYDYCDIL ECEEECMHCS GENYDGKISK   180
TMSGLECQAW DSQSPHAHGY IPSKFPNKNL KKNYCRNPDR ELRPWCFTTD PNKRWELCDI   240
PRCTTPPPSS GPTYQCLKGT GENYRGNVAV TVSGHTCQHW SAQTPHTHNR TPENFPCKNL   300
DENYCRNPDG KRAPWCHTTN SQVRWEYCKI PSCDSSPVST EQLAPTAPPE LTPVVQDCYH   360
GDGQSYRGTS STTTTGKKCQ SWSSMTPHRH QKTPENYPNA GLTMNYCRNP DADKGPWCFT   420
TDPSVRWEYC NLKKCSGTEA SVVAPPPVVL LPDVETPSEE DCMFGNGKGY RGKRATTVTG   480
TPCQDWAAQE PHRHSIFTPE TNPRAGLEKN YCRNPDGDVG GPWCYTTNPR KLYDYCDVPQ   540
CAAPSFDCGK PQVEPKKCPG R                                             561

SEQ ID NO: 119         moltype = AA  length = 230
FEATURE                Location/Qualifiers
source                 1..230
                       mol_type = protein
                       organism = Homo sapiens
SEQUENCE: 119
VVGGCVAHPH SWPWQVSLRT RFGMHFCGGT LISPEWVLTA AHCLEKSPRP SSYKVILGAH    60
QEVNLEPHVQ EIEVSRLFLE PTRKDIALLK LSSPAVITDK VIPACLPSPN YVVADRTECF   120
ITGWGETQGT FGAGLLKEAQ LPVIENKVCN RYEFLNGRVQ STELCAGHLA GGTDSCQGDS   180
GGPLVCFEKD KYILQGVTSW GLGCARPNKP GVYVRVSRFV TWIEGVMRNN              230
```